US010206788B2

(12) United States Patent
Field et al.

(10) Patent No.: US 10,206,788 B2
(45) Date of Patent: Feb. 19, 2019

(54) EXPANDABLE INTERBODY DEVICES AND RELATED INSTRUMENTS AND METHODS FOR SPINAL FUSION SURGERY

(71) Applicant: Southern Spine, LLC, Macon, GA (US)

(72) Inventors: David C. Field, Snellville, GA (US); Mitchell Blenden, Macon, GA (US); Hugh F. Smisson, III, Macon, GA (US)

(73) Assignee: Southern Spine, LLC, Macon, GA (US)

( * ) Notice: Subject to any disclaimer, the term of this patent is extended or adjusted under 35 U.S.C. 154(b) by 0 days.

(21) Appl. No.: 15/387,191

(22) Filed: Dec. 21, 2016

(65) Prior Publication Data

US 2017/0172758 A1    Jun. 22, 2017

Related U.S. Application Data

(60) Provisional application No. 62/270,115, filed on Dec. 21, 2015.

(51) Int. Cl.
*A61F 2/44* (2006.01)
*A61F 2/46* (2006.01)
*A61F 2/30* (2006.01)

(52) U.S. Cl.
CPC ............ *A61F 2/4455* (2013.01); *A61F 2/442* (2013.01); *A61F 2/4611* (2013.01); *A61F 2002/30024* (2013.01); *A61F 2002/3055* (2013.01); *A61F 2002/30321* (2013.01); *A61F 2002/30471* (2013.01); *A61F 2002/30538* (2013.01); *A61F 2002/30555* (2013.01); *A61F 2002/30579* (2013.01); *A61F 2002/30624* (2013.01); *A61F 2002/30904* (2013.01); *A61F 2002/4623* (2013.01); *A61F 2002/4627* (2013.01); *A61F 2002/4629* (2013.01)

(58) Field of Classification Search
CPC .............................................. A61F 2002/4625
See application file for complete search history.

(56) References Cited

U.S. PATENT DOCUMENTS 8,303,658 B2 *  11/2012  Peterman ............. A61F 2/4455
                                                                      623/17.11

* cited by examiner

*Primary Examiner* — Eduardo C Robert
*Assistant Examiner* — Tara R Carter
(74) *Attorney, Agent, or Firm* — Eversheds Sutherland (US) LLP

(57) ABSTRACT

An interbody device may include a main body and an arm movably connected thereto. The device may have a first end, a second end opposite the first end in a direction of a longitudinal axis of the device, a first side, a second side opposite the first side in a direction of a first transverse axis of the device, a third side, and a fourth side opposite the third side in a direction of a second transverse axis of the device. An overall distance between the first side and the second side may increase along at least a majority of a length of the device in a direction from the first end toward the second end, and an overall distance between the third side and the fourth side may increase along at least a majority of the length in a direction from the second end toward the first end.

20 Claims, 42 Drawing Sheets

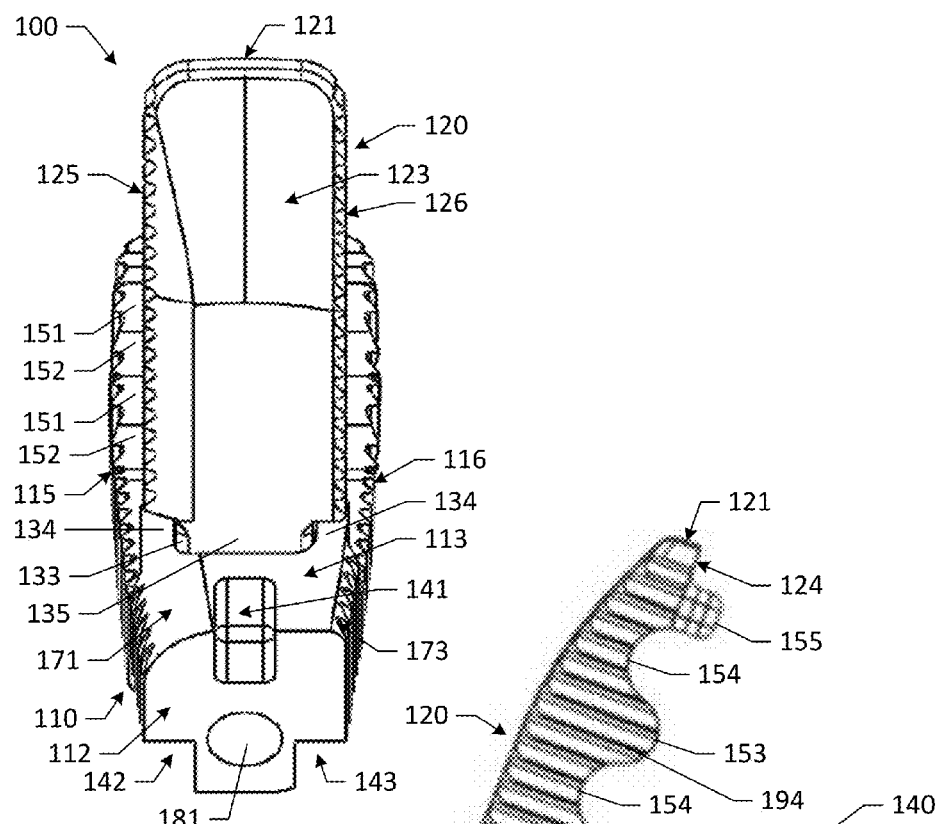
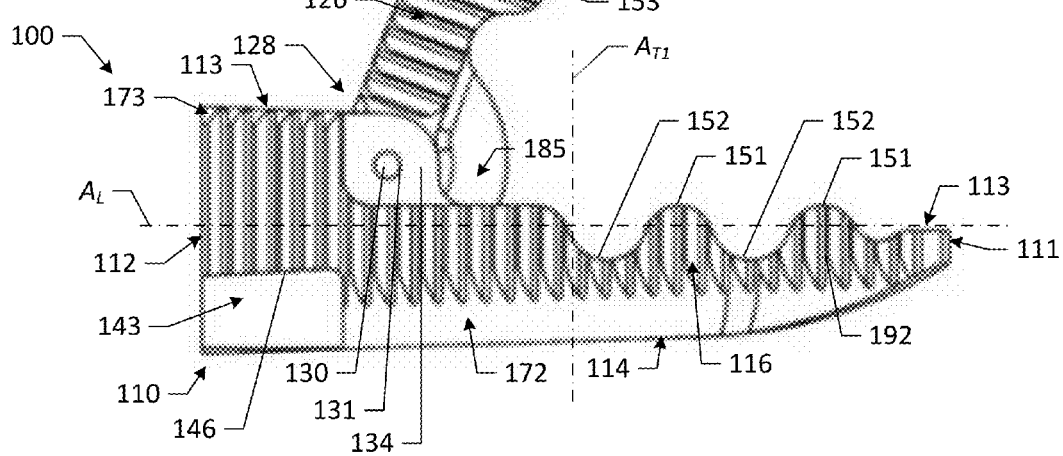
FIG. 1I
FIG. 1J

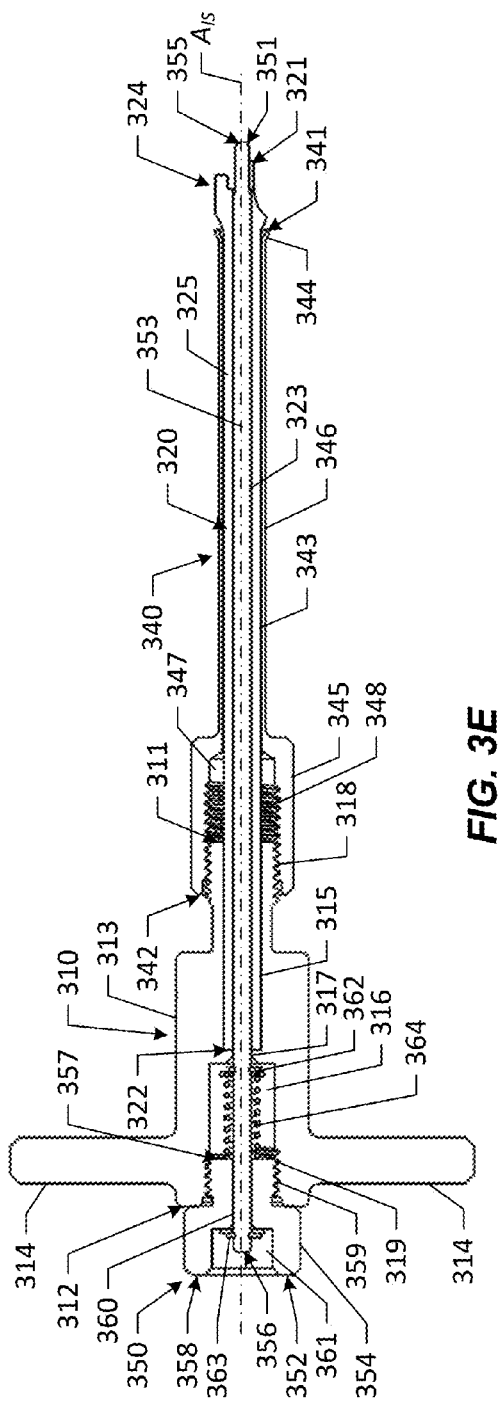
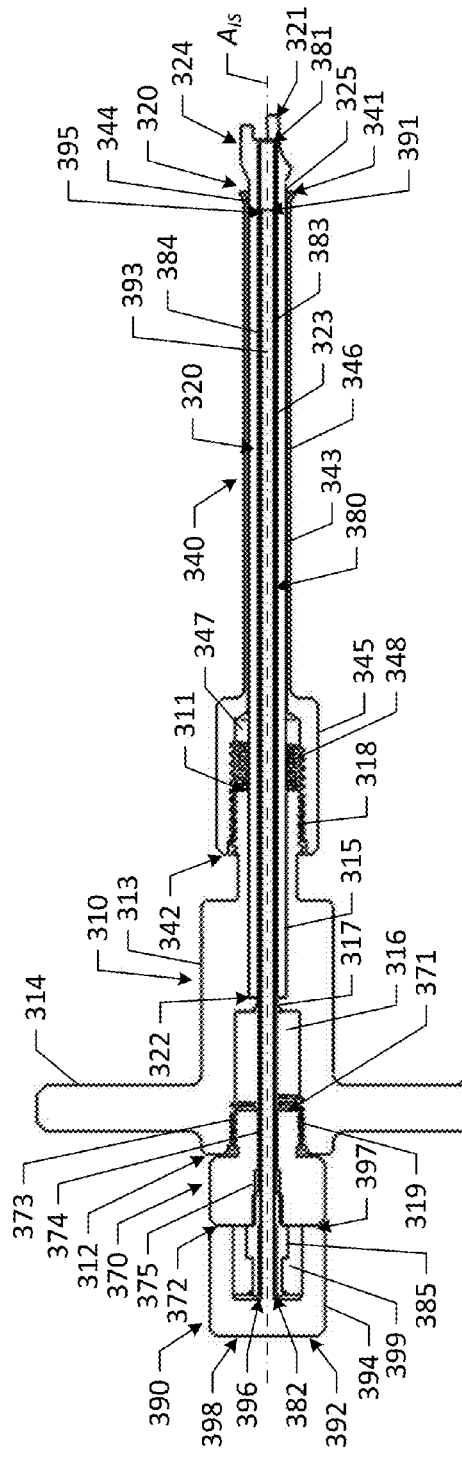
FIG. 3E
FIG. 3F

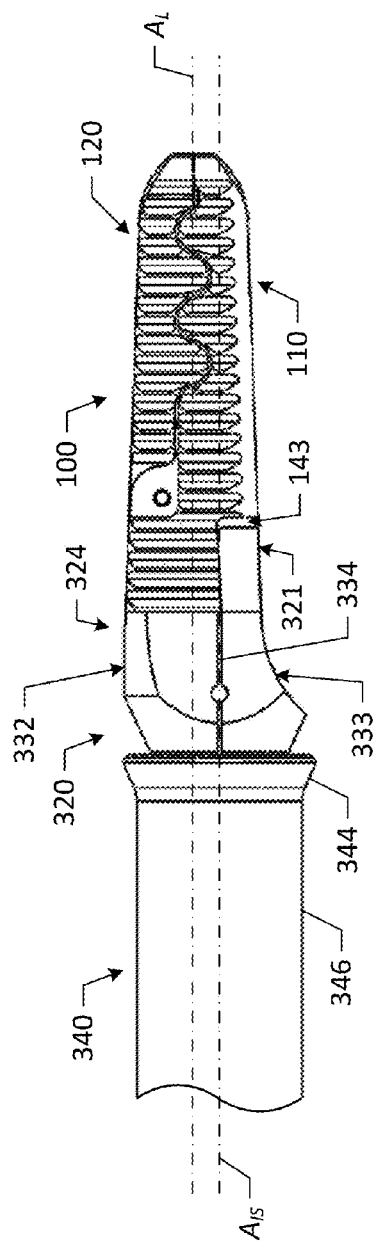
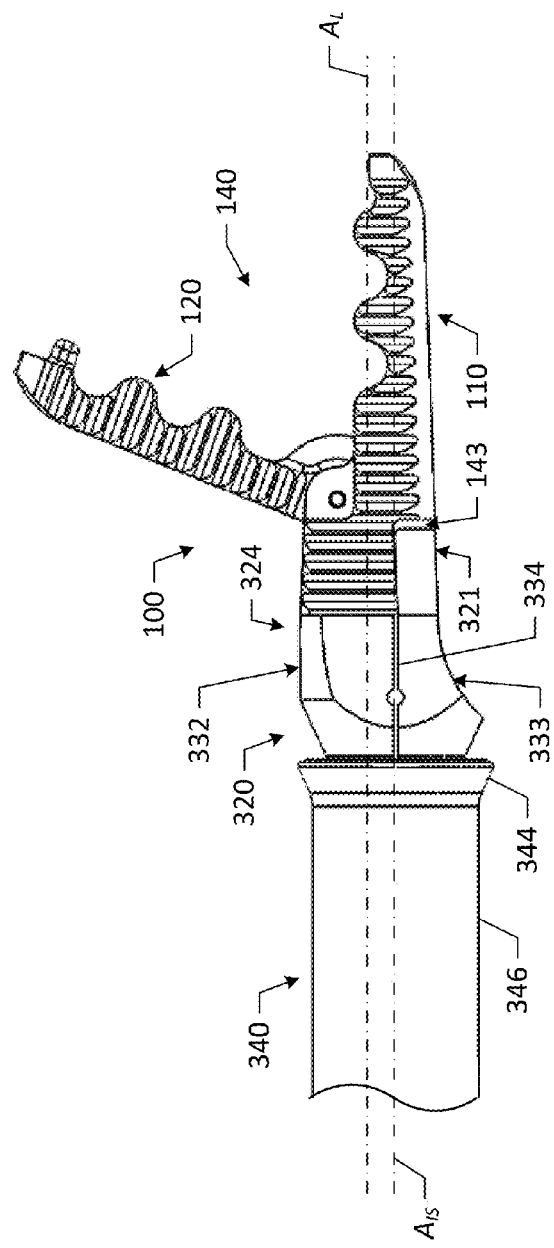

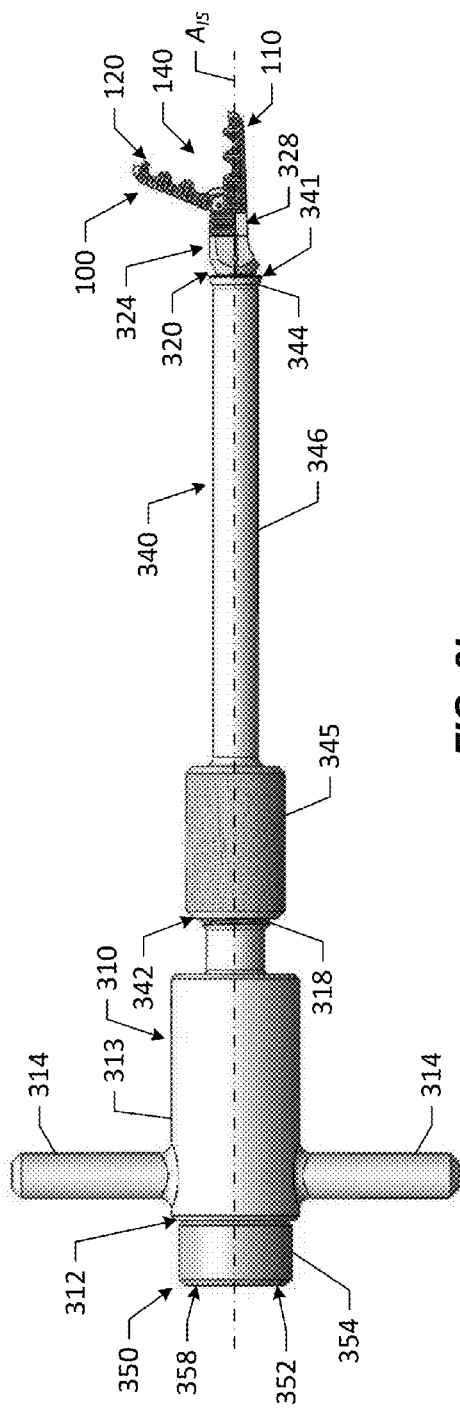
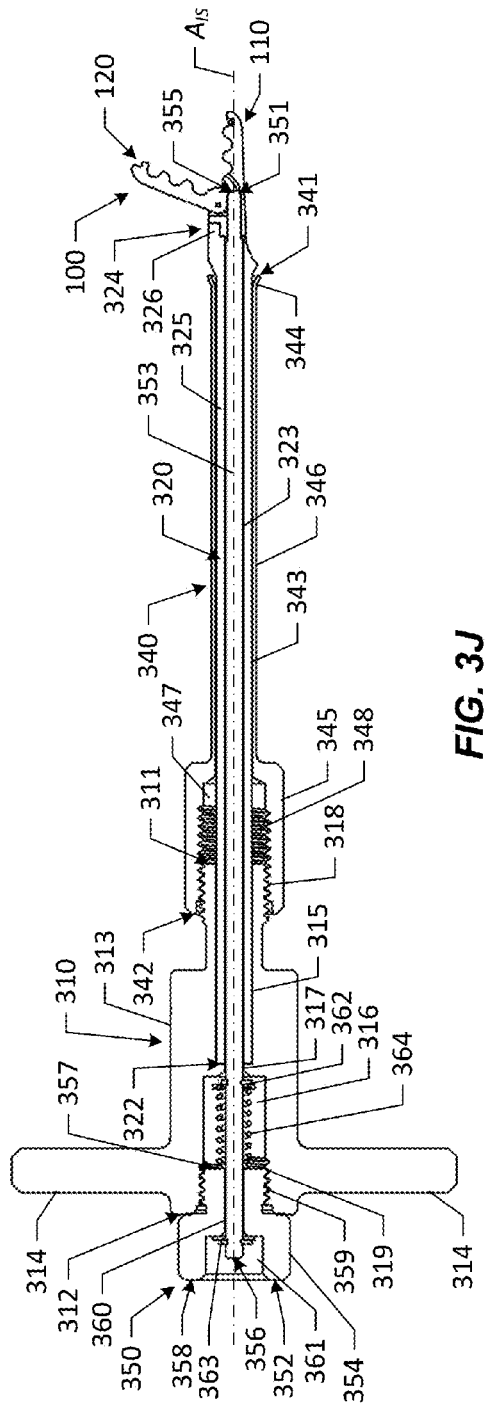
FIG. 3I
FIG. 3J

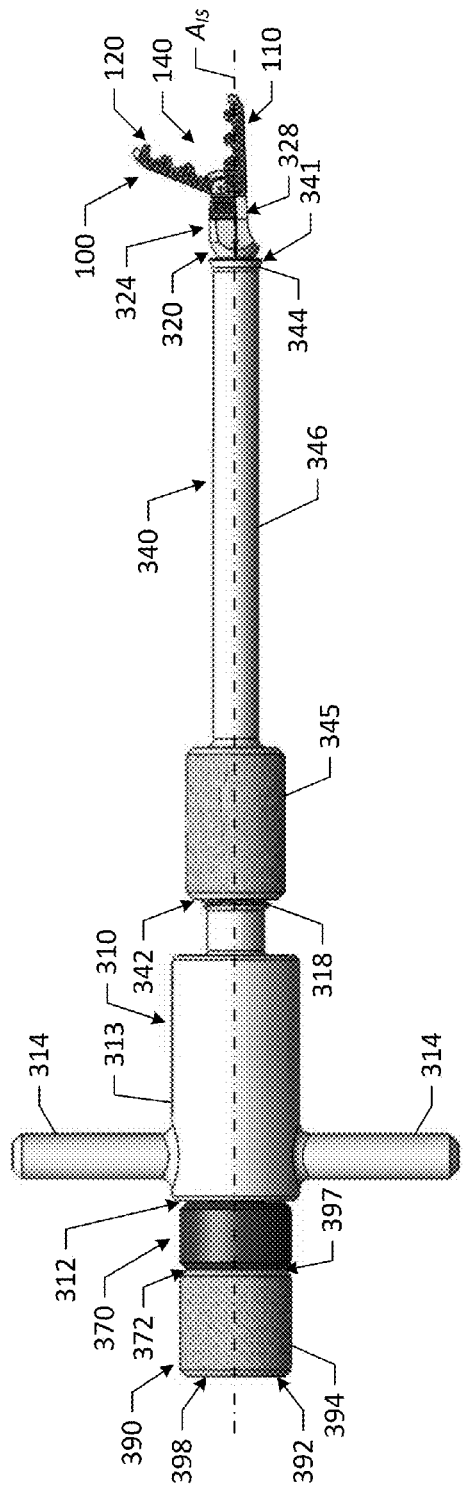
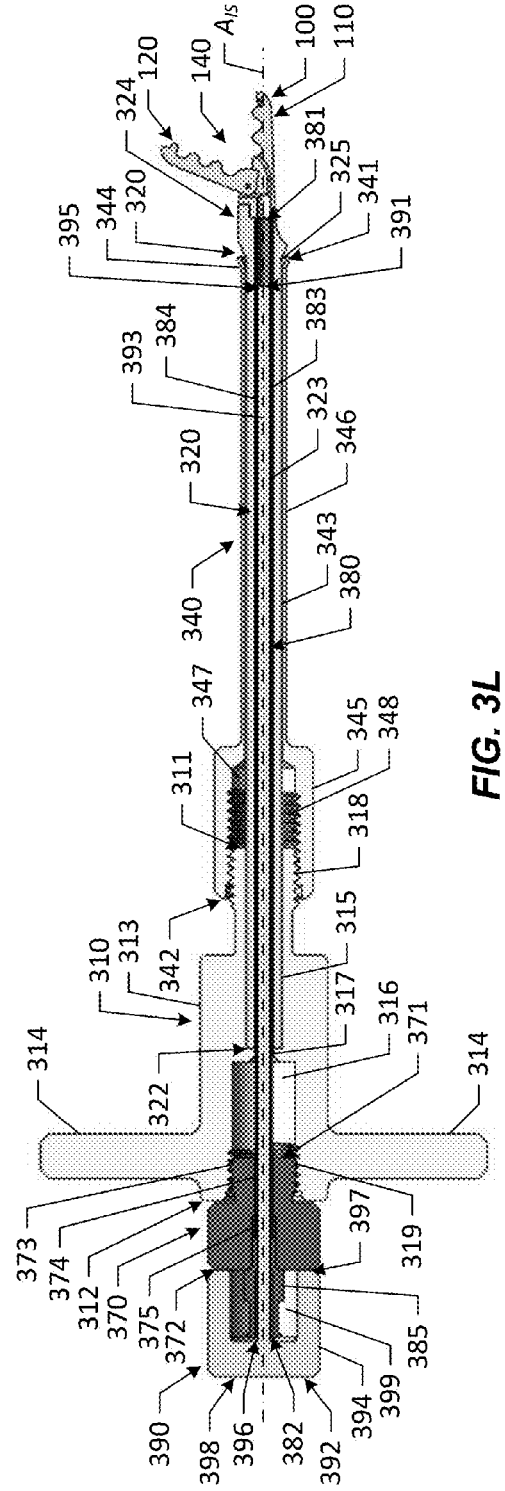
FIG. 3K
FIG. 3L

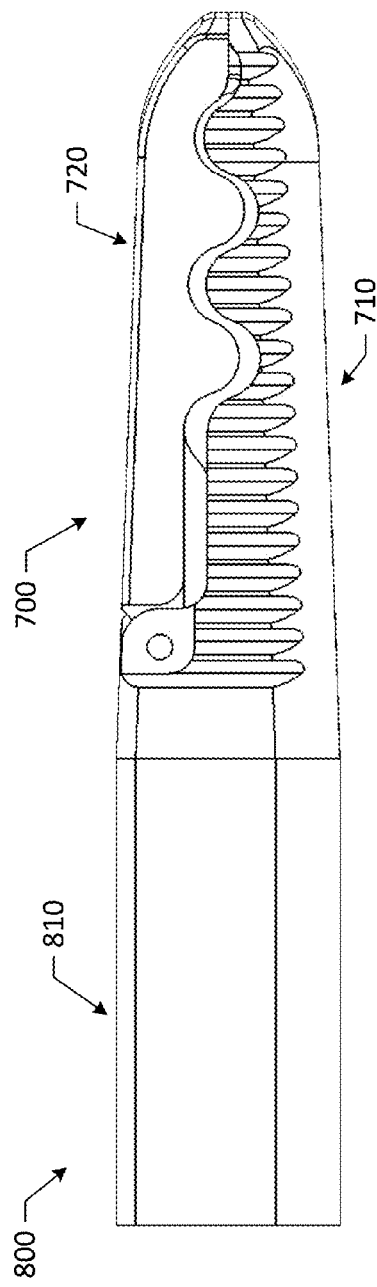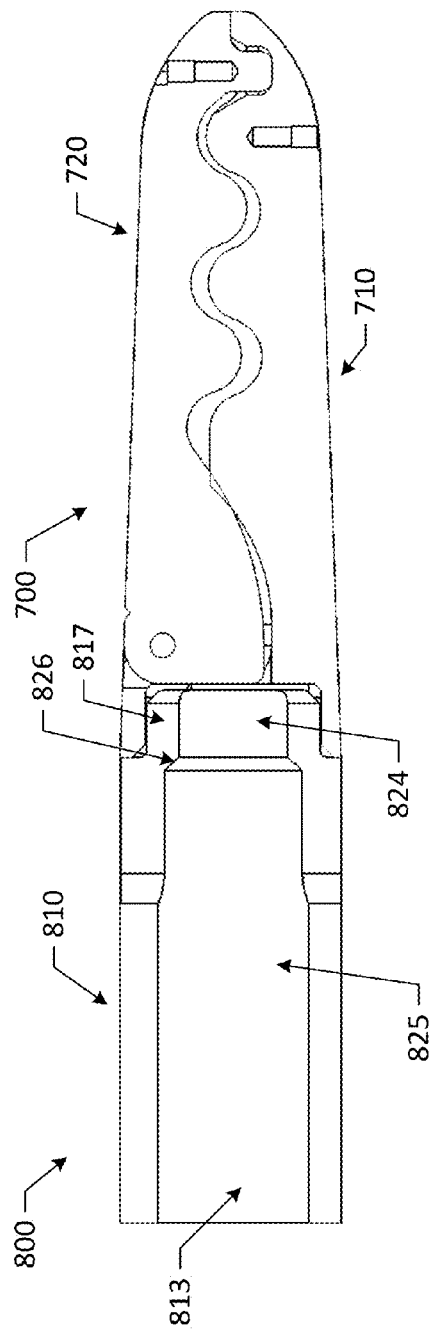
FIG. 8C
FIG. 8D

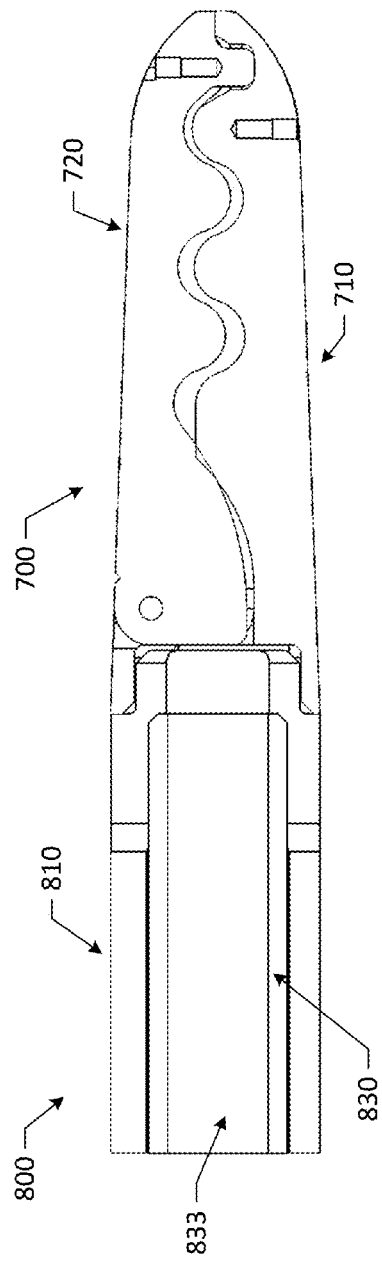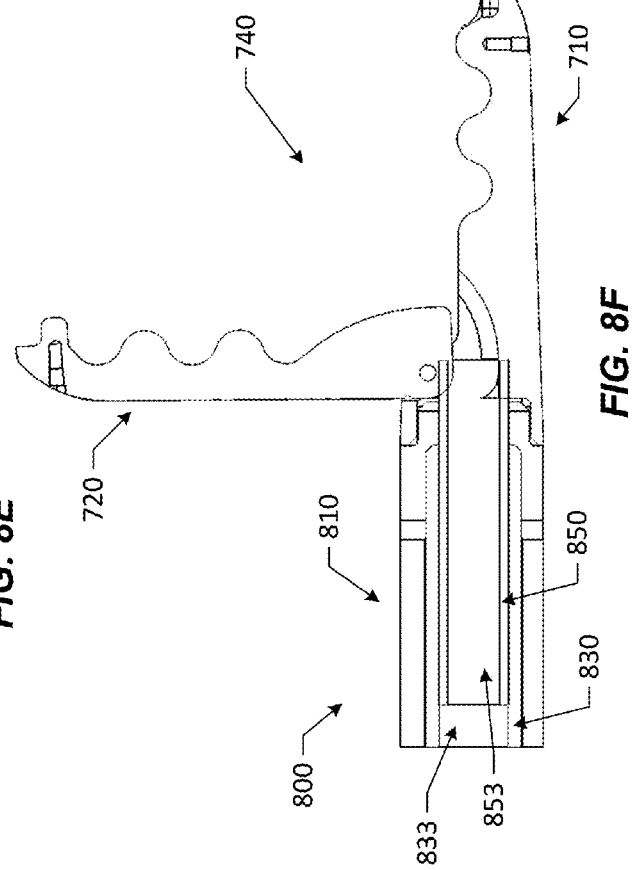

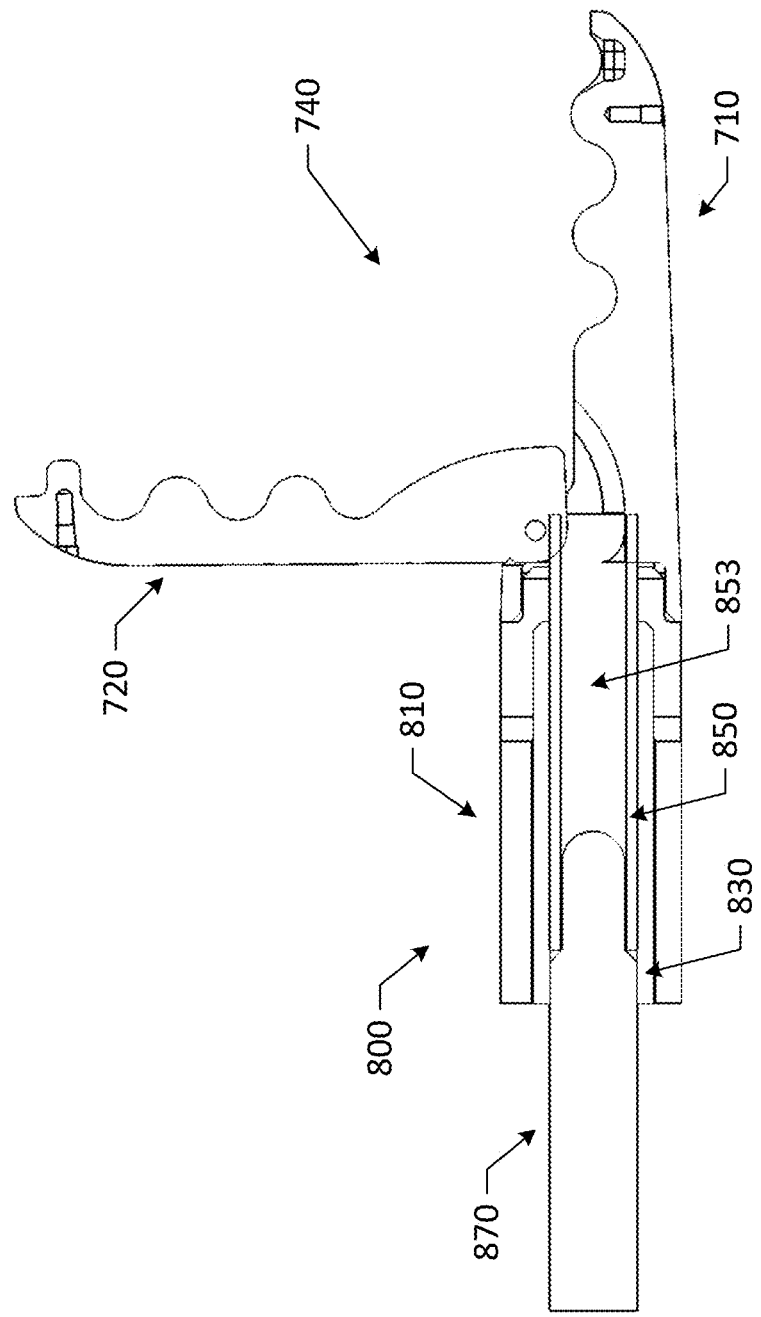

EXPANDABLE INTERBODY DEVICES AND RELATED INSTRUMENTS AND METHODS FOR SPINAL FUSION SURGERY

CROSS REFERENCES TO RELATED APPLICATIONS

This application claims priority benefit to U.S. Provisional Application No. 62/270,115, filed Dec. 21, 2015, the entire content of which is incorporated by reference herewith.

FIELD OF THE DISCLOSURE

The present disclosure relates generally to interbody devices, instruments, and methods for spinal surgery, and more particularly to expandable interbody devices and related instruments and methods for using such devices in spinal fusion surgery to restore and maintain normal spacing between adjacent vertebrae as well as provide lordosis correction.

BACKGROUND OF THE DISCLOSURE

Various types of implantable interbody devices, which also may be referred to as "spacers" or "cages," are commonly used in spinal fusion surgery to restore and maintain normal spacing between adjacent vertebrae. In particular, one or more interbody devices may be inserted into the intervertebral space, which also may be referred to as the "interbody space" or the "disc space," between two adjacent vertebrae to provide structural support and stabilization of the vertebrae. In addition to expanding the intervertebral space to its normal spacing or "height," interbody devices may realign the adjacent vertebrae such that the vertebrae follow the normal curvature of the spine. For example, in the lumbar region of the spine, interbody devices may provide correction of lordosis, the normal inward curvature of the lumbar region. Interbody devices may be used in the treatment of various spinal conditions, including spondylolisthesis, degenerative disc disease, and recurrent disc herniation. In many applications, interbody devices may be used in conjunction with additional hardware, such as pedicle screws and rods or plates, which provide additional structural support to stabilize the desired vertebrae and facilitate fusion therebetween.

In the lumbar region of the spine, interbody fusion (i.e., solid bone growth formed within the intervertebral space and connecting the adjacent vertebrae) may be achieved by a number of techniques, including posterior lumbar interbody fusion (PLIF), transforaminal lumbar interbody fusion (TLIF), extreme lateral interbody fusion (XLIF), and anterior lumbar interbody fusion (ALIF). The PLIF and TLIF techniques utilize a posterior approach, which generally requires removal of portions of the adjacent vertebrae in order to access the desired intervertebral space and allow for insertion of an interbody device therein. For example, complete or partial removal of the laminae and/or the facet joints may be required to provide a sufficient access window for subsequent removal of intervertebral disc material and insertion of the interbody device. The size of the access window necessary may be driven largely by the size of the interbody device being implanted. In some instances, distraction of the intervertebral space, via one or more instruments, may be required to allow for insertion of the interbody device therein. In other instances, the interbody device itself may distract the intervertebral space as the device is inserted therein. Upon insertion and positioning of the interbody device within the intervertebral space, the device may restore the normal spacing between the adjacent vertebrae and provide lordosis correction. According to the PLIF technique, two interbody devices generally are implanted, one in the left side of the intervertebral space and another in the right side of the intervertebral space. In contrast, the TLIF technique generally utilizes a single interbody device implanted in the middle of the intervertebral space via the right or left side of the spine.

In order to promote fusion between the adjacent vertebrae, bone graft (either autograft or allograft) or a bone graft substitute is commonly inserted into the intervertebral space. In some instances, the bone graft may be placed within one or more cavities of the interbody device, either before or after the device is inserted into the intervertebral space. Additionally or alternatively, the bone graft may be placed alongside the interbody device. Ultimately, the interbody device, itself or in combination with additional hardware, may provide the structural support necessary to maintain the normal spacing and alignment of the adjacent vertebrae until fusion is achieved between the vertebrae.

Various interbody devices and related instruments and methods have been developed for use in spinal fusion surgery. However, existing devices, instruments, and methods may suffer from several potential drawbacks. For example, certain existing interbody devices may be difficult to insert and position within the intervertebral space and/or may require significant distraction of the intervertebral space via separate instruments to allow for insertion and desired positioning. In particular, some interbody devices designed for insertion via a posterior approach and configured to provide lordosis correction may be challenging to insert and position within the intervertebral space without significant distraction via separate instruments, which may complicate the implantation procedure. Additionally, certain existing interbody devices may require a relatively large access window (created by removal of portions of the adjacent vertebrae) to allow for insertion of the device into the intervertebral space. In particular, some interbody devices designed for insertion via a posterior approach may have a relatively large insertion profile that necessitates complete or substantial removal of the laminae and/or the facet joints, which may complicate the implantation procedure, compromise the structural integrity of the affected vertebrae, and extend the post-operative healing process. According to certain designs, a large insertion profile may be driven by a large footprint of the interbody device in the transverse plane of the patient, which also may be referred to as the "axial" plane, as may be selected to provide desired structural support between the adjacent vertebrae.

Certain existing interbody devices may be configured for vertical expansion (i.e., expansion in the sagittal plane and/or the coronal plane of the patient) within the intervertebral space to restore normal spacing and alignment of the adjacent vertebrae, or may be configured for lateral expansion (i.e., expansion in the transverse plane of the patient) within the intervertebral space to provide an enlarged footprint for enhancing structural support of the vertebrae. Such expandable devices may have complicated designs including numerous parts that are susceptible to malfunction or failure during or after implantation of the device. Moreover, expandable interbody devices may include complex expansion mechanisms or may require the use of complex expansion instruments, which may complicate the implantation procedure and may lead to high manufacturing costs of the device and the instrument. Some laterally-expandable interbody devices may be configured to expand to a predetermined degree of expansion, lacking a means for controllably expanding the device to a user-determined degree of expansion as may be desired to accommodate a patient's anatomy. Additionally, some laterally-expandable interbody devices may not adequately support the adjacent vertebrae in the anterior and posterior regions of the intervertebral space in a manner that provides desired lordosis correction.

As described above, certain interbody devices may include one or more cavities configured to receive and contain bone graft or a bone graft substitute therein. However, the cavities of certain existing interbody devices, particularly non-expandable devices, may be relatively small, limiting the amount of bone graft that may be placed and contained therein and often necessitating placement of additional bone graft alongside the device, which may be susceptible to undesirable migration within and out of the intervertebral space. Certain expandable interbody devices may provide larger cavities for receiving bone graft, as compared to non-expandable devices. However, bone graft placed in the cavity of expandable interbody devices may be susceptible to undesirable migration out of the cavity and potentially out of the intervertebral space (such as posteriorly into the neural foramen or the spinal cord). Such migration may be of particular concern with expandable interbody devices that provide a cavity that is largely open in the posterior direction, especially when the device was inserted into the intervertebral space through and access window formed in the posterior of the spine.

A need therefore exists for improved interbody devices and related instruments and methods that address one or more of the above-described potential drawbacks of existing devices, instruments, and methods for spinal fusion surgery.

SUMMARY OF THE DISCLOSURE

Various embodiments described herein provide interbody devices and related instruments and methods for use in spinal fusion surgery to restore and maintain normal spacing between adjacent vertebrae as well as provide lordosis correction. According to one aspect, an interbody device is provided for implantation within an intervertebral space between a first vertebra and a second vertebra. In one embodiment, the interbody device may include a main body having an elongated shape, and an arm movably connected to the main body and having an elongated shape. The interbody device may have a first end, a second end disposed opposite the first end of the interbody device in a direction of a longitudinal axis of the interbody device, a first side, a second side disposed opposite the first side of the interbody device in a direction of a first transverse axis of the interbody device, a third side, and a fourth side disposed opposite the third side of the interbody device in a direction of a second transverse axis of the interbody device. An overall distance between the first side and the second side of the interbody device may increase along at least a majority of a length of the interbody device in a direction from the first end toward the second end of the interbody device, and an overall distance between the third side and the fourth side of the interbody device may increase along at least a majority of the length of the interbody device in a direction from the second end toward the first end of the interbody device.

In another embodiment, the interbody device may include a main body having an elongated shape, and an arm movably connected to the main body and having an elongated shape. The interbody device may have a first end, a second end disposed opposite the first end of the interbody device in a direction of a longitudinal axis of the interbody device, a first side, a second side disposed opposite the first side of the interbody device in a direction of a first transverse axis of the interbody device, a third side, and a fourth side disposed opposite the third side of the interbody device in a direction of a second transverse axis of the interbody device. An overall distance between the first side and the second side of the interbody device may increase along at least a majority of a length of the interbody device in a direction from the first end toward the second end of the interbody device, and an overall distance between the third side and the fourth side of the interbody device may be constant or substantially constant along at least a majority of the length of the interbody device.

In still another embodiment, the interbody device may include a main body having an elongated shape, and an arm movably connected to the main body and having an elongated shape. The interbody device may have a first end, a second end disposed opposite the first end of the interbody device in a direction of a longitudinal axis of the interbody device, a first side, a second side disposed opposite the first side of the interbody device in a direction of a first transverse axis of the interbody device, a third side, and a fourth side disposed opposite the third side of the interbody device in a direction of a second transverse axis of the interbody device. The interbody device may have a first overall distance between the first side and the second side of the interbody device at the first end of the interbody device, a second overall distance between the first side and the second side of the interbody device at the second end of the interbody device, and a third overall distance between the third side and the fourth side of the interbody device at the second end of the interbody device. The first overall distance may be less than each of the second overall distance and the third overall distance, and the third overall distance may be less than the second overall distance.

In another embodiment, the interbody device may include a main body having an elongated shape, and an arm movably connected to the main body and having an elongated shape. The interbody device may have a first end, a second end disposed opposite the first end of the interbody device in a direction of a longitudinal axis of the interbody device, a first side, a second side disposed opposite the first side of the interbody device in a direction of a first transverse axis of the interbody device, a third side, and a fourth side disposed opposite the third side of the interbody device in a direction of a second transverse axis of the interbody device. The interbody device may have a first overall distance between the first side and the second side of the interbody device at the first end of the interbody device, a second overall distance between the first side and the second side of the interbody device at the second end of the interbody device, a third overall distance between the third side and the fourth side of the interbody device at the second end of the interbody device, and a fourth overall distance between the third side and the fourth side of the interbody device at a location between the first end and the second end of the interbody device. The third overall distance may be less than the second overall distance, and the second overall distance may be less than the fourth overall distance.

In another embodiment, the interbody device may include a main body having an elongated shape, and an arm movably connected to the main body and having an elongated shape. A portion of a first side of the main body and a portion of a first side of the arm may define a first side of the interbody device. A second side of the main body may define a second side of the interbody device. A portion of a third side of the main body and a portion of a third side of the arm may define a third side of the interbody device. A portion of a fourth side of the main body and a portion of a fourth side of the arm may define a fourth side of the interbody device. An overall distance between the first side and the second side of the interbody device may increase along at least a majority of a length of the interbody device in a direction from a first end toward a second end of the interbody device, and an overall distance between the third side and the fourth side of the interbody device may increase along at least a majority of the length of the interbody device in a direction from the second end toward the first end of the interbody device.

In still another embodiment, the interbody device may include a main body having an elongated shape, and an arm movably connected to the main body and having an elongated shape. A portion of a first side of the main body and a portion of a first side of the arm may define a first side of the interbody device. A second side of the main body may define a second side of the interbody device. A portion of a third side of the main body and a portion of a third side of the arm may define a third side of the interbody device. A portion of a fourth side of the main body and a portion of a fourth side of the arm may define a fourth side of the interbody device. An overall distance between the first side and the second side of the interbody device may increase along at least a majority of a length of the interbody device in a direction from a first end toward a second end of the interbody device, and an overall distance between the third side and the fourth side of the interbody device may be constant or substantially constant along at least a majority of the length of the interbody device.

In another embodiment, the interbody device may include a main body having an elongated shape, and an arm movably connected to the main body and having an elongated shape. The main body may include a first end, a second end, a first side, a second side disposed opposite the first side of the main body, a third side, and a fourth side disposed opposite the third side of the main body. The arm may include a first end, a second end, a first side, a second side disposed opposite the first side of the arm, a third side, and a fourth side disposed opposite the third side of the arm. A portion of the first side of the main body and a portion of the first side of the arm may define a first side of the interbody device. The second side of the main body may define a second side of the interbody device. A portion of the third side of the main body and a portion of the third side of the arm may define a third side of the interbody device. A portion of the fourth side of the main body and a portion of the fourth side of the arm may define a fourth side of the interbody device. An overall distance between the first side and the second side of the interbody device may increase along at least a majority of a length of the interbody device in a direction from a first end toward a second end of the interbody device, and an overall distance between the third side and the fourth side of the interbody device may increase along at least a majority of the length of the interbody device in a direction from the second end toward the first end of the interbody device.

In still another embodiment, the interbody device may include a main body having an elongated shape, and an arm movably connected to the main body and having an elongated shape. The main body may include a first end, a second end, a first side, a second side disposed opposite the first side of the main body, a third side, and a fourth side disposed opposite the third side of the main body. The arm may include a first end, a second end, a first side, a second side disposed opposite the first side of the arm, a third side, and a fourth side disposed opposite the third side of the arm. A portion of the first side of the main body and a portion of the first side of the arm may define a first side of the interbody device. The second side of the main body may define a second side of the interbody device. A portion of the third side of the main body and a portion of the third side of the arm may define a third side of the interbody device. A portion of the fourth side of the main body and a portion of the fourth side of the arm may define a fourth side of the interbody device. An overall distance between the first side and the second side of the interbody device may increase along at least a majority of a length of the interbody device in a direction from a first end toward a second end of the interbody device, and an overall distance between the third side and the fourth side of the interbody device may be constant or substantially constant along at least a majority of the length of the interbody device.

According to another aspect, an instrument system is provided for implanting an interbody device within an intervertebral space between a first vertebra and a second vertebra. In one embodiment, the instrument system may include a handle, an inner tube removably attached to the handle, and an outer tube removably attached to the handle and extending at least partially over the inner tube. The inner tube may include a tubular body and an interbody device interface configured for releasably engaging the interbody device.

According to another aspect, a method is provided for implanting an interbody device within an intervertebral space between a first vertebra and a second vertebra of a patient. In one embodiment, the method may include the steps of inserting the interbody device into the intervertebral space, rotating the interbody device about a longitudinal axis of the interbody device within the intervertebral space, and expanding the interbody device within the intervertebral space by pivoting an arm of the interbody device with respect to a main body of the interbody device.

In another embodiment, the method may include the steps of providing the interbody device, inserting the interbody device into the intervertebral space, rotating the interbody device about a longitudinal axis of the interbody device within the intervertebral space, and expanding the interbody device within the intervertebral space. The interbody device may have a first end, a second end disposed opposite the first end of the interbody device in a direction of the longitudinal axis of the interbody device, a first side, a second side disposed opposite the first side of the interbody device in a direction of a first transverse axis of the interbody device, a third side, and a fourth side disposed opposite the third side of the interbody device in a direction of a second transverse axis of the interbody device. An overall distance between the first side and the second side of the interbody device increases along at least a majority of a length of the interbody device in a direction from the first end toward the second end of the interbody device. The interbody device may be inserted into the intervertebral space such that at least a portion of the first side of the interbody device engages one of the first vertebra and the second vertebra and at least a portion of the second side of the interbody device engages the other of the first vertebra and the second vertebra. The interbody device may be rotated about the longitudinal axis of the interbody device within the intervertebral space such that at least a portion of the third side of the interbody device engages one of the first vertebra and the second vertebra and at least a portion of the fourth side of the interbody device engages the other of the first vertebra and the second vertebra.

In still another embodiment, the method may include the steps of providing the interbody device, inserting the interbody device into the intervertebral space, rotating the interbody device about a longitudinal axis of the interbody device within the intervertebral space, and expanding the interbody device within the intervertebral space. The interbody device may have a first end, a second end disposed opposite the first end of the interbody device in a direction of the longitudinal axis of the interbody device, a first side, a second side disposed opposite the first side of the interbody device in a direction of a first transverse axis of the interbody device, a third side, and a fourth side disposed opposite the third side of the interbody device in a direction of a second transverse axis of the interbody device. The interbody device may have a first overall distance between the first side and the second side of the interbody device at the first end of the interbody device, a second overall distance between the first side and the second side of the interbody device at the second end of the interbody device, and a third overall distance between the third side and the fourth side of the interbody device at the second end of the interbody device. The first overall distance may be less than each of the second overall distance and the third overall distance, and the third overall distance may be less than the second overall distance. The interbody device may be inserted into the intervertebral space such that at least a portion of the first side of the interbody device engages one of the first vertebra and the second vertebra and at least a portion of the second side of the interbody device engages the other of the first vertebra and the second vertebra. The interbody device may be rotated about the longitudinal axis of the interbody device within the intervertebral space such that at least a portion of the third side of the interbody device engages one of the first vertebra and the second vertebra and at least a portion of the fourth side of the interbody device engages the other of the first vertebra and the second vertebra.

These and other aspects and embodiments of the present disclosure will be apparent or will become apparent to one of ordinary skill in the art upon review of the following detailed description when taken in conjunction with the several drawings and the appended claims.

BRIEF DESCRIPTION OF THE DRAWINGS

In describing the various embodiments of the present disclosure, reference is made to the accompanying drawings, which are not necessarily drawn to scale, and wherein:

FIG. 1I shows an end perspective view of the expandable interbody device of FIG. 1A in the expanded configuration.

FIG. 1J shows a side view of the expandable interbody device of FIG. 1A in the expanded configuration.

FIG. 3E shows a side cross-sectional view of a portion of the instrument system of FIG. 3A.

FIG. 3F shows a side cross-sectional view of a portion of the instrument system of FIG. 3A.

FIG. 3G shows a detailed side view of the distal portion of the instrument system of FIG. 3A and an expandable interbody device attached thereto and in a compact configuration.

FIG. 3H shows a detailed side view of the distal portion of the instrument system of FIG. 3A and the expandable interbody device attached thereto and in an expanded configuration.

FIG. 3I shows a side view of a portion of the instrument system of FIG. 3A and the expandable interbody device attached thereto and in the expanded configuration.

FIG. 3J shows a side cross-sectional view of a portion of the instrument system of FIG. 3A and the expandable interbody device attached thereto and in the expanded configuration.

FIG. 3K shows a side view of a portion of the instrument system of FIG. 3A and the expandable interbody device attached thereto and in the expanded configuration.

FIG. 3L shows a side cross-sectional view of a portion of the instrument system of FIG. 3A and the expandable interbody device attached thereto and in the expanded configuration.

FIG. 8C shows a side view of an outer tube of the instrument system of FIG. 8A and an expandable interbody device attached thereto and in a compact configuration.

FIG. 8D shows a side cross-sectional view of the outer tube of the instrument system of FIG. 8A and the expandable interbody device attached thereto and in the compact configuration.

FIG. 8E shows a side cross-sectional view of the outer tube and an intermediate tube of the instrument system of FIG. 8A and the expandable interbody device attached thereto and in the compact configuration.

FIG. 8F shows a side cross-sectional view of the outer tube, the intermediate tube, and an inner tube of the instrument system of FIG. 8A and the expandable interbody device attached thereto and in an expanded configuration.

FIG. 8G shows a side cross-sectional view of the outer tube, the intermediate tube, the inner tube, and a plunger of the instrument system of FIG. 8A and the expandable interbody device attached thereto and in the expanded configuration.

DETAILED DESCRIPTION OF THE DISCLOSURE

Figure 1A:
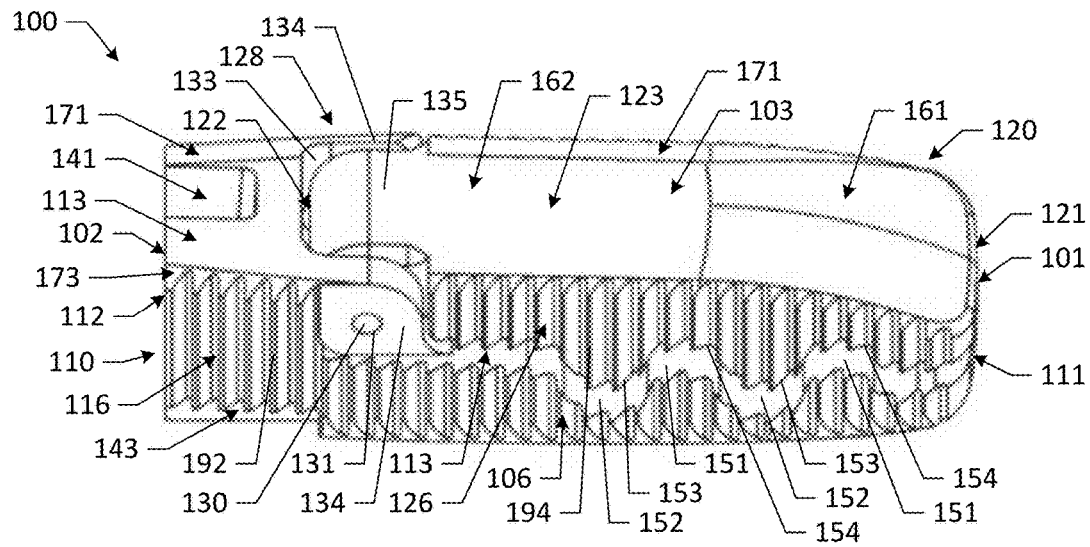
FIG. 1A shows a top perspective view of an expandable interbody device in accordance with one or more embodiments of the present disclosure, the expandable interbody device in a compact configuration.
Figure 1B:
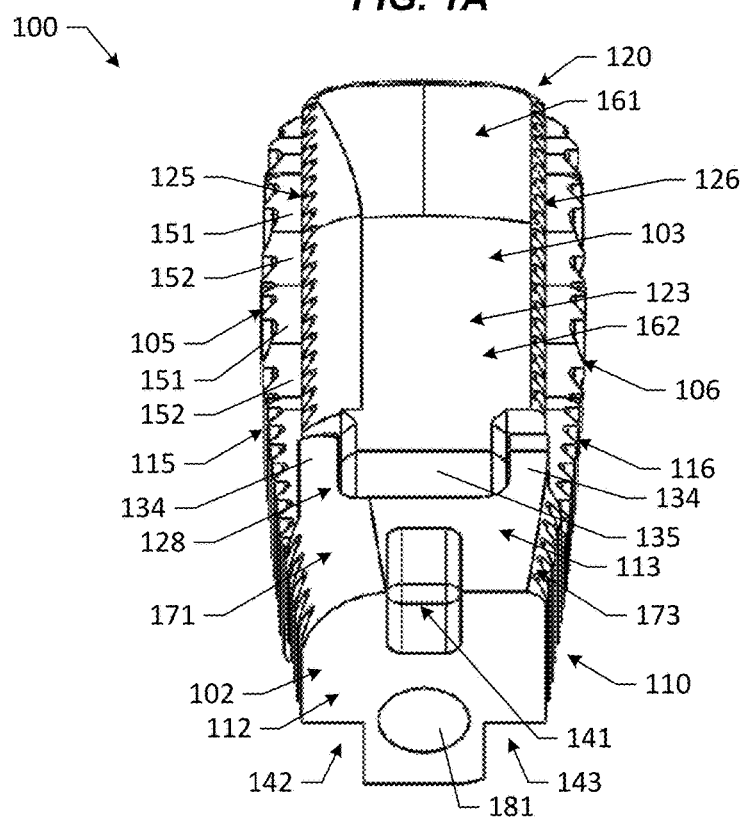
FIG. 1B shows an end perspective view of the expandable interbody device of FIG. 1A in the compact configuration.
Figure 1C:
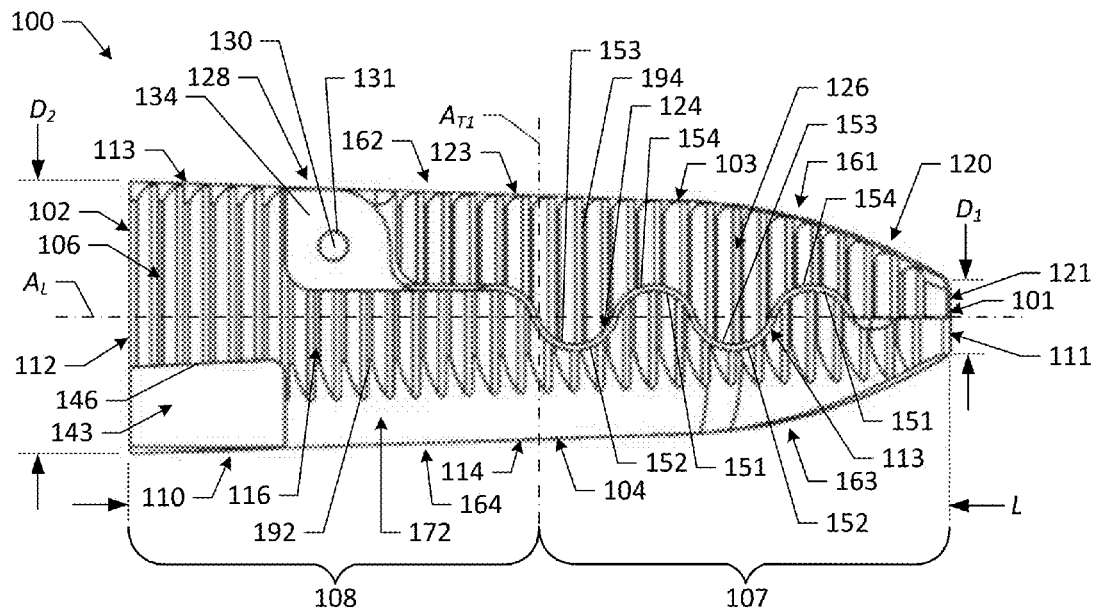
FIG. 1C shows a side view of the expandable interbody device of FIG. 1A in the compact configuration.
Figure 1D:
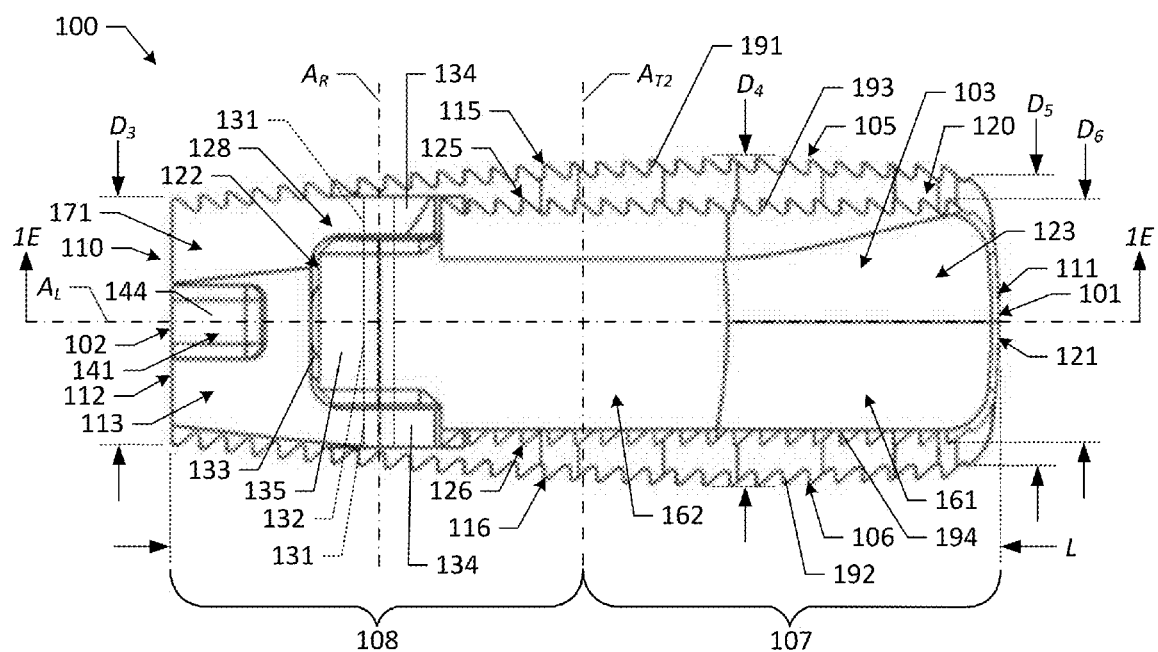
FIG. 1D shows a top view of the expandable interbody device of FIG. 1A in the compact configuration.
Figure 1E:
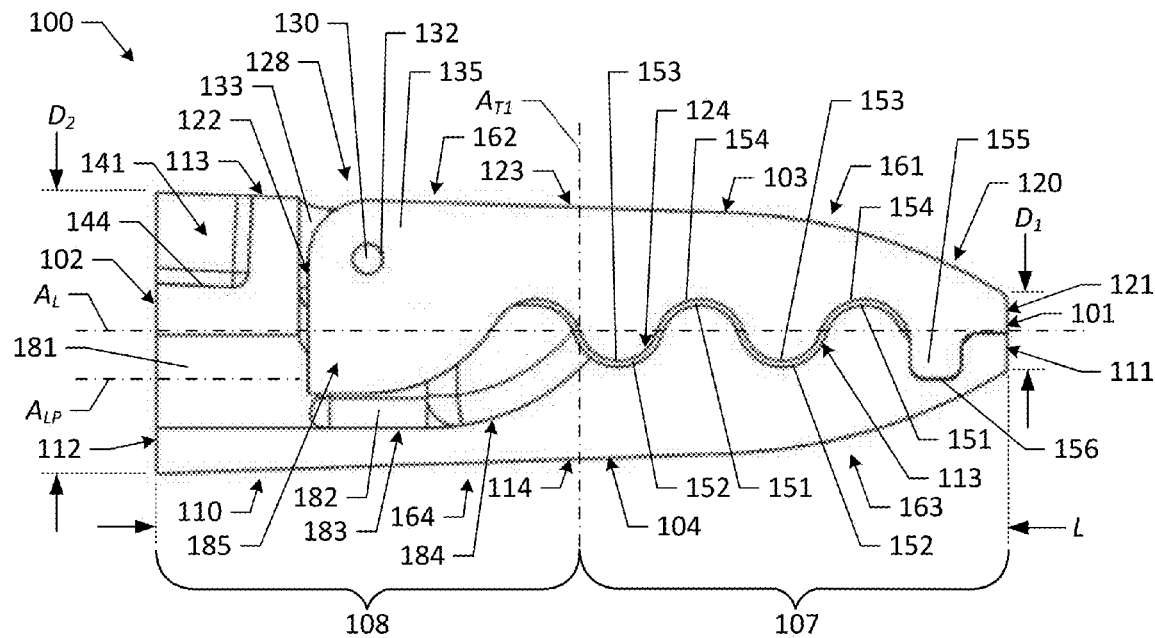
FIG. 1E shows a side cross-sectional view of the expandable interbody device of FIG. 1A in the compact configuration, taken along line 1E-1E of FIG. 1D.
Figure 1F:
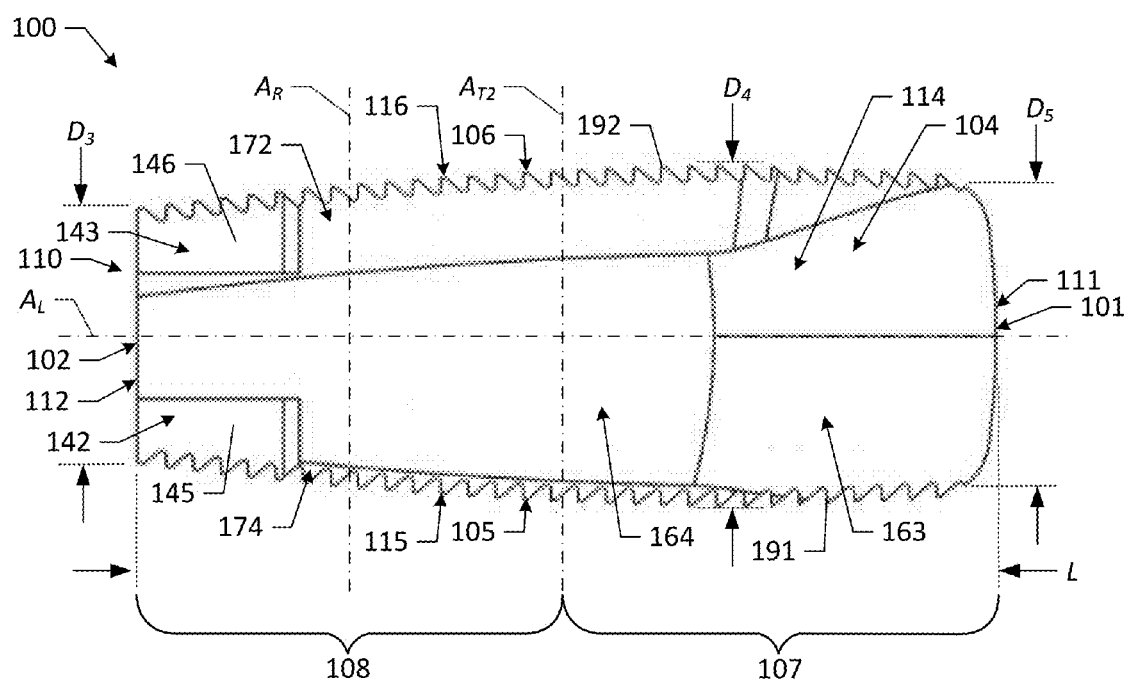
FIG. 1F shows a bottom view of the expandable interbody device of FIG. 1A in the compact configuration.
Figure 1G:
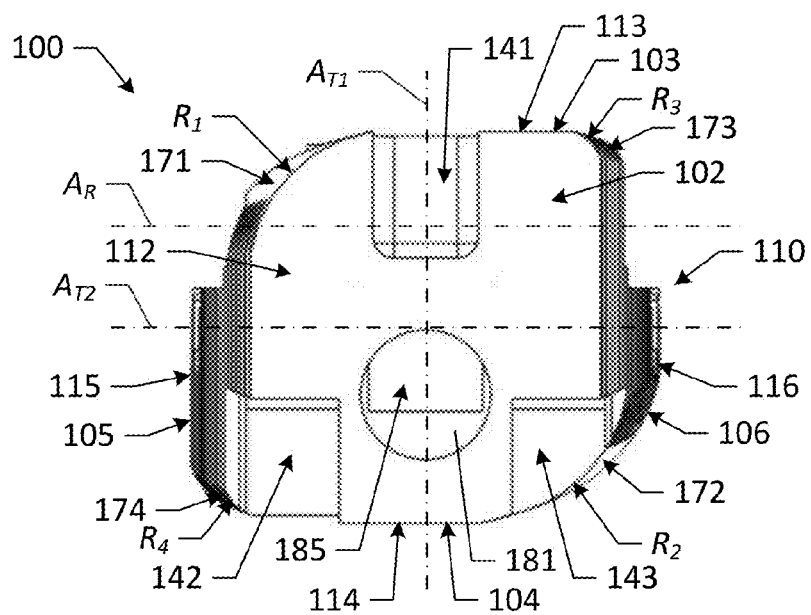
FIG. 1G shows an end view of the expandable interbody device of FIG. 1A in the compact configuration.
Figure 1H:
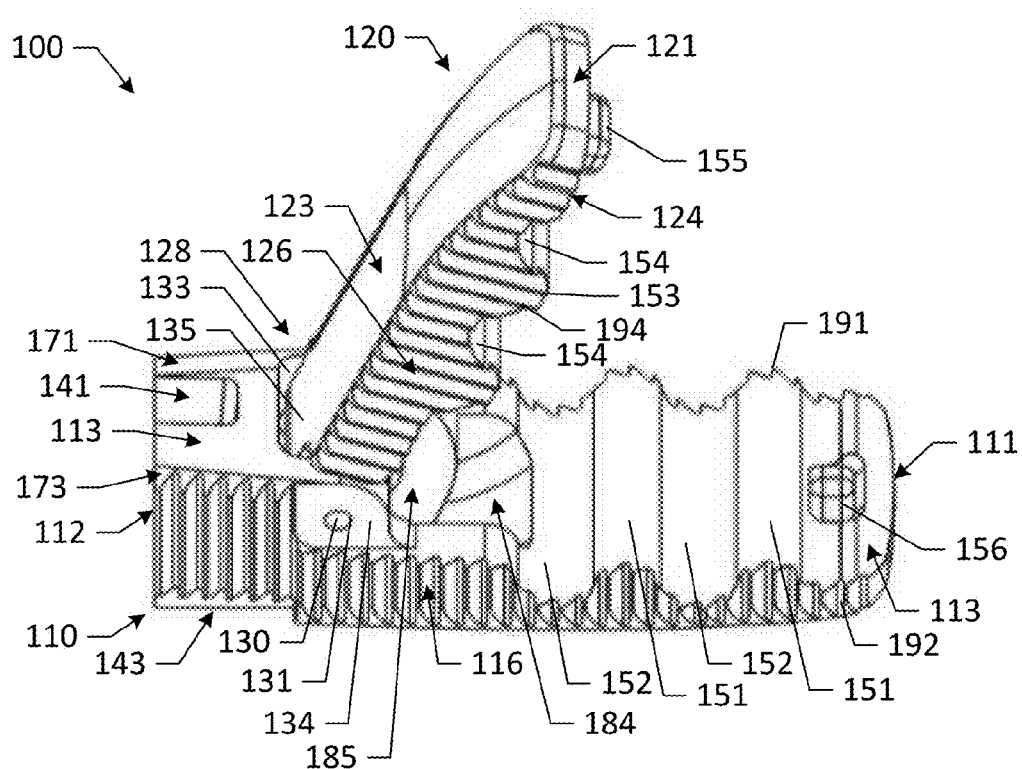
FIG. 1H shows a top perspective view of the expandable interbody device of FIG. 1A in an expanded configuration.
Figure 1K:
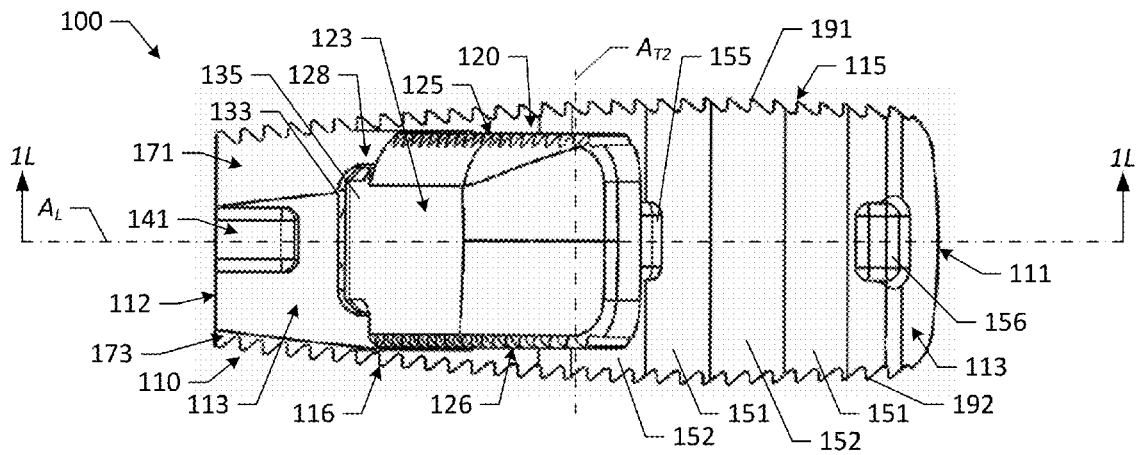
FIG. 1K shows a top view of the expandable interbody device of FIG. 1A in the expanded configuration.
Figure 1L:
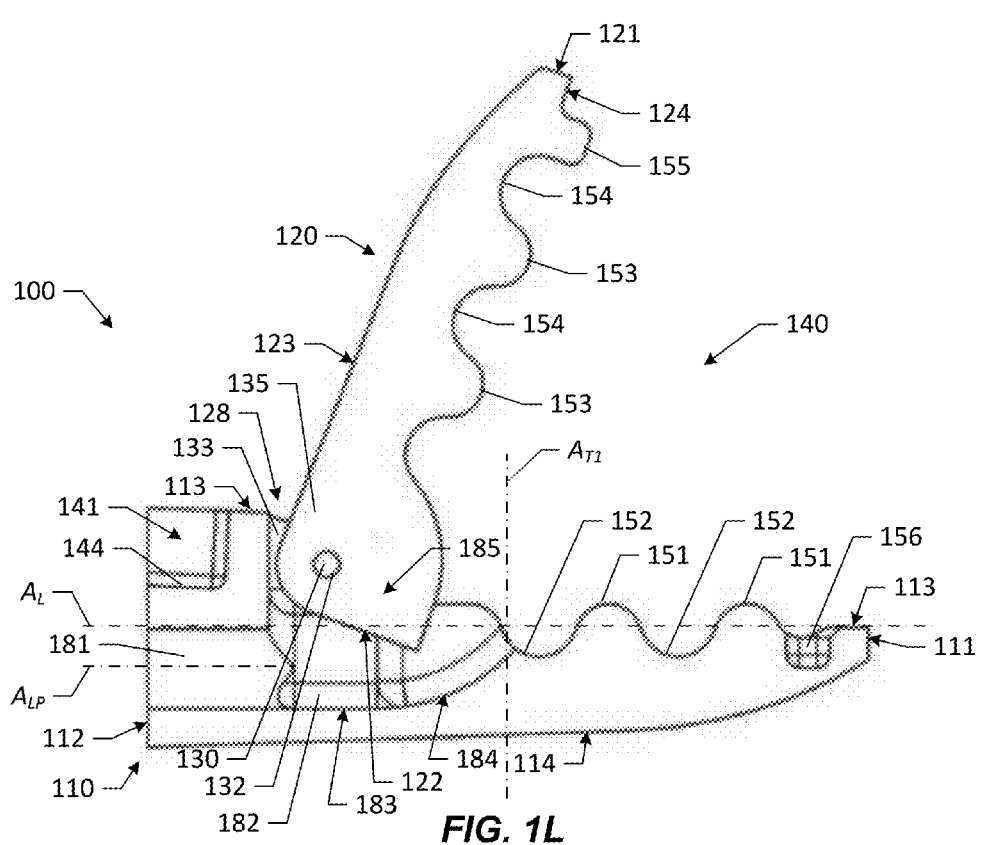
FIG. 1L shows a side cross-sectional view of the expandable interbody device of FIG. 1A in the expanded configuration, taken along line 1L-1L of FIG. 1K.
Figure 1M:
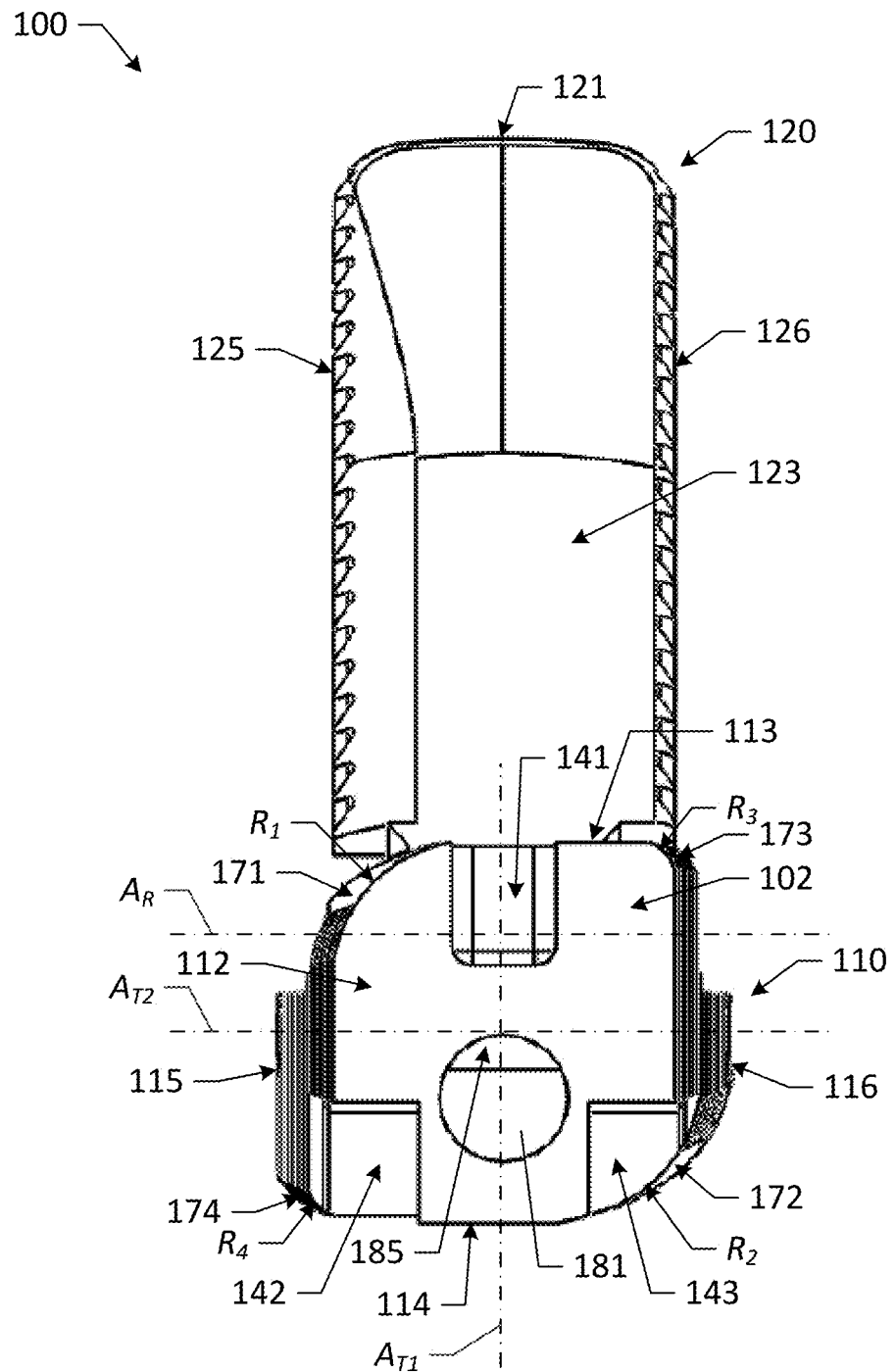
FIG. 1M shows an end view of the expandable interbody device of FIG. 1A in the expanded configuration.

Various embodiments of the present disclosure provide improved interbody devices and related instruments and methods for use in spinal fusion surgery to restore and maintain normal spacing between adjacent vertebrae as well as provide lordosis correction. Such devices, instruments, and methods may address one or more of the above-described potential drawbacks of existing technology for spinal fusion surgery.

Embodiments of the present disclosure are described herein below with reference to the accompanying drawings, in which some, but not all, embodiments are shown. Indeed, the interbody devices, instruments, and methods disclosed may be embodied in many different forms and should not be construed as limited to the embodiments set forth herein; rather, these embodiments are provided so that this disclosure is thorough and complete and fully conveys the scope of the devices, instruments, and methods to those skilled in the art. Like reference numbers refer to like elements throughout. The singular forms "a," "an," and "the" can refer to plural instances unless the context clearly dictates otherwise or unless explicitly stated.

As described in detail below, the embodiments of the present disclosure provide improved interbody devices and related instruments and methods for use in spinal fusion surgery to restore and maintain normal spacing between adjacent vertebrae as well as provide lordosis correction. In particular, some embodiments of the interbody device may provide ease of inserting and positioning the interbody device within the intervertebral space between the adjacent vertebrae, thereby reducing the complexity of the implantation procedure. In some embodiments, the interbody device itself may distract the intervertebral space during insertion and positioning of the interbody device within the intervertebral space, thereby eliminating the need for a separate instrument to distract the intervertebral space. Some embodiments of the interbody device may have a relatively small insertion profile and a relatively small insertion footprint in the transverse plane of the patient, and thus the interbody device may be inserted into the intervertebral space through a relatively small access window. Such a small access window may eliminate or minimize the need for removal of portions of the adjacent vertebrae, such as the laminae and/or the facet joints, in order to insert the interbody device into the intervertebral space. In this manner, the complexity of the implantation procedure may be reduced, the structural integrity of the adjacent vertebrae may be maintained, and the post-operative healing process may be shortened. Some embodiments of the interbody device may have a relatively large implantation footprint in the transverse plane of the patient after expansion of the interbody device within the intervertebral space, thereby providing enhanced support of the adjacent vertebrae. Additionally, some embodiments of the interbody device may have a relatively simple mechanical design including a limited number of components, thereby reducing the likelihood of malfunction of the interbody device during and after implantation. In some embodiments, the interbody device may include a relatively simple expansion mechanism, thereby reducing the complexity of the interbody device and the implantation procedure and also reducing manufacturing costs of the interbody device. Some embodiments of the interbody device may include an expansion mechanism that allows for controlled expansion of the interbody device to a user-determined degree of expansion, such that a user may select a degree of expansion that accommodates the anatomy of the patient. Moreover, some embodiments of the interbody device may, after expansion of the interbody device, provide desired support of the adjacent vertebrae along both the anterior region and the posterior region of the intervertebral space. Some embodiments of the interbody device may, after expansion of the interbody device, provide a relatively large cavity for receiving bone graft or a bone graft substitute therein, which may eliminate or reduce the need to place additional bone graft or a bone graft substitute alongside the interbody device. Further, some embodiments of the interbody device may inhibit undesirable migration of the bone graft or bone graft substitute out of the cavity of the interbody device, thereby reducing potential post-operative complications.

Some embodiments of the instrument for implanting an interbody device may provide ease of inserting and positioning the interbody device within the intervertebral space, rotating the interbody device about its longitudinal axis within the intervertebral space, expanding the interbody device within the intervertebral space, and delivering bone graft or a bone graft substitute into a cavity of the expanded interbody device, thereby reducing the complexity of the implantation procedure. In some embodiments, the instrument for implanting an interbody device may include a robust attachment mechanism for axially and rotatably coupling the interbody device to the instruments, which may allow for controlled insertion, positioning, and rotation of the interbody device within the intervertebral space. Additionally, some embodiments of the instrument for implanting an interbody device may have a relatively compact configuration, which may facilitate insertion of the interbody device into the intervertebral space through a relatively small access window. In some embodiments, the instrument for implanting an interbody device may include features that allow a user to easily transfer torque from the instrument to the interbody device, which may facilitate rotation of the interbody device within the intervertebral space. Some embodiments of the instrument for implanting an interbody device may include an expansion mechanism that allows for controlled expansion of the interbody device to a user-determined degree of expansion. In some embodiments, the instrument for implanting an interbody device may include a mechanism for limiting an expansion force applied by the instrument to the interbody device, thereby preventing application of excessive expansion forces that may compromise the structural integrity of the interbody device. Further, some embodiments of the instruments for implanting an interbody device may include a mechanism that allows for controlled delivery of bone graft or a bone graft substitute into a cavity of the expanded interbody device and that provides an indication of an amount of the bone graft or bone graft substitute that has been delivered into the cavity.

According to one aspect, an interbody device is provided for implantation within an intervertebral space between a first vertebra and a second vertebra. In one embodiment, the interbody device may include a main body having an elongated shape, and an arm movably connected to the main body and having an elongated shape. The interbody device may have a first end, a second end disposed opposite the first end of the interbody device in a direction of a longitudinal axis of the interbody device, a first side, a second side disposed opposite the first side of the interbody device in a direction of a first transverse axis of the interbody device, a third side, and a fourth side disposed opposite the third side of the interbody device in a direction of a second transverse axis of the interbody device. An overall distance between the first side and the second side of the interbody device may increase along at least a majority of a length of the interbody device in a direction from the first end toward the second end of the interbody device, and an overall distance between the third side and the fourth side of the interbody device may increase along at least a majority of the length of the interbody device in a direction from the second end toward the first end of the interbody device.

In some embodiments, the arm may be movable with respect to the main body from a compact position to an expanded position. In some embodiments, the arm may be pivotally connected to the main body via a hinge connection. In some embodiments, the arm may be pivotable with respect to the main body from a compact position to an expanded position. In some embodiments, the hinge connection may be positioned closer to the second end of the interbody device than the first end of the interbody device. In some embodiments, the hinge connection may be spaced apart from the second end of the interbody device. In some embodiments, a rotational axis of the hinge connection may extend perpendicular to the longitudinal axis of the interbody device. In some embodiments, the hinge connection may include a pin extending through one or more apertures defined in the main body and through one or more apertures defined in the arm. In some embodiments, the hinge connection may include a hinge recess defined between a pair of hinge supports of the main body, and a hinge tab of the arm may be movably disposed within the hinge recess. In some embodiments, the main body may include a port extending from the second end of the interbody device toward the first end of the interbody device. In some embodiments, the main body further may include a channel in communication with the port, the channel may extend from the port toward the first end of the interbody device. In some embodiments, the channel may include a straight portion and a ramped portion. In some embodiments, the straight portion of the channel may be positioned adjacent to the port and may extend parallel to the longitudinal axis of the interbody device. In some embodiments, the ramped portion of the channel may be positioned adjacent to the straight portion of the channel and may extend away from the second side of the interbody device and toward the first side of the interbody device. In some embodiments, at least a portion of the hinge tab of the arm may be movably disposed within the channel of the main body. In some embodiments, at least a portion of the hinge tab of the arm may be movably disposed adjacent to the port of the main body.

In some embodiments, the main body may include a plurality of ribs positioned along a first side of the main body and a plurality of grooves defined in the first side of the main body, the arm may include a plurality of ribs positioned along a second side of the arm and a plurality of grooves defined in the second side of the arm, each of the ribs of the main body may be positioned within a respective groove of the arm when the arm is in the compact position, and each of the ribs of the arm may be positioned within a respective groove of the main body when the arm is in the compact position. In some embodiments, each of the ribs and the grooves of the main body may extend perpendicular to the longitudinal axis of the interbody device, and each of the ribs and the grooves of the arm may extend perpendicular to the longitudinal axis of the interbody device. In some embodiments, the main body may include a pocket defined in a first side of the main body, the arm may include a protrusion defined in a second side of the arm, and the protrusion of the arm may be positioned within the pocket of the main body when the arm is in the compact position. In some embodiments, the pocket of the main body and the protrusion of the arm may be positioned closer to the first end of the interbody device than the second end of the interbody device. In some embodiments, the main body may include a plurality of recesses extending from the second end of the interbody device toward the first end of the interbody device and configured for receiving mating features of an instrument. In some embodiments, the first transverse axis of the interbody device may be perpendicular to the longitudinal axis of the interbody device, and the second transverse axis of the interbody device may be perpendicular to each of the longitudinal axis and the first transverse axis of the interbody device.

In some embodiments, the main body may have a first end, a second end disposed opposite the first end of the main body, a first side, a second side disposed opposite the first side of the main body, a third side, and a fourth side disposed opposite the third side of the main body, and the arm may have a first end, a second end disposed opposite the first end of the arm, a first side, a second side disposed opposite the first side of the arm, a third side, and a fourth side disposed opposite the third side of the arm. In some embodiments, the first end of the interbody device may be defined by at least one of the first end of the main body and the first end of the arm. In some embodiments, the second end of the interbody device may be defined by at least one of the second end of the main body and the second end of the arm. In some embodiments, the first side of the interbody device may be defined by at least a portion of the first side of the main body and at least a portion of the first side of the arm. In some embodiments, the second side of the interbody device may be defined by at least a portion of the second side of the main body. In some embodiments, the third side of the interbody device may be defined by at least a portion of the third side of the main body and at least a portion of the third side of the arm, and the fourth side of the interbody device may be defined by at least a portion of the fourth side of the main body and at least a portion of the fourth side of the arm.

In some embodiments, the first side of the interbody device may include a flat portion and a curved portion, and the second side of the interbody device may include a flat portion and a curved portion. In some embodiments, the curved portion of the first side of the interbody device may be positioned closer to the first end of the interbody device than the flat portion of the first side of the interbody device, and the curved portion of the second side of the interbody device may be positioned closer to the first end of the interbody device than the flat portion of the second side of the interbody device. In some embodiments, the first side of the main body and the first side of the arm each may include one or more smooth surfaces, and the second side of the main body may include one or more smooth surfaces. In some embodiments, the main body may include a first plurality of teeth positioned along the third side of the main body, and a second plurality of teeth positioned along the fourth side of the main body, and the arm may include a third plurality of teeth positioned along the third side of the arm, and a fourth plurality of teeth positioned along the fourth side of the arm. In some embodiments, each of the first plurality of teeth may extend perpendicular to the longitudinal axis of the interbody device, each of the second plurality of teeth may extend perpendicular to the longitudinal axis of the interbody device, each of the third plurality of teeth may extend perpendicular to the longitudinal axis of the interbody device, and each of the fourth plurality of teeth may extend perpendicular to the longitudinal axis of the interbody device.

In some embodiments, the interbody device may include a first transition portion positioned along an interface of the first side and the third side of the interbody device and having a first radius of curvature, a second transition portion positioned along an interface of the second side and the fourth side of the interbody device and having a second radius of curvature, a third transition portion positioned along an interface of the first side and the fourth side of the interbody device and having a third radius of curvature, and a fourth transition portion positioned along an interface of the second side and the third side of the interbody device and having a fourth radius of curvature. In some embodiments, the first radius of curvature may be greater than each of the third radius of curvature and the fourth radius of curvature, and the second radius of curvature may be greater than each of the third radius of curvature and the fourth radius of curvature. In some embodiments, the first radius of curvature may be equal to the second radius of curvature, and the third radius of curvature may be equal to the fourth radius of curvature.

In some embodiments, the interbody device may have a first overall distance between the first side and the second side of the interbody device at the first end of the interbody device, the interbody device may have a second overall distance between the first side and the second side of the interbody device at the second end of the interbody device, and the first overall distance may be less than the second overall distance. In some embodiments, the interbody device may have a third overall distance between the third side and the fourth side of the interbody device at the second end of the interbody device, the interbody device may have a fourth overall distance between the third side and the fourth side of the interbody device at a location between the first end and the second end of the interbody device, and the interbody device may have a fifth overall distance between the third side and the fourth side of the interbody device at the first end of the interbody device. In some embodiments, the third overall distance may be less than each of the fourth overall distance and the fifth overall distance, and the fifth overall distance may be less than the fourth overall distance. In some embodiments, the third overall distance may be less than the second overall distance. In some embodiments, the second overall distance may be less than the fourth overall distance. In some embodiments, the second overall distance may be less than the fifth overall distance. In some embodiments, the first overall distance may be less than each of the second overall distance, the third overall distance, the fourth overall distance, and the fifth overall distance.

In some embodiments, an overall distance between the third side and the fourth side of the arm may be constant or substantially constant along at least a majority of a length of the arm. In some embodiments, the arm may have a sixth overall distance between the third side and the fourth side of the arm which is constant or substantially constant along the at least a majority of the length of the arm. In some embodiments, the sixth overall distance may be equal to the third overall distance. In some embodiments, the sixth overall distance may be less than each of the fourth overall distance and the fifth overall distance. In some embodiments, the first overall distance may be less than the sixth overall distance, and the sixth overall distance may be less than the second overall distance. In some embodiments, the overall distance between the first side and the second side of the interbody device may increase along the entire length of the interbody device in the direction from the first end toward the second end of the interbody device. In some embodiments, the overall distance between the third side and the fourth side of the interbody device may increase along only a portion of the length of the interbody device from the second end toward the first end of the interbody device.

In another embodiment, the interbody device may include a main body having an elongated shape, and an arm movably connected to the main body and having an elongated shape. The interbody device may have a first end, a second end disposed opposite the first end of the interbody device in a direction of a longitudinal axis of the interbody device, a first side, a second side disposed opposite the first side of the interbody device in a direction of a first transverse axis of the interbody device, a third side, and a fourth side disposed opposite the third side of the interbody device in a direction of a second transverse axis of the interbody device. An overall distance between the first side and the second side of the interbody device may increase along at least a majority of a length of the interbody device in a direction from the first end toward the second end of the interbody device, and an overall distance between the third side and the fourth side of the interbody device may be constant or substantially constant along at least a majority of the length of the interbody device.

In some embodiments, the arm may be movable with respect to the main body from a compact position to an expanded position. In some embodiments, the arm may be pivotally connected to the main body via a hinge connection. In some embodiments, the arm may be pivotable with respect to the main body from a compact position to an expanded position. In some embodiments, the hinge connection may be positioned closer to the second end of the interbody device than the first end of the interbody device. In some embodiments, the hinge connection may be spaced apart from the second end of the interbody device. In some embodiments, a rotational axis of the hinge connection may extend perpendicular to the longitudinal axis of the interbody device. In some embodiments, the hinge connection may include a pin extending through one or more apertures defined in the main body and through one or more apertures defined in the arm. In some embodiments, the hinge connection may include a hinge recess defined between a pair of hinge supports of the main body, and a hinge tab of the arm may be movably disposed within the hinge recess. In some embodiments, the main body may include a port extending from the second end of the interbody device toward the first end of the interbody device. In some embodiments, the main body further may include a channel in communication with the port, the channel may extend from the port toward the first end of the interbody device. In some embodiments, the channel may include a straight portion and a ramped portion. In some embodiments, the straight portion of the channel may be positioned adjacent to the port and may extend parallel to the longitudinal axis of the interbody device. In some embodiments, the ramped portion of the channel may be positioned adjacent to the straight portion of the channel and may extend away from the second side of the interbody device and toward the first side of the interbody device. In some embodiments, at least a portion of the hinge tab of the arm may be movably disposed within the channel of the main body. In some embodiments, at least a portion of the hinge tab of the arm may be movably disposed adjacent to the port of the main body.

In some embodiments, the main body may include a plurality of ribs positioned along a first side of the main body and a plurality of grooves defined in the first side of the main body, the arm may include a plurality of ribs positioned along a second side of the arm and a plurality of grooves defined in the second side of the arm, each of the ribs of the main body may be positioned within a respective groove of the arm when the arm is in the compact position, and each of the ribs of the arm may be positioned within a respective groove of the main body when the arm is in the compact position. In some embodiments, each of the ribs and the grooves of the main body may extend perpendicular to the longitudinal axis of the interbody device, and each of the ribs and the grooves of the arm may extend perpendicular to the longitudinal axis of the interbody device. In some embodiments, the main body may include a pocket defined in a first side of the main body, the arm may include a protrusion defined in a second side of the arm, and the protrusion of the arm may be positioned within the pocket of the main body when the arm is in the compact position. In some embodiments, the pocket of the main body and the protrusion of the arm may be positioned closer to the first end of the interbody device than the second end of the interbody device. In some embodiments, the main body may include a plurality of recesses extending from the second end of the interbody device toward the first end of the interbody device and configured for receiving mating features of an instrument. In some embodiments, the first transverse axis of the interbody device may be perpendicular to the longitudinal axis of the interbody device, and the second transverse axis of the interbody device may be perpendicular to each of the longitudinal axis and the first transverse axis of the interbody device.

In some embodiments, the main body may have a first end, a second end disposed opposite the first end of the main body, a first side, a second side disposed opposite the first side of the main body, a third side, and a fourth side disposed opposite the third side of the main body, and the arm may have a first end, a second end disposed opposite the first end of the arm, a first side, a second side disposed opposite the first side of the arm, a third side, and a fourth side disposed opposite the third side of the arm. In some embodiments, the first end of the interbody device may be defined by at least one of the first end of the main body and the first end of the arm. In some embodiments, the second end of the interbody device may be defined by at least one of the second end of the main body and the second end of the arm. In some embodiments, the first side of the interbody device may be defined by at least a portion of the first side of the main body and at least a portion of the first side of the arm. In some embodiments, the second side of the interbody device may be defined by at least a portion of the second side of the main body. In some embodiments, the third side of the interbody device may be defined by at least a portion of the third side of the main body and at least a portion of the third side of the arm, and the fourth side of the interbody device may be defined by at least a portion of the fourth side of the main body and at least a portion of the fourth side of the arm.

In some embodiments, the first side of the interbody device may include a flat portion and a curved portion, and the second side of the interbody device may include a flat portion and a curved portion. In some embodiments, the curved portion of the first side of the interbody device may be positioned closer to the first end of the interbody device than the flat portion of the first side of the interbody device, and the curved portion of the second side of the interbody device may be positioned closer to the first end of the interbody device than the flat portion of the second side of the interbody device. In some embodiments, the first side of the main body and the first side of the arm each may include one or more smooth surfaces, and the second side of the main body may include one or more smooth surfaces. In some embodiments, the main body may include a first plurality of teeth positioned along the third side of the main body, and a second plurality of teeth positioned along the fourth side of the main body, and the arm may include a third plurality of teeth positioned along the third side of the arm, and a fourth plurality of teeth positioned along the fourth side of the arm. In some embodiments, each of the first plurality of teeth may extend perpendicular to the longitudinal axis of the interbody device, each of the second plurality of teeth may extend perpendicular to the longitudinal axis of the interbody device, each of the third plurality of teeth may extend perpendicular to the longitudinal axis of the interbody device, and each of the fourth plurality of teeth may extend perpendicular to the longitudinal axis of the interbody device. In some embodiments, the first plurality of teeth may include a first distal-most tooth, the third plurality of teeth may include a third distal-most tooth, and the first distal-most tooth may be positioned closer to the first end of the interbody device than the third distal-most tooth. In some embodiments, the second plurality of teeth may include a second distal-most tooth, the fourth plurality of teeth may include a fourth distal-most tooth, and the second distal-most tooth may be positioned closer to the first end of the interbody device than the fourth distal-most tooth.

In some embodiments, the interbody device may include a first transition portion positioned along an interface of the first side and the third side of the interbody device and having a first radius of curvature, a second transition portion positioned along an interface of the second side and the fourth side of the interbody device and having a second radius of curvature, a third transition portion positioned along an interface of the first side and the fourth side of the interbody device and having a third radius of curvature, and a fourth transition portion positioned along an interface of the second side and the third side of the interbody device and having a fourth radius of curvature. In some embodiments, the first radius of curvature may be greater than each of the third radius of curvature and the fourth radius of curvature, and the second radius of curvature may be greater than each of the third radius of curvature and the fourth radius of curvature. In some embodiments, the first radius of curvature may be equal to the second radius of curvature, and the third radius of curvature may be equal to the fourth radius of curvature.

In some embodiments, the interbody device may have a first overall distance between the first side and the second side of the interbody device at the first end of the interbody device, the interbody device may have a second overall distance between the first side and the second side of the interbody device at the second end of the interbody device, and the first overall distance may be less than the second overall distance. In some embodiments, the interbody device may have a third overall distance between the third side and the fourth side of the interbody device which is constant or substantially constant along the at least a majority of the length of the interbody device. In some embodiments, the third overall distance may be less than the second overall distance. In some embodiments, the first overall distance may be less than the third overall distance.

In some embodiments, an overall distance between the third side and the fourth side of the arm may be constant or substantially constant along at least a majority of a length of the arm. In some embodiments, the arm may have a fourth overall distance between the third side and the fourth side of the arm which is constant or substantially constant along the at least a majority of the length of the arm. In some embodiments, the fourth overall distance may be equal to the third overall distance. In some embodiments, the fourth overall distance may be less than the second overall distance. In some embodiments, the first overall distance may be less than the fourth overall distance, and the fourth overall distance may be less than the second overall distance. In some embodiments, the overall distance between the first side and the second side of the interbody device may increase along the entire length of the interbody device in the direction from the first end toward the second end of the interbody device. In some embodiments, the overall distance between the third side and the fourth side of the interbody device may be constant or substantially constant along the entire length of the interbody device. In some embodiments, the overall distance between the third side and the fourth side of the interbody device is constant or substantially constant along only a portion of the length of the interbody device.

In still another embodiment, the interbody device may include a main body having an elongated shape, and an arm movably connected to the main body and having an elongated shape. The interbody device may have a first end, a second end disposed opposite the first end of the interbody device in a direction of a longitudinal axis of the interbody device, a first side, a second side disposed opposite the first side of the interbody device in a direction of a first transverse axis of the interbody device, a third side, and a fourth side disposed opposite the third side of the interbody device in a direction of a second transverse axis of the interbody device. The interbody device may have a first overall distance between the first side and the second side of the interbody device at the first end of the interbody device, a second overall distance between the first side and the second side of the interbody device at the second end of the interbody device, and a third overall distance between the third side and the fourth side of the interbody device at the second end of the interbody device. The first overall distance may be less than each of the second overall distance and the third overall distance, and the third overall distance may be less than the second overall distance.

In some embodiments, the interbody device may have a fourth overall distance between the third side and the fourth side of the interbody device at a location between the first end and the second end of the interbody device, and the third overall distance may be less than the fourth overall distance. In some embodiments, the second overall distance may be less than the fourth overall distance. In some embodiments, the interbody device may have a fifth overall distance between the third side and the fourth side of the interbody device at the first end of the interbody device, and the fifth overall distance may be less than the fourth overall distance. In some embodiments, the third overall distance may be less than the fifth overall distance.

In another embodiment, the interbody device may include a main body having an elongated shape, and an arm movably connected to the main body and having an elongated shape. The interbody device may have a first end, a second end disposed opposite the first end of the interbody device in a direction of a longitudinal axis of the interbody device, a first side, a second side disposed opposite the first side of the interbody device in a direction of a first transverse axis of the interbody device, a third side, and a fourth side disposed opposite the third side of the interbody device in a direction of a second transverse axis of the interbody device. The interbody device may have a first overall distance between the first side and the second side of the interbody device at the first end of the interbody device, a second overall distance between the first side and the second side of the interbody device at the second end of the interbody device, a third overall distance between the third side and the fourth side of the interbody device at the second end of the interbody device, and a fourth overall distance between the third side and the fourth side of the interbody device at a location between the first end and the second end of the interbody device. The third overall distance may be less than the second overall distance, and the second overall distance may be less than the fourth overall distance.

In some embodiments, the first overall distance may be less than the second overall distance. In some embodiments, the first overall distance may be less than the third overall distance. In some embodiments, the interbody device may have a fifth overall distance between the third side and the fourth side of the interbody device at the first end of the interbody device, and the fifth overall distance may be less than the fourth overall distance. In some embodiments, the third overall distance may be less than the fifth overall distance.

In another embodiment, the interbody device may include a main body having an elongated shape, and an arm movably connected to the main body and having an elongated shape. A portion of a first side of the main body and a portion of a first side of the arm may define a first side of the interbody device. A second side of the main body may define a second side of the interbody device. A portion of a third side of the main body and a portion of a third side of the arm may define a third side of the interbody device. A portion of a fourth side of the main body and a portion of a fourth side of the arm may define a fourth side of the interbody device. An overall distance between the first side and the second side of the interbody device may increase along at least a majority of a length of the interbody device in a direction from a first end toward a second end of the interbody device, and an overall distance between the third side and the fourth side of the interbody device may increase along at least a majority of the length of the interbody device in a direction from the second end toward the first end of the interbody device.

In still another embodiment, the interbody device may include a main body having an elongated shape, and an arm movably connected to the main body and having an elongated shape. A portion of a first side of the main body and a portion of a first side of the arm may define a first side of the interbody device. A second side of the main body may define a second side of the interbody device. A portion of a third side of the main body and a portion of a third side of the arm may define a third side of the interbody device. A portion of a fourth side of the main body and a portion of a fourth side of the arm may define a fourth side of the interbody device. An overall distance between the first side and the second side of the interbody device may increase along at least a majority of a length of the interbody device in a direction from a first end toward a second end of the interbody device, and an overall distance between the third side and the fourth side of the interbody device may be constant or substantially constant along at least a majority of the length of the interbody device.

In another embodiment, the interbody device may include a main body having an elongated shape, and an arm movably connected to the main body and having an elongated shape. The main body may include a first end, a second end, a first side, a second side disposed opposite the first side of the main body, a third side, and a fourth side disposed opposite the third side of the main body. The arm may include a first end, a second end, a first side, a second side disposed opposite the first side of the arm, a third side, and a fourth side disposed opposite the third side of the arm. A portion of the first side of the main body and a portion of the first side of the arm may define a first side of the interbody device. The second side of the main body may define a second side of the interbody device. A portion of the third side of the main body and a portion of the third side of the arm may define a third side of the interbody device. A portion of the fourth side of the main body and a portion of the fourth side of the arm may define a fourth side of the interbody device. An overall distance between the first side and the second side of the interbody device may increase along at least a majority of a length of the interbody device in a direction from a first end toward a second end of the interbody device, and an overall distance between the third side and the fourth side of the interbody device may increase along at least a majority of the length of the interbody device in a direction from the second end toward the first end of the interbody device.

In still another embodiment, the interbody device may include a main body having an elongated shape, and an arm movably connected to the main body and having an elongated shape. The main body may include a first end, a second end, a first side, a second side disposed opposite the first side of the main body, a third side, and a fourth side disposed opposite the third side of the main body. The arm may include a first end, a second end, a first side, a second side disposed opposite the first side of the arm, a third side, and a fourth side disposed opposite the third side of the arm. A portion of the first side of the main body and a portion of the first side of the arm may define a first side of the interbody device. The second side of the main body may define a second side of the interbody device. A portion of the third side of the main body and a portion of the third side of the arm may define a third side of the interbody device. A portion of the fourth side of the main body and a portion of the fourth side of the arm may define a fourth side of the interbody device. An overall distance between the first side and the second side of the interbody device may increase along at least a majority of a length of the interbody device in a direction from a first end toward a second end of the interbody device, and an overall distance between the third side and the fourth side of the interbody device may be constant or substantially constant along at least a majority of the length of the interbody device.

In another embodiment, the interbody device may include a main body having an elongated shape, and an arm movably connected to the main body and having an elongated shape. The interbody device may have a first end, a second end disposed opposite the first end of the interbody device in a direction of a longitudinal axis of the interbody device, a first side, a second side disposed opposite the first side of the interbody device in a direction of a first transverse axis of the interbody device, a third side, and a fourth side disposed opposite the third side of the interbody device in a direction of a second transverse axis of the interbody device. In some embodiments, the main body may include a port extending from the second end of the interbody device toward the first end of the interbody device. In some embodiments, the port may include a number of threads configured for engaging mating threads of an instrument system. In some embodiments, the interbody device may further include a number of markers formed of a radiodense or radiopaque material. In some embodiments, the number of markers may include a first marker disposed within the main body and a second marker disposed within the arm. In some embodiments, the first marker may be positioned near a first end of the main body, and the second marker may be positioned near a first end of the arm.

According to another aspect, an instrument system is provided for implanting an interbody device within an intervertebral space between a first vertebra and a second vertebra. In one embodiment, the instrument system may include a handle, an inner tube removably attached to the handle, and an outer tube removably attached to the handle and extending at least partially over the inner tube. The inner tube may include a tubular body and an interbody device interface configured for releasably engaging the interbody device.

In some embodiments, the handle may include a first bore defined therein and extending from a distal end of the handle toward a proximal end of the handle, and a proximal portion of the inner tube is removably received within the first bore of the handle. In some embodiments, the inner tube may be axially and rotatably coupled to the handle via a locking mechanism. In some embodiments, the interbody device interface may include a plurality of protrusions spaced apart from one another and configured for engaging mating features of the interbody device. In some embodiments, a distal portion of the inner tube may include a first part, a second part, and a slot extending between the first part and the second part, and the first part and the second part may be configured to deflect away from one another and away from a longitudinal axis of the inner tube.

In some embodiments, the outer tube may include a bore defined therein and extending from a proximal end of the outer tube toward a distal end of the outer tube, and a distal portion of the handle may be removably received within the bore of the outer tube. In some embodiments, the outer tube may be removably attached to the handle via a plurality of threads of the outer tube and a plurality of threads of the handle. In some embodiments, the outer tube may include a tapered interface positioned at a distal end of the outer tube. In some embodiments, the outer tube may be movable with respect to the handle and the inner tube between a distal position in which the tapered interface engages or is positioned near the interbody device interface and a proximal position in which the tapered interface is spaced apart from the interbody device interface.

In some embodiments, the instrument system may further include an expansion plunger configured for advancing at least partially through the handle, the inner tube, and the outer tube. In some embodiments, the expansion plunger may include a shaft and a knob attached to the shaft. In some embodiments, the shaft may be movably attached to the knob. In some embodiments, the shaft may be configured to translate axially with respect to the knob between an extended position and a retracted position. In some embodiments, the expansion plunger may further include a spring configured to bias the shaft toward the expanded position. In some embodiments, the handle may include a second bore defined therein and extending from a proximal end of the handle toward a distal end of the handle, and a distal portion of the knob may be configured for advancing at least partially into the second bore of the handle. In some embodiments, the knob may be configured for removably attaching to the handle via a plurality of threads of the knob and a plurality of threads of the handle.

In some embodiments, the instrument system may further include a cap configured for attaching to the handle. In some embodiments, the handle may include a second bore defined therein and extending from a proximal end of the handle toward a distal end of the handle, and a distal portion of the cap may be configured for advancing at least partially into the second bore of the handle. In some embodiments, the cap may be configured for removably attaching to the handle via a plurality of threads of the cap and a plurality of threads of the handle. In some embodiments, the instrument system may further include a bone graft tube configured for advancing at least partially through the cap, the handle, the inner tube, and the outer tube. In some embodiments, the bone graft tube may include a tubular body extending from a distal end of the bone graft tube toward a proximal end of the bone graft tube, and an inlet port extending from the proximal end of the bone graft tube toward the distal end of the bone graft tube. In some embodiments, the instrument system may further include a bone graft plunger configured for advancing at least partially through the bone graft tube, the cap, the handle, the inner tube, and the outer tube. In some embodiments, the bone graft plunger may include a shaft extending from a distal end of the bone graft plunger toward a proximal end of the bone graft plunger, and a knob extending from the proximal end of the bone graft plunger toward the distal end of the bone graft plunger. In some embodiments, the shaft may be rigidly attached to the knob. In some embodiments, the knob may include a bore defined therein and extending from a distal end of the knob toward a proximal end of the knob, and the bore of the knob may be configured for receiving at least a portion of the inlet port of the bone graft plunger.

According to another aspect, a method is provided for implanting an interbody device within an intervertebral space between a first vertebra and a second vertebra of a patient. In one embodiment, the method may include the steps of inserting the interbody device into the intervertebral space, rotating the interbody device about a longitudinal axis of the interbody device within the intervertebral space, and expanding the interbody device within the intervertebral space by pivoting an arm of the interbody device with respect to a main body of the interbody device.

In some embodiments, the interbody device may have a first end, a second end disposed opposite the first end of the interbody device in a direction of the longitudinal axis of the interbody device, a first side, a second side disposed opposite the first side of the interbody device in a direction of a first transverse axis of the interbody device, a third side, and a fourth side disposed opposite the third side of the interbody device in a direction of a second transverse axis of the interbody device. In some embodiments, an overall distance between the first side and the second side of the interbody device may increase along at least a majority of a length of the interbody device in a direction from the first end toward the second end of the interbody device. In some embodiments, the overall distance between the first side and the second side of the interbody device may increase along the entire length of the interbody device in the direction from the first end toward the second end of the interbody device. In some embodiments, an overall distance between the third side and the fourth side of the interbody device may increase along at least a majority of the length of the interbody device in a direction from the second end toward the first end of the interbody device. In some embodiments, the overall distance between the third side and the fourth side of the interbody device may increase along only a portion of the length of the interbody device from the second end toward the first end of the interbody device.

In some embodiments, the interbody device may have a first overall distance between the first side and the second side of the interbody device at the first end of the interbody device, and a second overall distance between the first side and the second side of the interbody device at the second end of the interbody device, and the first overall distance may be less than the second overall distance. In some embodiments, the interbody device may have a third overall distance between the third side and the fourth side of the interbody device at the second end of the interbody device, a fourth overall distance between the third side and the fourth side of the interbody device at a location between the first end and the second end of the interbody device, and a fifth overall distance between the third side and the fourth side of the interbody device at the first end of the interbody device. In some embodiments, the third overall distance may be less than each of the fourth overall distance and the fifth overall distance, and the fifth overall distance may be less than the fourth overall distance. In some embodiments, the third overall distance may be less than the second overall distance. In some embodiments, the second overall distance may be less than the fourth overall distance. In some embodiments, the second overall distance may be less than the fifth overall distance. In some embodiments, the first overall distance may be less than each of the second overall distance, the third overall distance, the fourth overall distance, and the fifth overall distance. In some embodiments, an overall distance between a third side and a fourth side of the arm may be constant or substantially constant along at least a majority of a length of the arm. In some embodiments, the arm may have a sixth overall distance between the third side and the fourth side of the arm which is constant or substantially constant along the at least a majority of the length of the arm. In some embodiments, the sixth overall distance may be equal to the third overall distance. In some embodiments, the sixth overall distance may be less than each of the fourth overall distance and the fifth overall distance. In some embodiments, the first overall distance may be less than the sixth overall distance, and the sixth overall distance may be less than the second overall distance.

In some embodiments, inserting the interbody device into the intervertebral space may include inserting the interbody device into the intervertebral space via a posterior approach. In some embodiments, inserting the interbody device into the intervertebral space may include distracting the intervertebral space via the interbody device. In some embodiments, distracting the intervertebral space may include over-distracting a posterior portion of the intervertebral space. In some embodiments, inserting the interbody device into the intervertebral space may include engaging one of the first vertebra and the second vertebra with at least a portion of the first side of the interbody device and engaging the other of the first vertebra and the second vertebra with at least a portion of the second side of the interbody device. In some embodiments, rotating the interbody device within the intervertebral space may include rotating the interbody device approximately ninety degrees about the longitudinal axis of the interbody device. In some embodiments, rotating the interbody device within the intervertebral space may include engaging one of the first vertebra and the second vertebra with at least a portion of the third side of the interbody device and engaging the other of the first vertebra and the second vertebra with at least a portion of the fourth side of the interbody device. In some embodiments, expanding the interbody device within the intervertebral space may include laterally expanding the interbody device within the intervertebral space. In some embodiments, expanding the interbody device within the intervertebral space may include engaging one of the first vertebra and the second vertebra with at least a portion of a third side of the arm of the interbody device and engaging the other of the first vertebra and the second vertebra with at least a portion of a fourth side of the arm of the interbody device. In some embodiments, pivoting the arm of the interbody device with respect to the main body of the interbody device may include pivoting the arm medially with respect to the main body. In some embodiments, the method further may include delivering bone graft or a bone graft substitute into a cavity of the interbody device. In some embodiments, the cavity of the interbody device may be defined between the arm and the main body of the interbody device. In some embodiments, delivering the bone graft or the bone graft substitute into the cavity of the interbody device may include advancing the bone graft or the bone graft substitute through a port and a channel of the interbody device.

In another embodiment, the method may include the steps of providing the interbody device, inserting the interbody device into the intervertebral space, rotating the interbody device about a longitudinal axis of the interbody device within the intervertebral space, and expanding the interbody device within the intervertebral space. The interbody device may have a first end, a second end disposed opposite the first end of the interbody device in a direction of the longitudinal axis of the interbody device, a first side, a second side disposed opposite the first side of the interbody device in a direction of a first transverse axis of the interbody device, a third side, and a fourth side disposed opposite the third side of the interbody device in a direction of a second transverse axis of the interbody device. An overall distance between the first side and the second side of the interbody device increases along at least a majority of a length of the interbody device in a direction from the first end toward the second end of the interbody device. The interbody device may be inserted into the intervertebral space such that at least a portion of the first side of the interbody device engages one of the first vertebra and the second vertebra and at least a portion of the second side of the interbody device engages the other of the first vertebra and the second vertebra. The interbody device may be rotated about the longitudinal axis of the interbody device within the intervertebral space such that at least a portion of the third side of the interbody device engages one of the first vertebra and the second vertebra and at least a portion of the fourth side of the interbody device engages the other of the first vertebra and the second vertebra.

In some embodiments, the overall distance between the first side and the second side of the interbody device may increase along the entire length of the interbody device in the direction from the first end toward the second end of the interbody device. In some embodiments, an overall distance between the third side and the fourth side of the interbody device may increase along at least a majority of the length of the interbody device in a direction from the second end toward the first end of the interbody device. In some embodiments, an overall distance between the third side and the fourth side of the interbody device may be constant or substantially constant along at least a majority of the length of the interbody device. In some embodiments, the interbody device may include a main body having an elongated shape, and an arm movably connected to the main body and having an elongated shape.

In still another embodiment, the method may include the steps of providing the interbody device, inserting the interbody device into the intervertebral space, rotating the interbody device about a longitudinal axis of the interbody device within the intervertebral space, and expanding the interbody device within the intervertebral space. The interbody device may have a first end, a second end disposed opposite the first end of the interbody device in a direction of the longitudinal axis of the interbody device, a first side, a second side disposed opposite the first side of the interbody device in a direction of a first transverse axis of the interbody device, a third side, and a fourth side disposed opposite the third side of the interbody device in a direction of a second transverse axis of the interbody device. The interbody device may have a first overall distance between the first side and the second side of the interbody device at the first end of the interbody device, a second overall distance between the first side and the second side of the interbody device at the second end of the interbody device, and a third overall distance between the third side and the fourth side of the interbody device at the second end of the interbody device. The first overall distance may be less than each of the second overall distance and the third overall distance, and the third overall distance may be less than the second overall distance. The interbody device may be inserted into the intervertebral space such that at least a portion of the first side of the interbody device engages one of the first vertebra and the second vertebra and at least a portion of the second side of the interbody device engages the other of the first vertebra and the second vertebra. The interbody device may be rotated about the longitudinal axis of the interbody device within the intervertebral space such that at least a portion of the third side of the interbody device engages one of the first vertebra and the second vertebra and at least a portion of the fourth side of the interbody device engages the other of the first vertebra and the second vertebra.

In some embodiments, an overall distance between the first side and the second side of the interbody device may increase along at least a majority of a length of the interbody device in a direction from the first end toward the second end of the interbody device. In some embodiments, an overall distance between the third side and the fourth side of the interbody device may increase along at least a majority of a length of the interbody device in a direction from the second end toward the first end of the interbody device. In some embodiments, an overall distance between the third side and the fourth side of the interbody device may be constant or substantially constant along at least a majority of a length of the interbody device. In some embodiments, the interbody device may include a main body having an elongated shape, and an arm movably connected to the main body and having an elongated shape.

Expandable Interbody Devices

Referring now to the drawings of the present disclosure, FIGS. 1A-1M illustrate an expandable interbody device 100 (which also may be referred to as an "interbody spacer," an "interbody cage," a "spacer," or a "cage") according to one or more embodiments of the disclosure. The interbody device 100 may be configured for implantation within an intervertebral space (which also may be referred to as an "interbody space" or a "disc space") between two adjacent vertebrae to provide structural support and stabilization of the vertebrae. As described in detail below, the interbody device 100 may be used in spinal fusion surgery to restore and maintain normal spacing or "height" between the adjacent vertebrae and to realign the adjacent vertebrae such that the vertebrae follow the normal curvature of the spine. In some embodiments, the interbody device 100 may be configured for use in the lumbar region of the spine, such that the interbody device 100 provides correction of lordosis, the normal inward curvature of the lumbar region. Additionally, in some embodiments, the interbody device 100 may be well suited for implantation via a posterior approach, as may be utilized according to the PLIF technique or the TLIF technique. However, it will be appreciated that the interbody device 100 may be implanted via other approaches, such as an anterior approach or a lateral approach, and according to other known techniques. Further, the interbody device 100 may alternatively be configured for use in the thoracic region or the cervical region of the spine. The interbody device 100 may be used in the treatment of various spinal conditions, including spondylolisthesis, degenerative disc disease, and recurrent disc herniation. In certain applications, the interbody device 100 may be used in conjunction with additional hardware, such as pedicle screws and rods or plates, which may provide additional structural support to stabilize the desired vertebrae and facilitate fusion therebetween. As described in detail below, bone graft or a bone graft substitute may be placed within one or more cavities defined by the interbody device 100 to promote fusion between the adjacent vertebrae. Ultimately, the interbody device 100, itself or in combination with additional hardware, may provide the structural support necessary to maintain normal spacing and alignment of the adjacent vertebrae until fusion is achieved between the vertebrae.

The expandable interbody device 100 may have an elongated shape defining a longitudinal axis $A_L$, a first transverse axis $A_{T1}$ that is perpendicular to the longitudinal axis $A_L$, and a second transverse axis $A_{T2}$ that is perpendicular to each of the longitudinal axis $A_L$ and the first transverse axis $A_{T1}$. As shown, the interbody device 100 may include a first end 101 (which also may be referred to as a "distal end" or a "leading end," with reference to an orientation in which the device 100 is inserted into an intervertebral space) and a second end 102 (which also may be referred to as a "proximal end" or a "trailing end," with reference to the orientation in which the device 100 is inserted into an intervertebral space) disposed opposite the first end 101 in the direction of the longitudinal axis $A_L$. The interbody device 100 also may include a first side 103 extending from the first end 101 to the second end 102, and a second side 104 disposed opposite the first side 103 in the direction of the first transverse axis $A_{T1}$ and extending from the first end 101 to the second end 102. The interbody device 100 further may include a third side 105 extending from the first end 101 to the second end 102 and from the first side 103 to the second side 104, and a fourth side 106 disposed opposite the third side 105 in the direction of the second transverse axis $A_{T2}$ and extending from the first end 101 to the second end 102 and from the first side 103 to the second side 104. As shown, the interbody device 100 may have a length L from the first end 101 to the second end 102 of the device 100 in the direction of the longitudinal axis $A_L$. The interbody device 100 may include a first half 107 (which also may be referred to as a "distal half") extending from the first end 101 to a midpoint of the device 100 in the direction of the longitudinal axis $A_L$, and a second half 108 (which also may be referred to as a "proximal half") extending from the second end 102 to the midpoint of the device 100 in the direction of the longitudinal axis $A_L$.

As shown, the interbody device 100 may include a main body 110 having an elongated shape extending along the longitudinal axis $A_L$ of the device 100. The main body 110 may include a first end 111 (which also may be referred to as a "distal end" or a "leading end") and a second end 112 (which also may be referred to as a "proximal end" or a "trailing end") disposed opposite the first end 111 in the direction of the longitudinal axis $A_L$. The main body 110 also may include a first side 113 extending from the first end 111 to the second end 112, and a second side 114 disposed opposite the first side 113 in the direction of the first transverse axis $A_{T1}$ and extending from the first end 111 to the second end 112. The main body 110 further may include a third side 115 extending from the first end 111 to the second end 112 and from the first side 113 to the second side 114, and a fourth side 116 disposed opposite the third side 115 in the direction of the second transverse axis $A_{T2}$ and extending from the first end 111 to the second end 112 and from the first side 113 to the second side 114.

The interbody device 100 also may include an arm 120 having an elongated shape extending along the longitudinal axis $A_L$ of the device 100. The arm 120 may include a first end 121 (which also may be referred to as a "distal end" or a "leading end") and a second end 122 (which also may be referred to as a "proximal end" or a "trailing end") disposed opposite the first end 121 in the direction of the longitudinal axis $A_L$. The arm 120 also may include a first side 123 extending from the first end 121 to the second end 122, and a second side 124 disposed opposite the first side 123 in the direction of the first transverse axis $A_{T1}$ and extending from the first end 121 to the second end 122. The arm 120 further may include a third side 125 extending from the first end 121 to the second end 122 and from the first side 123 to the second side 124, and a fourth side 126 disposed opposite the third side 125 in the direction of the second transverse axis $A_{T2}$ and extending from the first end 121 to the second end 122 and from the first side 123 to the second side 124.

As shown, the first end 101 of the interbody device 100 may be defined by the first end 111 of the main body 110 and the first end 121 of the arm 120. In this manner, the first end 111 of the main body 110 and the first end 121 of the arm 120 may be aligned with one another along the longitudinal axis $A_L$ of the interbody device 100. Alternatively, the first end 101 of the interbody device 100 may be defined by the first end 111 of the main body 110 or by the first end 121 of the arm 120. In this manner, the first end 111 of the main body 110 and the first end 121 of the arm 120 may be offset from one another along the longitudinal axis $A_L$ of the interbody device 100. In some embodiments, as shown, the first end 101 of the interbody device 100 may extend perpendicular to the longitudinal axis $A_L$ (and parallel to the first transverse axis $A_{T1}$ and the second transverse axis $A_{T2}$) of the interbody device 100. As shown, the second end 102 of the interbody device 100 may be defined by the second end 112 of the main body 110. In this manner, the second end 112 of the main body 110 and the second end 122 of the arm 120 may be offset from one another along the longitudinal axis $A_L$ of the interbody device 100. Alternatively, the second end 102 of the interbody device 100 may be defined by the second end 112 of the main body 110 and the second end 122 of the arm 120. In this manner, the second end 112 of the main body 110 and the second end 122 of the arm 120 may be aligned with one another along the longitudinal axis $A_L$ of the interbody device 100. As another alternative, the second end 102 of the interbody device 100 may be defined by the second end 122 of the arm 120. In this manner, the second end 112 of the main body 110 and the second end 122 of the arm 120 may be offset from one another along the longitudinal axis $A_L$ of the interbody device 100. In some embodiments, as shown, the second end 102 of the interbody device 100 may extend perpendicular to the longitudinal axis $A_L$ (and parallel to the first transverse axis $A_{T1}$ and the second transverse axis $A_{T2}$) of the interbody device 100.

As shown, the first side 103 of the interbody device 100 may be defined by at least a portion of the first side 113 of the main body 110 and at least a portion of the first side 123 of the arm 120. In some embodiments, as shown, the first side 103 of the interbody device 100 may be defined by a proximal portion of the first side 113 of the main body 110 and the entire first side 123 of the arm 120. Alternatively, the first side 103 of the interbody device 100 may be defined by the entire first side 113 of the main body 110 or by the entire first side 123 of the arm 120. As shown, the second side 104 of the interbody device 100 may be defined by the entire second side 114 of the main body 110. Alternatively, the second side 104 of the interbody device 100 may be defined by the entire second side 124 of the arm 120. As another alternative, the second side 104 of the interbody device 100 may be defined by at least a portion of the second side 114 of the main body 110 and at least a portion of the second side 124 of the arm 120. As shown, the third side 105 of the interbody device 100 may be defined by at least a portion of the third side 115 of the main body 110 and at least a portion of the third side 125 of the arm 120. In some embodiments, as shown, the third side 105 of the interbody device 100 may be defined by the entire third side 115 of the main body 110 and a distal portion of the third side 125 of the arm 120. Alternatively, the third side 105 of the interbody device 100 may be defined by the entire third side 115 of the main body 110 or by the entire third side 125 of the arm 120. As shown, the fourth side 106 of the interbody device 100 may be defined by at least a portion of the fourth side 116 of the main body 110 and at least a portion of the fourth side 126 of the arm 120. In some embodiments, as shown, the fourth side 106 of the interbody device 100 may be defined by the entire fourth side 116 of the main body 110 and a distal portion of the fourth side 126 of the arm 120. Alternatively, the fourth side 106 of the interbody device 100 may be defined by the entire fourth side 116 of the main body 110 or by the entire fourth side 126 of the arm 120.

As shown, the main body 110 and the arm 120 may be movably connected to one another. In particular, the arm 120 may be movable with respect to the main body 110 between a compact position (which also may be referred to as an "insertion position"), as shown in FIGS. 1A-1G, and an expanded position (which also may be referred to as an "implantation position"), as shown in FIGS. 1H-1M. In this manner, the interbody device 100 may be movable between a compact configuration (which also may be referred to as an "insertion configuration") in which the arm 120 is in the compact position, as shown in FIGS. 1A-1G, and an expanded configuration (which also may be referred to as an "implantation configuration") in which the arm 120 is in the expanded position, as shown in FIGS. 1H-1M.

In particular, the main body 110 and the arm 120 may be pivotally connected to one another via a hinge connection 128, such that the arm 120 may pivot relative to the main body 110 between the compact position and the expanded position. As shown, the hinge connection 128 may be positioned within the second half 108 of the interbody device 100. In particular, the hinge connection 128 may be positioned near but spaced apart from the second end 102 of the interbody device 100, as shown. Alternatively, the hinge connection 128 may be positioned at or adjacent to the second end 102 of the interbody device 100. In some embodiments, as shown, the hinge connection 128 may include a pin 130 extending through a one or more apertures 131 defined in the main body 110 and through one or more apertures 132 defined in the arm 120. As shown, the hinge connection 128 also may include a hinge recess 133 defined between a pair of hinge supports 134 of the main body 110, and a hinge tab 135 of the arm 120. The hinge supports 134 may be disposed along the third side 115 and the fourth side 116 of the main body 110, respectively, and may extend to the first side 113 of the main body 110, as shown. One of the apertures 131 may be defined in one of the hinge supports 134, and another aperture 131 may be defined in the other hinge support 134. The hinge tab 135 may be positioned at or near the second end 122 of the arm 120 and may extend to the first side 123, the second side 124, the third side 125, and the fourth side 126 of the arm 120, as shown. The one or more apertures 132 may be defined in the hinge tab 135. As shown, the hinge tab 135 of the arm 120 may be movably disposed within the hinge recess 133 of the main body 110. In some embodiments, the pin 130 may be press-fit into the one or more apertures 131 of the main body 110 and may have a sliding fit within the one or more apertures 132 of the arm 120. In other embodiments, the pin 130 may be press-fit into the one or more apertures 132 of the arm 120 and may have a sliding fit within the one or more apertures 131 of the main body 110. As shown, a rotational axis $A_R$ of the hinge connection 128 (i.e., a longitudinal axis of the pin 130) may extend parallel to the second transverse axis $A_{T2}$ of the device 100 and perpendicular to the longitudinal axis $A_L$ and the first transverse axis $A_{T1}$ of the device 100.

Figure 1N:
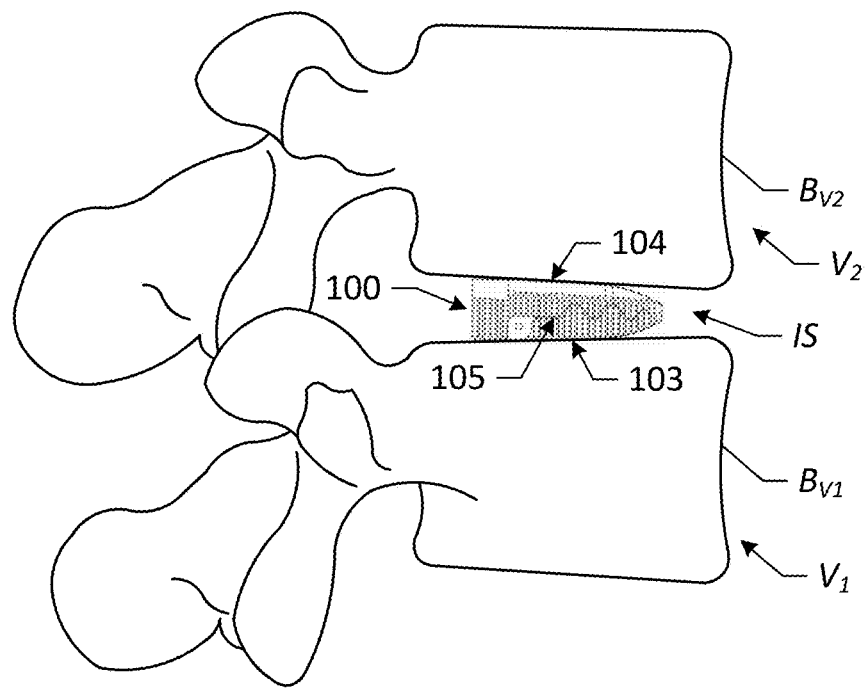
FIG. 1N shows a side view of the expandable interbody device of FIG. 1A positioned within an intervertebral space between an inferior vertebra and a superior vertebra, the expandable interbody device in an insertion orientation and the compact configuration.
Figure 1O:
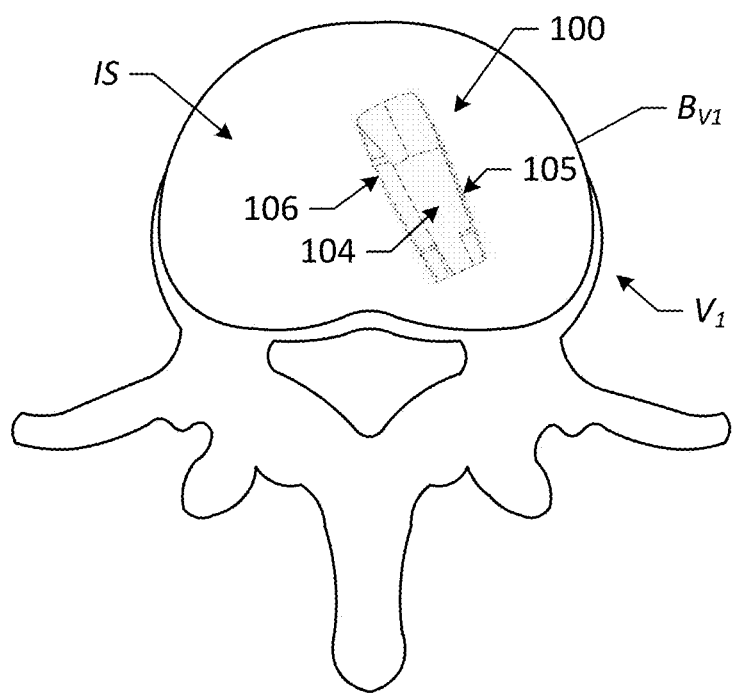
FIG. 1O shows a top view of the expandable interbody device of FIG. 1A positioned within the intervertebral space above the inferior vertebra, the expandable interbody device in the insertion orientation and the compact configuration.

Additional features of the main body 110, the arm 120, and the overall expandable interbody device 100 may be best understood in view of an intended method of implanting the interbody device 100 within an intervertebral space IS between a first vertebra $V_1$ (which also may be referred to as an "inferior vertebra") and an adjacent second vertebra $V_2$ (which also may be referred to as a "superior vertebra"), as shown in FIGS. 1N-1S. The interbody device 100 initially may be inserted into and positioned within the intervertebral space IS while the device 100 is an "insertion orientation" and the compact configuration, as shown in FIGS. 1N and 1O. When the interbody device 100 is in the insertion orientation within the intervertebral space IS, the longitudinal axis $A_L$ and the second transverse axis $A_{T2}$ of the device 100 may extend substantially parallel to the transverse plane of the patient, and the first transverse axis $A_{T1}$ of the device 100 may extend substantially parallel to the sagittal plane and the coronal plane of the patient. In this manner, upon insertion of the interbody device 100 within the intervertebral space IS, respective portions of the first side 103 and the second side 104 of the device 100 each may engage one of the adjacent vertebrae $V_1$, $V_2$.

In some embodiments, as shown, at least a portion of the first side 103 of the device 100 may engage a first body $B_{V1}$ of the first vertebra $V_1$, and at least a portion of the second side 104 of the device 100 may engage a second body $B_{V2}$ of the second vertebra $V_2$. In other words, in such embodiments, when the interbody device 100 is in the insertion orientation within the intervertebral space IS, the first side 103 of the device 100 is oriented in the caudal direction of the patient, and the second side 104 of the device 100 is oriented in the cephalad direction of the patient. For reasons described below, such insertion orientation may be used when the illustrated embodiment of the interbody device 100 is being inserted from the right side of the patient's spine, as shown in FIGS. 1N-1S, although such insertion orientation also may be used when the interbody device 100 is being inserted from the left side of the patient's spine according to other embodiments of the device 100. According to the illustrated embodiment of the interbody device 100, when the device 100 is in the insertion orientation within the intervertebral space IS, at least a portion of the first side 113 of the main body 110 and at least a portion of the first side 123 of the arm 120 may engage the first body $B_{V1}$ of the first vertebra $V_1$, and at least a portion of the second side 114 of the main body 110 may engage the second body $B_{V2}$ of the second vertebra $V_2$.

In other embodiments, at least a portion of the second side 104 of the device 100 may engage the first body $B_{V1}$ of the first vertebra $V_1$, and at least a portion of the first side 103 of the device 100 may engage the second body $B_{V2}$ of the second vertebra $V_2$. In other words, in such embodiments, when the interbody device 100 is in the insertion orientation within the intervertebral space IS, the second side 104 of the device 100 is oriented in the caudal direction of the patient, and the first side 103 of the device 100 is oriented in the cephalad direction of the patient. For reasons described below, such insertion orientation may be used when the illustrated embodiment of the interbody device 100 is being inserted from the left side of the patient's spine, although such insertion orientation also may be used when the interbody device 100 is being inserted from the right side of the patient's spine according to other embodiments of the device 100. According to the illustrated embodiment of the interbody device 100, when the device 100 is in the insertion orientation within the intervertebral space IS, at least a portion of the second side 114 of the main body 110 may engage the first body $B_{V1}$ of the first vertebra $V_1$, and at least a portion of the first side 113 of the main body 110 and at least a portion of the first side 123 of the arm 120 may engage the second body $B_{V2}$ of the second vertebra $V_2$.

Figure 1P:
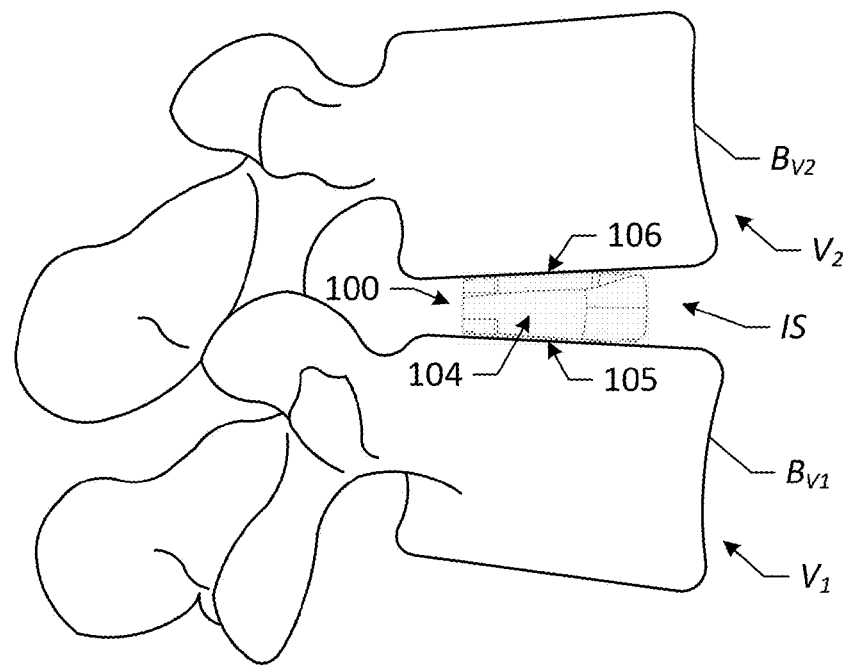
FIG. 1P shows a side view of the expandable interbody device of FIG. 1A positioned within the intervertebral space between the inferior vertebra and the superior vertebra, the expandable interbody device in an implantation orientation and the compact configuration.
Figure 1Q:
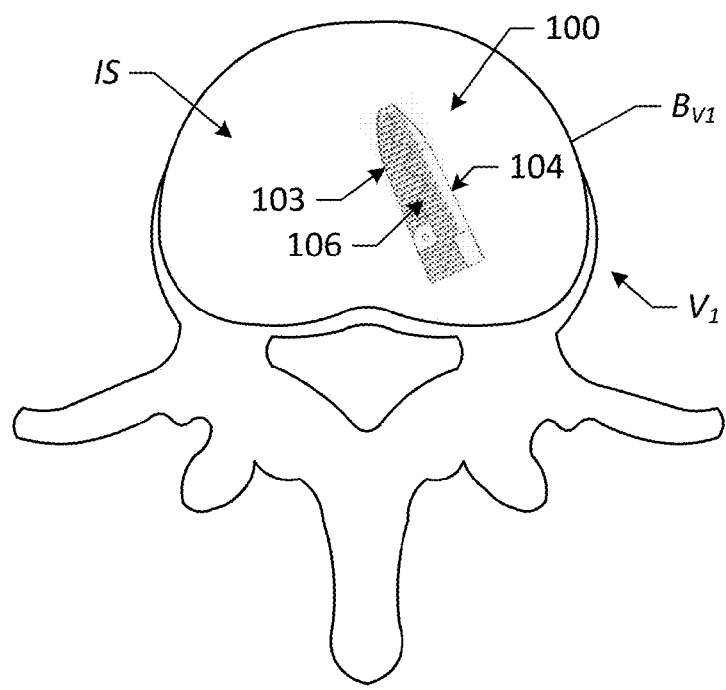
FIG. 1Q shows a top view of the expandable interbody device of FIG. 1A positioned within the intervertebral space above the inferior vertebra, the expandable interbody device in the implantation orientation and the compact configuration.

After inserting and positioning the interbody device 100 within the intervertebral space IS and while maintaining the device 100 in the compact configuration, the device 100 may be rotated approximately ninety (90) degrees about the longitudinal axis $A_L$ of the device 100 from the insertion orientation to an "implantation orientation," as shown in FIGS. 1P and 1Q. In some embodiments, as shown, the device 100 may be rotated clockwise (when viewed from the second end 102 of the device 100) from the insertion orientation to the implantation orientation. In other embodiments, the device 100 may be rotated counter clockwise (when viewed from the second end 102 of the device 100) from the insertion orientation to the implantation orientation. When the interbody device 100 is in the implantation orientation, the longitudinal axis $A_L$ and the first transverse axis $A_{T1}$ of the device 100 may extend substantially parallel to the transverse plane of the patient, and the second transverse axis $A_{T2}$ of the device 100 may extend substantially parallel to the sagittal plane and the coronal plane of the patient. In this manner, upon rotation of the interbody device 100 within the intervertebral space IS from the insertion orientation to the implantation orientation, respective portions of the third side 105 and the fourth side 106 of the device 100 each may engage one of the adjacent vertebrae $V_1$, $V_2$.

In some embodiments, as shown, at least a portion of the third side 105 of the device 100 may engage the first body $B_{V1}$ of the first vertebra $V_1$, and at least a portion of the fourth side 106 of the device 100 may engage the second body $B_{V2}$ of the second vertebra $V_2$. In other words, in such embodiments, when the interbody device 100 is in the implantation orientation within the intervertebral space IS, the third side 105 of the device 100 is oriented in the caudal direction of the patient, and the fourth side 106 of the device 100 is oriented in the cephalad direction of the patient. For reasons described below, such implantation orientation may be used when the interbody device 100 has been inserted from the right side of the patient's spine, as shown in FIGS. 1N-1S, although such implantation orientation also may be used when the interbody device 100 is being inserted from the left side of the patient's spine according to other embodiments. According to the illustrated embodiment of the interbody device 100, when the device 100 is in the implantation orientation within the intervertebral space IS, at least a portion of the third side 115 of the main body 110 may engage the first body $B_{V1}$ of the first vertebra $V_1$, and at least a portion of the fourth side 116 of the main body 110 may engage the second body $B_{V2}$ of the second vertebra $V_2$. Meanwhile, the third side 125 of the arm 120 may be oriented toward but spaced apart from (i.e., not engaging) the first body $B_{V1}$ of the first vertebra $V_1$, and the fourth side 126 of the arm 120 may be oriented toward but spaced apart from the second body $B_{V2}$ of the second vertebra $V_2$.

In other embodiments, at least a portion of the fourth side 106 of the device 100 may engage the first body $B_{V1}$ of the first vertebra $V_1$, and at least a portion of the third side 105 of the device 100 may engage the second body $B_{V2}$ of the second vertebra $V_2$. In other words, in such embodiments, when the interbody device 100 is in the implantation orientation within the intervertebral space IS, the fourth side 106 of the device 100 is oriented in the caudal direction of the patient, and the third side 105 of the device 100 is oriented in the cephalad direction of the patient. For reasons described below, such implantation orientation may be used when the interbody device 100 has been inserted from the left side of the patient's spine, although such implantation orientation also may be used when the interbody device 100 is being inserted from the right side of the patient's spine according to other embodiments. According to the illustrated embodiment of the interbody device 100, when the device 100 is in the implantation orientation within the intervertebral space IS, at least a portion of the fourth side 116 of the main body 110 may engage the first body $B_{V1}$ of the first vertebra $V_1$, and at least a portion of the third side 115 of the main body 110 may engage the second body $B_{V2}$ of the second vertebra $V_2$. Meanwhile, the fourth side 126 of the arm 120 may be oriented toward but spaced apart from the first body $B_{V1}$ of the first vertebra $V_1$, and the third side 125 of the arm 120 may be oriented toward but spaced apart from the second body $B_{V2}$ of the second vertebra $V_2$.

Figure 1R:
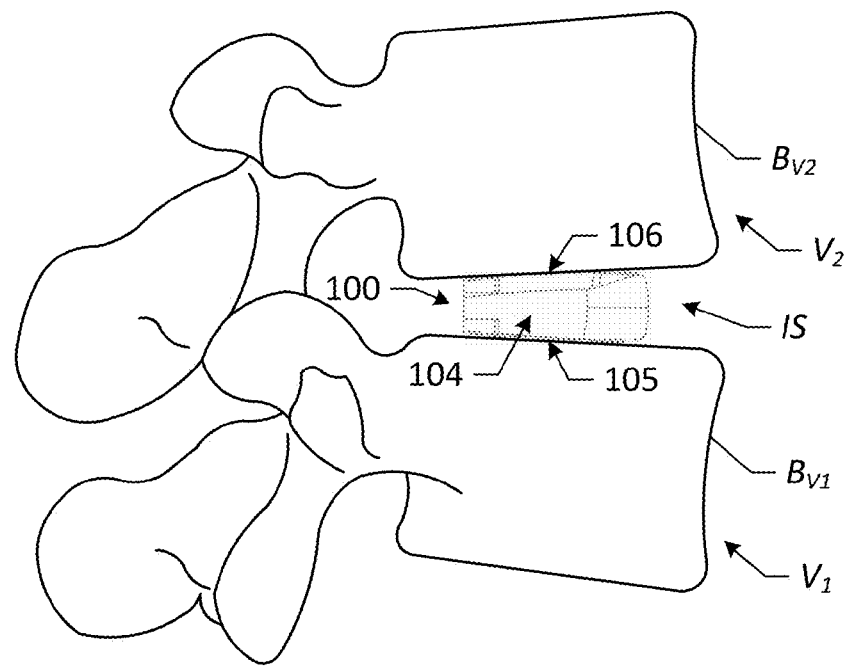
FIG. 1R shows a side view of the expandable interbody device of FIG. 1A positioned within the intervertebral space between the inferior vertebra and the superior vertebra, the expandable interbody device in the implantation orientation and the expanded configuration.
Figure 1S:
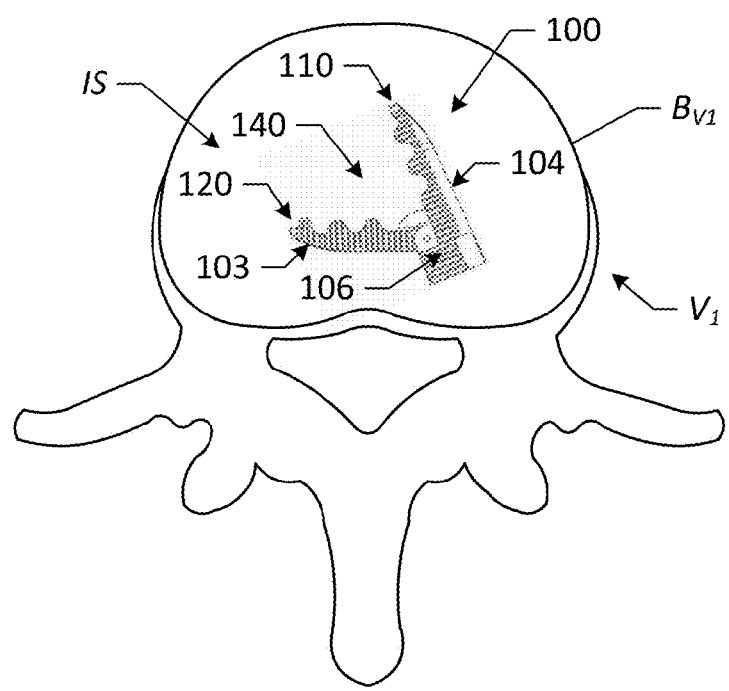
FIG. 1S shows a top view of the expandable interbody device of FIG. 1A positioned within the intervertebral space above the inferior vertebra, the expandable interbody device in the implantation orientation and the expanded configuration.

After rotating the interbody device 100 within the intervertebral space IS from the insertion orientation to the implantation orientation, the device 100 may be expanded from the compact configuration to the expanded configuration, as shown in FIGS. 1R and 1S. In this manner, the arm 120 may be moved with respect to the main body 110 from the compact position to the expanded position. In particular, the arm 120 may be pivoted medially with respect to the main body 110 about the hinge connection 128 from the compact position to the expanded position. The degree of expansion of the interbody device 100 (i.e., the degree which the arm 120 is pivoted with respect to the main body 110) may be determined by the user, based on the anatomy of the patient and the desired correction of the adjacent vertebrae $V_1$, $V_2$. Upon expansion of the interbody device 100 within the intervertebral space IS from the compact configuration to the expanded configuration, respective portions of the third side 105 and the fourth side 106 of the device 100 each may engage one of the adjacent vertebrae $V_1$, $V_2$.

In some embodiments, as shown, at least a portion of the third side 105 of the device 100 may engage the first body $B_{V1}$ of the first vertebra $V_1$, and at least a portion of the fourth side 106 of the device 100 may engage the second body $B_{V2}$ of the second vertebra $V_2$. According to the illustrated embodiment of the interbody device 100, when the device 100 is in the implantation orientation and the expanded configuration within the intervertebral space IS, at least a portion of the third side 115 of the main body 110 and at least a portion of the third side 125 of the arm 120 may engage the first body $B_{V1}$ of the first vertebra $V_1$, and at least a portion of the fourth side 116 of the main body 110 and at least a portion of the fourth side 126 of the arm 120 may engage the second body $B_{V2}$ of the second vertebra $V_2$. In some embodiments, as shown, when the interbody device 100 is in the implantation orientation and the expanded configuration within the intervertebral space IS, the main body 110 may be positioned partially within a posterior portion, such as a posterior half, of the intervertebral space IS and partially within an anterior portion, such as an anterior half, of the intervertebral space IS, and the arm 120 may be positioned entirely within the posterior portion, such as the posterior half, of the intervertebral space IS. In this manner, at least portions of the third side 115 of the main body 110 may engage part of a posterior portion, such as a posterior half, of the first body $B_{V1}$ of the first vertebra $V_1$ and part of an anterior portion, such as an anterior half, of the first body $B_{V1}$ of the first vertebra $V_1$, at least portions of the fourth side 116 of the main body 110 may engage part of a posterior portion, such as a posterior half, of the second body $B_{V2}$ of the second vertebra $V_2$ and part of an anterior portion, such as an anterior half, of the second body $B_{V2}$ of the second vertebra $V_2$, at least a portion of the third side 125 of the arm 120 may engage part of the posterior portion of the first body $B_{V1}$ of the first vertebra $V_1$, and at least a portion of the fourth side 126 of the arm 120 may engage part of the posterior portion of the second body $B_{V2}$ of the second vertebra $V_2$.

In other embodiments, at least a portion of the fourth side 106 of the device 100 may engage the first body $B_{V1}$ of the first vertebra $V_1$, and at least a portion of the third side 105 of the device 100 may engage the second body $B_{V2}$ of the second vertebra $V_2$. According to the illustrated embodiment of the interbody device 100, when the device 100 is in the implantation orientation and the expanded configuration within the intervertebral space IS, at least a portion of the fourth side 116 of the main body 110 and at least a portion of the fourth side 126 of the arm 120 may engage the first body $B_{V1}$ of the first vertebra $V_1$, and at least a portion of the third side 115 of the main body 110 and at least a portion of the third side 125 of the arm 120 may engage the second body $B_{V2}$ of the second vertebra $V_2$. In some embodiments, when the interbody device 100 is in the implantation orientation and the expanded configuration within the intervertebral space IS, the main body 110 may be positioned partially within a posterior portion, such as a posterior half, of the intervertebral space IS and partially within an anterior portion, such as an anterior half, of the intervertebral space IS, and the arm 120 may be positioned entirely within the posterior portion, such as the posterior half, of the intervertebral space IS. In this manner, at least portions of the fourth side 116 of the main body 110 may engage part of a posterior portion, such as a posterior half, of the first body $B_{V1}$ of the first vertebra $V_1$ and part of an anterior portion, such as an anterior half, of the first body $B_{V1}$ of the first vertebra $V_1$, at least portions of the third side 115 of the main body 110 may engage part of a posterior portion, such as a posterior half, of the second body $B_{V2}$ of the second vertebra $V_2$ and part of an anterior portion, such as an anterior half, of the second body $B_{V2}$ of the second vertebra $V_2$, at least a portion of the fourth side 126 of the arm 120 may engage part of the posterior portion of the first body $B_{V1}$ of the first vertebra $V_1$, and at least a portion of the third side 125 of the arm 120 may engage part of the posterior portion of the second body $B_{V2}$ of the second vertebra $V_2$.

As shown, when the interbody device 100 is in the implantation orientation and the expanded configuration within the intervertebral space IS, the main body 110 and the arm 120 may define a cavity 140 (which also may be referred to as a "space" or a "gap") therebetween. In particular, the cavity 140 may be defined between a portion of the first side 113 of the main body 110 and a portion of the second side 124 of the arm 120. As described in detail below, bone graft or a bone graft substitute may be placed within the cavity 140 to promote fusion between the first vertebra $V_1$ and the second vertebra $V_2$.

The expandable interbody device 100 may include one or more engagement features configured for engaging mating features of an instrument system, such as the instrument system 300 described below, used for implanting the device 100 within the intervertebral space IS. For example, the main body 110 may include one or more recesses configured for engaging mating features of the instrument. In particular, as shown, the main body 110 may include a first recess 141, a second recess 142, and a third recess 143 (which also may be referred to as a "first notch," a "second notch," and a "third notch," respectively) defined in the second end 112 of the main body 110 and spaced apart from one another. The first recess 141 may extend to the first side 113 of the main body 110, and the first recess 141 may be spaced apart from each of the third side 115 and the fourth side 116 of the main body 110 and centered therebetween. As shown, the first recess 141 may have a generally rectangular cross-sectional shape and may include an inner surface 144 that is angled inward toward the longitudinal axis $A_L$ of the device 100 in a direction from the second end 112 toward the first end 111 of the main body 110. The second recess 142 may extend to each of the second side 114 and the third side 115 of the main body 110, and the second recess 142 may be spaced apart from the fourth side 116 of the main body 110. As shown, the second recess 142 may have a generally rectangular cross-sectional shape and may include an inner surface 145 that is angled inward toward the longitudinal axis $A_L$ of the device 100 in a direction from the second end 112 toward the first end 111 of the main body 110. The third recess 143 may extend to each of the second side 114 and the fourth side 116 of the main body 110, and the third recess 143 may be spaced apart from the third side 115 of the main body 110.

As shown, the third recess 143 may have a generally rectangular cross-sectional shape and may include an inner surface 146 that is angled inward toward the longitudinal axis $A_L$ of the device 100 in a direction from the second end 112 toward the first end 111 of the main body 110.

The main body 110 and the arm 120 may include a number of features that engage and mate with one another when the expandable interbody device 100 is in the compact configuration, which may minimize the access window required for insertion of the device 100 into the intervertebral space IS and may enhance the structural integrity of the device 100 during insertion into the intervertebral space IS. In particular, the main body 110 may include a plurality of ribs 151 positioned along the first side 113 of the main body 110 and a plurality of grooves 152 defined in the first side 113 of the main body 110. As shown, the ribs 151 and the grooves 152 may be positioned along and defined in a distal portion of the first side 113 of the main body 110. In a similar manner, the arm 120 may include a plurality of ribs 153 positioned along the second side 124 of the arm 120 and a plurality of grooves 154 defined in the second side 122 of the arm 120. As shown, the ribs 153 and the grooves 154 may be positioned along and defined in a distal portion of the second side 124 of the arm 120. When the interbody device 100 is in the compact configuration, each of the ribs 151 of the main body 110 may be positioned within a respective groove 154 of the arm 120, and each of the ribs 153 of the arm 120 may be positioned within a respective groove 152 of the main body 110. As shown, each of the ribs 151, 153 and each of the grooves 152, 154 may extend perpendicular to the longitudinal axis $A_L$ and the first transverse axis $A_{T1}$ (and parallel the second transverse axis $A_{T2}$) of the interbody device 100. In other words, each of the ribs 151, 153 and each of the grooves 152, 154 may have a length extending perpendicular to the longitudinal axis $A_L$ and the first transverse axis $A_{T1}$ (and parallel the second transverse axis $A_{T2}$) of the interbody device 100 and a width extending parallel to the longitudinal axis $A_L$ (and perpendicular to first transverse axis $A_{T1}$ and the second transverse axis $A_{T2}$) of the interbody device 100. As shown, the ribs 151, 153 and the grooves 152, 154 each may have a rounded or semi-circular cross-sectional shape when viewed from the third side 105 and the fourth side 106 of the interbody device 100.

The arm 120 also may include a protrusion 155 (which also may be referred to as a "tooth") positioned along the second side 124 of the arm 120, and the main body 110 may include a pocket 156 (which also may be referred to as a "recess") defined in the first side 113 of the main body 110. In particular, the protrusion 155 may be positioned along a distal portion of the second side 124 of the arm 120, and the pocket 156 may be defined in a distal portion of the first side 113 of the main body 110. When the interbody device 100 is in the compact configuration, the protrusion 155 of the arm 120 may be received within the pocket 156 of the main body 110. As shown, the protrusion 155 may be positioned near but spaced apart from the first end 121 of the arm 120, and the protrusion 155 may be spaced apart from each of the third side 125 and the fourth side 126 of the arm 120 and centered therebetween. In a similar manner, the pocket 156 may be positioned near but spaced apart from the first end 111 of the main body 110, and the pocket 156 may be spaced apart from each of the third side 115 and the fourth side 116 of the main body 110 and centered therebetween. In various embodiments, the protrusion 155 and the pocket 156 may be sized and configured such that the protrusion 155 and the pocket 156 form a loose fit, a close fit, or an interference fit when the interbody device 100 is in the compact configuration. The engagement between the protrusion 155 and the pocket 156 may enhance the structural integrity of the interbody device 100 during insertion of the device 100 into the intervertebral space IS. In particular, as the first end 101 of the interbody device 100 is inserted into the intervertebral space IS, a portion of the insertion forces acting on the device 100 as it contacts the vertebrae $V_1$, $V_2$ may be carried by the protrusion 155 and the pocket 156. In this manner, the protrusion 155 and the pocket 156 may shield the hinge connection 128 from such portion of insertion forces.

The interbody device 100 may include a number of features that cooperate with the vertebrae $V_1$, $V_2$ to facilitate insertion of the device 100 into the intervertebral space IS and positioning of the device 100 therein. In particular, the first side 103 and the second side 104 of the interbody device 100 may include one or more smooth surfaces configured for slidably engaging one of the first body $B_{V1}$ of the first vertebrae $V_1$ and the second body $B_{V2}$ of the second vertebrae $V_2$ as the device 100 is inserted into and positioned within the intervertebral space IS. In this manner, as shown, the portion of the first side 113 of the main body 110 and the portion of the first side 123 of the arm 120 that define the first side 103 of the interbody device 100 may include one or more smooth surfaces configured for slidably engaging one of the first body $B_{V1}$ and the second body $B_{V2}$. In a similar manner, as shown, the second side 114 of the main body 110 that defines the second side 104 of the interbody device 100 may include one or more smooth surfaces configured for slidably engaging one of the first body $B_{V1}$ and the second body $B_{V2}$. The smooth surfaces of the main body 110 and the arm 120 may reduce friction generated between the interbody device 100 and the first body $B_{V1}$ and the second body $B_{V2}$, thereby reducing forces required to insert the device 100 into and position the device 100 within the intervertebral space IS.

As described above, upon insertion of the interbody device 100 within the intervertebral space IS, respective portions of the first side 103 and the second side 104 of the device 100 each may engage one of the adjacent vertebrae $V_1$, $V_2$. As shown, an overall distance D between the first side 103 and the second side 104 of the interbody device 100 in the direction of the first transverse axis $A_{T1}$ (which also may be referred to as an "overall height" of the interbody device 100 when the device 100 is in the insertion orientation and the compact configuration, or simply an "overall insertion height") may vary along the length L of the device 100 in the direction of the longitudinal axis $A_L$. In particular, the overall distance D between the first side 103 and the second side 104 of the device 100 may increase along at least a majority of the length L of the device 100 in the direction from the first end 101 toward the second end 102 of the device 100. In this manner, the interbody device 100 may have a first overall distance $D_1$ (which also may be referred to as a "minimum overall distance" or a "minimum overall height") between the first side 103 and the second side 104 of the device 100 at a first location along the length L of the device 100 positioned closer to the first end 101 of the device 100 and a second overall distance $D_2$ (which also may be referred to as a "maximum overall distance" or a "maximum overall height") between the first side 103 and the second side 104 of the device 100 at a second location along the length L of the device 100 positioned closer to the second end 102 of the device 100, wherein the first overall distance $D_1$ is less than the second overall distance $D_2$. In some embodiments, as shown, the overall distance D between the first side 103 and the second side 104 of the device 100 may increase along the entire length L of the device 100 in the direction from the first end 101 toward the second end 102 of the device 100. In this manner, as shown, the interbody device 100 may have a first overall distance $D_1$ (which also may be referred to as a "minimum overall distance" or a "minimum overall height") between the first side 103 and the second side 104 of the device 100 at the first end 101 of the device 100 and a second overall distance $D_2$ (which also may be referred to as a "maximum overall distance" or a "maximum overall height") between the first side 103 and the second side 104 of the device 100 at the second end 102 of the device 100, wherein the first overall distance $D_1$ is less than the second overall distance $D_2$. In other embodiments, the overall distance D between the first side 103 and the second side 104 of the device 100 may increase along only a portion of the length L of the device 100 in the direction from the first end 101 toward the second end 102 of the device 100. It will be understood that the variation of the overall distance D between the first side 103 and the second side 104 of the interbody device 100 in the direction of the longitudinal axis $A_L$ may ease initial insertion of the device 100 into the intervertebral space IS and may facilitate gradual distraction of the intervertebral space IS as the device 100 is fully inserted therein.

Herein, use of the term "overall distance" with respect to the first side 103 and the opposite second side 104 of the interbody device 100 at a particular location along the length L of the device 100 in the direction of the longitudinal axis $A_L$ refers to a distance in the direction of the first transverse axis $A_{T1}$ between a portion of the first side 103 positioned furthest from the longitudinal axis $A_L$ in the direction of the first transverse axis $A_{T1}$ at the particular location along the length L of the device 100 and a portion of the second side 104 positioned furthest from the longitudinal axis $A_L$ in the direction of the first transverse axis $A_{T1}$ at the particular location along the length L of the device 100. As described above, in some embodiments, as shown, the first side 103 of the device 100 may be defined by a portion of the first side 113 of the main body 110 and a portion of the first side 123 of the arm 120, and the second side 104 of the device 100 may be defined by the second side 114 of the main body 110. According to the illustrated embodiment, at certain locations along the length L of the device 100, the overall distance D between the first side 103 and the second side 104 of the device 100 may be defined by the first side 113 and the second side 114 of the main body 110, and at other locations along the length L of the device 100, the overall distance D between the first side 103 and the second side 104 of the device 100 may be defined by the first side 123 of the arm 120 and the second side 114 of the main body 110.

In some embodiments, the first side 103 of the interbody device 100 may include a curved portion 161 and a flat portion 162. As shown, the curved portion 161 may be positioned adjacent the first end 101 of the device 100, and the flat portion 162 may be positioned adjacent to the second end 102 of the device 100. The curved portion 161 may extend from the first end 101 of the device 100 to the flat portion 162, and the flat portion 162 may extend from the curved portion 161 to the second end 102 of the device 100. As shown, the curved portion 161 of the first side 103 of the device 100 may be defined by a portion of the first side 123 of the arm 120, and the flat portion 162 of the first side 103 of the device 100 may be defined by a portion of the first side 123 of the arm 120 and a portion of the first side 113 of the main body 110. In other embodiments, the entire first side 103 of the interbody device 100 may have a curved shape extending from the first end 101 to the second end 102 of the device 100. In still other embodiments, the entire first side 103 of the interbody device 100 may have a flat shape extending from the first end 101 to the second end 102 of the device 100. In some embodiments, the second side 104 of the interbody device 100 may include a curved portion 163 and a flat portion 164. As shown, the curved portion 163 may be positioned adjacent the first end 101 of the device 100, and the flat portion 164 may be positioned adjacent to the second end 102 of the device 100. The curved portion 163 may extend from the first end 101 of the device 100 to the flat portion 164, and the flat portion 164 may extend from the curved portion 163 to the second end 102 of the device 100. As shown, the curved portion 163 of the second side 104 of the device 100 may be defined by a portion of the second side 114 of the main body 110, and the flat portion 164 may be defined by another portion of the second side 114 of the main body 110. In other embodiments, the entire second side 104 of the interbody device 100 may have a curved shape extending from the first end 101 to the second end 102 of the device 100. In still other embodiments, the entire second side 104 of the interbody device 100 may have a flat shape extending from the first end 101 to the second end 102 of the device 100. It will be understood that during implantation of the interbody device 100, the curved portions 161, 163 and the flat portions 162, 164 of the first side 103 and the second side 104 of the device 100 may ease initial insertion of the device 100 into the intervertebral space IS and may facilitate gradual distraction of the intervertebral space IS as the device 100 is fully inserted therein.

The interbody device 100 may include a number of features that cooperate with the vertebrae $V_1$, $V_2$ to facilitate rotation of the device 100 from the insertion orientation to the implantation orientation within the intervertebral space IS. In particular, the interbody device 100 may include a number of transition portions positioned along respective interfaces between adjacent sides of the device 100. As shown, the interbody device 100 may include a first transition portion 171, a second transition portion 172, a third transition portion 173, and a fourth transition portion 174. The first transition portion 171 may be positioned along the interface between the first side 103 and the third side 105 of the device 100, the second transition portion 172 may be positioned along the interface between the second side 104 and the fourth side 106 of the device 100, the third transition portion 173 may be positioned along the interface between the first side 103 and the fourth side 106 of the device 100, and the fourth transition portion 174 may be positioned along the interface between the second side 104 and the third side 105 of the device 100. In some embodiments, each of the transition portions 171, 172, 173, 174 may extend along the entire length L of the device 100 from the first end 101 to the second end 102 of the device 100. In some embodiments, some or all of the transition portions 171, 172, 173, 174 may extend along only a portion of the length L of the device 100. In some such embodiments, each of the transition portions 171, 172, 173, 174 may extend from the second end 102 of the device 100 to respective intermediate locations along the length L of the device 100 spaced apart from the first end 101 of the device 100.

As shown, each of the transition portions 171, 172, 173, 174 may have a curved shape extending along the respective interfaces between the sides of the device 100. The first transition portion 171 may have a first radius of curvature $R_1$, the second transition portion 172 may have a second radius of curvature $R_2$, the third transition portion 173 may have a third radius of curvature $R_3$, and the fourth transition portion 174 may have a fourth radius of curvature $R_4$. In some embodiments, as shown, the first radius of curvature $R_1$ may be equal to the second radius of curvature $R_2$, the third radius of curvature $R_3$ may be equal to the fourth radius of curvature $R_4$, and the first radius of curvature $R_1$ may be different than the third radius of curvature $R_3$.

In some embodiments, as shown, the first radius of curvature $R_1$ may be greater than each of the third radius of curvature $R_3$ and the fourth radius of curvature $R_4$, and the second radius of curvature $R_2$ may be greater than each of the third radius of curvature $R_3$ and the fourth radius of curvature $R_4$. It will be understood that such relationships between the radii of curvature of the transition portions 171, 172, 173, 174 may facilitate clockwise rotation of the device 100 (when viewed from the second end 102 of the device 100) by ninety (90) degrees about the longitudinal axis $A_L$ of the device 100 from the insertion orientation to the implantation orientation within the intervertebral space IS, and may inhibit further clockwise rotation (i.e., rotation beyond ninety degrees) of the device 100 beyond the implantation orientation.

In other embodiments, the first radius of curvature $R_1$ may be less than each of the third radius of curvature $R_3$ and the fourth radius of curvature $R_4$, and the second radius of curvature $R_2$ may be less than each of the third radius of curvature $R_3$ and the fourth radius of curvature $R_4$. It will be understood that such relationships between the radii of curvature of the transition portions 171, 172, 173, 174 may facilitate counter clockwise rotation of the device 100 (when viewed from the second end 102 of the device 100) by ninety (90) degrees about the longitudinal axis $A_L$ of the device 100 from the insertion orientation to the implantation orientation within the intervertebral space IS, and may inhibit further counter clockwise rotation (i.e., rotation beyond ninety degrees) of the device 100 beyond the implantation orientation.

As described above, upon rotation of the interbody device 100 within the intervertebral space IS from the insertion orientation to the implantation orientation, respective portions of the third side 105 and the fourth side 106 of the device 100 each may engage one of the adjacent vertebrae $V_1$, $V_2$. As shown, an overall distance D between the third side 105 and the fourth side 106 of the interbody device 100 in the direction of the second transverse axis $A_{T2}$ (which also may be referred to as an "overall height" of the interbody device 100 when the device 100 is in the implantation orientation, or simply an "overall implantation height") may vary along the length L of the device 100 in the direction of the longitudinal axis $A_L$. In particular, the overall distance D between the third side 105 and the fourth side 106 of the device 100 may increase along at least a majority of the length L of the device 100 in the direction from the second end 102 toward the first end 101 of the device 100. In this manner, the interbody device 100 may have a third overall distance $D_3$ (which also may be referred to as a "minimum overall distance" or a "minimum overall height") between the third side 105 and the fourth side 106 of the device 100 at a first location along the length L of the device 100 positioned closer to the second end 102 of the device 100 and a fourth overall distance $D_4$ (which also may be referred to as a "maximum overall distance" or a "maximum overall height") between the third side 105 and the fourth side 106 of the device 100 at a second location along the length L of the device 100 positioned closer to the first end 101 of the device 100, wherein the third overall distance $D_3$ is less than the fourth overall distance $D_4$. In some embodiments, as shown, the overall distance D between the third side 105 and the fourth side 106 of the device 100 may increase along a majority of the length L of the device 100 in the direction from the second end 102 toward the first end 101 of the device 100 and may decrease along a minority of the length L of the device 100 in the direction from the second end 102 toward the first end 101 of the device 100. In this manner, as shown, the interbody device 100 may have a third overall distance $D_3$ (which also may be referred to as a "minimum overall distance" or a "minimum overall height") between the third side 105 and the fourth side 106 of the device 100 at the second end 102 of the device 100, a fourth overall distance $D_4$ (which also may be referred to as a "maximum overall distance" or a "maximum overall height") between the third side 105 and the fourth side 106 of the device 100 an intermediate location along the length L of the device 100 positioned closer to the first end 101 of the device 100, and a fifth overall distance $D_5$ (which also may be referred to as an "intermediate overall distance" or an "intermediate overall height") between the third side 105 and the fourth side 106 of the device 100 at the first end 101 of the device 100, wherein the third overall distance $D_3$ is less than the fourth overall distance $D_4$, and wherein the fifth overall distance $D_5$ is less than the fourth overall distance $D_4$. In some such embodiments, as shown, the third overall distance $D_3$ may be less than the fifth overall distance $D_5$. In other embodiments, the overall distance D between the third side 105 and the fourth side 106 of the device 100 may increase along the entire length L of the device 100 in the direction from the second end 102 toward the first end 101 of the device 100. It will be understood that the variation of the overall distance D between the third side 105 and the fourth side 106 of the interbody device 100 in the direction of the longitudinal axis $A_L$ may facilitate realignment of the adjacent vertebrae $V_1$, $V_2$ such that the vertebrae $V_1$, $V_2$ follow the normal curvature of the spine. For example, when the interbody device 100 is implanted in the lumbar region of the spine, the variation of the overall distance D between the third side 105 and the fourth side 106 of the device 100 may provide correction of lordosis, the normal inward curvature of the lumbar region.

Herein, use of the term "overall distance" with respect to the third side 105 and the opposite fourth side 106 of the interbody device 100 at a particular location along the length L of the device 100 in the direction of the longitudinal axis $A_L$ refers to a distance in the direction of the second transverse axis $A_{T2}$ between a portion of the third side 105 positioned furthest from the longitudinal axis $A_L$ in the direction of the second transverse axis $A_{T2}$ at the particular location along the length L of the device 100 and a portion of the fourth side 106 positioned furthest from the longitudinal axis $A_L$ in the direction of the second transverse axis $A_{T2}$ at the particular location along the length L of the device 100. As described above, in some embodiments, as shown, the third side 105 of the device 100 may be defined by a portion of the third side 115 of the main body 110 and a portion of the third side 125 of the arm 120, and the fourth side 106 of the device 100 may be defined by a portion of the fourth side 116 of the main body 110 and a portion of the fourth side 126 of the arm 120. According to the illustrated embodiment, at locations along the length L of the device 100, the overall distance D between the third side 105 and the fourth side 106 of the device 100 may be defined by the third side 115 and the fourth side 116 of the main body 110.

The interbody device 100 may include a number of features that cooperate with one another and mating features of an instrument system, such as the instrument system 300 described below, to facilitate expansion of the device 100 from the compact configuration to the expanded configuration within the intervertebral space IS. In particular, the main body 110 may include a port 181 (which also may be referred to as a "hole" or a "thru hole") defined in the second end 112 of the main body 110 and extending distally from the second end 112 toward the first end 111 of the main body 110. As shown, the port 181 may be spaced apart from each of the first side 113, the second side 114, the third side 115, and the fifth side 116 of the main body 110. Additionally, the port 181 may be spaced apart from each of the first recess 141, the second recess 142, and the third recess 143 of the main body 110. As shown, the port 181 may have a cylindrical shape and a circular cross-sectional shape when viewed from an end of the port 181. The port 181 may define a longitudinal axis $A_{LP}$, which may extend parallel to the longitudinal axis $A_L$ (and perpendicular to the first transverse axis $A_{T1}$ and the second transverse axis $A_{T2}$) of the interbody device 100. The main body 110 also may include a channel 182 defined therein and in direct communication with the port 181. As shown, the channel 182 may be positioned adjacent to the port 181 and distally with respect to the port 181. In other words, the proximal end of the channel 182 may be positioned adjacent to the distal end of the port 181. As shown, the channel 182 may extend distally from the port 181 toward the first end 111 of the main body 110. The channel 182 may include a straight portion 183 and a ramped portion 184. The straight portion 183 may be positioned adjacent to the port 181 and may extend in a straight (i.e., linear) manner parallel to the longitudinal axis $A_L$ of the interbody device 100. The ramped portion 184 may be positioned adjacent to the straight portion 183 and distally therefrom and may extend in a ramped manner away from the second side 114 and toward the first side 113 of the main body 110. In some embodiments, as shown, the ramped portion 184 may have a curved shape extending away from the second side 114 and toward the first side 113 of the main body 110. In other embodiments, the ramped portion 184 may have a flat shape extending away from the second side 114 and toward the first side 113 of the main body 110.

As shown, when the interbody device 100 is in the compact configuration, the hinge tab 135 of the arm 120 may be positioned at least partially within the channel 182 at or near the distal end of the port 181. In particular, an actuator portion 185 (which also may be referred to as a "keel") of the hinge tab 135 may be positioned within the channel 182 at or near the distal end of the port 181. During implantation of the interbody device 100, the device 100 may be expanded from the compact configuration to the expanded configuration by inserting a mating feature of an instrument into the port 181 and advancing the mating feature distally through the port 181 and at least partially through the channel 182. As the mating feature is advanced in this manner, the mating feature may contact and move the actuator portion 185 of the hinge tab 135 at least partially out of the channel 182, thereby causing the arm 120 to pivot with respect to the main body 110 about the rotational axis $A_R$ of the hinge connection 128 from the compact position to the expanded position. The degree of expansion of the interbody device 100 may be determined by the extent to which the mating feature is advanced through the channel 182. In some embodiments, the arm 120 may be configured to pivot about the rotational axis $A_R$ of the hinge connection 128 until the hinge tab 135 contacts the hinge recess 133. In this manner, the hinge tab 135 and the hinge recess 133 may be configured to limit a maximum degree of expansion of the interbody device 100.

As described above, upon expansion of the interbody device 100 within the intervertebral space IS, respective portions of the third side 125 and the fourth side 126 of the arm 120 each may engage one of the adjacent vertebrae $V_1$, $V_2$. As shown, an overall distance D between the third side 125 and the fourth side 126 of the arm 120 in the direction of the second transverse axis $A_{T2}$ (which also may be referred to as an "overall height" of the arm 120 when the device 100 is in the implantation orientation, or simply an "overall implantation height") may be constant or substantially constant along at least a portion of the length L of the arm 120 in the direction of the longitudinal axis $A_L$ of the device 100. In particular, the overall distance D between the third side 125 and the fourth side 126 of the arm 120 may be constant or substantially constant along at least a majority of the length L of the arm 120. In this manner, as shown, the arm 120 may have a sixth overall distance $D_6$ (which also may be referred to as a "constant overall distance" or a "constant overall height") between the third side 125 and the fourth side 126 of the arm 120, which may be constant or substantially constant along at least a majority of the length L of the arm 120. In some embodiments, as shown, the region of the constant or substantially constant sixth overall distance $D_6$ between the third side 125 and the fourth side 126 of the arm 120 may extend along the length L of the arm 120 from a first location positioned at or near the first end 121 of the arm 120 to a second location positioned adjacent to or near the hinge tab 135 of the arm 120. It will be understood that the constant or substantially constant nature of the overall distance D between the third side 125 and the fourth side 126 of the arm 120 along at least a majority of the length L of the arm 120 may provide desired support of the posterior portions of the adjacent vertebrae $V_1$, $V_2$ when the interbody device 100 is in the expanded configuration within the intervertebral space IS.

Herein, use of the term "overall distance" with respect to the third side 125 and the opposite fourth side 126 of the arm 120 at a particular location along the length L of the arm 120 in the direction of the longitudinal axis $A_L$ of the interbody device 100 refers to a distance in the direction of the second transverse axis $A_{T2}$ between a portion of the third side 125 positioned furthest from the longitudinal axis $A_L$ in the direction of the second transverse axis $A_{T2}$ at the particular location along the length L of the arm 120 and a portion of the fourth side 126 positioned furthest from the longitudinal axis $A_L$ in the direction of the second transverse axis $A_{T2}$ at the particular location along the length L of the arm 120.

Certain relationships between the first overall distance $D_1$, the second overall distance $D_2$, the third overall distance $D_3$, the fourth overall distance $D_4$, the fifth overall distance $D_5$, and the sixth overall distance $D_6$ may facilitate implantation of the interbody device 100 within the intervertebral space IS as well as use of the device 100 to restore and maintain normal spacing of the adjacent vertebrae $V_1$, $V_2$ and to realign the adjacent vertebrae $V_1$, $V_2$ such that the vertebrae $V_1$, $V_2$ follow the normal curvature of the spine. In some embodiments, as shown, the first overall distance $D_1$ may be less than the second overall distance $D_2$, which may ease initial insertion of the interbody device 100 into the intervertebral space IS and may facilitate gradual distraction of the intervertebral space IS as the device 100 is fully inserted therein. In some embodiments, as shown, the third overall distance $D_3$ may be less than the fourth overall distance $D_4$, the fifth overall distance $D_5$ may be less than the fourth overall distance $D_4$, and the third overall distance $D_3$ may be less than the fifth overall distance $D_5$, which may facilitate realignment of the adjacent vertebrae $V_1$, $V_2$ such that the vertebrae $V_1$, $V_2$ follow the normal curvature of the spine. In some embodiments, as shown, the sixth overall distance $D_6$ may be equal to the third overall distance $D_3$, which may provide desired support of the posterior portions of the adjacent vertebrae $V_1$, $V_2$ when the interbody device 100 is in the expanded configuration within the intervertebral space IS. In some embodiments, as shown, the third overall distance $D_3$ may be less than the second overall distance $D_2$, which may cause the interbody device 100 to over-distract the posterior portion of the intervertebral space IS upon insertion of the device 100 therein and may facilitate rotation of the device 100 from the insertion orientation to the implantation orientation within the intervertebral space IS.

In some embodiments, as shown, the overall distances may have the following relationships: the first overall distance $D_1$ may be less than each of the second overall distance $D_2$, the third overall distance $D_3$, the fourth overall distance $D_4$, the fifth overall distance $D_5$, and the sixth overall distance $D_6$; the second overall distance $D_2$ may be less than each of the fourth overall distance $D_4$ and the fifth overall distance $D_5$ and greater than each of the first overall distance $D_1$, the third overall distance $D_3$, and the sixth overall distance $D_6$; the third overall distance $D_3$ may be less than each of the second overall distance $D_2$, the fourth overall distance $D_4$, and the fifth overall distance $D_5$, greater than the first overall distance $D_1$, and equal to the sixth overall distance $D_6$; the fourth overall distance $D_4$ may be greater than each of the first overall distance $D_1$, the second overall distance $D_2$, the third overall distance $D_3$, the fifth overall distance $D_5$, and the sixth overall distance $D_6$; the fifth overall distance $D_5$ may be less than the fourth overall distance $D_4$ and greater than each of the first overall distance $D_1$, the second overall distance $D_2$, the third overall distance $D_3$, the fifth overall distance $D_5$, and the sixth overall distance $D_6$; and the sixth overall distance $D_6$ may be less than the each of the second overall distance $D_2$, the fourth overall distance $D_4$, and the fifth overall distance $D_5$, greater than the first overall distance $D_1$, and equal to the third overall distance $D_3$.

The interbody device 100 may include a number of features that cooperate with the vertebrae $V_1$, $V_2$ to maintain an implanted position of the device 100 within the intervertebral space IS (i.e., to prevent migration of the device 100 within the intervertebral space IS). In particular, the main body 110 may include a first plurality of teeth 191 (which also may be referred to as "ridges") positioned along the third side 115 of the main body 110, and a second plurality of teeth 192 (which also may be referred to as "ridges") positioned along the fourth side 116 of the main body 110. As shown, the first plurality of teeth 191 and the second plurality of teeth 192 each may extend along a majority of the length L of the main body 110. In a similar manner, the arm 120 may include a third plurality of teeth 193 (which also may be referred to as "ridges") positioned along the third side 125 of the arm 120, and a fourth plurality of teeth 194 (which also may be referred to as "ridges") positioned along the fourth side 126 of the arm 120. As shown, the third plurality of teeth 193 and the fourth plurality of teeth 194 each may extend along a majority of the length L of the arm 120.

As shown, each of the teeth 191, 192, 193, 194 may extend perpendicular to the longitudinal axis $A_L$ and the second transverse axis $A_{T2}$ (and parallel the first transverse axis $A_{T1}$) of the interbody device 100. In other words, each of the teeth 191, 192, 193, 194 may have a length extending perpendicular to the longitudinal axis $A_L$ and the second transverse axis $A_{T2}$ (and parallel the first transverse axis $A_{T1}$) of the interbody device 100 and a width extending parallel to the longitudinal axis $A_L$ (and perpendicular to first transverse axis $A_{T1}$ and the second transverse axis $A_{T2}$) of the interbody device 100. As shown, each of the teeth 191, 192, 193, 194 may have a generally V-shaped cross-sectional shape when viewed from the first side 103 and the second side 104 of the interbody device. In particular, each of the teeth 191, 192, 193, 194 may have a distal face and a proximal face that meet at an edge of the tooth 191, 192, 193, 194. As shown, the distal face of the tooth 191, 192, 193, 194 may be angled inward toward the longitudinal axis $A_L$ of the interbody device 100 in a direction from the second end 102 toward the first end 101 of the device 100, and the proximal face of the tooth 191, 192, 193, 194 may be oriented perpendicular to the longitudinal axis $A_L$ of the device 100.

During implantation of the interbody device 100, the teeth 191, 192, 193, 194 may engage and grip the adjacent vertebrae $V_1$, $V_2$. In particular, the teeth 191, 192 of the main body 110 may engage and grip the adjacent vertebrae $V_1$, $V_2$ upon rotation of the interbody device 100 from the insertion orientation to the implantation orientation. The teeth 193, 194 of the arm 120 subsequently may engage and grip the adjacent vertebrae $V_1$, $V_2$ upon expansion of the interbody device 100 from the compact configuration to the expanded configuration. It will be understood that the engagement between the teeth 191, 192, 193, 194 and the adjacent vertebrae $V_1$, $V_2$ may maintain the interbody device 100 in a desired position within the intervertebral space IS (i.e., prevent migration of the device 100 within the intervertebral space IS). Additionally, the engagement between the teeth 191, 192, 193, 194 and the adjacent vertebrae $V_1$, $V_2$ may maintain the interbody device 100 in a desired expansion state (i.e., prevent the arm 120 from moving with respect to the main body 110). In some embodiments, the third side 115 and the fourth side 116 of the main body 110 and/or the third side 125 and the fourth side 126 of the arm 120 may include other forms of texturing (other than teeth) along the surfaces thereof for engaging and gripping the vertebrae $V_1$, $V_2$, as well as promoting bone growth along and/or into such surfaces, upon implantation of the device 100.

As described above, upon expansion of the interbody device 100 within the intervertebral space IS, the main body 110 and the arm 120 may define the cavity 140 therebetween, and bone graft or a bone graft substitute may be placed within the cavity 140 to promote fusion between the adjacent vertebrae $V_1$, $V_2$. The interbody device 100 may include a number of features that facilitate delivery of the bone graft or bone graft substitute to the cavity 140. In particular, the port 181 and the channel 182 may be used to deliver the bone graft or bone graft substitute to the cavity 140. As described above, when the interbody device 100 is expanded from the compact configuration to the expanded configuration, the actuator portion 185 of the hinge tab 135 may move at least partially out of the channel 182. Accordingly, the port 181 and the channel 182 may provide a pathway for delivering the bone graft or bone graft substitute through the proximal portion of the interbody device 100 and into the cavity 140. An instrument system, such as the instrument system 300 described below, may be used to advance the bone graft or bone graft substitute through the port 181 and the channel 182 and into the cavity 140.

The interbody device 100 may be formed of various biocompatible materials. In some embodiments, the main body 110 and the arm 120 may be formed of polyether ether ketone (PEEK), although other suitable polymers may be used. In some embodiments, the main body 110 and the arm 120 may be formed of titanium, although other suitable metals may be used. In some embodiments, the pin 130 may be formed of stainless steel, although other suitable metals or polymers may be used. In some embodiments, the main body 110 and/or the arm 120, or at least portions thereof, may be formed of a porous material configured to facilitate bone growth therein.

FIGS. 2A-2M illustrate an expandable interbody device 200 (which also may be referred to as an "interbody spacer," an "interbody cage," a "spacer," or a "cage") according to one or more embodiments of the disclosure. The interbody device 200 may be configured for implantation within an intervertebral space between two adjacent vertebrae to provide structural support and stabilization of the vertebrae. The interbody device 200 generally may be configured and used in a manner similar to the interbody device 100 described above, although certain differences in the configuration and use of the interbody device 200 are described below. Corresponding features of the interbody device 200 may be indicated by corresponding reference numbers in the drawings.

The expandable interbody device 200 may have an elongated shape defining a longitudinal axis $A_L$, a first transverse axis $A_{T1}$ that is perpendicular to the longitudinal axis $A_L$, and a second transverse axis $A_{T2}$ that is perpendicular to each of the longitudinal axis $A_L$ and the first transverse axis $A_{T1}$. As shown, the interbody device 200 may include a first end 201 (which also may be referred to as a "distal end" or a "leading end," with reference to an orientation in which the device 200 is inserted into an intervertebral space) and a second end 202 (which also may be referred to as a "proximal end" or a "trailing end," with reference to the orientation in which the device 200 is inserted into an intervertebral space) disposed opposite the first end 201 in the direction of the longitudinal axis $A_L$. The interbody device 200 also may include a first side 203 extending from the first end 201 to the second end 202, and a second side 204 disposed opposite the first side 203 in the direction of the first transverse axis $A_{T1}$ and extending from the first end 201 to the second end 202. The interbody device 200 further may include a third side 205 extending from the first end 201 to the second end 202 and from the first side 203 to the second side 204, and a fourth side 206 disposed opposite the third side 205 in the direction of the second transverse axis $A_{T2}$ and extending from the first end 201 to the second end 202 and from the first side 203 to the second side 204. As shown, the interbody device 200 may have a length L from the first end 201 to the second end 202 of the device 200 in the direction of the longitudinal axis $A_L$. The interbody device 200 may include a first half 207 (which also may be referred to as a "distal half") extending from the first end 201 to a midpoint of the device 200 in the direction of the longitudinal axis $A_L$, and a second half 208 (which also may be referred to as a "proximal half") extending from the second end 202 to the midpoint of the device 200 in the direction of the longitudinal axis $A_L$.

As shown, the interbody device 200 may include a main body 210 having an elongated shape extending along the longitudinal axis $A_L$ of the device 200. The main body 210 may include a first end 211 (which also may be referred to as a "distal end" or a "leading end") and a second end 212 (which also may be referred to as a "proximal end" or a "trailing end") disposed opposite the first end 211 in the direction of the longitudinal axis $A_L$. The main body 210 also may include a first side 213 extending from the first end 211 to the second end 212, and a second side 214 disposed opposite the first side 213 in the direction of the first transverse axis $A_{T1}$ and extending from the first end 211 to the second end 212. The main body 210 further may include a third side 215 extending from the first end 211 to the second end 212 and from the first side 213 to the second side 214, and a fourth side 216 disposed opposite the third side 215 in the direction of the second transverse axis $A_{T2}$ and extending from the first end 211 to the second end 212 and from the first side 213 to the second side 214.

The interbody device 200 also may include an arm 220 having an elongated shape extending along the longitudinal axis $A_L$ of the device 200. The arm 220 may include a first end 221 (which also may be referred to as a "distal end" or a "leading end") and a second end 222 (which also may be referred to as a "proximal end" or a "trailing end") disposed opposite the first end 221 in the direction of the longitudinal axis $A_L$. The arm 220 also may include a first side 223 extending from the first end 221 to the second end 222, and a second side 224 disposed opposite the first side 223 in the direction of the first transverse axis $A_{T1}$ and extending from the first end 221 to the second end 222. The arm 220 further may include a third side 225 extending from the first end 221 to the second end 222 and from the first side 223 to the second side 224, and a fourth side 226 disposed opposite the third side 225 in the direction of the second transverse axis $A_{T2}$ and extending from the first end 221 to the second end 222 and from the first side 223 to the second side 224.

As shown, the first end 201 of the interbody device 200 may be defined by the first end 211 of the main body 110 and the first end 221 of the arm 220. In this manner, the first end 211 of the main body 210 and the first end 221 of the arm 220 may be aligned with one another along the longitudinal axis $A_L$ of the interbody device 200. Alternatively, the first end 201 of the interbody device 200 may be defined by the first end 211 of the main body 210 or by the first end 221 of the arm 220. In this manner, the first end 211 of the main body 210 and the first end 221 of the arm 220 may be offset from one another along the longitudinal axis $A_L$ of the interbody device 200. In some embodiments, as shown, the first end 201 of the interbody device 200 may extend perpendicular to the longitudinal axis $A_L$ (and parallel to the first transverse axis $A_{T1}$ and the second transverse axis $A_{T2}$) of the interbody device 200. As shown, the second end 202 of the interbody device 200 may be defined by the second end 212 of the main body 210. In this manner, the second end 212 of the main body 210 and the second end 222 of the arm 220 may be offset from one another along the longitudinal axis $A_L$ of the interbody device 200. Alternatively, the second end 202 of the interbody device 200 may be defined by the second end 212 of the main body 210 and the second end 222 of the arm 220. In this manner, the second end 212 of the main body 210 and the second end 222 of the arm 220 may be aligned with one another along the longitudinal axis $A_L$ of the interbody device 200. As another alternative, the second end 202 of the interbody device 200 may be defined by the second end 222 of the arm 220. In this manner, the second end 212 of the main body 210 and the second end 222 of the arm 220 may be offset from one another along the longitudinal axis $A_L$ of the interbody device 200. In some embodiments, as shown, the second end 202 of the interbody device 200 may extend perpendicular to the longitudinal axis $A_L$ (and parallel to the first transverse axis $A_{T1}$ and the second transverse axis $A_{T2}$) of the interbody device 200.

As shown, the first side 203 of the interbody device 200 may be defined by at least a portion of the first side 213 of the main body 210 and at least a portion of the first side 223 of the arm 220. In some embodiments, as shown, the first side 203 of the interbody device 200 may be defined by a proximal portion of the first side 213 of the main body 210 and the entire first side 223 of the arm 220. Alternatively, the first side 203 of the interbody device 200 may be defined by the entire first side 213 of the main body 210 or by the entire first side 223 of the arm 220. As shown, the second side 204 of the interbody device 200 may be defined by the entire second side 214 of the main body 210. Alternatively, the second side 204 of the interbody device 200 may be defined by the entire second side 224 of the arm 220. As another alternative, the second side 204 of the interbody device 200 may be defined by at least a portion of the second side 214 of the main body 210 and at least a portion of the second side 224 of the arm 220. As shown, the third side 205 of the interbody device 200 may be defined by at least a portion of the third side 215 of the main body 210 and at least a portion of the third side 225 of the arm 220. In some embodiments, as shown, the third side 205 of the interbody device 200 may be defined by the entire third side 215 of the main body 210 and a distal portion of the third side 225 of the arm 220. Alternatively, the third side 205 of the interbody device 200 may be defined by the entire third side 215 of the main body 210 or by the entire third side 225 of the arm 220. As shown, the fourth side 206 of the interbody device 200 may be defined by at least a portion of the fourth side 216 of the main body 210 and at least a portion of the fourth side 226 of the arm 220. In some embodiments, as shown, the fourth side 206 of the interbody device 200 may be defined by the entire fourth side 216 of the main body 210 and a distal portion of the fourth side 226 of the arm 220. Alternatively, the fourth side 206 of the interbody device 200 may be defined by the entire fourth side 216 of the main body 210 or by the entire fourth side 226 of the arm 220.

As shown, the main body 210 and the arm 220 may be movably connected to one another. In particular, the arm 220 may be movable with respect to the main body 210 between a compact position (which also may be referred to as an "insertion position"), as shown in FIGS. 2A-2G, to an expanded position (which also may be referred to as an "implantation position"), as shown in FIGS. 2H-2M. In this manner, the interbody device 200 may be movable between a compact configuration (which also may be referred to as an "insertion configuration") in which the arm 220 is in the compact position, as shown in FIGS. 2A-2G, and an expanded configuration (which also may be referred to as an "implantation configuration") in which the arm 220 is in the expanded position, as shown in FIGS. 2H-2M.

In particular, the main body 210 and the arm 220 may be pivotally connected to one another via a hinge connection 228, such that the arm 220 may pivot relative to the main body 210 between the compact position and the expanded position. As shown, the hinge connection 228 may be positioned within the second half 208 of the interbody device 200. In particular, the hinge connection 228 may be positioned near but spaced apart from the second end 202 of the interbody device 200, as shown. Alternatively, the hinge connection 228 may be positioned at or adjacent to the second end 202 of the interbody device 200. In some embodiments, as shown, the hinge connection 228 may include a pin 230 extending through a one or more apertures 231 defined in the main body 210 and through one or more apertures 232 defined in the arm 220. As shown, the hinge connection 228 also may include a hinge recess 233 defined between a pair of hinge supports 234 of the main body 210, and a hinge tab 235 of the arm 220. The hinge supports 234 may be disposed along the third side 215 and the fourth side 216 of the main body 210, respectively, and may extend to the first side 213 of the main body 210, as shown. One of the apertures 231 may be defined in one of the hinge supports 234, and another aperture 231 may be defined in the other hinge support 234. The hinge tab 235 may be positioned at or near the second end 222 of the arm 220 and may extend to the first side 223, the second side 224, the third side 225, and the fourth side 226 of the arm 220, as shown. The one or more apertures 232 may be defined in the hinge tab 235. As shown, the hinge tab 235 of the arm 220 may be movably disposed within the hinge recess 233 of the main body 210. In some embodiments, the pin 230 may be press-fit into the one or more apertures 231 of the main body 210 and may have a sliding fit within the one or more apertures 232 of the arm 220. In other embodiments, the pin 230 may be press-fit into the one or more apertures 232 of the arm 220 and may have a sliding fit within the one or more apertures 231 of the main body 210. As shown, a rotational axis $A_R$ of the hinge connection 228 (i.e., a longitudinal axis of the pin 230) may extend parallel to the second transverse axis $A_{T2}$ of the device 200 and perpendicular to the longitudinal axis $A_L$ and the first transverse axis $A_{T1}$ of the device 200.

Figure 2A:
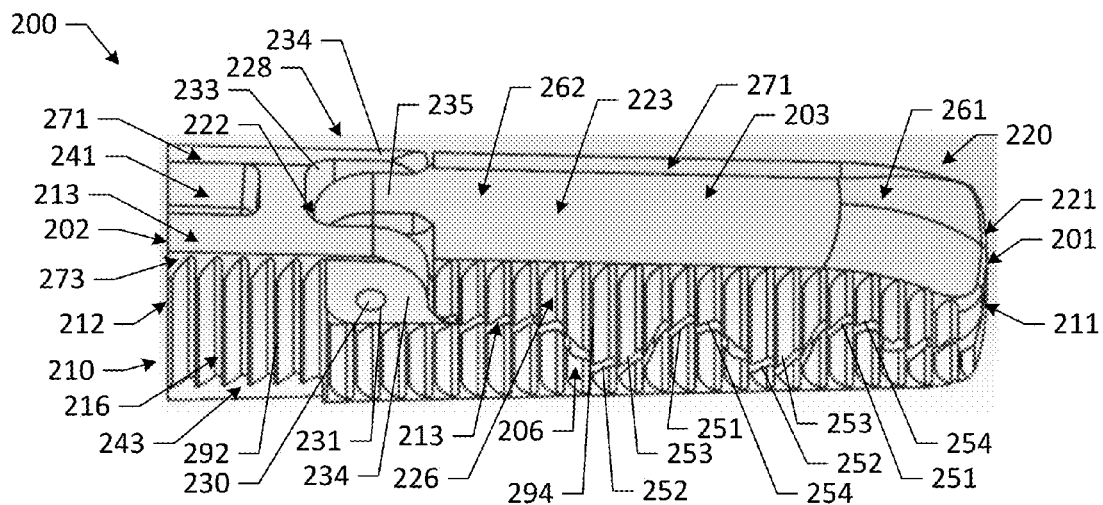
FIG. 2A shows a top perspective view of an expandable interbody device in accordance with one or more embodiments of the present disclosure, the expandable interbody device in a compact configuration.
Figure 2B:
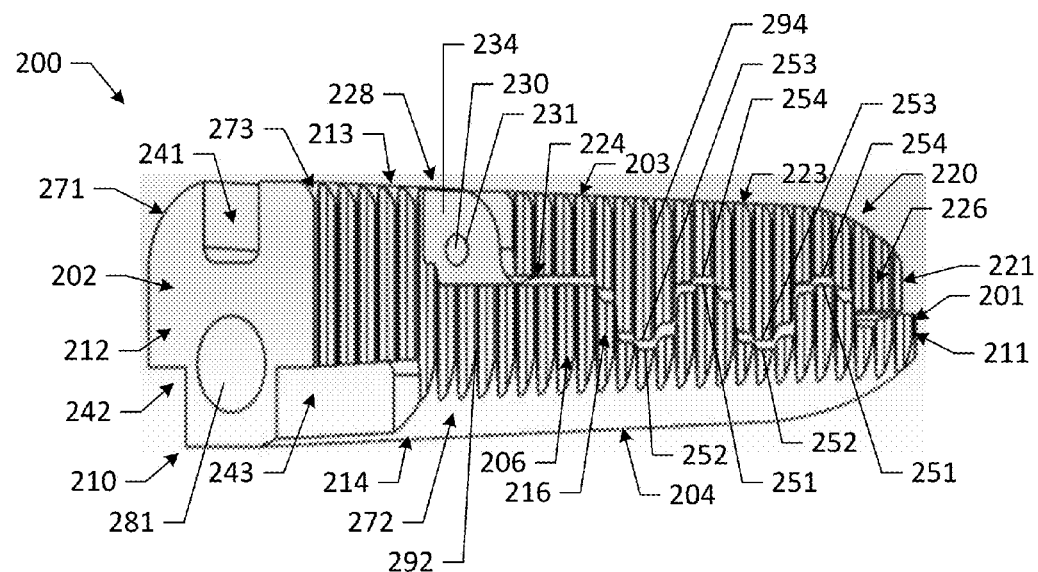
FIG. 2B shows an end perspective view of the expandable interbody device of FIG. 2A in the compact configuration.
Figure 2C:
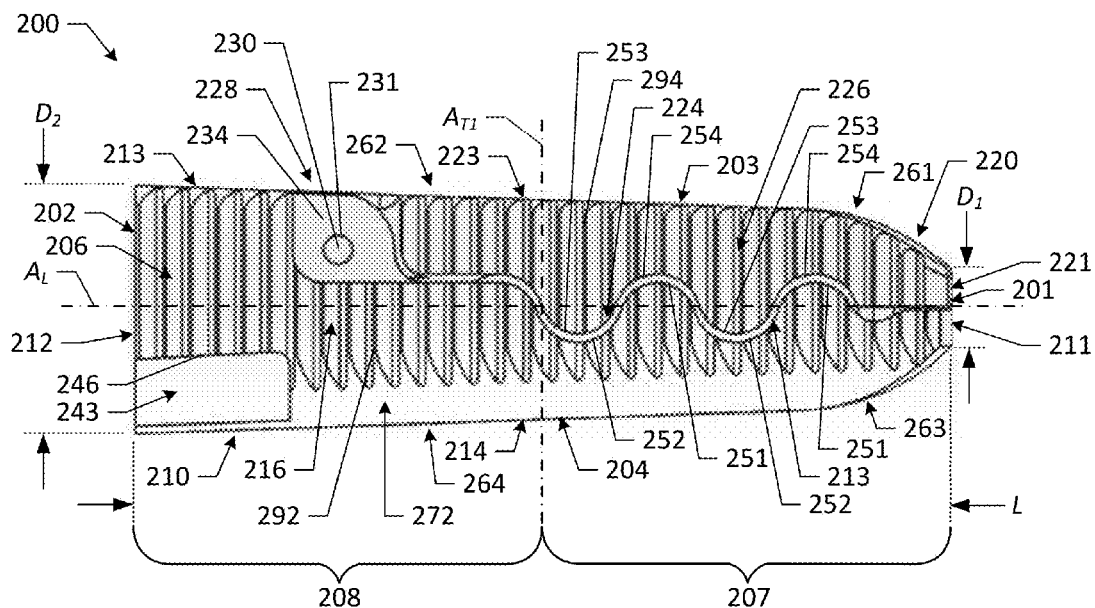
FIG. 2C shows a side view of the expandable interbody device of FIG. 2A in the compact configuration.
Figure 2D:
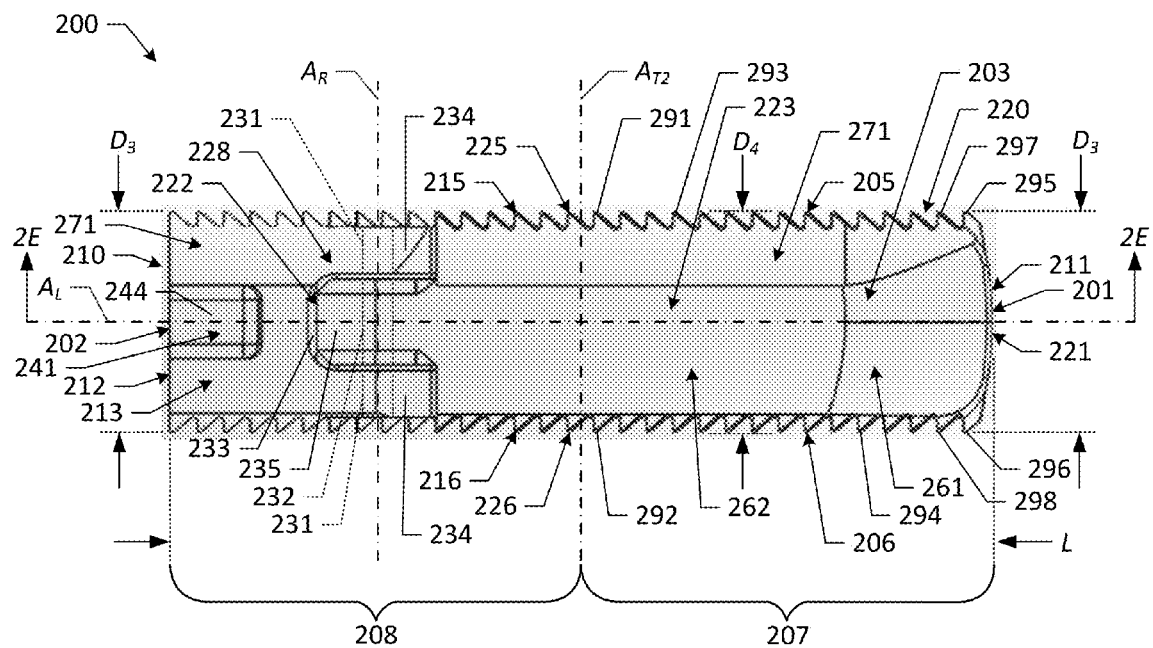
FIG. 2D shows a top view of the expandable interbody device of FIG. 2A in the compact configuration.
Figure 2E:
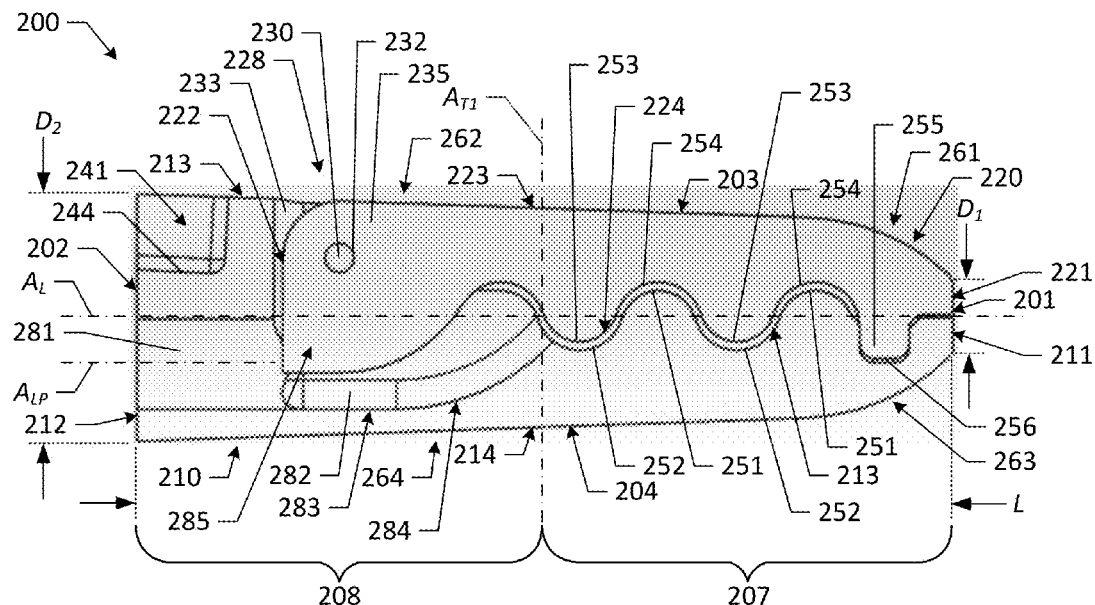
FIG. 2E shows a side cross-sectional view of the expandable interbody device of FIG. 2A in the compact configuration, taken along line 2E-2E of FIG. 2D.
Figure 2F:
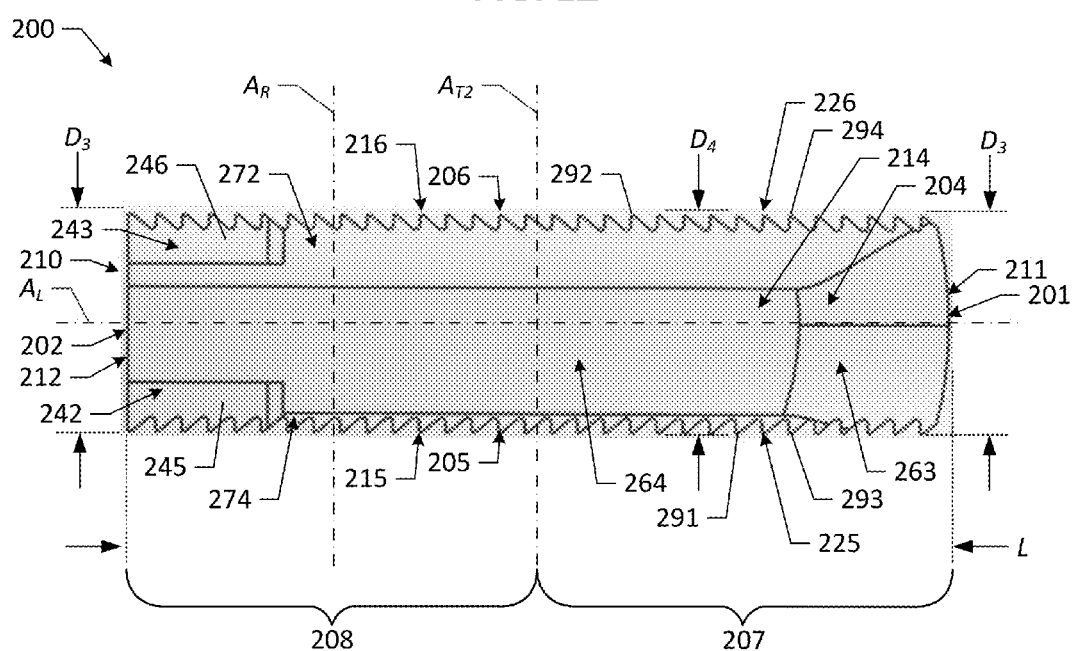
FIG. 2F shows a bottom view of the expandable interbody device of FIG. 2A in the compact configuration.
Figure 2G:
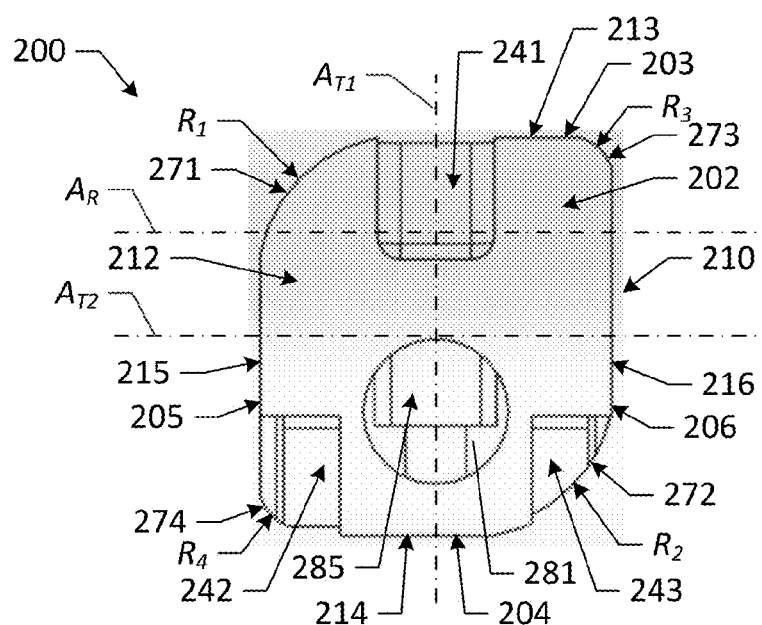
FIG. 2G shows an end view of the expandable interbody device of FIG. 2A in the compact configuration.
Figure 2H:
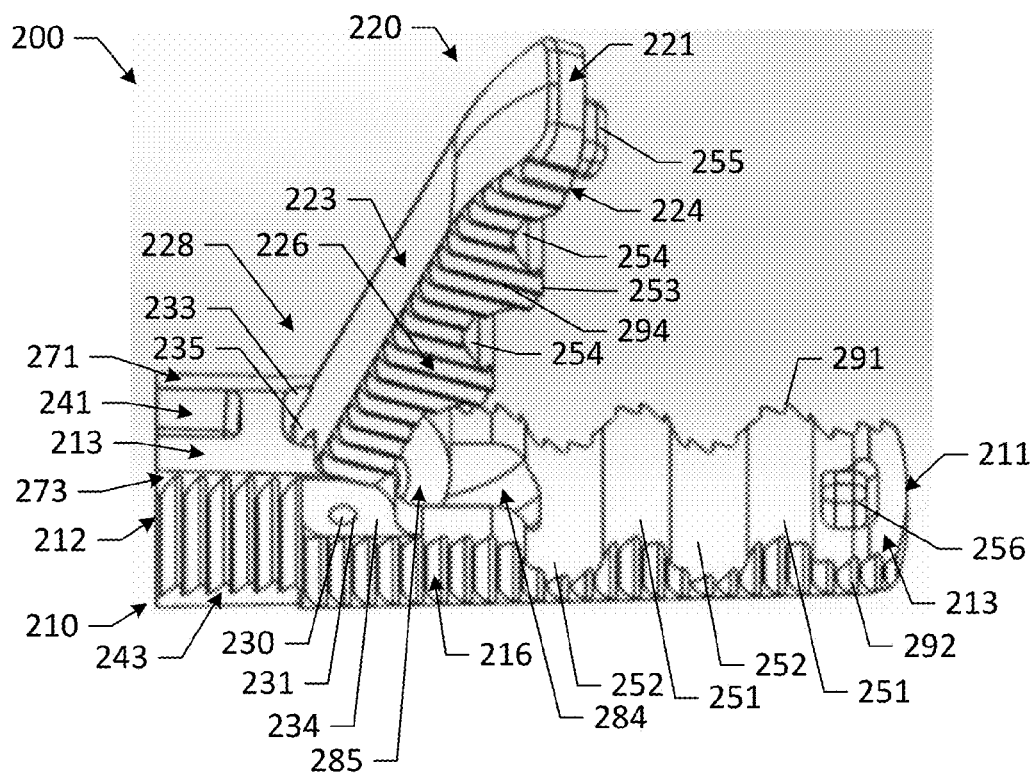
FIG. 2H shows a top perspective view of the expandable interbody device of FIG. 2A in an expanded configuration.
Figure 2I:
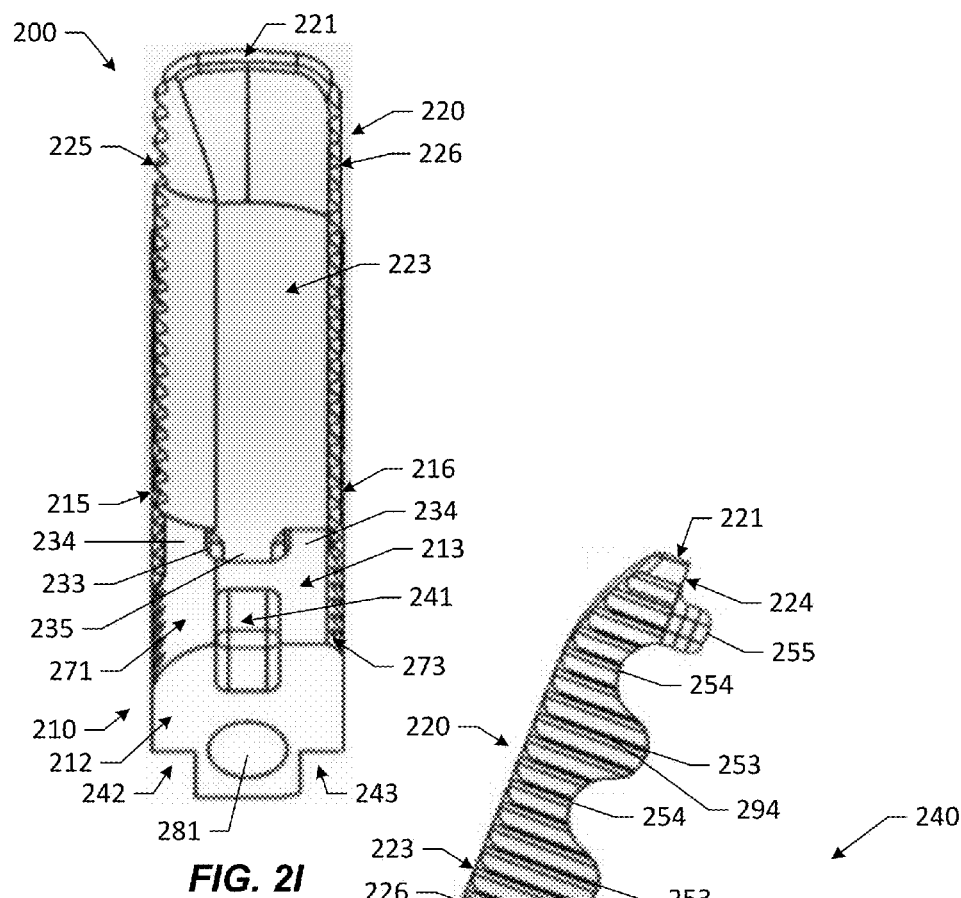
FIG. 2I shows an end perspective view of the expandable interbody device of FIG. 2A in the expanded configuration.
Figure 2J:
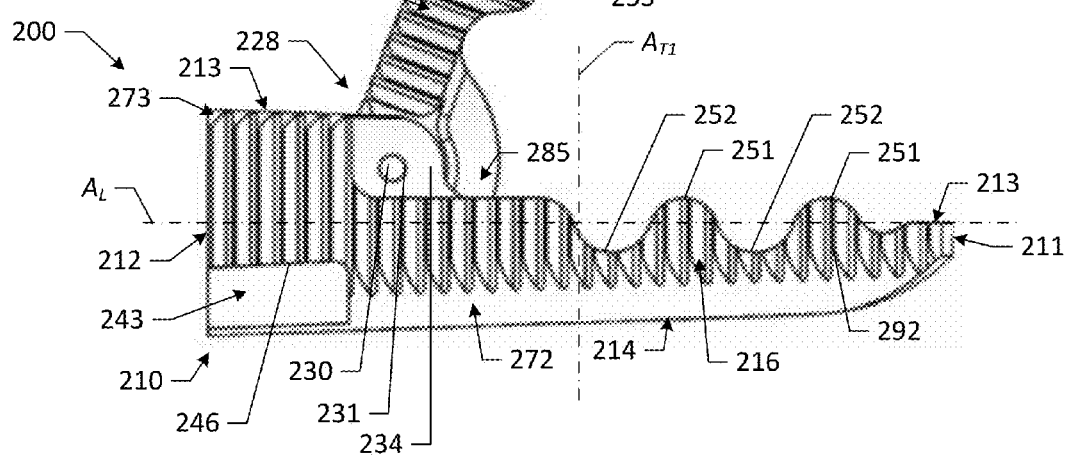
FIG. 2J shows a side view of the expandable interbody device of FIG. 2A in the expanded configuration.
Figure 2K:
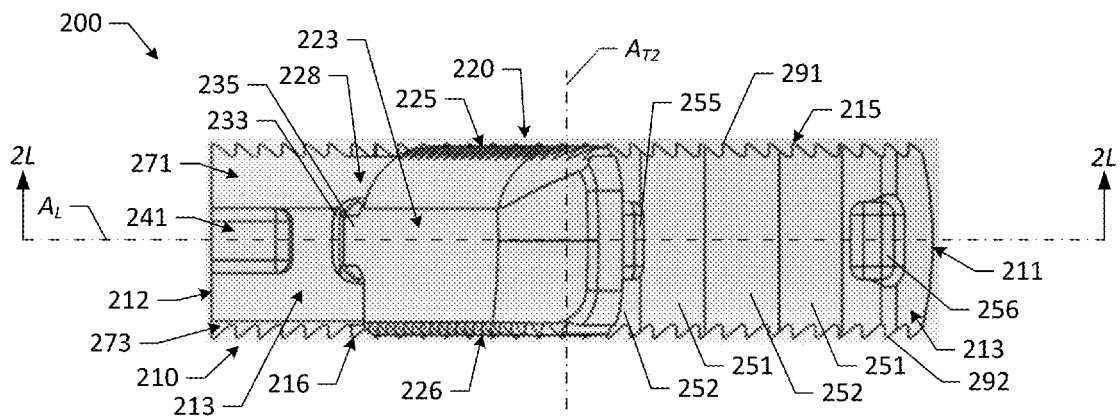
FIG. 2K shows a top view of the expandable interbody device of FIG. 2A in the expanded configuration.
Figure 2L:
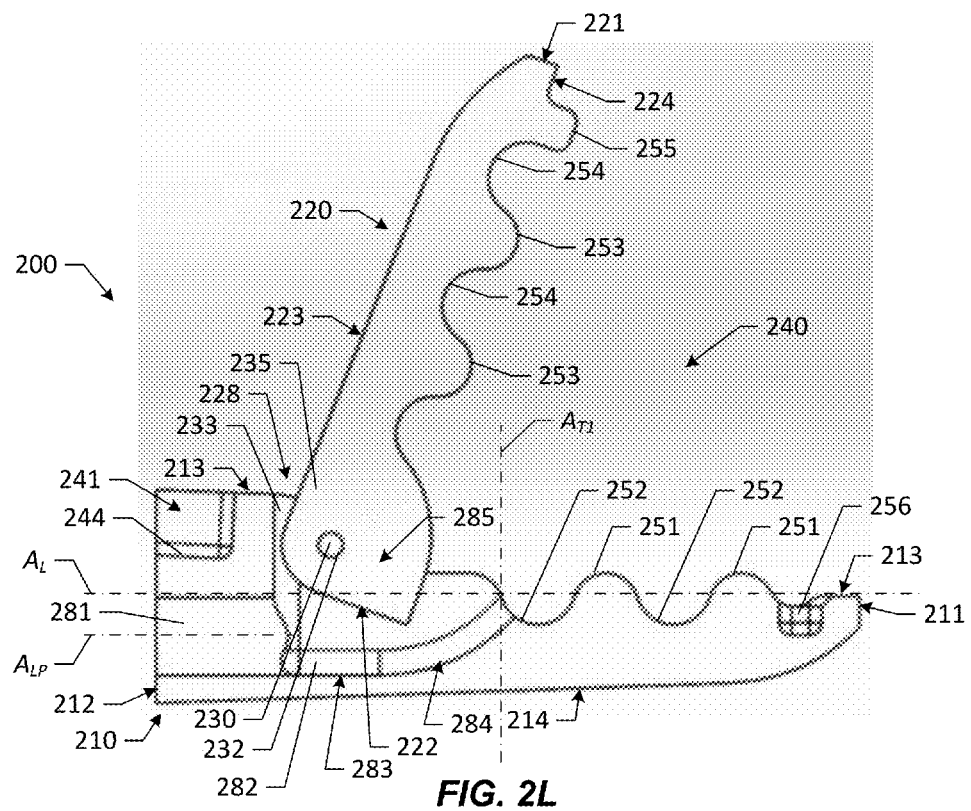
FIG. 2L shows a side cross-sectional view of the expandable interbody device of FIG. 2A in the expanded configuration, taken along line 2L-2L of FIG. 2K.
Figure 2M:
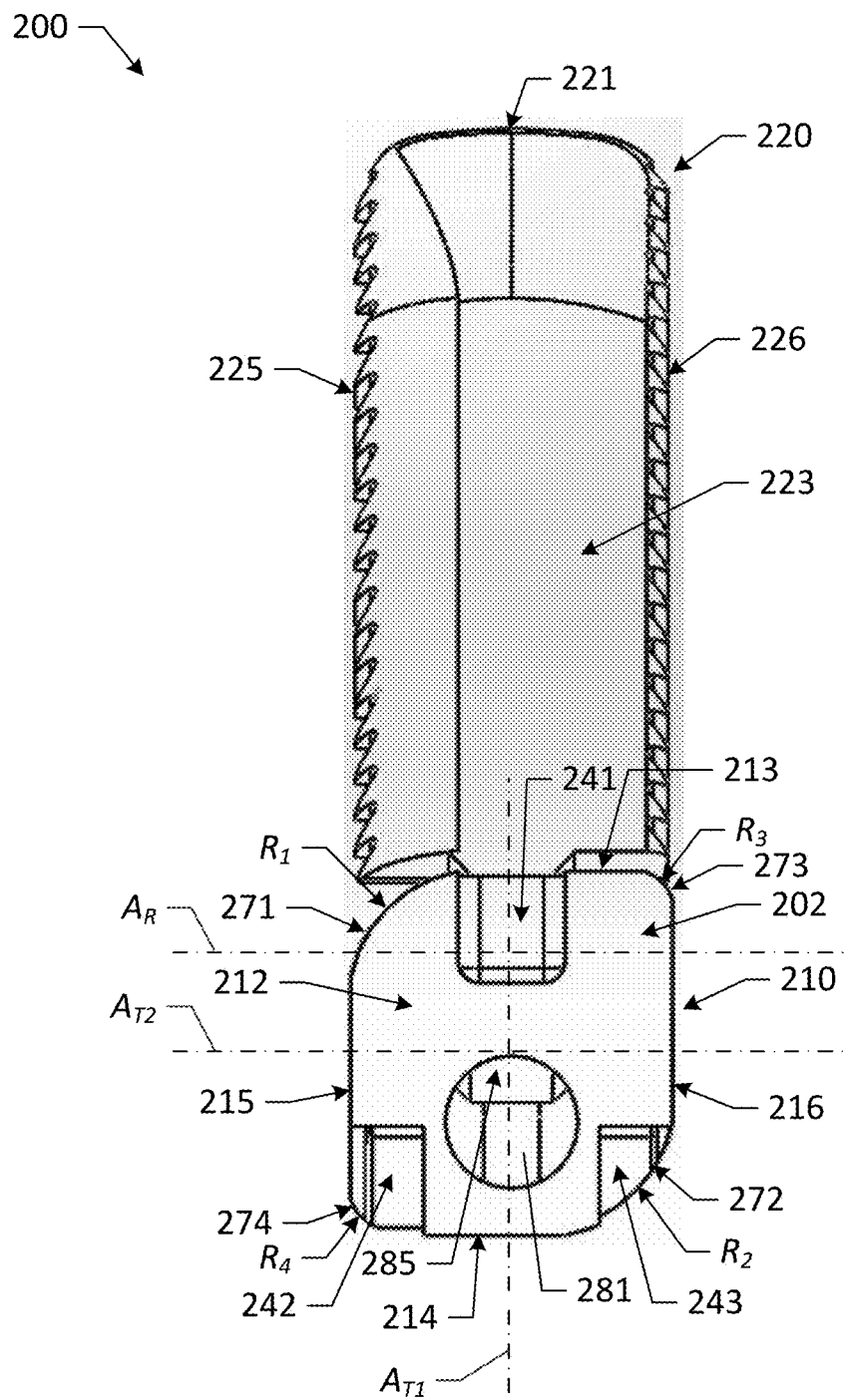
FIG. 2M shows an end view of the expandable interbody device of FIG. 2A in the expanded configuration.
Figure 2N:
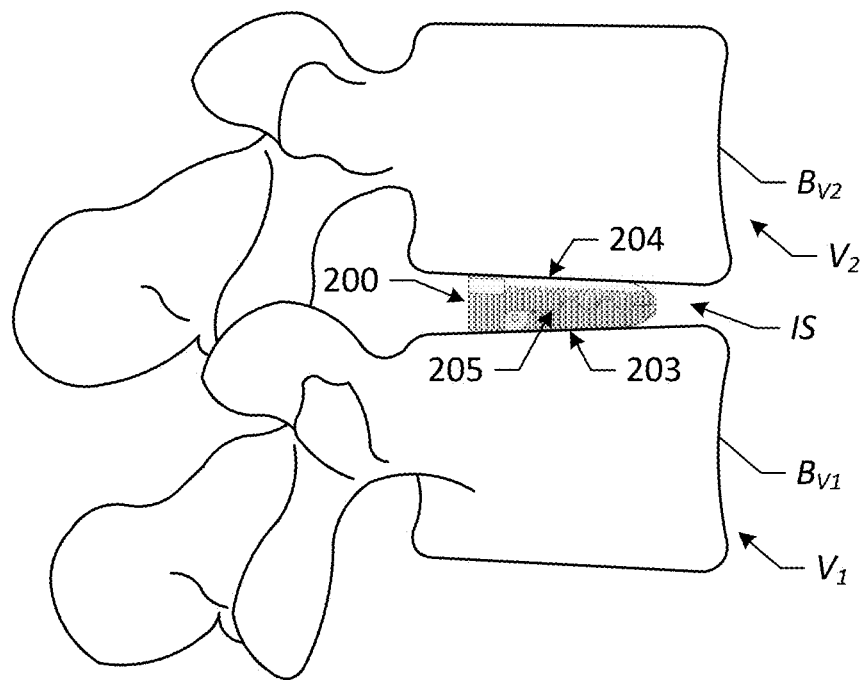
FIG. 2N shows a side view of the expandable interbody device of FIG. 2A positioned within an intervertebral space between an inferior vertebra and a superior vertebra, the expandable interbody device in an insertion orientation and the compact configuration.
Figure 2O:
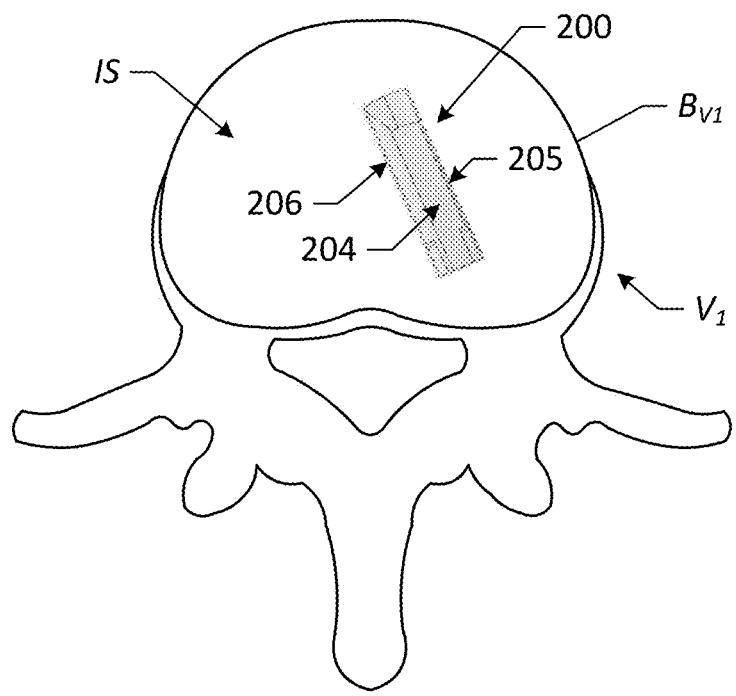
FIG. 2O shows a top view of the expandable interbody device of FIG. 2A positioned within the intervertebral space above the inferior vertebra, the expandable interbody device in the insertion orientation and the compact configuration.

Additional features of the main body 210, the arm 220, and the overall expandable interbody device 200 may be best understood in view of an intended method of implanting the interbody device 200 within an intervertebral space IS between a first vertebra $V_1$ (which also may be referred to as an "inferior vertebra") and an adjacent second vertebra $V_2$ (which also may be referred to as a "superior vertebra"), as shown in FIGS. 2N-2S. The interbody device 200 initially may be inserted into and positioned within the intervertebral space IS while the device 200 is an "insertion orientation" and the compact configuration, as shown in FIGS. 2N and 2O. When the interbody device 200 is in the insertion orientation within the intervertebral space IS, the longitudinal axis $A_L$ and the second transverse axis $A_{T2}$ of the device 200 may extend substantially parallel to the transverse plane of the patient, and the first transverse axis $A_{T1}$ of the device 200 may extend substantially parallel to the sagittal plane and the coronal plane of the patient. In this manner, upon insertion of the interbody device 200 within the intervertebral space IS, respective portions of the first side 203 and the second side 204 of the device 200 each may engage one of the adjacent vertebrae $V_1$, $V_2$.

In some embodiments, as shown, at least a portion of the first side 203 of the device 200 may engage a first body $B_{V1}$ of the first vertebra $V_1$, and at least a portion of the second side 204 of the device 200 may engage a second body $B_{V2}$ of the second vertebra $V_2$. In other words, in such embodiments, when the interbody device 200 is in the insertion orientation within the intervertebral space IS, the first side 203 of the device 200 is oriented in the caudal direction of the patient, and the second side 204 of the device 200 is oriented in the cephalad direction of the patient. For reasons described below, such insertion orientation may be used when the illustrated embodiment of the interbody device 200 is being inserted from the right side of the patient's spine, as shown in FIGS. 2N-2S, although such insertion orientation also may be used when the interbody device 200 is being inserted from the left side of the patient's spine according to other embodiments of the device 200. According to the illustrated embodiment of the interbody device 200, when the device 200 is in the insertion orientation within the intervertebral space IS, at least a portion of the first side 213 of the main body 210 and at least a portion of the first side 223 of the arm 220 may engage the first body $B_{V1}$ of the first vertebra $V_1$, and at least a portion of the second side 214 of the main body 210 may engage the second body $B_{V2}$ of the second vertebra $V_2$.

In other embodiments, at least a portion of the second side 204 of the device 200 may engage the first body $B_{V1}$ of the first vertebra $V_1$, and at least a portion of the first side 203 of the device 200 may engage the second body $B_{V2}$ of the second vertebra $V_2$. In other words, in such embodiments, when the interbody device 200 is in the insertion orientation within the intervertebral space IS, the second side 204 of the device 200 is oriented in the caudal direction of the patient, and the first side 203 of the device 200 is oriented in the cephalad direction of the patient. For reasons described below, such insertion orientation may be used when the illustrated embodiment of the interbody device 200 is being inserted from the left side of the patient's spine, although such insertion orientation also may be used when the interbody device 200 is being inserted from the right side of the patient's spine according to other embodiments of the device 200. According to the illustrated embodiment of the interbody device 200, when the device 200 is in the insertion orientation within the intervertebral space IS, at least a portion of the second side 214 of the main body 210 may engage the first body $B_{V1}$ of the first vertebra $V_1$, and at least a portion of the first side 213 of the main body 210 and at least a portion of the first side 223 of the arm 220 may engage the second body $B_{V2}$ of the second vertebra $V_2$.

Figure 2P:
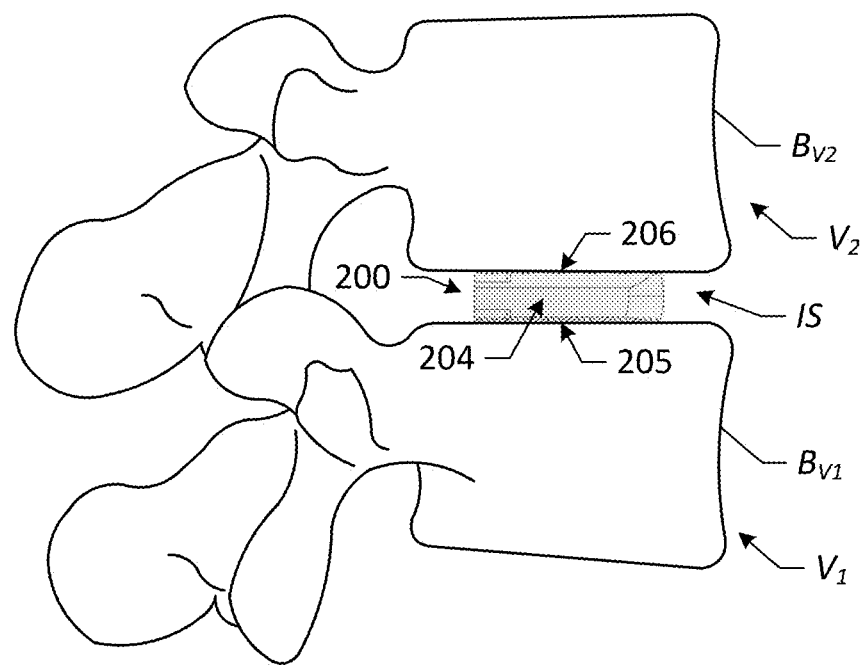
FIG. 2P shows a side view of the expandable interbody device of FIG. 2A positioned within the intervertebral space between the inferior vertebra and the superior vertebra, the expandable interbody device in an implantation orientation and the compact configuration.
Figure 2Q:
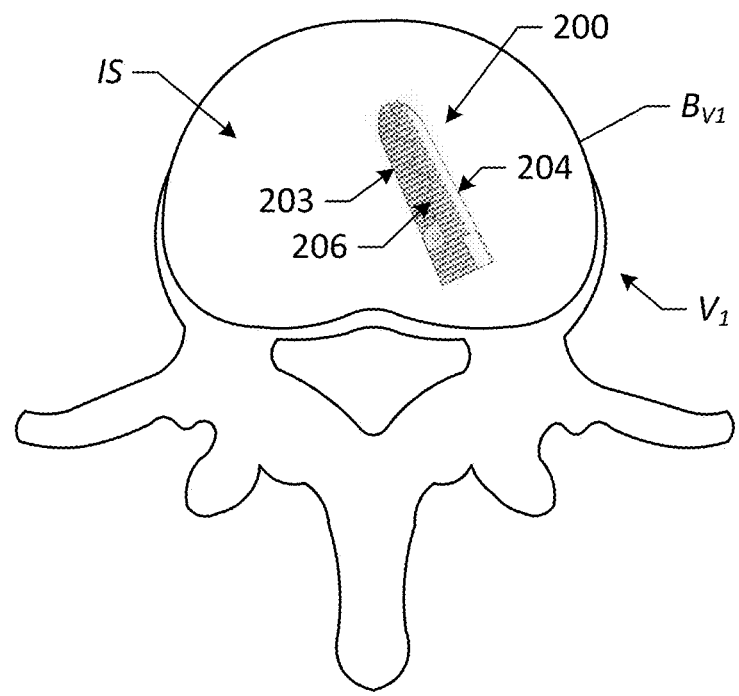
FIG. 2Q shows a top view of the expandable interbody device of FIG. 2A positioned within the intervertebral space above the inferior vertebra, the expandable interbody device in the implantation orientation and the compact configuration.

After inserting and positioning the interbody device 200 within the intervertebral space IS and while maintaining the device 200 in the compact configuration, the device 200 may be rotated approximately ninety (90) degrees about the longitudinal axis $A_L$ of the device 200 from the insertion orientation to an "implantation orientation," as shown in FIGS. 2P and 2Q. In some embodiments, as shown, the device 200 may be rotated clockwise (when viewed from the second end 202 of the device 200) from the insertion orientation to the implantation orientation. In other embodiments, the device 200 may be rotated counter clockwise (when viewed from the second end 202 of the device 200) from the insertion orientation to the implantation orientation. When the interbody device 200 is in the implantation orientation, the longitudinal axis $A_L$ and the first transverse axis $A_{T1}$ of the device 200 may extend substantially parallel to the transverse plane of the patient, and the second transverse axis $A_{T2}$ of the device 200 may extend substantially parallel to the sagittal plane and the coronal plane of the patient. In this manner, upon rotation of the interbody device 200 within the intervertebral space IS from the insertion orientation to the implantation orientation, respective portions of the third side 205 and the fourth side 206 of the device 200 each may engage one of the adjacent vertebrae $V_1$, $V_2$.

In some embodiments, as shown, at least a portion of the third side 205 of the device 200 may engage the first body $B_{V1}$ of the first vertebra $V_1$, and at least a portion of the fourth side 206 of the device 200 may engage the second body $B_{V2}$ of the second vertebra $V_2$. In other words, in such embodiments, when the interbody device 200 is in the implantation orientation within the intervertebral space IS, the third side 205 of the device 200 is oriented in the caudal direction of the patient, and the fourth side 206 of the device 200 is oriented in the cephalad direction of the patient. For reasons described below, such implantation orientation may be used when the interbody device 200 has been inserted from the right side of the patient's spine, as shown in FIGS. 2N-2S, although such implantation orientation also may be used when the interbody device 200 is being inserted from the left side of the patient's spine according to other embodiments. According to the illustrated embodiment of the interbody device 200, when the device 200 is in the implantation orientation within the intervertebral space IS, at least a portion of the third side 215 of the main body 210 and at least a portion of the third side 225 of the arm 220 each may engage the first body $B_{V1}$ of the first vertebra $V_1$, and at least a portion of the fourth side 216 of the main body 210 and at least a portion of the fourth side 226 of the arm 220 each may engage the second body $B_{V2}$ of the second vertebra $V_2$.

In other embodiments, at least a portion of the fourth side 206 of the device 200 may engage the first body $B_{V1}$ of the first vertebra $V_1$, and at least a portion of the third side 205 of the device 200 may engage the second body $B_{V2}$ of the second vertebra $V_2$. In other words, in such embodiments, when the interbody device 200 is in the implantation orientation within the intervertebral space IS, the fourth side 206 of the device 200 is oriented in the caudal direction of the patient, and the third side 205 of the device 200 is oriented in the cephalad direction of the patient. For reasons described below, such implantation orientation may be used when the interbody device 200 has been inserted from the left side of the patient's spine, although such implantation orientation also may be used when the interbody device 200 is being inserted from the right side of the patient's spine according to other embodiments. According to the illustrated embodiment of the interbody device 200, when the device 200 is in the implantation orientation within the intervertebral space IS, at least a portion of the fourth side 216 of the main body 210 and at least a portion of the fourth side 226 of the arm 220 each may engage the first body $B_{V1}$ of the first vertebra $V_1$, and at least a portion of the third side 215 of the main body 210 and at least a portion of the third side 225 of the arm 220 each may engage the second body $B_{V2}$ of the second vertebra $V_2$.

Figure 2R:
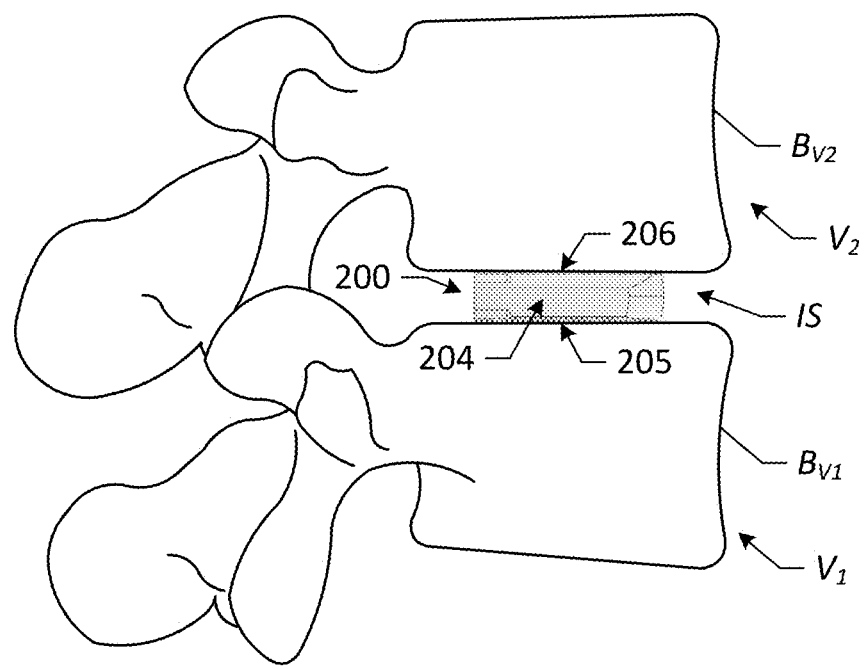
FIG. 2R shows a side view of the expandable interbody device of FIG. 2A positioned within the intervertebral space between the inferior vertebra and the superior vertebra, the expandable interbody device in the implantation orientation and the expanded configuration.
Figure 2S:
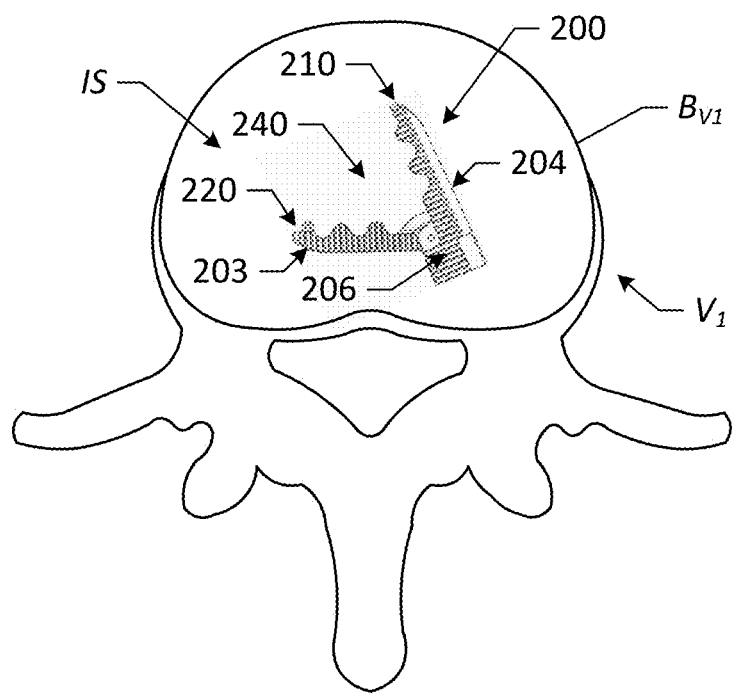
FIG. 2S shows a top view of the expandable interbody device of FIG. 2A positioned within the intervertebral space above the inferior vertebra, the expandable interbody device in the implantation orientation and the expanded configuration.
Figure 3A:
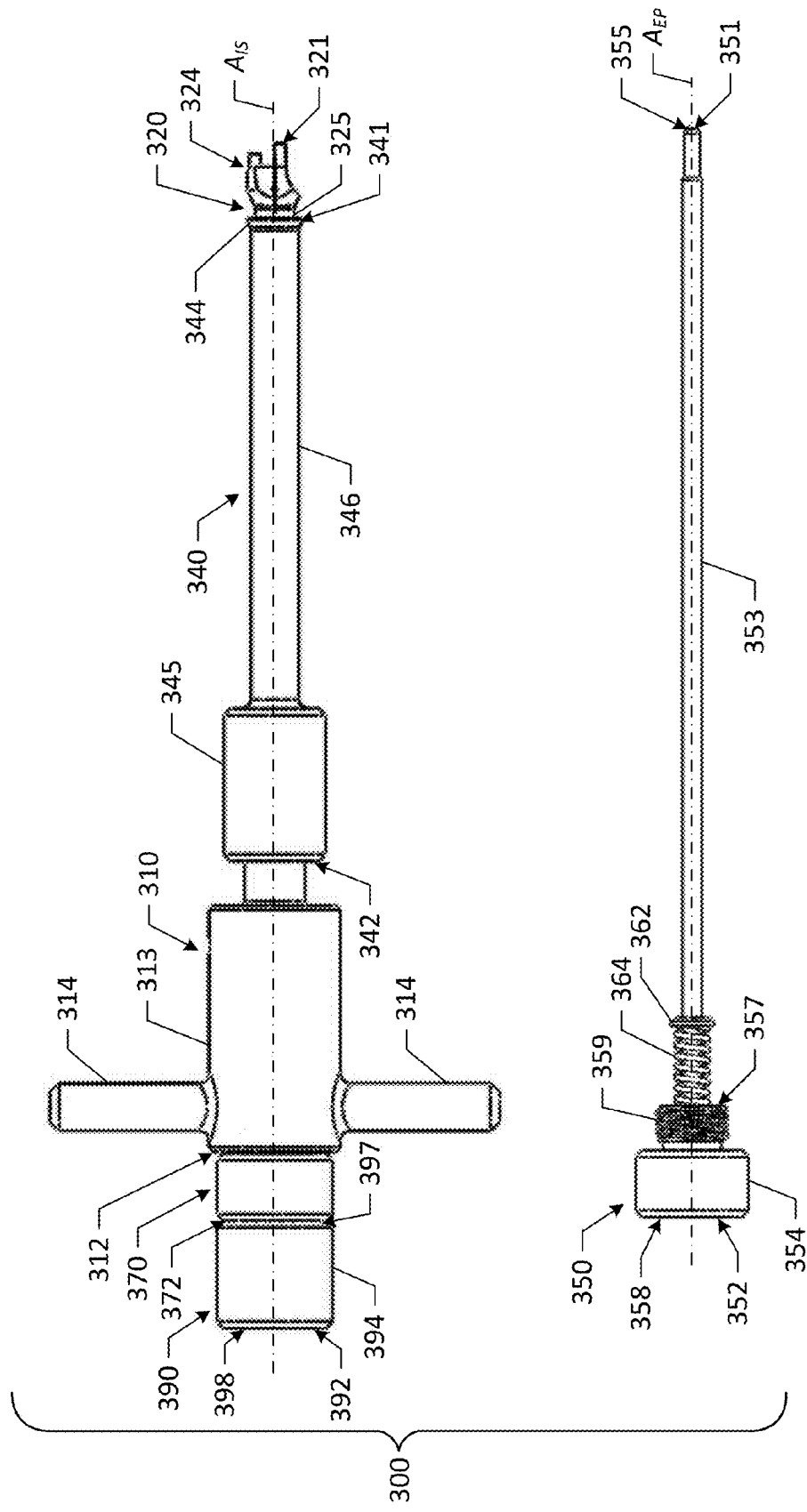
FIG. 3A shows a side view of an instrument system for inserting and positioning an expandable interbody device in an intervertebral space, rotating the interbody device within the intervertebral space, expanding the interbody device within the intervertebral space, and delivering bone graft into a cavity of the expanded interbody device.
Figure 3B:
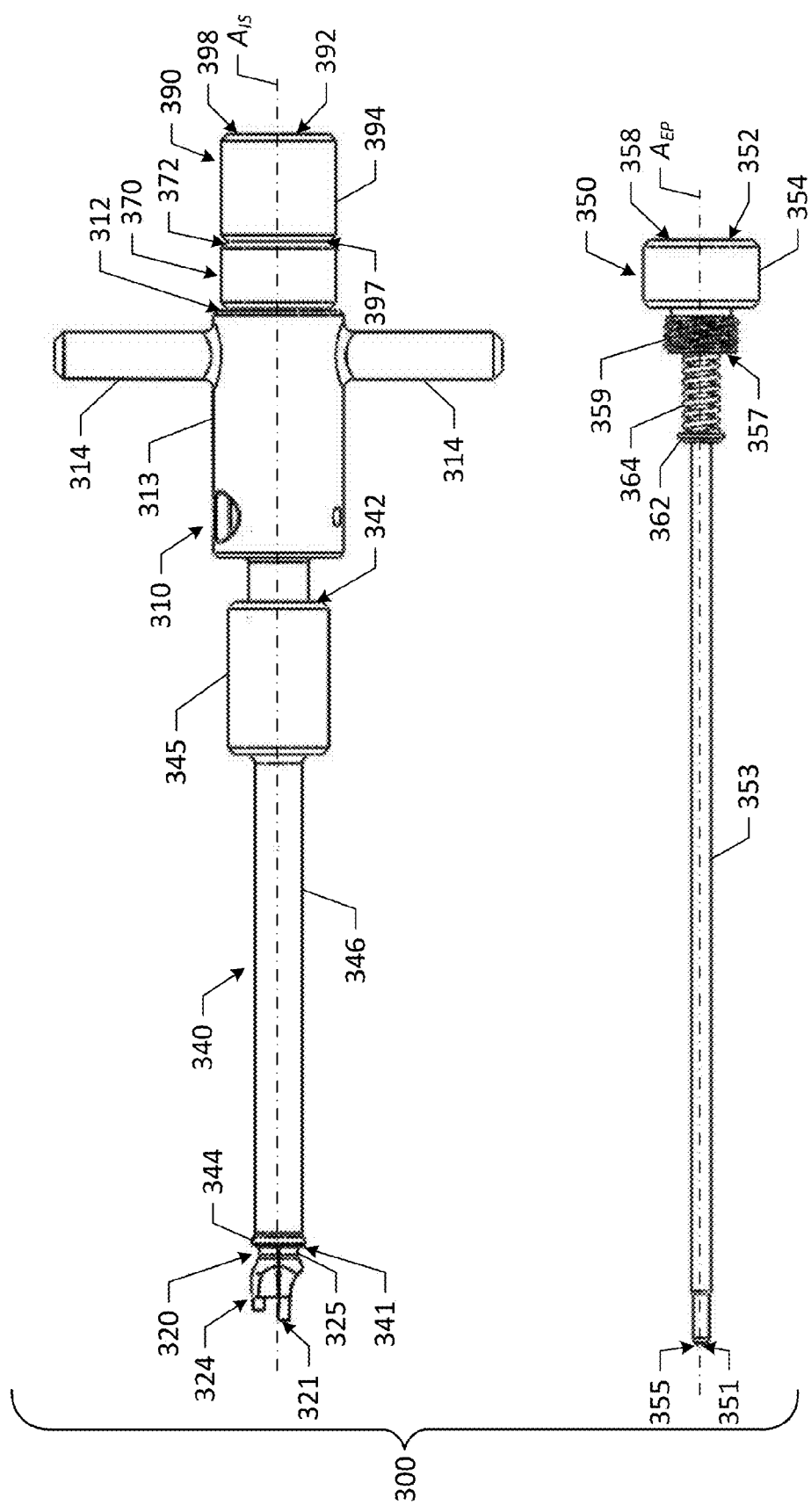
FIG. 3B shows a side view of the instrument system of FIG. 3A.
Figure 3C:
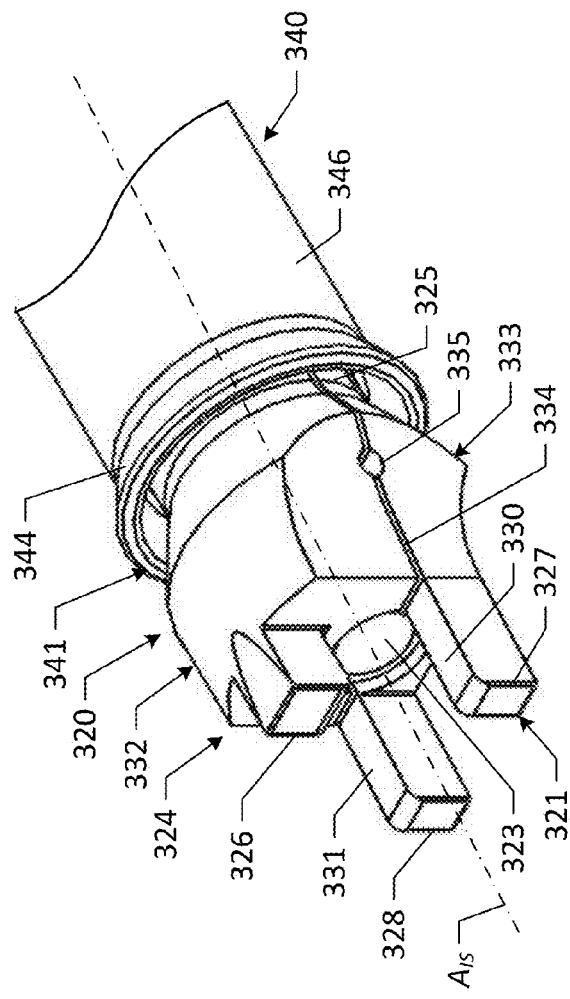
FIG. 3C shows a detailed perspective view of a distal portion of the instrument system of FIG. 3A.
Figure 3D:
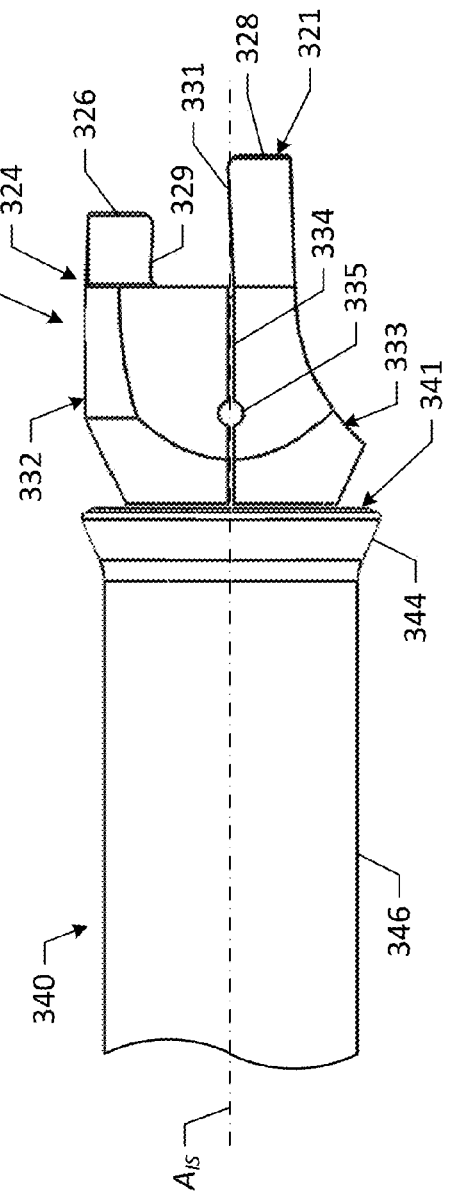
FIG. 3D shows a detailed side view of the distal portion of the instrument system of FIG. 3A.

After rotating the interbody device 200 within the intervertebral space IS from the insertion orientation to the implantation orientation, the device may be expanded from the compact configuration to the expanded configuration, as shown in FIGS. 2R and 2S. In this manner, the arm 220 may be moved with respect to the main body 210 from the compact position to the expanded position. In particular, the arm 220 may be pivoted medially with respect to the main body 210 about the hinge connection 228 from the compact position to the expanded position. The degree of expansion of the interbody device 200 (i.e., the degree which the arm 220 is pivoted with respect to the main body 210) may be determined by the user, based on the anatomy of the patient and the desired correction of the adjacent vertebrae $V_1$, $V_2$. Upon expansion of the interbody device 200 within the intervertebral space IS from the compact configuration to the expanded configuration, respective portions of the third side 205 and the fourth side 206 of the device 200 each may engage one of the adjacent vertebrae $V_1$, $V_2$.

In some embodiments, as shown, at least a portion of the third side 205 of the device 200 may engage the first body $B_{V1}$ of the first vertebra $V_1$, and at least a portion of the fourth side 206 of the device 200 may engage the second body $B_{V2}$ of the second vertebra $V_2$. According to the illustrated embodiment of the interbody device 200, when the device 200 is in the implantation orientation and the expanded configuration within the intervertebral space IS, at least a portion of the third side 215 of the main body 210 and at least a portion of the third side 225 of the arm 220 each may engage the first body $B_{V1}$ of the first vertebra $V_1$, and at least a portion of the fourth side 216 of the main body 210 and at least a portion of the fourth side 226 of the arm 220 each may engage the second body $B_{V2}$ of the second vertebra $V_2$. In some embodiments, as shown, when the interbody device 200 is in the implantation orientation and the expanded configuration within the intervertebral space IS, the main body 210 may be positioned partially within a posterior portion, such as a posterior half, of the intervertebral space IS and partially within an anterior portion, such as an anterior half, of the intervertebral space IS, and the arm 220 may be positioned entirely within the posterior portion, such as the posterior half, of the intervertebral space IS. In this manner, at least portions of the third side 215 of the main body 210 may engage part of a posterior portion, such as a posterior half, of the first body $B_{V1}$ of the first vertebra $V_1$ and part of an anterior portion, such as an anterior half, of the first body $B_{V1}$ of the first vertebra $V_1$, at least portions of the fourth side 216 of the main body 210 may engage part of a posterior portion, such as a posterior half, of the second body $B_{V2}$ of the second vertebra $V_2$ and part of an anterior portion, such as an anterior half, of the second body $B_{V2}$ of the second vertebra $V_2$, at least a portion of the third side 225 of the arm 220 may engage part of the posterior portion of the first body $B_{V1}$ of the first vertebra $V_1$, and at least a portion of the fourth side 226 of the arm 220 may engage part of the posterior portion of the second body $B_{V2}$ of the second vertebra $V_2$.

In other embodiments, at least a portion of the fourth side 206 of the device 200 may engage the first body $B_{V1}$ of the first vertebra $V_1$, and at least a portion of the third side 205 of the device 200 may engage the second body $B_{V2}$ of the second vertebra $V_2$. According to the illustrated embodiment of the interbody device 200, when the device 200 is in the implantation orientation and the expanded configuration within the intervertebral space IS, at least a portion of the fourth side 216 of the main body 210 and at least a portion of the fourth side 226 of the arm 220 each may engage the first body $B_{V1}$ of the first vertebra $V_1$, and at least a portion of the third side 215 of the main body 210 and at least a portion of the third side 225 of the arm 220 each may engage the second body $B_{V2}$ of the second vertebra $V_2$. In some embodiments, as shown, when the interbody device 200 is in the implantation orientation and the expanded configuration within the intervertebral space IS, the main body 210 may be positioned partially within a posterior portion, such as a posterior half, of the intervertebral space IS and partially within an anterior portion, such as an anterior half, of the intervertebral space IS, and the arm 220 may be positioned entirely within the posterior portion, such as the posterior half, of the intervertebral space IS. In this manner, at least portions of the fourth side 216 of the main body 210 may engage part of a posterior portion, such as a posterior half, of the first body $B_{V1}$ of the first vertebra $V_1$ and part of an anterior portion, such as an anterior half, of the first body $B_{V1}$ of the first vertebra $V_1$, at least portions of the third side 215 of the main body 210 may engage part of a posterior portion, such as a posterior half, of the second body $B_{V2}$ of the second vertebra $V_2$ and part of an anterior portion, such as an anterior half, of the second body $B_{V2}$ of the second vertebra $V_2$, at least a portion of the fourth side 226 of the arm 220 may engage part of the posterior portion of the first body $B_{V1}$ of the first vertebra $V_1$, and at least a portion of the third side 225 of the arm 220 may engage part of the posterior portion of the second body $B_{V2}$ of the second vertebra $V_2$.

As shown, when the interbody device 200 is in the implantation orientation and the expanded configuration within the intervertebral space IS, the main body 210 and the arm 220 may define a cavity 240 (which also may be referred to as a "space" or a "gap") therebetween. In particular, the cavity 240 may be defined between a portion of the first side 213 of the main body 210 and a portion of the second side 224 of the arm 220. As described in detail below, bone graft or a bone graft substitute may be placed within the cavity 240 to promote fusion between the first vertebra $V_1$ and the second vertebra $V_2$.

The main body 210 and the arm 220 may include a number of features that engage and mate with one another when the expandable interbody device 200 is in the compact configuration, which may minimize the access window required for insertion of the device 200 into the intervertebral space IS and may enhance the structural integrity of the device 200 during insertion into the intervertebral space IS. In particular, the main body 210 may include a plurality of ribs 251 positioned along the first side 213 of the main body 210 and a plurality of grooves 252 defined in the first side 213 of the main body 110. As shown, the ribs 251 and the grooves 252 may be positioned along and defined in a distal portion of the first side 213 of the main body 210. In a similar manner, the arm 220 may include a plurality of ribs 253 positioned along the second side 224 of the arm 220 and a plurality of grooves 254 defined in the second side 222 of the arm 220. As shown, the ribs 253 and the grooves 254 may be positioned along and defined in a distal portion of the second side 224 of the arm 220. When the interbody device 200 is in the compact configuration, each of the ribs 251 of the main body 210 may be positioned within a respective groove 254 of the arm 220, and each of the ribs 253 of the arm 220 may be positioned within a respective groove 252 of the main body 210. As shown, each of the ribs 251, 253 and each of the grooves 252, 254 may extend perpendicular to the longitudinal axis $A_L$ and the first transverse axis $A_{T1}$ (and parallel the second transverse axis $A_{T2}$) of the interbody device 200. In other words, each of the ribs 251, 253 and each of the grooves 252, 254 may have a length extending perpendicular to the longitudinal axis $A_L$ and the first transverse axis $A_{T1}$ (and parallel the second transverse axis $A_{T2}$) of the interbody device 200 and a width extending parallel to the longitudinal axis $A_L$ (and perpendicular to first transverse axis $A_{T1}$ and the second transverse axis $A_{T2}$) of the interbody device 200. As shown, the ribs 251, 253 and the grooves 252, 254 each may have a rounded or semi-circular cross-sectional shape when viewed from the third side 205 and the fourth side 206 of the interbody device 200.

The arm 220 also may include a protrusion 255 (which also may be referred to as a "tooth") positioned along the second side 224 of the arm 220, and the main body 210 may include a pocket 256 (which also may be referred to as a "recess") defined in the first side 213 of the main body 210. In particular, the protrusion 255 may be positioned along a distal portion of the second side 224 of the arm 220, and the pocket 256 may be defined in a distal portion of the first side 213 of the main body 210. When the interbody device 200 is in the compact configuration, the protrusion 255 of the arm 220 may be received within the pocket 256 of the main body 210. As shown, the protrusion 255 may be positioned near but spaced apart from the first end 221 of the arm 220, and the protrusion 255 may be spaced apart from each of the third side 225 and the fourth side 226 of the arm 220 and centered therebetween. In a similar manner, the pocket 256 may be positioned near but spaced apart from the first end 211 of the main body 210, and the pocket 256 may be spaced apart from each of the third side 215 and the fourth side 216 of the main body 210 and centered therebetween. In various embodiments, the protrusion 255 and the pocket 256 may be sized and configured such that the protrusion 255 and the pocket 256 form a loose fit, a close fit, or an interference fit when the interbody device 200 is in the compact configuration. The engagement between the protrusion 255 and the pocket 256 may enhance the structural integrity of the interbody device 200 during insertion of the device 200 into the intervertebral space IS. In particular, as the first end 201 of the interbody device 200 is inserted into the intervertebral space IS, a portion of the insertion forces acting on the device 200 as it contacts the vertebrae $V_1$, $V_2$ may be carried by the protrusion 255 and the pocket 256. In this manner, the protrusion 255 and the pocket 256 may shield the hinge connection 228 from such portion of insertion forces.

The interbody device 200 may include a number of features that cooperate with the vertebrae $V_1$, $V_2$ to facilitate insertion of the device 200 into the intervertebral space IS and positioning of the device 200 therein. In particular, the first side 203 and the second side 204 of the interbody device 200 may include one or more smooth surfaces configured for slidably engaging one of the first body $B_{V1}$ of the first vertebrae $V_1$ and the second body $B_{V2}$ of the second vertebrae $V_2$ as the device 200 is inserted into and positioned within the intervertebral space IS. In this manner, as shown, the portion of the first side 213 of the main body 210 and the portion of the first side 223 of the arm 220 that define the first side 203 of the interbody device 200 may include one or more smooth surfaces configured for slidably engaging one of the first body $B_{V1}$ and the second body $B_{V2}$. In a similar manner, as shown, the second side 214 of the main body 210 that defines the second side 204 of the interbody device 200 may include one or more smooth surfaces configured for slidably engaging one of the first body $B_{V1}$ and the second body $B_{V2}$. The smooth surfaces of the main body 210 and the arm 220 may reduce friction generated between the interbody device 200 and the first body $B_{V1}$ and the second body $B_{V2}$, thereby reducing forces required to insert the device 200 into and position the device 200 within the intervertebral space IS.

As described above, upon insertion of the interbody device 200 within the intervertebral space IS, respective portions of the first side 203 and the second side 204 of the device 200 each may engage one of the adjacent vertebrae $V_1$, $V_2$. As shown, an overall distance D between the first side 203 and the second side 204 of the interbody device 200 in the direction of the first transverse axis $A_{T1}$ (which also may be referred to as an "overall height" of the interbody device 200 when the device 200 is in the insertion orientation and the compact configuration, or simply an "overall insertion height") may vary along the length L of the device 200 in the direction of the longitudinal axis $A_L$. In particular, the overall distance D between the first side 203 and the second side 204 of the device 200 may increase along at least a majority of the length L of the device 200 in the direction from the first end 201 toward the second end 202 of the device 200. In this manner, the interbody device 200 may have a first overall distance $D_1$ (which also may be referred to as a "minimum overall distance" or a "minimum overall height") between the first side 203 and the second side 204 of the device 200 at a first location along the length L of the device 200 positioned closer to the first end 201 of the device 200 and a second overall distance $D_2$ (which also may be referred to as a "maximum overall distance" or a "maximum overall height") between the first side 203 and the second side 204 of the device 200 at a second location along the length L of the device 200 positioned closer to the second end 202 of the device 200, wherein the first overall distance $D_1$ is less than the second overall distance $D_2$. In some embodiments, as shown, the overall distance D between the first side 203 and the second side 204 of the device 200 may increase along the entire length L of the device 200 in the direction from the first end 201 toward the second end 202 of the device 200. In this manner, as shown, the interbody device 200 may have a first overall distance $D_1$ (which also may be referred to as a "minimum overall distance" or a "minimum overall height") between the first side 203 and the second side 204 of the device 200 at the first end 201 of the device 200 and a second overall distance $D_2$ (which also may be referred to as a "maximum overall distance" or a "maximum overall height") between the first side 203 and the second side 204 of the device 200 at the second end 202 of the device 200, wherein the first overall distance $D_1$ is less than the second overall distance $D_2$. In other embodiments, the overall distance D between the first side 203 and the second side 204 of the device 200 may increase along only a portion of the length L of the device 200 in the direction from the first end 201 toward the second end 202 of the device 200. It will be understood that the variation of the overall distance D between the first side 203 and the second side 204 of the interbody device 200 in the direction of the longitudinal axis $A_L$ may ease initial insertion of the device 200 into the intervertebral space IS and may facilitate gradual distraction of the intervertebral space IS as the device 200 is fully inserted therein.

Herein, use of the term "overall distance" with respect to the first side 203 and the opposite second side 204 of the interbody device 200 at a particular location along the length L of the device 200 in the direction of the longitudinal axis $A_L$ refers to a distance in the direction of the first transverse axis $A_{T1}$ between a portion of the first side 203 positioned furthest from the longitudinal axis $A_L$ in the direction of the first transverse axis $A_{T1}$ at the particular location along the length L of the device 200 and a portion of the second side 204 positioned furthest from the longitudinal axis $A_L$ in the direction of the first transverse axis $A_{T1}$ at the particular location along the length L of the device 200. As described above, in some embodiments, as shown, the first side 203 of the device 200 may be defined by a portion of the first side 213 of the main body 210 and a portion of the first side 223 of the arm 220, and the second side 204 of the device 200 may be defined by the second side 214 of the main body 210. According to the illustrated embodiment, at certain locations along the length L of the device 200, the overall distance D between the first side 203 and the second side 204 of the device 200 may be defined by the first side 213 and the second side 214 of the main body 210, and at other locations along the length L of the device 200, the overall distance D between the first side 203 and the second side 204 of the device 200 may be defined by the first side 223 of the arm 220 and the second side 214 of the main body 210.

In some embodiments, the first side 203 of the interbody device 200 may include a curved portion 261 and a flat portion 262. As shown, the curved portion 261 may be positioned adjacent the first end 201 of the device 200, and the flat portion 262 may be positioned adjacent to the second end 202 of the device 200. The curved portion 261 may extend from the first end 201 of the device 200 to the flat portion 262, and the flat portion 262 may extend from the curved portion 261 to the second end 202 of the device 200. As shown, the curved portion 261 of the first side 203 of the device 200 may be defined by a portion of the first side 223 of the arm 220, and the flat portion 262 of the first side 203 of the device 200 may be defined by a portion of the first side 223 of the arm 220 and a portion of the first side 213 of the main body 210. In other embodiments, the entire first side 203 of the interbody device 200 may have a curved shape extending from the first end 201 to the second end 202 of the device 200. In still other embodiments, the entire first side 203 of the interbody device 200 may have a flat shape extending from the first end 201 to the second end 202 of the device 200. In some embodiments, the second side 204 of the interbody device 200 may include a curved portion 263 and a flat portion 264. As shown, the curved portion 263 may be positioned adjacent the first end 201 of the device 200, and the flat portion 264 may be positioned adjacent to the second end 202 of the device 200. The curved portion 263 may extend from the first end 201 of the device 200 to the flat portion 264, and the flat portion 264 may extend from the curved portion 263 to the second end 202 of the device 200. As shown, the curved portion 263 of the second side 204 of the device 200 may be defined by a portion of the second side 214 of the main body 210, and the flat portion 264 may be defined by another portion of the second side 214 of the main body 210. In other embodiments, the entire second side 204 of the interbody device 200 may have a curved shape extending from the first end 201 to the second end 202 of the device 200. In still other embodiments, the entire second side 204 of the interbody device 200 may have a flat shape extending from the first end 201 to the second end 202 of the device 200. It will be understood that during implantation of the interbody device 200, the curved portions 261, 263 and the flat portions 262, 264 of the first side 203 and the second side 204 of the device 200 may ease initial insertion of the device 200 into the intervertebral space IS and may facilitate gradual distraction of the intervertebral space IS as the device 200 is fully inserted therein.

The interbody device 200 may include a number of features that cooperate with the vertebrae $V_1$, $V_2$ to facilitate rotation of the device 200 from the insertion orientation to the implantation orientation within the intervertebral space IS. In particular, the interbody device 200 may include a number of transition portions positioned along respective interfaces between adjacent sides of the device 200. As shown, the interbody device 200 may include a first transition portion 271, a second transition portion 272, a third transition portion 273, and a fourth transition portion 274. The first transition portion 271 may be positioned along the interface between the first side 203 and the third side 205 of the device 200, the second transition portion 272 may be positioned along the interface between the second side 204 and the fourth side 206 of the device 200, the third transition portion 273 may be positioned along the interface between the first side 203 and the fourth side 206 of the device 200, and the fourth transition portion 274 may be positioned along the interface between the second side 204 and the third side 205 of the device 200. In some embodiments, each of the transition portions 271, 272, 273, 274 may extend along the entire length L of the device 200 from the first end 201 to the second end 202 of the device 200. In some embodiments, some or all of the transition portions 271, 272, 273, 274 may extend along only a portion of the length L of the device 200. In some such embodiments, each of the transition portions 271, 272, 273, 274 may extend from the second end 202 of the device 200 to respective intermediate locations along the length L of the device 200 spaced apart from the first end 201 of the device 200.

As shown, each of the transition portions 271, 272, 273, 274 may have a curved shape extending along the respective interfaces between the sides of the device 200. The first transition portion 271 may have a first radius of curvature $R_1$, the second transition portion 272 may have a second radius of curvature $R_2$, the third transition portion 273 may have a third radius of curvature $R_3$, and the fourth transition portion 274 may have a fourth radius of curvature $R_4$. In some embodiments, as shown, the first radius of curvature $R_1$ may be equal to the second radius of curvature $R_2$, the third radius of curvature $R_3$ may be equal to the fourth radius of curvature $R_4$, and the first radius of curvature $R_1$ may be different than the third radius of curvature $R_3$.

In some embodiments, as shown, the first radius of curvature $R_1$ may be greater than each of the third radius of curvature $R_3$ and the fourth radius of curvature $R_4$, and the second radius of curvature $R_2$ may be greater than each of the third radius of curvature $R_3$ and the fourth radius of curvature $R_4$. It will be understood that such relationships between the radii of curvature of the transition portions 271, 272, 273, 274 may facilitate clockwise rotation of the device 200 (when viewed from the second end 202 of the device 200) by ninety (90) degrees about the longitudinal axis $A_L$ of the device 200 from the insertion orientation to the implantation orientation within the intervertebral space IS, and may inhibit further clockwise rotation (i.e., rotation beyond ninety degrees) of the device 200 beyond the implantation orientation.

In other embodiments, the first radius of curvature $R_1$ may be less than each of the third radius of curvature $R_3$ and the fourth radius of curvature $R_4$, and the second radius of curvature $R_2$ may be less than each of the third radius of curvature $R_3$ and the fourth radius of curvature $R_4$. It will be understood that such relationships between the radii of curvature of the transition portions 271, 272, 273, 274 may facilitate counter clockwise rotation of the device 200 (when viewed from the second end 202 of the device 200) by ninety (90) degrees about the longitudinal axis $A_L$ of the device 200 from the insertion orientation to the implantation orientation within the intervertebral space IS, and may inhibit further counter clockwise rotation (i.e., rotation beyond ninety degrees) of the device 200 beyond the implantation orientation.

As described above, upon rotation of the interbody device 200 within the intervertebral space IS from the insertion orientation to the implantation orientation, respective portions of the third side 205 and the fourth side 206 of the device 200 each may engage one of the adjacent vertebrae $V_1$, $V_2$. As shown, an overall distance D between the third side 205 and the fourth side 206 of the interbody device 200 in the direction of the second transverse axis $A_{T2}$ (which also may be referred to as an "overall height" of the interbody device 200 when the device 200 is in the implantation orientation, or simply an "overall implantation height") may be constant or substantially constant along at least a portion of the length L of the device 200 in the direction of the longitudinal axis $A_L$. In particular, the overall distance D between the third side 205 and the fourth side 206 of the interbody device 200 may be constant or substantially constant along at least a majority of the length L of the device 200. In this manner, as shown, the interbody device 200 may have a third overall distance $D_3$ (which also may be referred to as a "constant overall distance" or a "constant overall height") between the third side 205 and the fourth side 206 of the device 200, which may be constant or substantially constant along at least a majority of the length L of the device 200. In some embodiments, as shown, the region of the constant or substantially constant third overall distance $D_3$ may extend along the entire length L of the device 200 from the first end 201 to the second end 202 of the device 200. In other embodiments, the region of the constant or substantially constant third overall distance $D_3$ may extend along only a portion of the length L of the device 200. It will be understood that the constant or substantially constant nature of the overall distance D between the third side 205 and the fourth side 206 of the interbody device 200 along at least a majority of the length L of the device 200 may facilitate realignment of the adjacent vertebrae $V_1$, $V_2$ such that the vertebrae $V_1$, $V_2$ follow the normal curvature of the spine. For example, when the interbody device 200 is implanted in the lumbar region of the spine, the constant or substantially constant nature of the overall distance D between the third side 205 and the fourth side 206 of the device 200 may provide correction of lordosis, the normal inward curvature of the lumbar region.

Herein, use of the term "overall distance" with respect to the third side 205 and the opposite fourth side 206 of the interbody device 200 at a particular location along the length L of the device 200 in the direction of the longitudinal axis $A_L$ refers to a distance in the direction of the second transverse axis $A_{T2}$ between a portion of the third side 205 positioned furthest from the longitudinal axis $A_L$ in the direction of the second transverse axis $A_{T2}$ at the particular location along the length L of the device 200 and a portion of the fourth side 206 positioned furthest from the longitudinal axis $A_L$ in the direction of the second transverse axis $A_{T2}$ at the particular location along the length L of the device 200. As described above, in some embodiments, as shown, the third side 205 of the device 200 may be defined by a portion of the third side 215 of the main body 210 and a portion of the third side 225 of the arm 120, and the fourth side 206 of the device 200 may be defined by a portion of the fourth side 216 of the main body 210 and a portion of the fourth side 226 of the arm 220. According to the illustrated embodiment, at locations along the length L of the device 200, the overall distance D between the third side 205 and the fourth side 206 of the device 200 may be defined by the third side 215 and the fourth side 216 of the main body 210.

The interbody device 200 may include a number of features that cooperate with one another and mating features of an instrument system, such as the instrument system 300 described below, to facilitate expansion of the device 200 from the compact configuration to the expanded configuration within the intervertebral space IS. In particular, the main body 210 may include a port 281 (which also may be referred to as a "hole" or a "thru hole") defined in the second end 212 of the main body 210 and extending distally from the second end 212 toward the first end 211 of the main body 210. As shown, the port 281 may be spaced apart from each of the first side 213, the second side 214, the third side 215, and the fifth side 216 of the main body 210. Additionally, the port 281 may be spaced apart from each of the first recess 241, the second recess 242, and the third recess 243 of the main body 210. As shown, the port 281 may have a cylindrical shape and a circular cross-sectional shape when viewed from an end of the port 281. The port 281 may define a longitudinal axis $A_{LP}$, which may extend parallel to the longitudinal axis $A_L$ (and perpendicular to the first transverse axis $A_{T1}$ and the second transverse axis $A_{T2}$) of the interbody device 200. The main body 210 also may include a channel 282 defined therein and in direct communication with the port 281. As shown, the channel 282 may be positioned adjacent to the port 281 and distally with respect to the port 281. In other words, the proximal end of the channel 282 may be positioned adjacent to the distal end of the port 281. As shown, the channel 282 may extend distally from the port 281 toward the first end 211 of the main body 210. The channel 282 may include a straight portion 283 and a ramped portion 284. The straight portion 283 may be positioned adjacent to the port 281 and may extend in a straight (i.e., linear) manner parallel to the longitudinal axis $A_L$ of the interbody device 200. The ramped portion 284 may be positioned adjacent to the straight portion 283 and distally therefrom and may extend in a ramped manner away from the second side 214 and toward the first side 213 of the main body 210. In some embodiments, as shown, the ramped portion 284 may have a curved shape extending away from the second side 214 and toward the first side 213 of the main body 210. In other embodiments, the ramped portion 284 may have a flat shape extending away from the second side 214 and toward the first side 213 of the main body 210.

As shown, when the interbody device 200 is in the compact configuration, the hinge tab 235 of the arm 220 may be positioned at least partially within the channel 282 at or near the distal end of the port 281. In particular, an actuator portion 285 (which also may be referred to as a "keel") of the hinge tab 235 may be positioned within the channel 282 at or near the distal end of the port 281. During implantation of the interbody device 200, the device 200 may be expanded from the compact configuration to the expanded configuration by inserting a mating feature of an instrument into the port 281 and advancing the mating feature distally through the port 281 and at least partially through the channel 282. As the mating feature is advanced in this manner, the mating feature may contact and move the actuator portion 285 of the hinge tab 235 at least partially out of the channel 282, thereby causing the arm 220 to pivot with respect to the main body 210 about the rotational axis $A_R$ of the hinge connection 228 from the compact position to the expanded position. The degree of expansion of the interbody device 200 may be determined by the extent to which the mating feature is advanced through the channel 282. In some embodiments, the arm 220 may be configured to pivot about the rotational axis $A_R$ of the hinge connection 228 until the hinge tab 235 contacts the hinge recess 233. In this manner, the hinge tab 235 and the hinge recess 233 may be configured to limit a maximum degree of expansion of the interbody device 200.

As described above, upon expansion of the interbody device 200 within the intervertebral space IS, respective portions of the third side 225 and the fourth side 226 of the arm 220 each may engage one of the adjacent vertebrae $V_1$, $V_2$. As shown, an overall distance D between the third side 225 and the fourth side 226 of the arm 220 in the direction of the second transverse axis $A_{T2}$ (which also may be referred to as an "overall height" of the arm 220 when the device 200 is in the implantation orientation, or simply an "overall implantation height") may be constant or substantially constant along at least a portion of the length L of the arm 220 in the direction of the longitudinal axis $A_L$ of the device 200. In particular, the overall distance D between the third side 225 and the fourth side 226 of the arm 220 may be constant or substantially constant along at least a majority of the length L of the arm 220. In this manner, as shown, the arm 220 may have a fourth overall distance $D_4$ (which also may be referred to as a "constant overall distance" or a "constant overall height") between the third side 225 and the fourth side 226 of the arm 220, which may be constant or substantially constant along at least a majority of the length L of the arm 220. In some embodiments, as shown, the region of the constant or substantially constant fourth overall distance $D_4$ between the third side 225 and the fourth side 226 of the arm 220 may extend along the length L of the arm 220 from a first location positioned at or near the first end 221 of the arm 220 to a second location positioned adjacent to or near the hinge tab 235 of the arm 220. It will be understood that the constant or substantially constant nature of the overall distance D between the third side 225 and the fourth side 226 of the arm 220 along at least a majority of the length L of the arm 220 may provide desired support of the posterior portions of the adjacent vertebrae $V_1$, $V_2$ when the interbody device 200 is in the expanded configuration within the intervertebral space IS.

Herein, use of the term "overall distance" with respect to the third side 225 and the opposite fourth side 226 of the arm 220 at a particular location along the length L of the arm 220 in the direction of the longitudinal axis $A_L$ of the interbody device 200 refers to a distance in the direction of the second transverse axis $A_{T2}$ between a portion of the third side 225 positioned furthest from the longitudinal axis $A_L$ in the direction of the second transverse axis $A_{T2}$ at the particular location along the length L of the arm 220 and a portion of the fourth side 226 positioned furthest from the longitudinal axis $A_L$ in the direction of the second transverse axis $A_{T2}$ at the particular location along the length L of the arm 220.

Certain relationships between the first overall distance $D_1$, the second overall distance $D_2$, the third overall distance $D_3$, and the fourth overall distance $D_4$ may facilitate implantation of the interbody device 200 within the intervertebral space IS as well as use of the device 200 to restore and maintain normal spacing of the adjacent vertebrae $V_1$, $V_2$ and to realign the adjacent vertebrae $V_1$, $V_2$ such that the vertebrae $V_1$, $V_2$ follow the normal curvature of the spine. In some embodiments, as shown, the first overall distance $D_1$ may be less than the second overall distance $D_2$, which may ease initial insertion of the interbody device 200 into the intervertebral space IS and may facilitate gradual distraction of the intervertebral space IS as the device 200 is fully inserted therein. In some embodiments, as shown, the fourth overall distance $D_4$ may be equal to the third overall distance $D_3$, which may provide desired support of the posterior portions of the adjacent vertebrae $V_1$, $V_2$ when the interbody device 200 is in the expanded configuration within the intervertebral space IS. In some embodiments, the fourth overall distance $D_4$ may be less than the third overall distance $D_3$, which may facilitate expansion of the interbody device 200 from the compact configuration to the expanded configuration and may provide desired support of the posterior portions of the adjacent vertebrae $V_1$, $V_2$ when the interbody device 200 is in the expanded configuration within the intervertebral space IS. In some embodiments, as shown, the third overall distance $D_3$ may be less than the second overall distance $D_2$, which may cause the interbody device 200 to over-distract the posterior portion of the intervertebral space IS upon insertion of the device 200 therein and may facilitate rotation of the device 200 from the insertion orientation to the implantation orientation within the intervertebral space IS.

In some embodiments, as shown, the overall distances may have the following relationships: the first overall distance $D_1$ may be less than each of the second overall distance $D_2$, the third overall distance $D_3$, and the fourth overall distance $D_4$; the second overall distance $D_2$ may be greater than each of the first overall distance $D_1$, the third overall distance $D_3$, and the fourth overall distance $D_4$; the third overall distance $D_3$ may be less than the second overall distance $D_2$, greater than the first overall distance $D_1$, and equal to the fourth overall distance $D_4$; and the fourth overall distance $D_4$ may be less than the second overall distance $D_2$, greater than the first overall distance $D_1$, and equal to the third overall distance $D_3$.

The interbody device 200 may include a number of features that cooperate with the vertebrae $V_1$, $V_2$ to maintain an implanted position of the device 200 within the intervertebral space IS (i.e., to prevent migration of the device 200 within the intervertebral space IS). In particular, the main body 210 may include a first plurality of teeth 291 (which also may be referred to as "ridges") positioned along the third side 215 of the main body 210, and a second plurality of teeth 292 (which also may be referred to as "ridges") positioned along the fourth side 216 of the main body 210. As shown, the first plurality of teeth 291 and the second plurality of teeth 292 each may extend along a majority of the length L of the main body 210. In a similar manner, the arm 220 may include a third plurality of teeth 293 (which also may be referred to as "ridges") positioned along the third side 225 of the arm 220, and a fourth plurality of teeth 294 (which also may be referred to as "ridges") positioned along the fourth side 226 of the arm 220. As shown, the third plurality of teeth 293 and the fourth plurality of teeth 294 each may extend along a majority of the length L of the arm 220.

As shown, each of the teeth 291, 292, 293, 294 may extend perpendicular to the longitudinal axis $A_L$ and the second transverse axis $A_{T2}$ (and parallel the first transverse axis $A_{T1}$) of the interbody device 200. In other words, each of the teeth 291, 292, 293, 294 may have a length extending perpendicular to the longitudinal axis $A_L$ and the second transverse axis $A_{T2}$ (and parallel the first transverse axis $A_{T1}$) of the interbody device 200 and a width extending parallel to the longitudinal axis $A_L$ (and perpendicular to first transverse axis $A_{T1}$ and the second transverse axis $A_{T2}$) of the interbody device 200. As shown, each of the teeth 291, 292, 293, 294 may have a generally V-shaped cross-sectional shape when viewed from the first side 203 and the second side 204 of the interbody device 200. In particular, each of the teeth 291, 292, 293, 294 may have a distal face and a proximal face that meet at an edge of the tooth 291, 292, 293, 294. As shown, the distal face of the tooth 291, 292, 293, 294 may be angled inward toward the longitudinal axis $A_L$ of the interbody device 200 in a direction from the second end 202 toward the first end 201 of the device 200, and the proximal face of the tooth 291, 292, 293, 294 may be oriented perpendicular to the longitudinal axis $A_L$ of the device 200.

As shown, the first plurality of teeth 291 may include a distal-most tooth 295 (i.e., a tooth positioned closest to the first end 211 of the main body 210), the second plurality of teeth 292 may include a distal-most tooth 296 (i.e., a tooth positioned closest to the first end 211 of the main body 210), the third plurality of teeth 293 may include a distal-most tooth 297 (i.e., a tooth positioned closest to the first end 221 of the arm 220), and the fourth plurality of teeth 294 may include a distal-most tooth 298 (i.e., a tooth positioned closest to the first end 221 of the arm 220). In some embodiments, as shown, the distal-most tooth 295 of the third side 215 of the main body 210 may be positioned distally with respect to the distal-most tooth 297 of the third side 225 of the arm 220 along the length L of the interbody device 200. In other embodiments, the distal-most tooth 295 of the third side 215 of the main body 210 may be aligned with the distal-most tooth 297 of the third side 225 of the arm 220 along the length L of the interbody device 200. In some embodiments, as shown, the distal-most tooth 296 of the fourth side 216 of the main body 210 may be positioned distally with respect to the distal-most tooth 298 of the fourth side 226 of the arm 220 along the length L of the interbody device 200. In other embodiments, the distal-most tooth 296 of the fourth side 216 of the main body 210 may be aligned with the distal-most tooth 298 of the fourth side 226 of the arm 220 along the length L of the interbody device 200.

During implantation of the interbody device 200, the teeth 291, 292, 293, 294 may engage and grip the adjacent vertebrae $V_1$, $V_2$. In particular, the teeth 291, 292 of the main body 210 may engage and grip the adjacent vertebrae $V_1$, $V_2$ upon rotation of the interbody device 200 from the insertion orientation to the implantation orientation. In some embodiments, the teeth 293, 294 of the arm 220 may engage and grip the adjacent vertebrae $V_1$, $V_2$ upon rotation of the interbody device 200 from the insertion orientation to the implantation orientation. In some embodiments, the teeth 293, 294 of the arm 220 subsequently may engage and grip the adjacent vertebrae $V_1$, $V_2$ upon expansion of the interbody device 200 from the compact configuration to the expanded configuration. It will be understood that the engagement between the teeth 291, 292, 293, 294 and the adjacent vertebrae $V_1$, $V_2$ may maintain the interbody device 200 in a desired position within the intervertebral space IS (i.e., prevent migration of the device 200 within the intervertebral space IS). Additionally, the engagement between the teeth 291, 292, 293, 294 and the adjacent vertebrae $V_1$, $V_2$ may maintain the interbody device 200 in a desired expansion state (i.e., prevent the arm 220 from moving with respect to the main body 210). In some embodiments, the third side 215 and the fourth side 216 of the main body 210 and/or the third side 225 and the fourth side 226 of the arm 220 may include other forms of texturing (other than teeth) along the surfaces thereof for engaging and gripping the vertebrae $V_1$, $V_2$, as well as promoting bone growth along and/or into such surfaces, upon implantation of the device 200.

As described above, upon expansion of the interbody device 200 within the intervertebral space IS, the main body 210 and the arm 220 may define the cavity 240 therebetween, and bone graft or a bone graft substitute may be placed within the cavity 240 to promote fusion between the adjacent vertebrae $V_1$, $V_2$. The interbody device 200 may include a number of features that facilitate delivery of the bone graft or bone graft substitute to the cavity 240. In particular, the port 281 and the channel 282 may be used to deliver the bone graft or bone graft substitute to the cavity 240. As described above, when the interbody device 200 is expanded from the compact configuration to the expanded configuration, the actuator portion 285 of the hinge tab 235 may move at least partially out of the channel 282. Accordingly, the port 281 and the channel 282 may provide a pathway for delivering the bone graft or bone graft substitute through the proximal portion of the interbody device 200 and into the cavity 240. An instrument system, such as the instrument system 300 described below, may be used to advance the bone graft or bone graft substitute through the port 281 and the channel 282 and into the cavity 240.

The interbody device 200 may be formed of various biocompatible materials. In some embodiments, the main body 210 and the arm 220 may be formed of polyether ether ketone (PEEK), although other suitable polymers may be used. In some embodiments, the main body 210 and the arm 220 may be formed of titanium, although other suitable metals may be used. In some embodiments, the pin 230 may be formed of stainless steel, although other suitable metals or polymers may be used. In some embodiments, the main body 210 and/or the arm 220, or at least portions thereof, may be formed of a porous material configured to facilitate bone growth therein.

Instrument Systems for Implantation of Expandable Interbody Devices

FIGS. 3A-3F illustrate an instrument system 300 (which also may be referred to simply as an "instrument") for implantation of an expandable interbody device, according to one or more embodiments of the disclosure. In particular, the instrument system 300 may be configured for inserting and positioning the expandable interbody device in an intervertebral space, rotating the interbody device within the intervertebral space, expanding the interbody device within the intervertebral space, and delivering bone graft or a bone graft substitute into a cavity of the expanded interbody device. The instrument system 300 may be configured for use with the expandable interbody device 100 and the expandable interbody device 200 described above. FIGS. 3G-3L illustrate use of the instrument system 300 with the expandable interbody device 100 and how certain features of the instrument system 300 interact with mating features of the interbody device 100. It will be understood that the instrument system 300 may be used in a similar manner with the expandable interbody device 200.

The instrument system 300 may have an elongated shape defining a longitudinal axis $A_{IS}$. As shown, the instrument system 300 may include a handle 310, an inner tube 320, an outer tube 340, an expansion plunger 350, a cap 370, a bone graft tube 380, and a bone graft plunger 390. As described below, certain portions of the handle 310, the inner tube 320, the outer tube 340, the expansion plunger 350, the cap 370, the bone graft tube 380, and the bone graft plunger 390 may be configured to cooperate with one another and to interact with an expandable interbody device, such as the expandable interbody device 100 or the expandable interbody device 200, to insert and position the expandable interbody device in an intervertebral space, to rotate the interbody device within the intervertebral space, to expand the interbody device within the intervertebral space, and to deliver bone graft or a bone graft substitute into a cavity of the expanded interbody device. As also described below, certain portions of the handle 310, the inner tube 320, the outer tube 340, the expansion plunger 350, the cap 370, the bone graft tube 380, and the bone graft plunger 390 may be configured to attach to one another during use of the instrument system 300 and to detach from one another after use such that the instrument system 300 may be easily sterilized for subsequent use.

The handle 310 may have an elongated shape extending along a longitudinal axis $A_H$ of the handle 310. When the instrument system 300 is assembled for use, the longitudinal axis $A_H$ of the handle 310 may coincide with the longitudinal axis $A_{IS}$ of the instrument system 300. The handle 310 may include a first end 311 (which also may be referred to as a "distal end") and a second end 312 (which also may be referred to as a "proximal end") disposed opposite the first end 311 in the direction of the longitudinal axis $A_H$ of the handle 310. As shown, the handle 310 may include a body 313 extending along the longitudinal axis $A_H$ from the first end 311 to the second end 312 of the handle 310, and a pair of arms 314 extending radially outward from the body 313 with respect to the longitudinal axis $A_H$. The arms 314 may be positioned at or near the second end 312 of the handle 310. The body 313 may include a first bore 315 defined therein and extending along the longitudinal axis $A_H$ from the first end 311 toward the second end 312 of the handle 310, a second bore 316 defined therein and extending along the longitudinal axis $A_H$ from the second end 312 toward the first end 311 of the handle 310, and a third bore 317 defined therein and extending along the longitudinal axis $A_H$ from the first bore 315 to the second bore 316. The first bore 315, the second bore 316, and the third bore 317 each may have a cylindrical shape and a circular cross-sectional shape, although other shapes may be used. The first bore 315 may have a first diameter, the second bore 316 may have a second diameter, and the third bore 317 may have a third diameter. In some embodiments, as shown, the first diameter may be less than the second diameter and greater than the third diameter. As shown, the handle 310 may include a first plurality of threads 318 positioned at or near the first end 311 of the handle 310, and a second plurality of threads 319 positioned at or near the second end 312 of the handle 310. In some embodiments, as shown, the first plurality of threads 318 may be male threads disposed along an outer surface of the body 313, and the second plurality of threads 319 may be female threads disposed along an inner surface of the body 313. In particular, the second plurality of threads 319 may be disposed along an inner surface of the second bore 316, as shown.

The inner tube 320 may have an elongated shape extending along a longitudinal axis $A_{IT}$ of the inner tube 320. When the instrument system 300 is assembled for use, the longitudinal axis $A_{IT}$ of the inner tube 320 may coincide with the longitudinal axis $A_{IS}$ of the instrument system 300. The inner tube 320 may include a first end 321 (which also may be referred to as a "distal end"), a second end 322 (which also may be referred to as a "proximal end") disposed opposite the first end 321 in the direction of the longitudinal axis $A_{IT}$, and a cannula 323 (which also may be referred to as a "central aperture" or an "aperture") extending through the inner tube 320 along the longitudinal axis $A_{IT}$ from the first end 321 to the second end 322. As shown, the inner tube 320 may include an interbody device interface 324 (which also may be referred to as a "device interface") extending along the longitudinal axis $A_{IT}$ from the first end 321 toward the second end 322 of the inner tube 320, and a tubular body 325 extending from the second end 322 of the inner tube 320 to the interbody device interface 324. The inner tube 320 may be removably attached to the handle 310. In particular, as shown, a proximal portion of the tubular body 325 may be received within the first bore 315 of the handle 310 when the inner tube 320 is attached to the handle 310. The proximal portion of the tubular body 325 may be releasably secured within the first bore 315 via one or more locking mechanisms, such as one or more set screws, clips, latches, or other locking features. In this manner, the inner tube 320 may be axially and rotatably coupled to the handle 310 (i.e., the inner tube 320 may be restrained from axial and rotational movement with respect to the handle 310) such that the inner tube 320 may be positioned and rotated via the handle 310 during use of the instrument system 300, and the inner tube 320 may be separated from the handle 310 for sterilization.

As shown, the interbody device interface 324 may include a plurality of protrusions configured for releasably engaging mating features of an expandable interbody device. In particular, the interbody device interface 324 may include a first protrusion 326, a second protrusion 327, and a third protrusion 328 spaced apart from one another. The first protrusion 326 may be centered with respect to the longitudinal axis $A_{IT}$ of the inner tube 320, and the second protrusion 327 and the third protrusion 328 each may be offset from the longitudinal axis $A_{IT}$. As shown, the first protrusion 326, the second protrusion 327 and the third protrusion 328 each may have a generally rectangular cross-sectional shape. The first protrusion 326 may include an inner surface 329 that is angled inward toward the longitudinal axis $A_{IT}$ of the inner tube 320 in a direction from the second end 322 to the first end 321 of the inner tube 320. In a similar manner, the second protrusion 327 may include an inner surface 330 that is angled inward toward the longitudinal axis $A_{It}$ of the inner tube 320 in the direction from the second end 322 to the first end 321 of the inner tube 320, and the third protrusion 328 may include an inner surface 331 that is angled inward toward the longitudinal axis $A_{IT}$ of the inner tube 320 in the direction from the second end 322 to the first end 321 of the inner tube 320. As shown, when the instrument system 300 is used with the expandable interbody device 100, the protrusions 326, 327, 328 may engage and be received within the respective recesses 141, 142, 143 of the interbody device 100. In particular, the inner surface 329 of the first protrusion 326 may engage the inner surface 144 of the first recess 141, the inner surface 330 of the second protrusion 327 may engage the inner surface 145 of the second recess 142, and the inner surface 331 of the third protrusion 328 may engage the inner surface 146 of the third recess 143. As a result of such engagement between the angled inner surfaces 329, 330, 331 of the protrusions 326, 327, 328 and the angled inner surfaces 144, 145, 146 of the recesses 141, 142, 143, the interbody device 100 may be axially coupled to the interbody device interface 324 (i.e., the interbody device 100 may be restrained from axial movement with respect to the interbody device interface 324). Further, as a result of the multi-point engagement between the protrusions 326, 327, 328 and the recesses 141, 142, 143, the interbody device 100 may be rotatably coupled to the interbody device interface 324 (i.e., the interbody device 100 may be restrained from rotational movement with respect to the interbody device interface 324). In this manner, when the interbody device 100 is attached to the interbody device interface 324, the interbody device 100 may be positioned and rotated via the inner tube 320.

As shown, a distal portion of the inner tube 320 may have a split configuration. In particular, the distal portion of the inner tube 320 may include a first part 332 and a second part 333 that are separated from one another via a slot 334 extending therebetween. As shown, the first part 332 may include the first protrusion 326, and the second part 333 may include the second protrusion 327 and the third protrusion 328. The slot 334 may extend parallel to the longitudinal axis $A_{IT}$ of the inner tube 320. In this manner, the first part 332 and the second part 333 may be configured to deflect away from one another and away from the longitudinal axis $A_{IT}$ of the inner tube 320. Such deflection may facilitate insertion of the protrusions 326, 327, 328 of the interbody device interface 324 into the recesses 141, 142, 143, the interbody device 100. In some embodiments, as shown, the slot 334 may extend axially through the interbody device interface 324 and partially through the tubular body 325 of the inner tube 320. In some embodiments, as shown, the interbody device interface 324 may include one or more reliefs 335 defined therein along the slot 333 to facilitate deflection of the first part 332 and the second part 333 and reduce stress concentrations that may develop therein.

The outer tube 340 may have an elongated shape extending along a longitudinal axis $A_{OT}$ of the outer tube 340. When the instrument system 300 is assembled for use, the longitudinal axis $A_{OT}$ of the outer tube 340 may coincide with the longitudinal axis $A_{IS}$ of the instrument system 300. The outer tube 340 may include a first end 341 (which also may be referred to as a "distal end"), a second end 342 (which also may be referred to as a "proximal end") disposed opposite the first end 341 in the direction of the longitudinal axis $A_{OT}$ of the outer tube 340, and a cannula 343 (which also may be referred to as a "central aperture" or an "aperture") extending through the outer tube 340 along the longitudinal axis $A_{OT}$ from the first end 341 to the second end 342. As shown, the outer tube 340 may include a tapered interface 344 extending along the longitudinal axis $A_{OT}$ from the first end 341 toward the second end 342 of the outer tube 340, a knob 345 extending from the second end 342 toward the first end 341 of the outer tube 340, and a tubular body 346 extending from the tapered interface 344 to the knob 345. The outer tube 340 may include a bore 347 defined therein and extending along the longitudinal axis $A_{OT}$ from the second end 342 toward the first end 341 of the outer tube 340.

The outer tube 340 may be removably attached to the handle 310. In particular, a distal portion of the body 313 of the handle 310 may be received within the bore 347 of the outer tube 340 when the outer tube 340 is attached to the handle 310. The outer tube 340 may include a plurality of threads 348 positioned at or near the second end 342 of the outer tube 340 and configured for releasably engaging the first plurality of threads 318 of the handle 310. In some embodiments, as shown, the plurality of threads 348 may be female threads disposed along an inner surface of the bore 347. The engagement between the threads 348 of the outer tube 340 and the threads 318 of the handle 310 may allow the relative axial position of the outer tube 340 to be adjusted relative to the handle 310 and the inner tube 320 (i.e., the extent of engagement between the threads 348 and the threads 318 may be varied to adjust the axial position of the outer tube 340 relative to the handle 310 and the inner tube 320). In particular, the outer tube 340 may be adjusted between a first position (which also may be referred to as a "distal position" or a "locked position") in which the second end 342 of the outer tube 340 is spaced apart from the body 313 of the handle 310 and the tapered interface 344 of the outer tube 340 engages or is positioned near the interbody device interface 324 of the inner tube 320, and a second position (which also may be referred to as a "proximal position" or an "unlocked position") in which the second end 342 of the outer tube 340 engages or is positioned near the body 313 of the handle 310 and the tapered interface 344 of the outer tube 340 is spaced apart from the interbody device interface 324 of the inner tube 320. When the outer tube 340 is in the first position, the engagement between the tapered interface 344 and the interbody device interface 324 and/or the engagement between a distal portion of the tubular body 346 of the outer tube 340 and a distal portion of the tubular body 325 of the inner tube 320 may limit or prevent the first part 332 and the second part 333 from deflecting away from one another, thereby causing the interbody device 100 attached to the interbody device interface 324 to remain locked to the interbody device interface 324. When the outer tube 340 is in the second position, the spacing between the tapered interface 344 and the interbody device interface 324 and/or the spacing between the distal portion of the tubular body 346 of the outer tube 340 and the distal portion of the tubular body 325 of the inner tube 320 may allow the first part 332 and the second part 333 to deflect away from one another, thereby allowing the interbody device interface 324 to be removed from the attached interbody device 100. After use of the instrument system 300, the outer tube 340 may be removed from the handle 310, following removal of the inner tube 320 from the handle 310, by completely unthreading the threads 348 of the outer tube 340 and the threads 318 of the handle 310.

The expansion plunger 350 may have an elongated shape extending along a longitudinal axis $A_{EP}$ of the expansion plunger 350. When the expansion plunger 350 is used with the handle 310, the inner tube 320, and the outer tube 340, the longitudinal axis $A_{EP}$ of the expansion plunger 350 may coincide with the longitudinal axis $A_{IS}$ of the instrument system 300. The expansion plunger 350 may include a first end 351 (which also may be referred to as a "distal end") and a second end 352 (which also may be referred to as a "proximal end") disposed opposite the first end 351 in the direction of the longitudinal axis $A_{EP}$. As shown, the expansion plunger 350 may include a shaft 353 extending along the longitudinal axis $A_{EP}$ from the first end 351 toward the second end 352 of the expansion plunger 350, and a knob 354 extending from the second end 352 toward the first end 351 of the expansion plunger 350. The shaft 353 may include a first end 355 (which also may be referred to as a "distal end") and a second end 356 (which also may be referred to as a "proximal end") disposed opposite the first end 355 in the direction of the longitudinal axis $A_{EP}$. The knob 354 also may include a first end 357 (which also may be referred to as a "distal end") and a second end 358 (which also may be referred to as a "proximal end") disposed opposite the first end 357 in the direction of the longitudinal axis $A_{EP}$.

The expansion plunger 350 may be configured for advancing at least partially through the handle 310, the inner tube 320, and the outer tube 340 to facilitate expansion of the interbody device 100 attached to the interbody device interface 324. In particular, the shaft 353 may be configured for advancing at least partially through the bores 315, 316, 317 of the handle 310, the cannula 323 of the inner tube 320, and the cannula 343 of the outer tube 340, such that the first end 355 of the shaft 353 advances through the port 181 of the interbody device 100 and engages the actuator portion 185 of the hinge tab 135 of the arm 120. Upon further advancing of the shaft 353 through the handle 310, the inner tube 320, and the outer tube 340, the first end 355 of the shaft 353 may move the actuator portion 185 at least partially out of the channel 182, thereby causing the arm 120 to pivot with respect to the main body 110 from the compact position to the expanded position.

The knob 354 may be configured for advancing at least partially through the second bore 316 of the handle 310 to facilitate advancing of the shaft 353 through the handle 310, the inner tube 320, and the outer tube 340. As shown, the knob 354 may include a plurality of threads 359 positioned at or near the second end 358 of the knob 354 and configured for releasably engaging the second plurality of threads 319 of the handle 310. In some embodiments, as shown, the plurality of threads 359 may be male threads disposed along an outer surface of the knob 354. The engagement between the threads 359 of the knob 354 and the threads 319 of the handle 310 may facilitate advancing of the shaft 353 through the handle 310, the inner tube 320, and the outer tube 340. In particular, the engagement between the threads 359 of the knob 354 and the threads 319 of the handle 310 may provide mechanical advantage for controllably advancing the shaft 353 and thus controllably expanding the interbody device 100.

In some embodiments, as shown, the shaft 353 may be movably attached to the knob 354 of the expansion plunger 350. In particular, the shaft 353 may be configured to translate axially with respect to the knob 354 between an extended position and a retracted position. The knob 354 may include a first bore 360 defined therein and extending along the longitudinal axis $A_{EP}$ of the expansion plunger 350 from the first end 357 toward the second end 358 of the knob 354, and a second bore 361 defined therein and extending along the longitudinal axis $A_{EP}$ from the second end 358 to the first bore 360. As shown, respective portions of the shaft 353 may be movably received within the first bore 360 and the second bore 361 of the knob 354. Translational movement of the shaft 353 relative to the knob 354 may be limited and controlled by a pair of clips 362, 363 and a spring 364 of the expansion plunger 350. The first clip 362 may be attached to an intermediate portion of the shaft 353, and the second clip 363 may be attached at or near the second end 356 of the shaft 353. The spring 364, which may be a coiled compression spring, may be positioned between the first end 357 of the knob 354 and the first clip 362. The spring 364 may be preloaded between the first end 357 of the knob 354 and the first clip 362 such that the spring 364 biases the shaft 353 toward the extended position relative to the knob 354. As shown, the second clip 363 may limit translational movement of the shaft 353 relative to the knob 354 in the extended position. During use of the expansion plunger 350, if the force applied by the first end 355 of the shaft 353 to the actuator portion 185 of the hinge tab 135 exceeds the biasing force provided by the spring 364, upon further advancing of the knob 354 into the second bore 316 of the handle 310, the shaft 353 may move from the extended position toward the retracted position (i.e., the knob 354 and the shaft 353 may translate axially with respect to one another). In this manner, the attachment mechanism between the shaft 353 and the knob 354 may limit the force that may be applied by the first end 355 of the shaft 353 to the actuator portion 185 of the hinge tab 135. In other embodiments, the shaft 353 may be rigidly attached to the knob 354 of the expansion plunger 350.

The cap 370 may have an elongated shape extending along a longitudinal axis $A_C$ of the cap 370. When the cap 370 is used with the handle 310, the inner tube 320, and the outer tube 340, the longitudinal axis $A_C$ of the cap 370 may coincide with the longitudinal axis $A_{IS}$ of the instrument system 300. The cap 370 may include a first end 371 (which also may be referred to as a "distal end") and a second end 372 (which also may be referred to as a "proximal end") disposed opposite the first end 371 in the direction of the longitudinal axis $A_C$ of the cap 370. The cap 370 may be removably attached to the handle 310. In particular, as shown, a distal portion of the cap 370 may be received within the second bore 316 of the handle 310 when the cap 370 is attached to the handle 310. As shown, the cap 370 may include a plurality of threads 373 positioned at or near the first end 371 of the cap 370 and configured for releasably engaging the second plurality of threads 319 of the handle 310. In some embodiments, as shown, the plurality of threads 373 may be male threads disposed along an outer surface of the cap 370. The cap 370 also may include a first bore 374 defined therein and extending along the longitudinal axis $A_C$ of the cap 370 from the first end 371 toward the second end 372 of the cap 370, and a second bore 375 defined therein and extending along the longitudinal axis $A_C$ from the second end 372 to the first bore 371.

The bone graft tube 380 may have an elongated shape extending along a longitudinal axis $A_{BT}$ of the bone graft tube 380. When the bone graft tube 380 is used with the cap 370, the handle 310, the inner tube 320, and the outer tube 340, the longitudinal axis $A_{BT}$ of the bone graft tube 380 may coincide with the longitudinal axis $A_{IS}$ of the instrument system 300. The bone graft tube 380 may include a first end 381 (which also may be referred to as a "distal end"), a second end 382 (which also may be referred to as a "proximal end") disposed opposite the first end 381 in the direction of the longitudinal axis $A_{BT}$ of the bone graft tube 380, and a cannula 383 (which also may be referred to as a "central aperture" or an "aperture") extending through the bone graft tube 380 along the longitudinal axis $A_{BT}$ from the first end 381 to the second end 382. As shown, the bone graft tube 380 may include a tubular body 384 extending along the longitudinal axis $A_{BT}$ from the first end 381 toward the second end 382 of the bone graft tube 380, and an inlet port 385 extending from the second end 382 toward the first end 381 of the bone graft tube 380. In some embodiments, as shown, the tubular body 384 may be rigidly attached to the inlet port 385.

The bone graft tube 380 may be configured for advancing at least partially through the cap 370, the handle 310, the inner tube 320, and the outer tube 340 to facilitate delivery of bone graft or a bone graft substitute into the cavity 140 of the expanded interbody device 100 attached to the interbody device interface 324. In particular, the tubular body 384 may be configured for advancing at least partially through the bores 374, 375 of the cap 370, the bores 315, 316, 317 of the handle 310, the cannula 323 of the inner tube 320, and the cannula 343 of the outer tube 340, such that the first end 381 of the bone graft tube 380 abuts or is positioned near the second end 102 of the interbody device 100 and the cannula 383 of the bone graft tube 380 is in communication with the port 181 of the interbody device 100. The inlet port 385 may be configured for advancing at least partially through the second bore 375 of the cap 370. During use of the bone graft tube 380, bone graft or a bone graft substitute may be inserted within the cannula 383 of the bone graft tube 380 via the inlet port 385, either before or after the bone graft tube 380 is advanced at least partially through the cap 370, the handle 310, the inner tube 320, and the outer tube 340.

The bone graft plunger 390 may have an elongated shape extending along a longitudinal axis $A_{BP}$ of the bone graft plunger 390. When the bone graft plunger 390 is used with the bone graft tube 380, the cap 370, the handle 310, the inner tube 320, and the outer tube 340, the longitudinal axis $A_{BP}$ of the bone graft plunger 390 may coincide with the longitudinal axis $A_{IS}$ of the instrument system 300. The bone graft plunger 390 may include a first end 391 (which also may be referred to as a "distal end") and a second end 392 (which also may be referred to as a "proximal end") disposed opposite the first end 391 in the direction of the longitudinal axis $A_{BP}$. As shown, the bone graft plunger 390 may include a shaft 393 extending along the longitudinal axis $A_{BP}$ from the first end 391 toward the second end 392 of the bone graft plunger 390, and a knob 394 extending along the longitudinal axis $A_{BP}$ from the second end 392 toward the first end 391 of the bone graft plunger 390. The shaft 393 may include a first end 395 (which also may be referred to as a "distal end") and a second end 396 (which also may be referred to as a "proximal end") disposed opposite the first end 395 in the direction of the longitudinal axis $A_{BP}$. The knob 394 also may include a first end 397 (which also may be referred to as a "distal end") and a second end 398 (which also may be referred to as a "proximal end") disposed opposite the first end 397 in the direction of the longitudinal axis $A_{BP}$. The knob 394 also may include a bore 399 defined therein and extending along the longitudinal axis $A_{BP}$ of the instrument system 300 from the first end 397 toward the second end 398 of the knob 394. In some embodiments, as shown, the shaft 393 may be rigidly attached to the knob 394.

The bone graft plunger 390 may be configured for advancing at least partially through the bone graft tube 380, the cap 370, the handle 310, the inner tube 320, and the outer tube 340 to facilitate delivery of bone graft or a bone graft substitute into the cavity 140 of the expanded interbody device 100 attached to the interbody device interface 324. In particular, the shaft 393 may be configured for advancing at least partially through the cannula 383 of the bone graft tube 380, the bores 374, 375 of the cap 370, the bores 315, 316, 317 of the handle 310, the cannula 323 of the inner tube 320, and the cannula 343 of the outer tube 340, such that the first end 395 of the shaft 393 is positioned at or near the second end 102 of the interbody device 100. As the shaft 393 of the bone graft plunger 390 is advanced in this manner, the first end 395 of the shaft 393 may advance the bone graft or bone graft substitute through the cannula 383 of the bone graft tube 380, through the port 181 and the channel 182 of the interbody device 100, and into the cavity 140 between the main body 110 and the arm 120 of the expanded interbody device 100. During such advancement of the shaft 393, the distance between the knob 394 of the bone graft plunger 380 and the cap 370 may serve as an indicator of the amount of bone graft or bone graft substitute that has been delivered into the cavity 140 of the interbody device 100. As shown, the first end 397 of the knob 394 of the bone graft plunger 380 may eventually engage the second end 372 of the cap 370, thereby limiting advancement of the shaft 393 of the bone graft plunger 380 through the cannula 383 of the bone graft tube 380.

Methods for Implanting an Expandable Interbody Device

As described above, the expandable interbody device 100 and the expandable interbody device 200 may be implanted within an intervertebral space IS between a first vertebra $V_1$ and an adjacent second vertebra $V_2$, and the instrument system 300 may be used to facilitate such implantation. Described below are various embodiments of a method for implanting the expandable interbody device 100 during a spinal fusion surgery. It will be understood that the expandable interbody device 200 may be implanted via a similar method.

Generally described, a method for implanting the expandable interbody device 100 during a spinal fusion surgery may include the steps of inserting and positioning the interbody device 100 within the intervertebral space IS, rotating the interbody device 100 about its longitudinal axis $A_L$ within the intervertebral space IS, expanding the interbody device 100 within the intervertebral space IS, and delivering bone graft or a bone graft substitute into the cavity 140 of the expanded interbody device 100.

In some embodiments, the interbody device 100 may be implanted in the lumbar region of the spine (i.e., the adjacent vertebrae $V_1$, $V_2$ may be lumbar vertebrae). In other embodiments, the interbody device 100 may be implanted in the thoracic region or the cervical region of the spine (i.e., the adjacent vertebrae $V_1$, $V_2$ may be thoracic vertebrae or cervical vertebrae). In some embodiments, the interbody device 100 may be implanted via a posterior approach, for example, according to the PLIF technique or the TLIF technique. In other embodiments, the interbody device 100 may be implanted via an anterior approach or a lateral approach. In some embodiments, the interbody device 100 may be implanted along with additional hardware, such as pedicle screws and rods or plates.

Insertion of the interbody device 100 into the intervertebral space IS may be facilitated by the instrument system 300. Initially, the inner tube 320 and the outer tube 340 may be attached to the handle 310 as described above. The outer tube 340 may be moved to the second position relative to the handle 310 and the inner tube 320, and the interbody device 100 may be attached to the interbody device interface 324 of the inner tube 320. In particular, the protrusions 326, 327, 327 of the interbody device interface 324 may engage and be received within the respective recesses 141, 142, 143 of the interbody device 100. The outer tube 340 then may be moved from the second position to the first position relative to the handle 310 and the inner tube 320, such that the interbody device 100 is axially and rotatably coupled to the interbody device interface 324. With the interbody device 100 in the compact configuration, the handle 310 may be manipulated by a user to orient the device 100 in the insertion orientation with respect to the vertebrae $V_1$, $V_2$, insert the device 100 into the intervertebral space IS in the insertion orientation, and position the device 100 within the intervertebral space IS. When the interbody device 100 is in the insertion orientation within the intervertebral space IS, the longitudinal axis $A_L$ and the second transverse axis $A_{T2}$ of the device 100 may extend substantially parallel to the transverse plane of the patient, and the first transverse axis $A_{T1}$ of the device 100 may extend substantially parallel to the sagittal plane and the coronal plane of the patient. In this manner, upon insertion of the interbody device 100 within the intervertebral space IS, respective portions of the first side 103 and the second side 104 of the device 100 each may engage one of the adjacent vertebrae $V_1$, $V_2$.

In some embodiments, when the interbody device 100 is in the insertion orientation within the intervertebral space IS, at least a portion of the first side 103 of the device 100 may engage the first body $B_{V1}$ of the first vertebra $V_1$, and at least a portion of the second side 104 of the device 100 may engage the second body $B_{V2}$ of the second vertebra $V_2$. In other words, in such embodiments, when the interbody device 100 is in the insertion orientation within the intervertebral space IS, the first side 103 of the device 100 is oriented in the caudal direction of the patient, and the second side 104 of the device 100 is oriented in the cephalad direction of the patient. As described above, such insertion orientation may be used when the illustrated embodiment of the interbody device 100 is inserted from the right side of the patient's spine via a posterior approach. According to the illustrated embodiment of the interbody device 100, when the device 100 is in the insertion orientation within the intervertebral space IS, at least a portion of the first side 113 of the main body 110 and at least a portion of the first side 123 of the arm 120 may engage the first body $B_{V1}$ of the first vertebra $V_1$, and at least a portion of the second side 114 of the main body 110 may engage the second body $B_{V2}$ of the second vertebra $V_2$.

In other embodiments, when the interbody device 100 is in the insertion orientation within the intervertebral space IS, at least a portion of the second side 104 of the device 100 may engage the first body $B_{V1}$ of the first vertebra $V_1$, and at least a portion of the first side 103 of the device 100 may engage the second body $B_{V2}$ of the second vertebra $V_2$. In other words, in such embodiments, when the interbody device 100 is in the insertion orientation within the intervertebral space IS, the second side 104 of the device 100 is oriented in the caudal direction of the patient, and the first side 103 of the device 100 is oriented in the cephalad direction of the patient. As described above, such insertion orientation may be used when the illustrated embodiment of the interbody device 100 is inserted from the left side of the patient's spine via a posterior approach. According to the illustrated embodiment of the interbody device 100, when the device 100 is in the insertion orientation within the intervertebral space IS, at least a portion of the second side 114 of the main body 110 may engage the first body $B_{V1}$ of the first vertebra $V_1$, and at least a portion of the first side 113 of the main body 110 and at least a portion of the first side 123 of the arm 120 may engage the second body $B_{V2}$ of the second vertebra $V_2$.

Rotation of the interbody device 100 from the insertion orientation to the implantation orientation within the intervertebral space IS may be facilitated by the instrument system 300. In particular, the handle 310 may be rotated approximately ninety (90) degrees about the longitudinal axis $A_{IS}$ such that interbody device 100 rotates approximately ninety (90) degrees about the longitudinal axis $A_L$ within the intervertebral space IS from the insertion orientation to the implantation orientation. In some embodiments, the device 100 may be rotated clockwise (when viewed from the second end 102 of the device 100) from the insertion orientation to the implantation orientation. In other embodiments, the device 100 may be rotated counter clockwise (when viewed from the second end 102 of the device 100) from the insertion orientation to the implantation orientation. In some embodiments, when the interbody device 100 is in the implantation orientation, the arm 120 is oriented medially with respect to the main body 110. In other embodiments, when the interbody device 100 is in the implantation orientation, the main body 110 is oriented medially with respect to the arm 120. When the interbody device 100 is in the implantation orientation, the longitudinal axis $A_L$ and the first transverse axis $A_{T1}$ of the device 100 may extend substantially parallel to the transverse plane of the patient, and the second transverse axis $A_{T2}$ of the device 100 may extend substantially parallel to the sagittal plane and the coronal plane of the patient. In this manner, upon rotation of the interbody device 100 within the intervertebral space IS from the insertion orientation to the implantation orientation, respective portions of the third side 105 and the fourth side 106 of the device 100 each may engage one of the adjacent vertebrae $V_1$, $V_2$.

In some embodiments, when the interbody device 100 is in the implantation orientation, at least a portion of the third side 105 of the device 100 may engage the first body $B_{V1}$ of the first vertebra $V_1$, and at least a portion of the fourth side 106 of the device 100 may engage the second body $B_{V2}$ of the second vertebra $V_2$. In other words, in such embodiments, when the interbody device 100 is in the implantation orientation within the intervertebral space IS, the third side 105 of the device 100 is oriented in the caudal direction of the patient, and the fourth side 106 of the device 100 is oriented in the cephalad direction of the patient. As described above, such implantation orientation may be used when the interbody device 100 has been inserted from the right side of the patient's spine via a posterior approach. According to the illustrated embodiment of the interbody device 100, when the device 100 is in the implantation orientation within the intervertebral space IS, at least a portion of the third side 115 of the main body 110 may engage the first body $B_{V1}$ of the first vertebra $V_1$, and at least a portion of the fourth side 116 of the main body 110 may engage the second body $B_{V2}$ of the second vertebra $V_2$. Meanwhile, the third side 125 of the arm 120 may be oriented toward but spaced apart from (i.e., not engaging) the first body $B_{V1}$ of the first vertebra $V_1$, and the fourth side 126 of the arm 120 may be oriented toward but spaced apart from the second body $B_{V2}$ of the second vertebra $V_2$.

In other embodiments, when the interbody device 100 is in the implantation orientation, at least a portion of the fourth side 106 of the device 100 may engage the first body $B_{V1}$ of the first vertebra $V_1$, and at least a portion of the third side 105 of the device 100 may engage the second body $B_{V2}$ of the second vertebra $V_2$. In other words, in such embodiments, when the interbody device 100 is in the implantation orientation within the intervertebral space IS, the fourth side 106 of the device 100 is oriented in the caudal direction of the patient, and the third side 105 of the device 100 is oriented in the cephalad direction of the patient. As described above, such implantation orientation may be used when the interbody device 100 has been inserted from the left side of the patient's spine via a posterior approach. According to the illustrated embodiment of the interbody device 100, when the device 100 is in the implantation orientation within the intervertebral space IS, at least a portion of the fourth side 116 of the main body 110 may engage the first body $B_{V1}$ of the first vertebra $V_1$, and at least a portion of the third side 115 of the main body 110 may engage the second body $B_{V2}$ of the second vertebra $V_2$. Meanwhile, the fourth side 126 of the arm 120 may be oriented toward but spaced apart from the first body $B_{V1}$ of the first vertebra $V_1$, and the third side 125 of the arm 120 may be oriented toward but spaced apart from the second body $B_{V2}$ of the second vertebra $V_2$.

Expansion of the interbody device 100 from the compact configuration to the expanded configuration within the intervertebral space IS may be facilitated by the instrument system 300. As described above, the expansion plunger 350 may be advanced at least partially through the handle 310, the inner tube 320, and the outer tube 340. In particular, the shaft 353 may be advanced at least partially through the bores 315, 316, 317 of the handle 310, the cannula 323 of the inner tube 320, and the cannula 343 of the outer tube 340, and the knob 354 may be advanced at least partially through the second bore 316 of the handle 310. In some embodiments, the expansion plunger 350 may be controllably advanced via the threads 359 of the knob 354 and the threads 319 of the handle 310. The first end 355 of the shaft 353 may be advanced through the port 181 of the interbody device 100 and may engage the actuator portion 185 of the hinge tab 135 of the arm 120. Upon further advancing of the shaft 353 through the handle 310, the inner tube 320, and the outer tube 340, the first end 355 of the shaft 353 may move the actuator portion 185 at least partially out of the channel 182, thereby causing the arm 120 to pivot with respect to the main body 110 from the compact position to the expanded position. In some embodiments, the arm 120 may be pivoted medially with respect to the main body 110 about the hinge connection 128 from the compact position to the expanded position. The degree of expansion of the interbody device 100 (i.e., the degree which the arm 120 is pivoted with respect to the main body 110) may be determined by the user, based on the anatomy of the patient and the desired correction of the adjacent vertebrae $V_1$, $V_2$. For example, the device 100 may be expanded by the user such that the arm 120 is pivoted with respect to the main body 110 at an angle greater than zero degrees and up to ninety degrees. Upon expansion of the interbody device 100 within the intervertebral space IS from the compact configuration to the expanded configuration, respective portions of the third side 105 and the fourth side 106 of the device 100 each may engage one of the adjacent vertebrae $V_1$, $V_2$.

In some embodiments, when the interbody device 100 is in the expanded configuration within the intervertebral space IS, at least a portion of the third side 105 of the device 100 may engage the first body $B_{V1}$ of the first vertebra $V_1$, and at least a portion of the fourth side 106 of the device 100 may engage the second body $B_{V2}$ of the second vertebra $V_2$. According to the illustrated embodiment of the interbody device 100, when the device 100 is in the implantation orientation and the expanded configuration within the intervertebral space IS, at least a portion of the third side 115 of the main body 110 and at least a portion of the third side 125 of the arm 120 may engage the first body $B_{V1}$ of the first vertebra $V_1$, and at least a portion of the fourth side 116 of the main body 110 and at least a portion of the fourth side 126 of the arm 120 may engage the second body $B_{V2}$ of the second vertebra $V_2$. In some embodiments, when the interbody device 100 is in the expanded configuration within the intervertebral space IS, the main body 110 may be positioned partially within a posterior portion, such as a posterior half, of the intervertebral space IS and partially within an anterior portion, such as an anterior half, of the intervertebral space IS, and the arm 120 may be positioned entirely within the posterior portion, such as the posterior half, of the intervertebral space IS. In this manner, at least portions of the third side 115 of the main body 110 may engage part of a posterior portion, such as a posterior half, of the first body $B_{V1}$ of the first vertebra $V_1$ and part of an anterior portion, such as an anterior half, of the first body $B_{V1}$ of the first vertebra $V_1$, at least portions of the fourth side 116 of the main body 110 may engage part of a posterior portion, such as a posterior half, of the second body $B_{V2}$ of the second vertebra $V_2$ and part of an anterior portion, such as an anterior half, of the second body $B_{V2}$ of the second vertebra $V_2$, at least a portion of the third side 125 of the arm 120 may engage part of the posterior portion of the first body $B_{V1}$ of the first vertebra $V_1$, and at least a portion of the fourth side 126 of the arm 120 may engage part of the posterior portion of the second body $B_{V2}$ of the second vertebra $V_2$.

In other embodiments, when the interbody device 100 is in the expanded configuration within the intervertebral space IS, at least a portion of the fourth side 106 of the device 100 may engage the first body $B_{V1}$ of the first vertebra $V_1$, and at least a portion of the third side 105 of the device 100 may engage the second body $B_{V2}$ of the second vertebra $V_2$. According to the illustrated embodiment of the interbody device 100, when the device 100 is in the expanded configuration within the intervertebral space IS, at least a portion of the fourth side 116 of the main body 110 and at least a portion of the fourth side 126 of the arm 120 may engage the first body $B_{V1}$ of the first vertebra $V_1$, and at least a portion of the third side 115 of the main body 110 and at least a portion of the third side 125 of the arm 120 may engage the second body $B_{V2}$ of the second vertebra $V_2$. In some embodiments, when the interbody device 100 is in the implantation orientation and the expanded configuration within the intervertebral space IS, the main body 110 may be positioned partially within a posterior portion, such as a posterior half, of the intervertebral space IS and partially within an anterior portion, such as an anterior half, of the intervertebral space IS, and the arm 120 may be positioned entirely within the posterior portion, such as the posterior half, of the intervertebral space IS. In this manner, at least portions of the fourth side 116 of the main body 110 may engage part of a posterior portion, such as a posterior half, of the first body $B_{V1}$ of the first vertebra $V_1$ and part of an anterior portion, such as an anterior half, of the first body $B_{V1}$ of the first vertebra $V_1$, at least portions of the third side 115 of the main body 110 may engage part of a posterior portion, such as a posterior half, of the second body $B_{V2}$ of the second vertebra $V_2$ and part of an anterior portion, such as an anterior half, of the second body $B_{V2}$ of the second vertebra $V_2$, at least a portion of the fourth side 126 of the arm 120 may engage part of the posterior portion of the first body $B_{V1}$ of the first vertebra $V_1$, and at least a portion of the third side 125 of the arm 120 may engage part of the posterior portion of the second body $B_{V2}$ of the second vertebra $V_2$.

Delivery of bone graft or a bone graft substitute into the cavity 140 of the expanded interbody device 100 may be facilitated by the instrument system 300. After expansion of the interbody device 100, the expansion plunger 350 may be removed from the handle 310, the inner tube 320, and the outer tube 340. The cap 370 then may be attached to the handle 310, and the bone graft tube 380 may be advanced at least partially through the cap 370, the handle 310, the inner tube 320, and the outer tube 340. In particular, the tubular body 384 may be advanced at least partially through the bores 374, 375 of the cap 370, the bores 315, 316, 317 of the handle 310, the cannula 323 of the inner tube 320, and the cannula 343 of the outer tube 340, such that the first end 381 of the bone graft tube 380 abuts or is positioned near the second end 102 of the interbody device 100 and the cannula 383 of the bone graft tube 380 is in communication with the port 181 of the interbody device 100, and the inlet port 385 may be advanced at least partially through the second bore 375 of the cap 370. Either before or after such advancement of the bone graft tube 380, bone graft or a bone graft substitute may be inserted within the cannula 383 of the bone graft tube 380. The bone graft plunger 390 then may be advanced at least partially through the bone graft tube 380, the cap 370, the handle 310, the inner tube 320, and the outer tube 340. In particular, the shaft 393 may be advanced at least partially through the cannula 383 of the bone graft tube 380, the bores 374, 375 of the cap 370, the bores 315, 316, 317 of the handle 310, the cannula 323 of the inner tube 320, and the cannula 343 of the outer tube 340. As the shaft 393 of the bone graft plunger 390 is advanced in this manner, the first end 395 of the shaft 393 may advance the bone graft or bone graft substitute through the cannula 383 of the bone graft tube 380, through the port 181 and the channel 182 of the interbody device 100, and into the cavity 140 between the main body 110 and the arm 120 of the expanded interbody device 100.

After delivery of the bone graft or bone graft substitute into the cavity 140 of the expanded interbody device 100, the instrument system 300 may be detached from the device 100 and removed from the patient. In particular, the outer tube 340 may be moved to the second position relative to the handle 310 and the inner tube 320, such that the protrusions 326, 327, 327 of the interbody device interface 324 may disengage and be removed from the respective recesses 141, 142, 143 of the interbody device 100.

Additional aspects of various embodiments of the method for implanting the expandable interbody device 100 will be understood in view of the above description of the interbody device 100 and the instrument system 300 and the corresponding drawings. Ultimately, the implanted interbody device 100, itself or in combination with additional hardware, may provide the structural support necessary to maintain normal spacing and alignment of the adjacent vertebrae $V_1$, $V_2$, and the bone graft or bone graft substitute placed within the cavity 140 of the interbody device 100 may facilitate fusion between the adjacent vertebrae $V_1$, $V_2$.

Expandable Interbody Devices

Figure 4A:
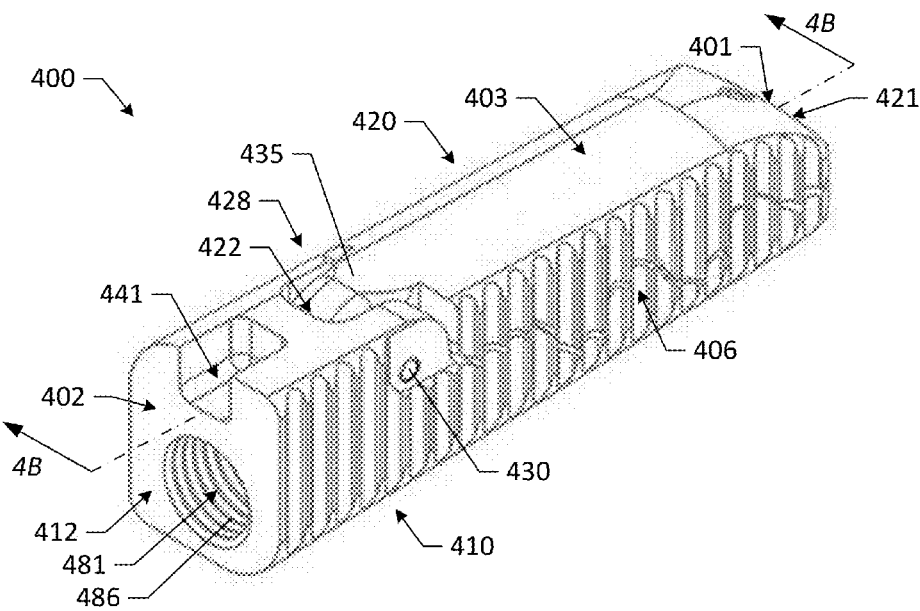
FIG. 4A shows a top perspective view of an expandable interbody device in accordance with one or more embodiments of the present disclosure, the expandable interbody device in a compact configuration.
Figure 4B:
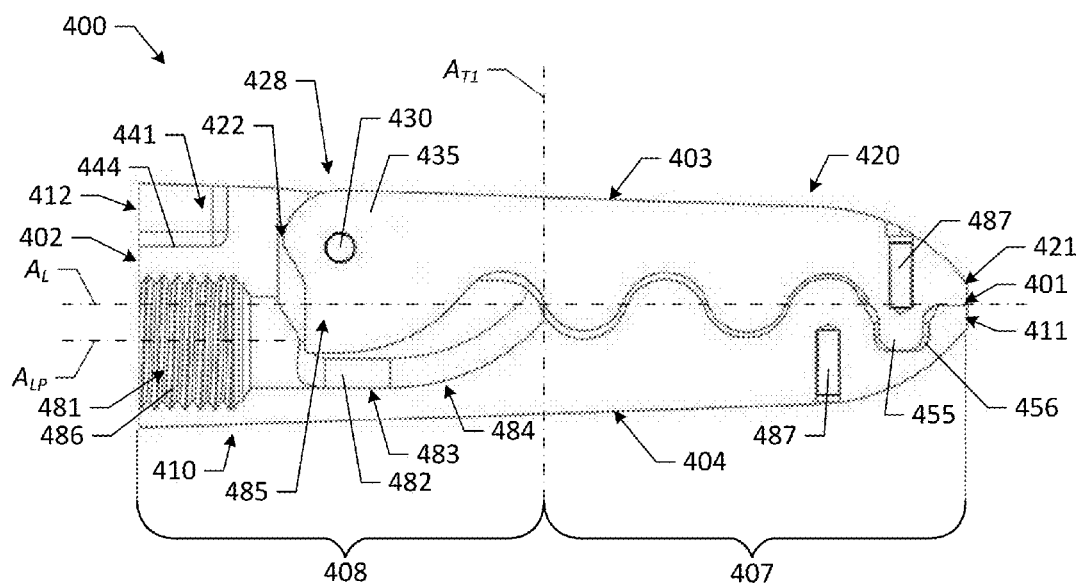
FIG. 4B shows a side cross-sectional view of the expandable interbody device of FIG. 4A in the compact configuration, taken along line 4B-4B of FIG. 4A.
Figure 4C:
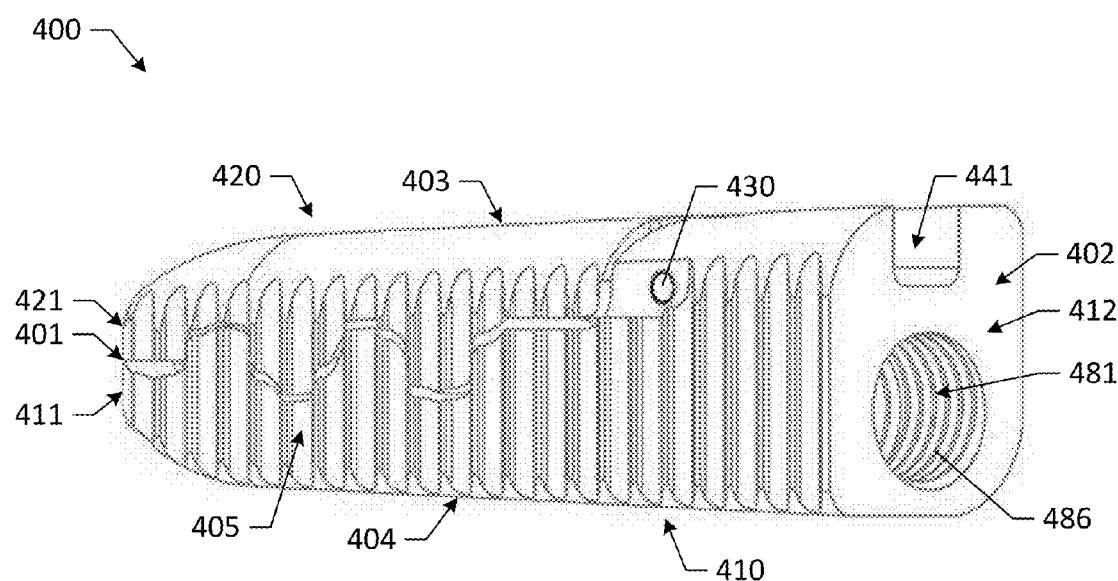
FIG. 4C shows an end perspective view of the expandable interbody device of FIG. 4A in the compact configuration.
Figure 5A:
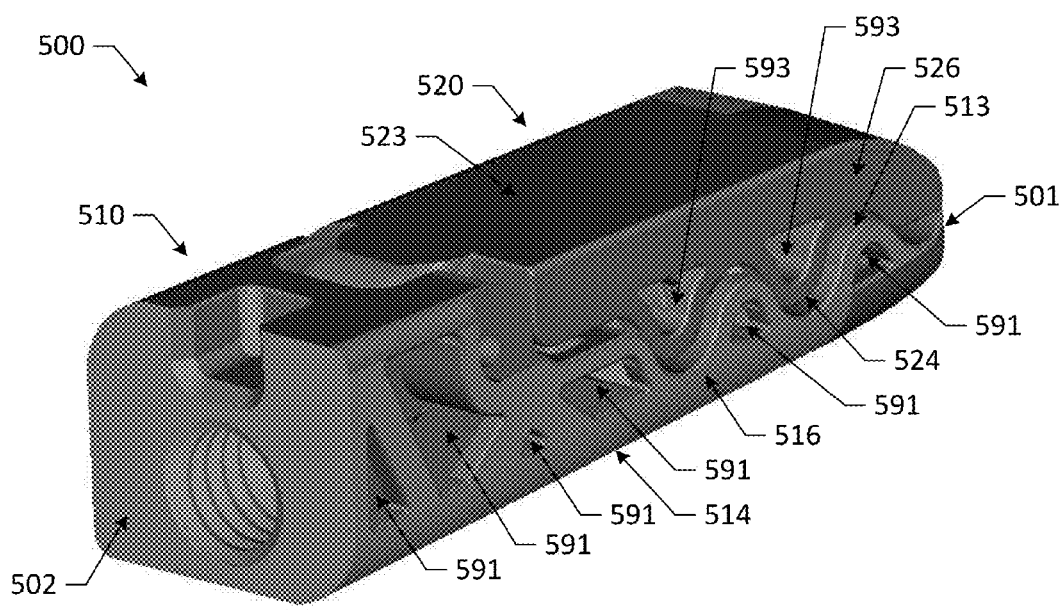
FIG. 5A shows a top perspective view of an expandable interbody device in accordance with one or more embodiments of the present disclosure, the expandable interbody device in a compact configuration.
Figure 5B:
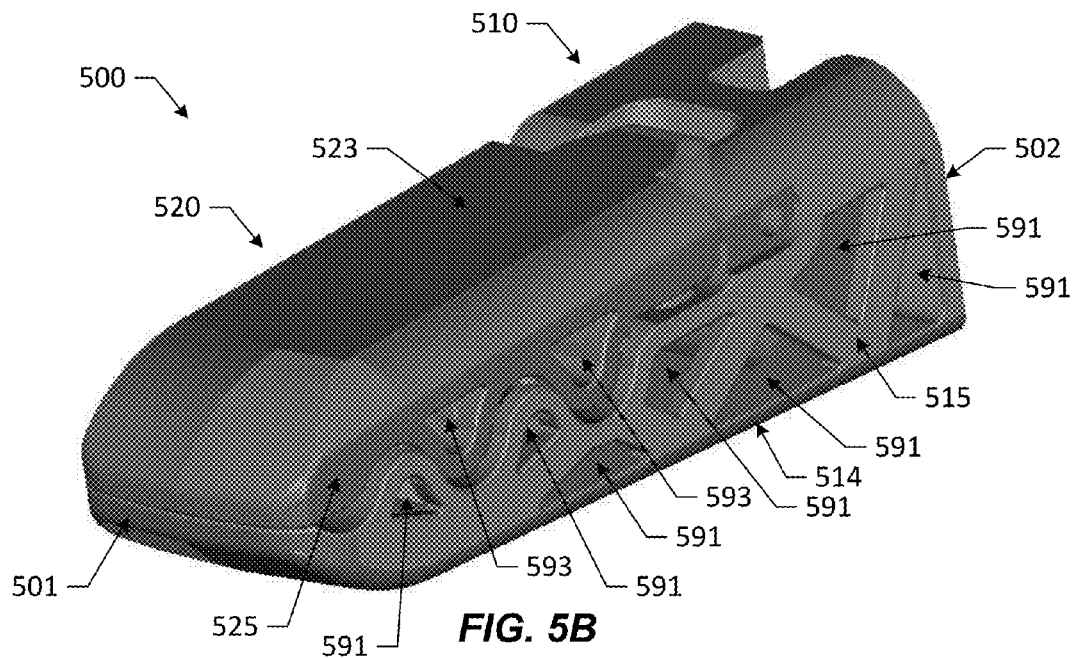
FIG. 5B shows a top perspective view of the expandable interbody device of FIG. 5A in the compact configuration.
Figure 5C:
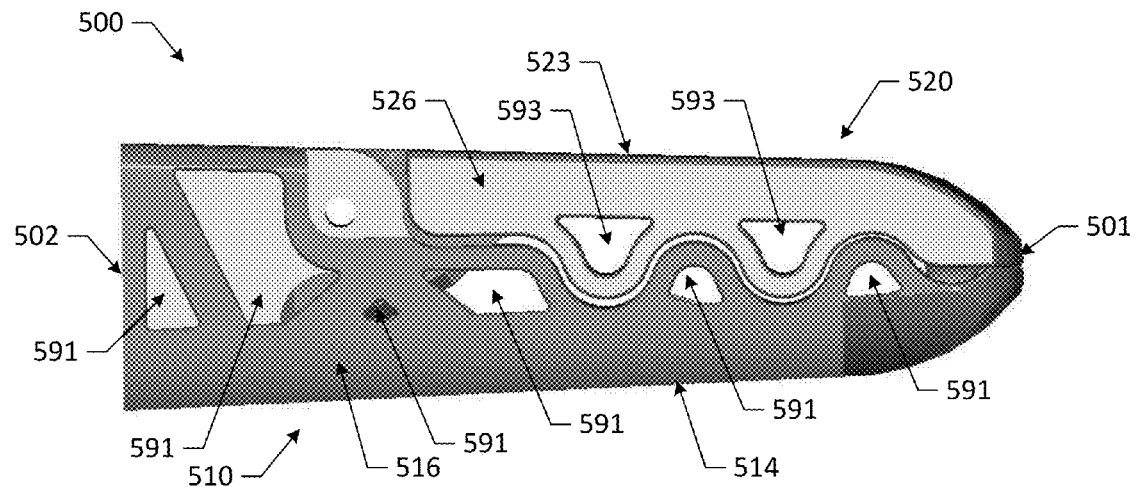
FIG. 5C shows a side view of the expandable interbody device of FIG. 5A in the compact configuration.
Figure 5D:
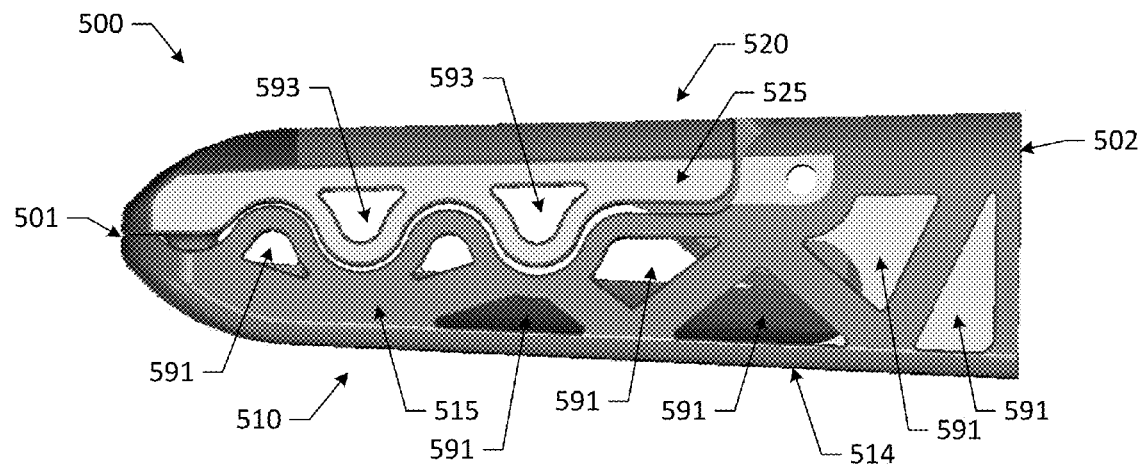
FIG. 5D shows a side view of the expandable interbody device of FIG. 5A in the compact configuration.
Figure 5E:
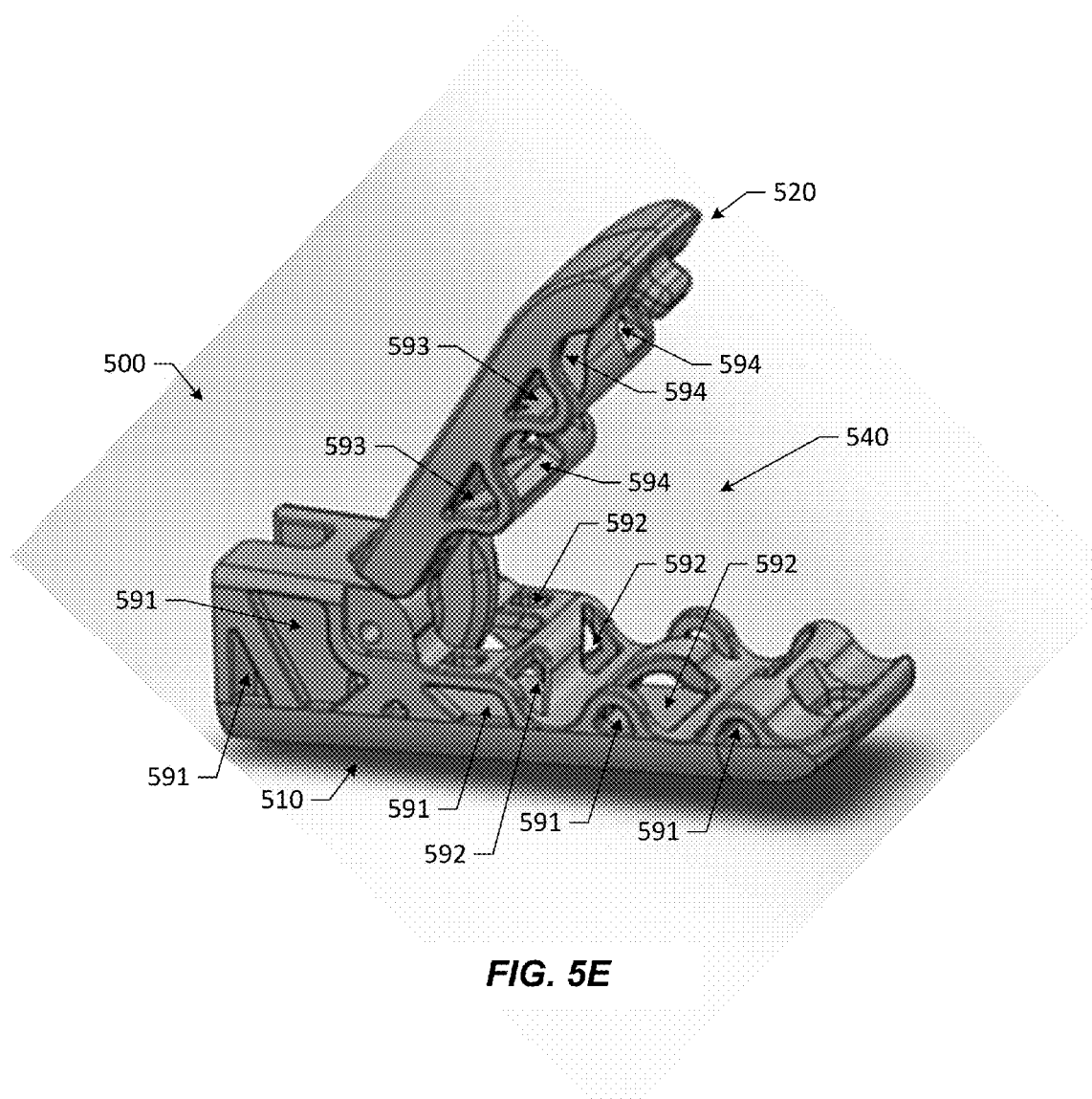
FIG. 5E shows a side perspective view of the expandable interbody device of FIG. 5A in an expanded configuration.
Figure 6A:
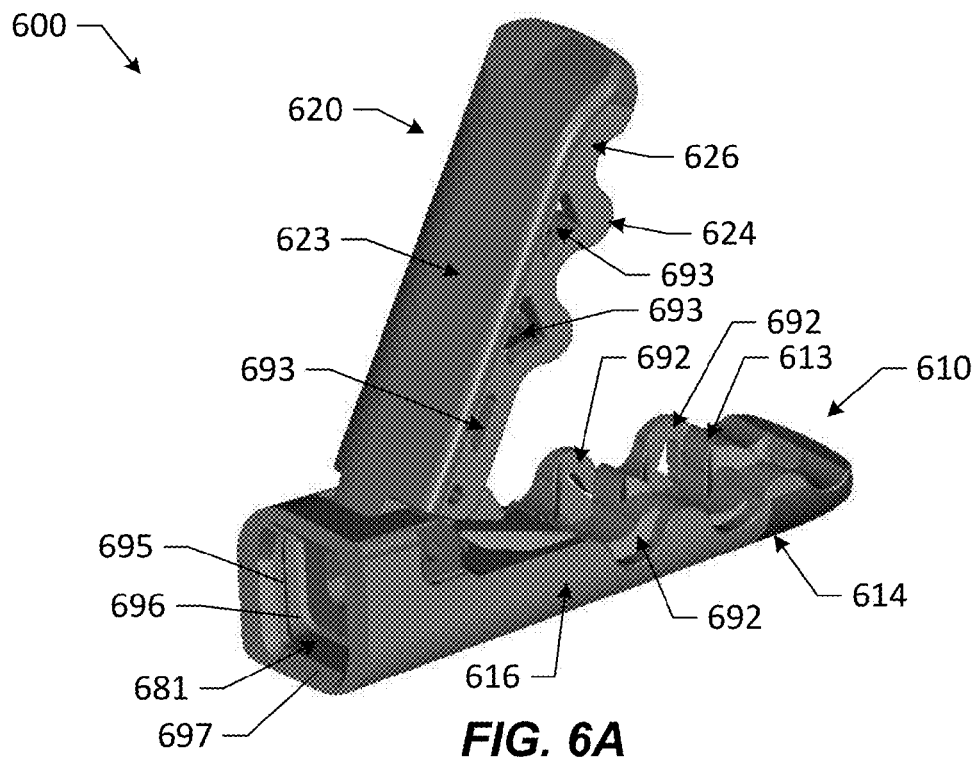
FIG. 6A shows a top perspective view of an expandable interbody device in accordance with one or more embodiments of the present disclosure, the expandable interbody device in an expanded configuration.
Figure 6B:
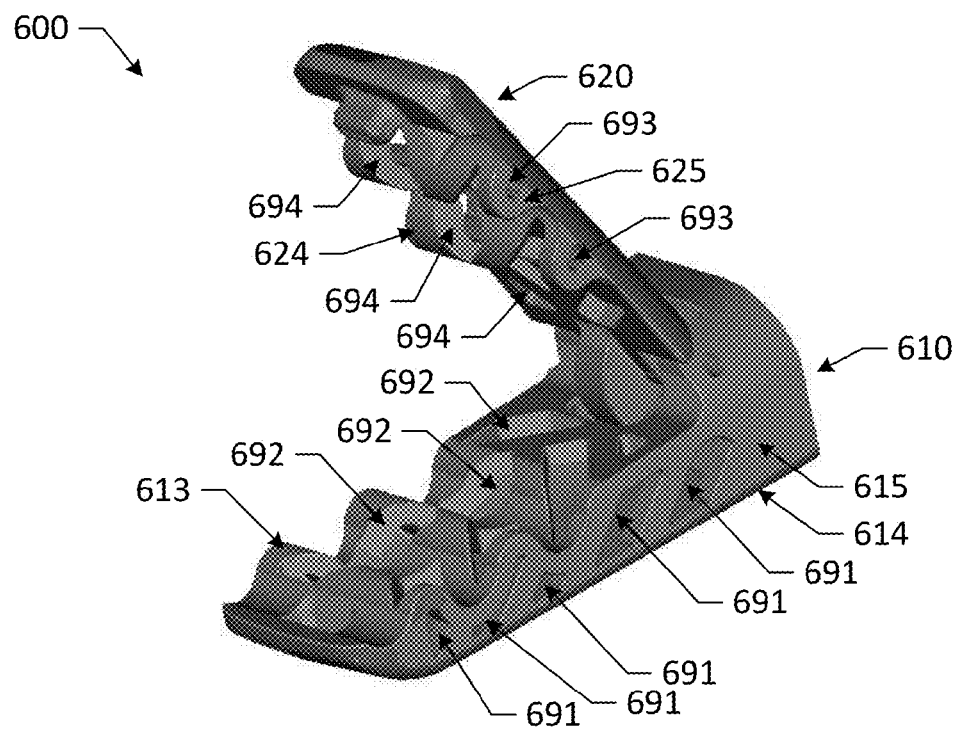
FIG. 6B shows a top perspective view of the expandable interbody device of FIG. 6A in the expanded configuration.
Figure 6C:
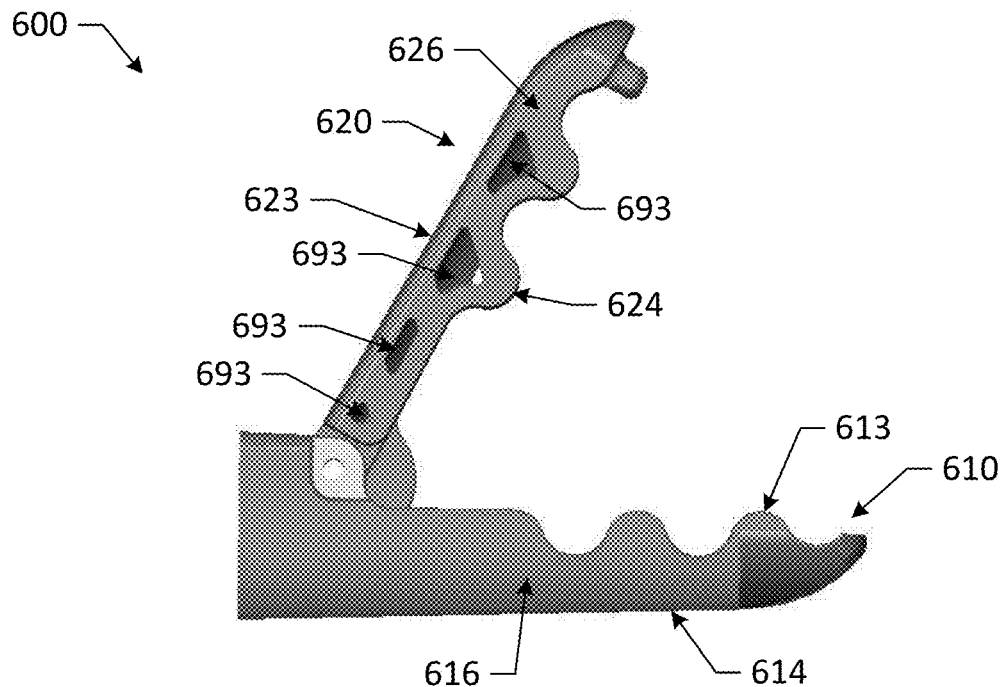
FIG. 6C shows a side view of the expandable interbody device of FIG. 6A in the expanded configuration.
Figure 6D:
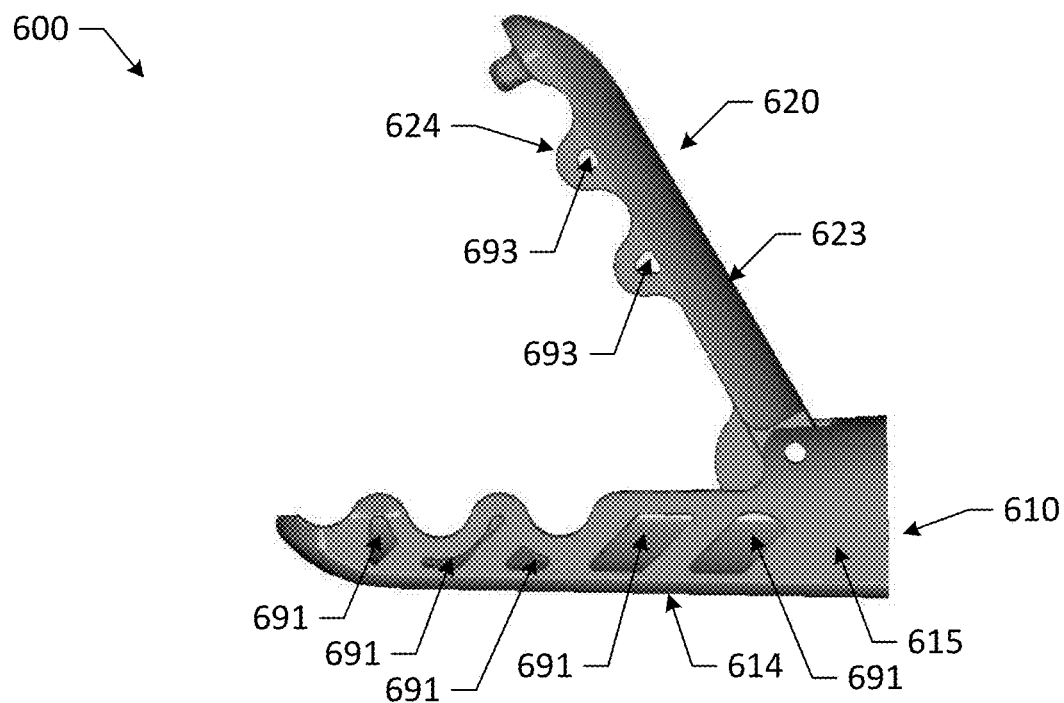
FIG. 6D shows a side view of the expandable interbody device of FIG. 6A in the expanded configuration.
Figures 6E, 6F:
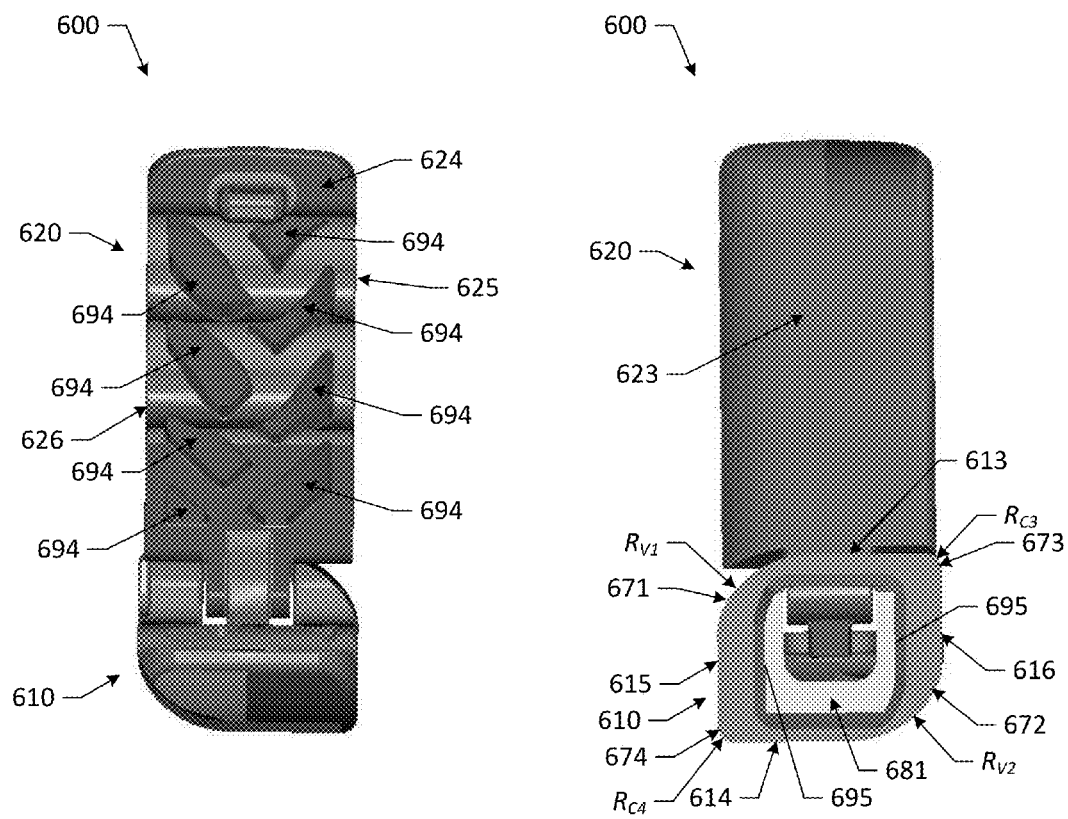
FIG. 6E shows an end view of the expandable interbody device of FIG. 6A in the expanded configuration.
FIG. 6F shows an end view of the expandable interbody device of FIG. 6A in the expanded configuration.
Figure 7A:
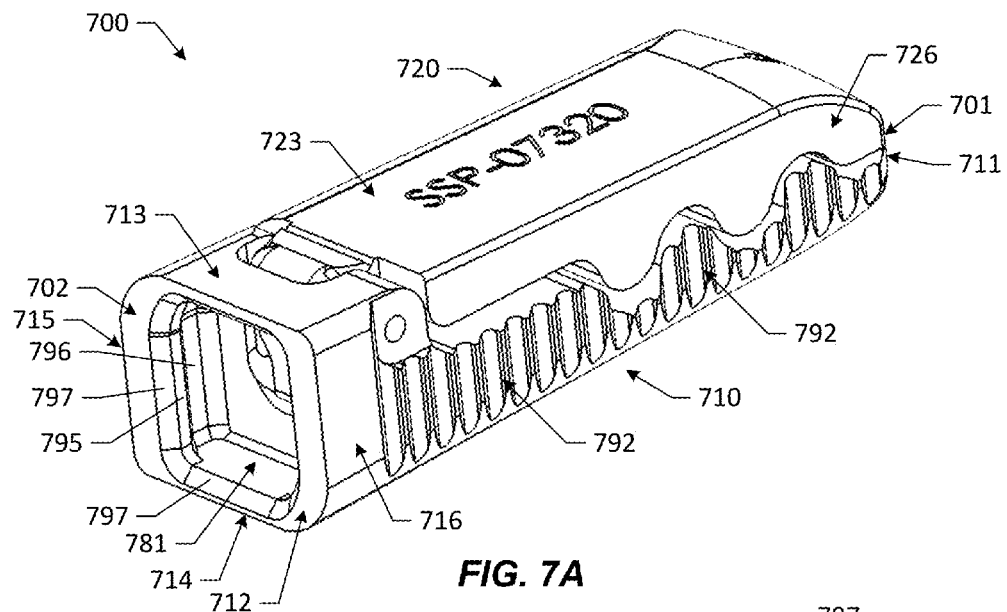
FIG. 7A shows a top perspective view of an expandable interbody device in accordance with one or more embodiments of the present disclosure, the expandable interbody device in a compact configuration.
Figure 7B:
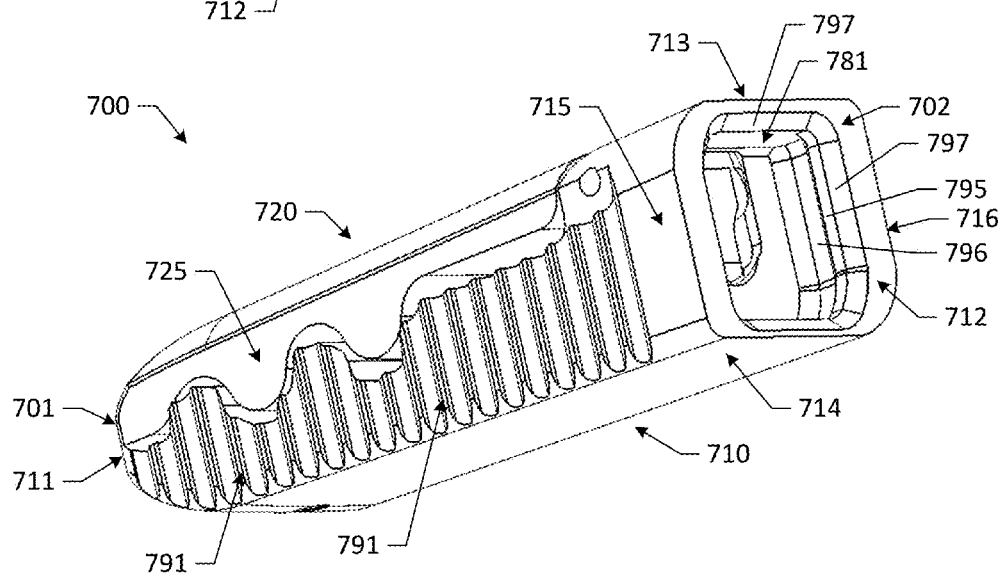
FIG. 7B shows a bottom perspective view of the expandable interbody device of FIG. 7A in the compact configuration.
Figure 7C:
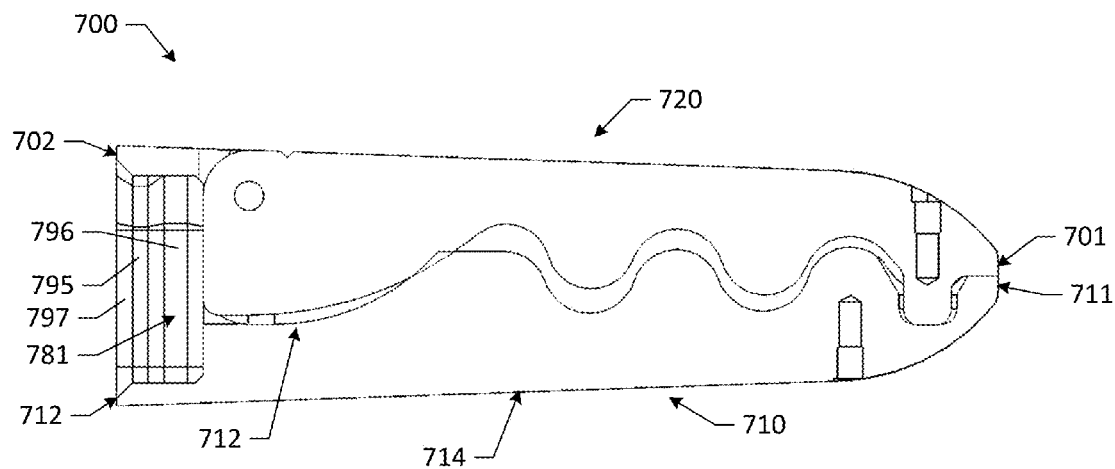
FIG. 7C shows a side cross-sectional view of the expandable interbody device of FIG. 7A in the compact configuration, taken along line 7C-7C of FIG. 7A.
Figure 7D:
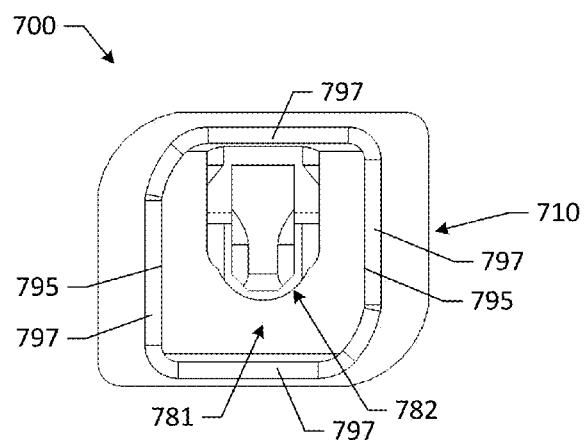
FIG. 7D shows an end view of the expandable interbody device of FIG. 7A in the compact configuration.
Figure 7E:
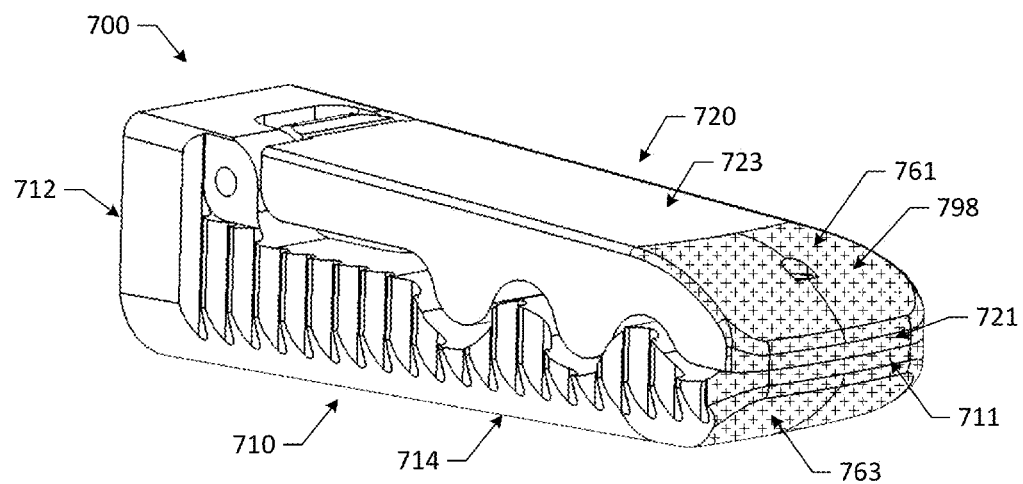
FIG. 7E shows a top perspective view of the expandable interbody device of FIG. 7A in the compact configuration, indicating polished regions of the device.
Figure 7F:
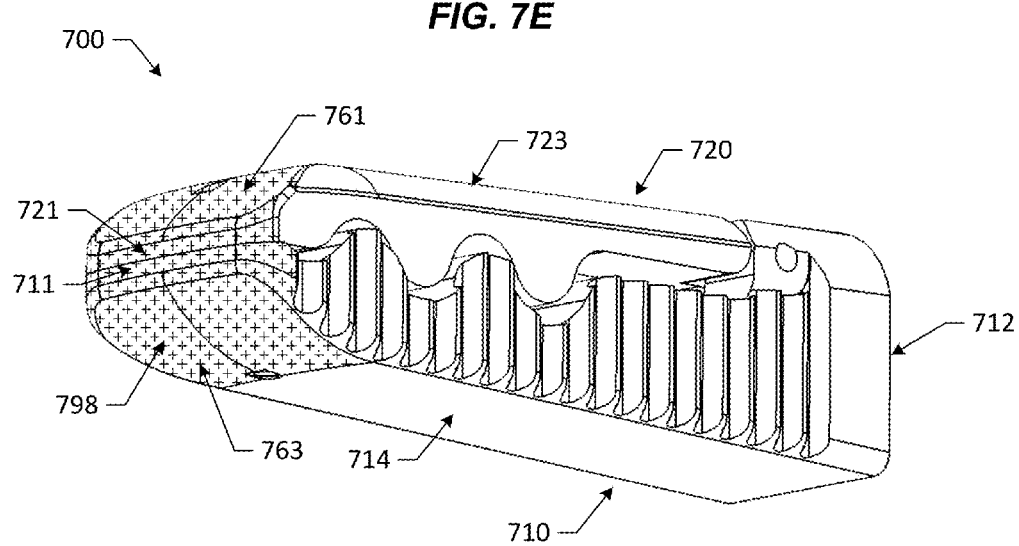
FIG. 7F shows a bottom perspective view of the expandable interbody device of FIG. 7A in the compact configuration, indicating polished regions of the device.

FIGS. 4A-4C illustrate an expandable interbody device 400 (which also may be referred to as an "interbody spacer," an "interbody cage," a "spacer," or a "cage") according to one or more embodiments of the disclosure. The interbody device 400 may be configured for implantation within an intervertebral space between two adjacent vertebrae to provide structural support and stabilization of the vertebrae. The interbody device 400 generally may be configured and used in a manner similar to the interbody devices 100, 200 described above, although certain differences in the configuration and use of the interbody device 400 are described below. Corresponding features of the interbody device 400 may be indicated by corresponding reference numbers in the drawings.

One difference between the interbody device 400 and the interbody devices 100, 200 relates to a first engagement feature configured for engaging a mating feature of an instrument system used for implanting the device 400 within the intervertebral space IS. A main body 410 of the interbody device 400 may include one or more recesses configured for engaging mating features of the instrument system. In particular, as shown, the main body 410 may include a first recess 441 (which also may be referred to as a "first notch") defined in a second end 412 of the main body 410. The first recess 441 may extend to a first side 413 of the main body 110, and the first recess 441 may be spaced apart from each of a third side 415 and a fourth side 416 of the main body 410 and centered therebetween. As shown, the first recess 441 may have a generally rectangular cross-sectional shape and may include an inner surface 444 that is oriented parallel or substantially parallel to a longitudinal axis $A_L$ of the device 400. The first recess 441 may be configured for receiving a mating protrusion of the instrument system, which may be generally similar to the first protrusion 326 of the instrument system 300 described above. In contrast to the interbody devices 100, 200, the main body 410 of the device 400 does not include a second recess or a third recess defined in the second end 412 of the main body 410.

Another difference between the interbody device 400 and the interbody devices 100, 200 relates to a second engagement feature configured for engaging a mating feature of the instrument system used for implanting the device 400 within the intervertebral space IS. As shown, the main body 410 may include a port 481 (which also may be referred to as a "hole" or a "thru hole") defined in the second end 412 of the main body 410. The port 481 may be spaced apart from each of the first side 413, the second side 414, the third side 415, and the fifth side 416 of the main body 410. Additionally, the port 481 may be spaced apart from the first recess 441 of the main body 410. As shown, the port 481 may have a cylindrical shape and a circular cross-sectional shape when viewed from an end of the port 481. The port 481 may define a longitudinal axis $A_{LP}$, which may extend parallel to the longitudinal axis $A_L$ (and perpendicular to a first transverse axis $A_{T1}$ and a second transverse axis $A_{T2}$) of the interbody device 400. The main body 410 also may include a channel 482 defined therein and in direct communication with the port 481. In contrast to the interbody devices 100, 200, the port 481 of the device 400 may include a plurality of threads 486. As shown, the threads 486 may be female threads defined along an inner circumferential surface of the port 481. The threads 486 of the port 481 may be configured for engaging mating threads of the instrument system. During implantation of the interbody device 400, the mating threads of the instrument system may engage the threads 486 of the port 481, and the mating protrusion of the instrument system may engage the first recess 441 of the main body 410. Such engagement may allow the interbody device 400 to be securely attached to the instruments system, such that the device 400 may be translated and rotated along with the instrument system. Notably, the threaded engagement between the threads 486 of the port 481 and the mating threads of the instrument system may eliminate the need for a second recess and a third recess defined in the second end 412 of the main body 410.

Yet another difference between the interbody device 400 and the interbody devices 100, 200 relates to features configured for facilitating visualization of the device 400 during implantation within the intervertebral space IS. In particular, the interbody device 400 may include one or more markers 487 configured to be visible via radiography or other medical imaging techniques that may be used during implantation of the interbody device 400. The markers 487 may be radiodense or radiopaque markers formed of a radiodense or radiopaque material. As shown, the interbody device 400 may include a first marker 487 disposed within the main body 410 and a second marker 487 disposed within an arm 420 of the device 400. The first marker 487 may be disposed near but spaced apart from a first end 411 of the main body 410, and the second marker 487 may be disposed near but spaced apart from a first end 421 of the arm 420, as shown. The markers 487 may be easily viewed via radiography or other medical imaging techniques as the interbody device 400 is inserted into and positioned within the intervertebral space IS, rotated within the intervertebral space IS, and expanded within the intervertebral space IS. It will be appreciated that the first and second markers 487 may be particularly useful in allowing a surgeon to visualize a degree of expansion of the interbody device 400 as the device 400 is moved from the compact configuration to the expanded configuration. Although the illustrated embodiment of the interbody device 400 includes two markers 487, the device 400 may include three or more markers 487 in other embodiments of the device 400. Moreover, it will be appreciated that the markers 487 may be disposed within or on other portions of the main body 410 and the arm 420.

In some embodiments, the overall distances between the opposite sides of the interbody device 400, the overall distances between the opposite sides of the main body 410, and the overall distances between the opposite sides of the arm 420 may have one or more of the various relationships (i.e., greater than, less than, or equal) and configurations (i.e., varying or remaining constant along a portion thereof) described above with respect to the interbody device 100. In this manner, the relative insertion heights and implantation heights of the portions of the interbody device 400 may be as described with respect to interbody device 100, and upon implantation, the device 400 may orient the vertebral bodies of the adjacent vertebrae at an acute angle such that the vertebrae are realigned to follow the normal curvature (e.g., lordosis) of the spine. In other embodiments, the overall distances between the opposite sides of the interbody device 400, the overall distances between the opposite sides of the main body 410, and the overall distances between the opposite sides of the arm 420 may have one or more of the various relationships and configurations described above with respect to the interbody device 200. In this manner, the relative insertion heights and implantation heights of the portions of the interbody device 400 may be as described with respect to interbody device 200, and upon implantation, the device 400 may orient the vertebral bodies of the adjacent vertebrae parallel (i.e., at a zero-degree angle) or substantially parallel to one another such that the vertebrae are realigned to follow the normal curvature of the spine.

Additional differences between the interbody device 400 and the interbody devices 100, 200 described above will be appreciated from the respective drawings. Further, it will be appreciated that the different features and functionality of the interbody device 400 may be incorporated into the above-described interbody devices in a similar manner.

The interbody device 400 may be formed of various biocompatible materials. In some embodiments, the main body 410 and the arm 420 may be formed of polyether ether ketone (PEEK), although other suitable polymers may be used. In some embodiments, the main body 410 and the arm 420 may be formed of titanium, although other suitable metals may be used. In some embodiments, the pin 430 may be formed of stainless steel, although other suitable metals or polymers may be used. In some embodiments, the main body 410 and/or the arm 420, or at least portions thereof, may be formed of a porous material configured to facilitate bone growth therein.

FIGS. 5A-5E illustrate an expandable interbody device 500 (which also may be referred to as an "interbody spacer," an "interbody cage," a "spacer," or a "cage") according to one or more embodiments of the disclosure. The interbody device 500 may be configured for implantation within an intervertebral space between two adjacent vertebrae to provide structural support and stabilization of the vertebrae. The interbody device 500 generally may be configured and used in a manner similar to the interbody devices 100, 200, 400 described above, although certain differences in the configuration and use of the interbody device 500 are described below. Corresponding features of the interbody device 500 may be indicated by corresponding reference numbers in the drawings.

One difference between the interbody device 500 and the interbody devices 100, 200, 400 relates to an "open architecture" structure configured for cooperating with the vertebrae $V_1$, $V_2$ to maintain an implanted position and expansion state of the device 500 within the intervertebral space IS (i.e., to prevent migration of the device 500 within the intervertebral space IS), for increasing a volume of bone growth achievable within the footprint of the device 500, and/or for promoting bone growth into and/or through portions of the device 500. In particular, a main body 510 and an arm 520 of the interbody device 500 may include a number of openings defined therein to provide the open architecture configuration. As described below, one or more of the openings may be configured for engaging the respective vertebrae $V_1$, $V_2$ to help maintain the implanted position and expansion state of the device 500, for increasing a volume of bone growth that may be achieved within the footprint of the device 500, and/or for allowing bone to grow into and/or through portions of the device 500.

The main body 510 may include a plurality of first openings 591 (which also may be referred to as "external openings") defined in the third side 515 and/or the fourth side 516 of the main body 510. In some embodiments, as shown, one or more of the first openings 591 may be defined in the third side 515 of the main body 510 and may extend from the third side 515 toward, but not to, the fourth side 516 of the main body 510 (i.e., such first openings 591 may terminate at a location between the third side 515 and the fourth side 516). In some embodiments, as shown, one or more of the first openings 591 may be defined in the fourth side 516 of the main body 510 and may extend from the fourth side 516 toward, but not to, the third side 515 of the main body 510 (i.e., such first openings 591 may terminate at a location between the fourth side 516 and the third side 515). In some embodiments, as shown, one or more of the first openings 591 may be defined in each of the third side 515 and the fourth side 516 of the main body 510, such that such first openings 591 extend through the main body 510 from the third side 515 to the fourth side 516 of the main body 510. In some embodiments, as shown, one or more of the first openings 591 defined in the third side 515 of the main body 510 may be in fluid communication with one or more of the first openings 591 defined in the fourth side 516 of the main body 510. As shown, each of the first openings 591 may be spaced apart from each of the first side 513 and the second side 514 of the main body 510.

The size and shape of the first openings 591 may vary depending on their location along the main body 510 and the shape of nearby features of the main body 510. In some embodiments, two or more of the first openings 591 may have the same size and/or the same shape. In some embodiments, all of the first openings 591 may have the same size and/or the same shape. In other embodiments, each of the first openings 591 may have a different size and/or a different shape. In some embodiments, the first openings 591 may be arranged in a repeating pattern extending along the third side 515 and/or the fourth side 516 of the main body 510. In some embodiments, the arrangement of the first openings 591 defined in the third side 515 of the main body 510 may be a mirror image of the arrangement of the first openings 591 defined in the fourth side 516 of the main body 510. In other embodiments, the arrangement of the first openings 591 defined in the third side 515 of the main body 510 may be different than the arrangement of the first openings 591 defined in the fourth side 516 of the main body 510. In some embodiments, the first openings 591 may be small, open pores defined in the third side 515 and/or the fourth side 516 of the main body 510. In other words, the third side 515 and/or the fourth side 516 of the main body 510 may be formed as a porous surface. In other embodiments, as shown, the first openings 591 may be larger gaps or voids defined between nearby features of the main body 510. In some embodiments, some of the first openings 591 may be small pores and some of the first openings 591 may be larger gaps or voids.

The main body 510 also may include a plurality of second openings 592 (which also may be referred to as "internal openings") defined in the first side 513 of the main body 510. In some embodiments, as shown, each of the second openings 592 may be defined in the first side 513 of the main body 510 and may extend from the first side 513 toward, but not to, the second side 514 of the main body 510 (i.e., the second openings 592 may terminate at a location between the first side 513 and the second side 514). In such embodiments, the second side 514 of the main body 510 may be formed as a solid surface, devoid of any openings. In other embodiments, one or more of the second openings 592 may extend through the main body 510 from the first side 513 to the second side 514 of the main body 510. In some embodiments, as shown, one or more of the second openings 592 may be in fluid communication with one or more of the first openings 591. In some embodiments, each of the second openings 592 may be in fluid communication with one or more of the first openings 591. As shown, each of the second openings 592 may be spaced apart from each of the third side 515 and the fourth side 516 of the main body 510.

The size and shape of the second openings 592 may vary depending on their location along the main body 510 and the shape of nearby features of the main body 510. In some embodiments, two or more of the second openings 592 may have the same size and/or the same shape. In some embodiments, all of the second openings 592 may have the same size and/or the same shape. In other embodiments, each of the second openings 592 may have a different size and/or a different shape. In some embodiments, the second openings 592 may be arranged in a repeating pattern extending along the first side 513 of the main body 510. In some embodiments, as shown, the arrangement of the second openings 592 may be symmetric about a plane extending through the longitudinal axis $A_L$ and the first transverse axis $A_{T1}$ of the interbody device 500. In other embodiments, the arrangement of the second openings 592 may be asymmetric about such a plane. In some embodiments, the second openings 592 may be small, open pores defined in the first side 513 of the main body 510. In other words, the first side 513 of the main body 510 may be formed as a porous surface. In other embodiments, as shown, the second openings 592 may be larger gaps or voids defined between nearby features of the main body 510. In some embodiments, some of the second openings 592 may be small pores and some of the second openings 592 may be larger gaps or voids.

In a similar manner, the arm 520 may include a plurality of first openings 593 (which also may be referred to as "external openings") defined in the third side 525 and/or the fourth side 526 of the arm 520. In some embodiments, one or more of the first openings 593 may be defined in the third side 525 of the arm 520 and may extend from the third side 525 toward, but not to, the fourth side 526 of the arm 520 (i.e., such first openings 593 may terminate at a location between the third side 525 and the fourth side 526). In some embodiments, one or more of the first openings 593 may be defined in the fourth side 526 of the arm 520 and may extend from the fourth side 526 toward, but not to, the third side 525 of the arm 520 (i.e., such first openings 593 may terminate at a location between the fourth side 526 and the third side 525). In some embodiments, as shown, one or more of the first openings 593 may be defined in each of the third side 525 and the fourth side 526 of the arm 520, such that such first openings 593 extend through the arm 520 from the third side 525 to the fourth side 526 of the arm 520. In some embodiments, as shown, one or more of the first openings 593 defined in the third side 525 of the arm 520 may be in fluid communication with one or more of the first openings 593 defined in the fourth side 526 of the arm 520. As shown, each of the first openings 593 may be spaced apart from each of the first side 523 and the second side 524 of the arm 520.

The size and shape of the first openings 593 may vary depending on their location along the arm 520 and the shape of nearby features of the arm 520. In some embodiments, two or more of the first openings 593 may have the same size and/or the same shape. In some embodiments, all of the first openings 593 may have the same size and/or the same shape. In other embodiments, each of the first openings 593 may have a different size and/or a different shape. In some embodiments, the first openings 593 may be arranged in a repeating pattern extending along the third side 525 and/or the fourth side 526 of the arm 520. In some embodiments, the arrangement of the first openings 593 defined in the third side 525 of the arm 520 may be a mirror image of the arrangement of the first openings 593 defined in the fourth side 526 of the arm 520. In other embodiments, the arrangement of the first openings 593 defined in the third side 525 of the arm 520 may be different than the arrangement of the first openings 593 defined in the fourth side 526 of the arm 520. In some embodiments, the first openings 593 may be small, open pores defined in the third side 525 and/or the fourth side 526 of the arm 520. In other words, the third side 525 and/or the fourth side 526 of the arm 520 may be formed as a porous surface. In other embodiments, as shown, the first openings 593 may be larger gaps or voids defined between nearby features of the arm 520. In some embodiments, some of the first openings 593 may be small pores and some of the first openings 593 may be larger gaps or voids.

The arm 520 also may include a plurality of second openings 594 (which also may be referred to as "internal openings") defined in the second side 524 of the arm 520. In some embodiments, as shown, each of the second openings 594 may be defined in the second side 524 of the arm 520 and may extend from the second side 524 toward, but not to, the first side 523 of the arm 520 (i.e., the second openings 594 may terminate at a location between the second side 524 and the first side 523). In such embodiments, the first side 523 of the arm 520 may be formed as a solid surface, devoid of any openings. In other embodiments, one or more of the second openings 594 may extend through the arm 520 from the second side 524 to the first side 523 of the arm 520. In some embodiments, as shown, one or more of the second openings 594 may be in fluid communication with one or more of the first openings 593 of the arm 520. In some embodiments, each of the second openings 594 may be in fluid communication with one or more of the first openings 593 of the arm 520. As shown, each of the second openings 594 may be spaced apart from each of the third side 525 and the fourth side 526 of the arm 520.

The size and shape of the second openings 594 may vary depending on their location along the arm 520 and the shape of nearby features of the arm 520. In some embodiments, two or more of the second openings 594 may have the same size and/or the same shape. In some embodiments, all of the second openings 594 may have the same size and/or the same shape. In other embodiments, each of the second openings 594 may have a different size and/or a different shape. In some embodiments, the second openings 594 may be arranged in a repeating pattern extending along the second side 524 of the arm 520. In some embodiments, as shown, the arrangement of the second openings 594 may be symmetric about a plane extending through the longitudinal axis $A_L$ and the first transverse axis $A_{T1}$ of the interbody device 500. In other embodiments, the arrangement of the second openings 594 may be asymmetric about such a plane. In some embodiments, the second openings 594 may be small, open pores defined in the second side 524 of the arm 520. In other words, the second side 524 of the arm 520 may be formed as a porous surface. In other embodiments, the second openings 594 may be larger gaps or voids defined between nearby features of the arm 520. In some embodiments, some of the second openings 594 may be small pores and some of the second openings 594 may be larger gaps or voids.

During use of the interbody device 500, one or more of the openings thereof may cooperate with the adjacent vertebrae $V_1$, $V_2$ and/or may facilitate bone growth between the vertebrae $V_1$, $V_2$ and about the device 500. In particular, when the interbody device 500 is positioned within the intervertebral space IS in the implantation orientation and the expanded configuration, the third side 515 of the main body 510 and the third side 525 of the arm 520 may engage one of the vertebrae $V_1$, $V_2$, and the fourth side 516 of the main body 510 and the fourth side 526 of the arm 520 may engage the other of the vertebrae $V_1$, $V_2$. In this manner, the first openings 591 of the main body 510 and the first openings 593 of the arm 520 may be positioned adjacent the respective vertebrae $V_1$, $V_2$, which may assist in maintaining the implanted position and expansion state of the device 500 within the intervertebral space IS. Such positioning of the first openings 591, 593 also may facilitate bone growth into and/or through the main body 510 and the arm 520 via the respective first openings 591, 593. Additionally, when the interbody device 500 is positioned within the intervertebral space IS in the implantation orientation and the expanded configuration, the second openings 592 of the main body 510 and the second openings 594 of the arm 520 may be positioned along and in fluid communication with a cavity 540 defined between the main body 510 and the arm 520. Such positioning of the second openings 592, 594 may facilitate bone growth into and/or through the main body 510 and the arm 520 via the respective second openings 592, 594, particularly when bone graft or a bone graft substitute is placed within the cavity 540. Furthermore, according to embodiments in which one or more of the second openings 592, 594 is in fluid communication with one or more of the respective first openings 591, 593, such communication provides additional pathways for bone growth through the main body 510 and the arm 520. Meanwhile, the solid configuration of the second side 514 of the main body 510 and the first side 523 of the arm 520 may function to generally contain the bone graft or bone graft substitute and the resulting bone growth within the overall footprint of the interbody device 500. In this manner, the main body 510 and the arm 520 may provide a partial containment area for bone material, inhibiting migration of the bone material and bone growth toward the spinal nerves. Ultimately, the open architecture of the interbody device 500 may increase a volume of bone growth achievable within the footprint of the device 500 and promote bone growth into and/or through the main body 510 and the arm 520, thereby enhancing the structural support and stabilization of the vertebrae $V_1$, $V_2$.

Another difference between the interbody device 500 and the interbody devices 100, 200, 400 relates to the relationship between the second overall distance $D_2$ (between the first side 503 and the second side 504 of the device 500) and the third overall distance $D_3$ (between the third side 505 and the fourth side 506 of the device 500) at the second end 502 of the device 500. In contrast to the interbody devices 100, 200, 400, the second overall distance $D_2$ of the interbody device 500 may be less than the third overall distance $D_3$. In this manner, the device 500 does not over-distract the posterior portion of the intervertebral space IS upon insertion of the device 500 therein. Instead, the device 500 may provide partial distraction of the posterior portion of the intervertebral space IS upon insertion of the device 500 therein and then further distraction of the posterior portion of the intervertebral space IS upon rotation of the device 500 therein.

In some embodiments, the overall distances between the opposite sides of the interbody device 500, the overall distances between the opposite sides of the main body 510, and the overall distances between the opposite sides of the arm 520 may have one or more of the various relationships (i.e., greater than, less than, or equal) and configurations (i.e., varying or remaining constant along a portion thereof) described above with respect to the interbody device 100. In this manner, the relative insertion heights and implantation heights of the portions of the interbody device 500 may be as described with respect to interbody device 100, and upon implantation, the device 500 may orient the vertebral bodies of the adjacent vertebrae at an acute angle such that the vertebrae are realigned to follow the normal curvature (e.g., lordosis) of the spine. In other embodiments, the overall distances between the opposite sides of the interbody device 500, the overall distances between the opposite sides of the main body 510, and the overall distances between the opposite sides of the arm 520 may have one or more of the various relationships and configurations described above with respect to the interbody device 200. In this manner, the relative insertion heights and implantation heights of the portions of the interbody device 500 may be as described with respect to interbody device 200, and upon implantation, the device 500 may orient the vertebral bodies of the adjacent vertebrae parallel (i.e., at a zero-degree angle) or substantially parallel to one another such that the vertebrae are realigned to follow the normal curvature of the spine.

Additional differences between the interbody device 500 and the interbody devices 100, 200, 400 described above will be appreciated from the respective drawings. Further, it will be appreciated that the different features and functionality of the interbody device 500 may be incorporated into the above-described interbody devices in a similar manner.

The interbody device 500 may be formed of various biocompatible materials. In some embodiments, the main body 510 and the arm 520 may be formed of polyether ether ketone (PEEK), although other suitable polymers may be used. In some embodiments, the main body 510 and the arm 520 may be formed of titanium, although other suitable metals may be used. As compared to other materials often used for interbody devices, titanium may provide the necessary strength required to accommodate the open architecture of the interbody device 500. In some embodiments, the pin 530 may be formed of stainless steel, although other suitable metals or polymers may be used. In some embodiments, at least portions of the main body 510 and the arm 520 may be formed of a porous material having small pores that mimic the mechanical structure of bone and encourage bone growth therein. In some embodiments, the main body and the arm 520 may be formed by direct metal laser sintering (DMLS), although other manufacturing techniques may be used. As compared to other manufacturing techniques often used to form interbody devices, DMLS may ease creation of the open architecture of the interbody device 500.

FIGS. 6A-6F illustrate an expandable interbody device 600 (which also may be referred to as an "interbody spacer," an "interbody cage," a "spacer," or a "cage") according to one or more embodiments of the disclosure. The interbody device 600 may be configured for implantation within an intervertebral space between two adjacent vertebrae to provide structural support and stabilization of the vertebrae. The interbody device 600 generally may be configured and used in a manner similar to the interbody devices 100, 200, 400, 500 described above, although certain differences in the configuration and use of the interbody device 600 are described below. Corresponding features of the interbody device 600 may be indicated by corresponding reference numbers in the drawings.

One difference between the interbody device 600 and the interbody devices 100, 200, 400 relates to an "open architecture" structure of the device 600. Similar to the interbody device 500, a main body 610 and an arm 620 of the interbody device 600 may include a number of openings defined therein to provide the open architecture configuration. One or more of the openings may be configured for engaging the respective vertebrae $V_1$, $V_2$ to help maintain the implanted position and expansion state of the device 600, for increasing a volume of bone growth that may be achieved within the footprint of the device 600, and/or for allowing bone to grow into and/or through portions of the device 600.

The main body 610 may include a plurality of first openings 691 (which also may be referred to as "external openings") defined in the third side 615 and/or the fourth side 616 of the main body 610. In some embodiments, as shown, one or more of the first openings 691 may be defined in the third side 615 of the main body 610 and may extend from the third side 615 toward, but not to, the fourth side 616 of the main body 610 (i.e., such first openings 691 may terminate at a location between the third side 615 and the fourth side 616). As shown, each of the first openings 691 may be spaced apart from each of the first side 613 and the second side 614 of the main body 610. The main body 610 also may include a plurality of second openings 692 (which also may be referred to as "internal openings") defined in the first side 613 of the main body 610. In some embodiments, as shown, each of the second openings 692 may be defined in the first side 613 of the main body 610 and may extend from the first side 613 toward, but not to, the second side 614 of the main body 610 (i.e., the second openings 692 may terminate at a location between the first side 613 and the second side 614). In such embodiments, the second side 614 of the main body 610 may be formed as a solid surface, devoid of any openings. In some embodiments, as shown, one or more of the second openings 692 may be in fluid communication with one or more of the first openings 691. As shown, each of the second openings 692 may be spaced apart from each of the third side 615 and the fourth side 616 of the main body 610. Alternative positions, configurations, size and shape relationships, and patterns of the first openings 691 and the second openings 692, such as those described above with respect to the interbody device 500, also may be used.

In a similar manner, the arm 620 may include a plurality of first openings 693 (which also may be referred to as "external openings") defined in the third side 625 and/or the fourth side 626 of the arm 620. In some embodiments, one or more of the first openings 693 may be defined in the third side 625 of the arm 620 and may extend from the third side 625 toward, but not to, the fourth side 626 of the arm 620 (i.e., such first openings 693 may terminate at a location between the third side 625 and the fourth side 626). In some embodiments, one or more of the first openings 693 may be defined in the fourth side 626 of the arm 620 and may extend from the fourth side 626 toward, but not to, the third side 625 of the arm 620 (i.e., such first openings 693 may terminate at a location between the fourth side 626 and the third side 625). As shown, each of the first openings 693 may be spaced apart from each of the first side 623 and the second side 624 of the arm 620. The arm 620 also may include a plurality of second openings 694 (which also may be referred to as "internal openings") defined in the second side 624 of the arm 620. In some embodiments, as shown, each of the second openings 694 may be defined in the second side 624 of the arm 620 and may extend from the second side 624 toward, but not to, the first side 623 of the arm 620 (i.e., the second openings 694 may terminate at a location between the second side 624 and the first side 623). In such embodiments, the first side 623 of the arm 620 may be formed as a solid surface, devoid of any openings. In some embodiments, one or more of the second openings 694 may be in fluid communication with one or more of the first openings 693 of the arm 620. As shown, each of the second openings 694 may be spaced apart from each of the third side 625 and the fourth side 626 of the arm 620. Alternative positions, configurations, size and shape relationships, and patterns of the first openings 693 and the second openings 694, such as those described above with respect to the interbody device 500, also may be used.

It will be appreciated that the open architecture of the interbody device 600 may increase a volume of bone growth achievable within the footprint of the device 600 and promote bone growth into and/or through the main body 610 and the arm 620, thereby enhancing the structural support and stabilization of the vertebrae $V_1$, $V_2$, in a manner similar to that described above with respect to interbody device 500. Additionally, the main body 610 and the arm 620 may provide a partial containment area for bone material, inhibiting migration of the bone material and bone growth toward the spinal nerves.

Another difference between the interbody device 600 and the interbody devices 100, 200, 400, 500 relates to engagement features configured for engaging mating features of an instrument system used for implanting the device 600 within the intervertebral space IS. As shown, the main body 610 may include a port 681 (which also may be referred to as a "hole" or a "thru hole") defined in the second end 612 of the main body 610. The port 681 may be spaced apart from each of the first side 613, the second side 614, the third side 615, and the fifth side 616 of the main body 610. As shown, the port 681 may have a generally rectangular cross-sectional shape with rounded or otherwise contoured corners, when viewed from an end of the port 681, although other shapes of the port 681 may be used in other embodiments. The port 681 may define a longitudinal axis $A_{LP}$, which may extend parallel to a longitudinal axis $A_L$ (and perpendicular to a first transverse axis $A_{T1}$ and a second transverse axis $A_{T2}$) of the interbody device 600. The main body 610 also may include a channel 682 defined therein and in direct communication with the port 681. In contrast to the interbody devices 100, 200, 400, 500, the port 681 of the device 600 may include one or more internal lips 695 positioned along one or more internal surfaces of the port 681 and extending inward toward the longitudinal axis $A_L$ of the interbody device 600. In some embodiments, as shown, the port 681 may include a pair of internal lips 695 positioned opposite one another along respective sides of the port 681. Although the internal lips 695 are shown as extending parallel to the first transverse axis $A_{T1}$ and perpendicular the second transverse axis $A_{T2}$ of the device 600, alternative orientations of the internal lips 695 may be used. In other embodiments, the port 681 may include three or more internal lips 695 spaced apart along the perimeter of the port 681 or may include a single internal lip 695 extending along the entirety or at least a majority of the perimeter of the port 681.

The port 681 also may include one or more internal recesses 696 positioned adjacent the internal lips 695 and between the internal lips 695 and the first end 611 of the main body 610 in the direction of the longitudinal axis $A_L$ of the device 600. In some embodiments, as shown, the port 681 may include a pair of internal recesses 696 positioned opposite one another along respective sides of the port 681 and corresponding to the pair of internal lips 695. In other embodiments, the port 681 may include three or more internal recesses 696 spaced apart along the perimeter of the port 681 or may include a single internal recess 696 extending along the entirety or at least a majority of the perimeter of the port 681. The port 681 further may include one or more lead-in surfaces 697 positioned along the second end 612 of the main body 610 and extending inward toward the longitudinal axis $A_L$ of the device 600 in a direction from the second end 612 toward the first end 611 of the main body 610. In some embodiments, as shown, the lead-in surfaces 697 may be flat, angled surfaces, although other configurations, such as rounded surfaces may be used in other embodiments. The internal lips 695, the internal recesses 696, and the lead-in surfaces 697 of the port 681 may be configured for engaging mating features of an instrument system, such as the instrument system 800 described below, during implantation of the interbody device 600. Such engagement may allow the device 600 to be securely attached to the instruments system, such that the device 600 may be translated and rotated along with the instrument system. Notably, the features of the port 681 may eliminate the need for external recesses or threads for attaching the device 600 to the instrument system and may allow the device 600 to be quickly attached to and detached from the instrument system.

Yet another difference between the interbody device 600 and the interbody devices 100, 200, 400, 500 relates to features that cooperate with the vertebrae $V_1$, $V_2$ to facilitate rotation of the device 600 from the insertion orientation to the implantation orientation within the intervertebral space IS. Similar to the above-described interbody devices, the device 600 may include a first transition portion 671 positioned along the interface between the first side 603 and the third side 605 of the device 600, a second transition portion 672 positioned along the interface between the second side 604 and the fourth side 606 of the device 600, a third transition portion 673 positioned along the interface between the first side 603 and the fourth side 606 of the device 600, and a fourth transition portion 674 positioned along the interface between the second side 604 and the third side 605 of the device 600. In some embodiments, each of the transition portions 671, 672, 673, 674 may extend along the entire length of the device 600 from the first end 601 to the second end 602 of the device 600. In some embodiments, some or all of the transition portions 671, 672, 673, 674 may extend along only a portion of the length of the device 600. In some such embodiments, each of the transition portions 671, 672, 673, 674 may extend from the second end 602 of the device 600 to respective intermediate locations along the length of the device 600 spaced apart from the first end 601 of the device 600.

As shown, each of the transition portions 671, 672, 673, 674 may have a curved shape extending along the respective interfaces between the sides of the device 600. In contrast to the interbody devices 100, 200, 400, 500, one or more of the transition portions 671, 672, 673, 674 of the device 600 may be formed as a spline having a variable radius of curvature. In some embodiments, as shown, the first transition portion 671 may have a variable first radius of curvature $R_{V1}$, the second transition portion 672 may have a variable second radius of curvature $R_{V2}$, the third transition portion 673 may have a constant third radius of curvature $R_{C3}$, and the fourth transition portion 674 may have a constant fourth radius of curvature $R_{C4}$. The variable first radius of curvature $R_{V1}$ of the first transition portion 671 may increase along the spline, from a minimum first radius of curvature $R_{1MIN}$ to a maximum first radius of curvature $R_{1MAX}$, in the direction from the third side 605 to the first side 603 of the device 600, and the variable second radius of curvature $R_{V2}$ of the second transition portion 672 may increase along the spline, from a minimum second radius of curvature $R_{2MIN}$ to a maximum second radius of curvature $R_{2MAX}$, in the direction from the fourth side 606 to the second side 604 of the device 600, as shown. In some embodiments, as shown, the minimum first radius of curvature $R_{1MIN}$ may be greater than each of the constant third radius of curvature $R_{C3}$ and the constant fourth radius of curvature $R_{C4}$, and the minimum second radius of curvature $R_{2MIN}$ may be greater than each of the constant third radius of curvature $R_{C3}$ and the constant fourth radius of curvature $R_{C4}$. In some embodiments, the minimum first radius of curvature $R_{1MIN}$ may be equal to the minimum second radius of curvature $R_{1MIN}$, and the maximum first radius of curvature $R_{1MAX}$ may be equal to the maximum second radius of curvature $R_{2MAX}$. In some embodiments, the variable first radius of curvature $R_{V1}$ may be a mirror image of the variable second radius of curvature $R_{V2}$. It will be understood that the foregoing relationships between the radii of curvature of the transition portions 671, 672, 673, 674 may facilitate clockwise rotation of the device 600 (when viewed from the second end 602 of the device 600) by ninety (90) degrees about the longitudinal axis $A_L$ of the device 600 from the insertion orientation to the implantation orientation within the intervertebral space IS, and may inhibit further clockwise rotation (i.e., rotation beyond ninety degrees) of the device 600 beyond the implantation orientation. Notably, the configuration of the variable first radius of curvature $R_{V1}$ and the variable second radius of curvature $R_{V2}$ may reduce the amount of torque required to rotate the device 600 from the insertion orientation to the implantation orientation within the intervertebral space IS.

In other embodiments, the configuration of the radii of curvature may be reversed, such that the first transition portion 671 has a constant first radius of curvature, the second transition portion 672 has a constant second radius of curvature, the third transition portion 673 has a variable third radius of curvature increasing along the spline thereof in the direction from the fourth side 606 to the first side 603 of the device 600, and the fourth transition portion 674 has a variable fourth radius of curvature increasing along the spline thereof in the direction from the third side 605 to the second side 604 of the device 600. Such configuration may facilitate counter clockwise rotation of the device 600 (when viewed from the second end 602 of the device 600) by ninety (90) degrees about the longitudinal axis $A_L$ of the device 600 from the insertion orientation to the implantation orientation within the intervertebral space IS, and may inhibit further counter clockwise rotation (i.e., rotation beyond ninety degrees) of the device 600 beyond the implantation orientation.

Another difference between the interbody device 600 and the interbody devices 100, 200, 400 relates to the relationship between the second overall distance $D_2$ (between the first side 603 and the second side 604 of the device 600) and the third overall distance $D_3$ (between the third side 605 and the fourth side 606 of the device 600) at the second end 602 of the device 600. Similar to the interbody device 500, the second overall distance $D_2$ of the interbody device 600 may be less than the third overall distance $D_3$. In this manner, the device 600 does not over-distract the posterior portion of the intervertebral space IS upon insertion of the device 600 therein. Instead, the device 600 may provide partial distraction of the posterior portion of the intervertebral space IS upon insertion of the device 600 therein and then further distraction of the posterior portion of the intervertebral space IS upon rotation of the device 600 therein.

In some embodiments, the overall distances between the opposite sides of the interbody device 600, the overall distances between the opposite sides of the main body 610, and the overall distances between the opposite sides of the arm 620 may have one or more of the various relationships (i.e., greater than, less than, or equal) and configurations (i.e., varying or remaining constant along a portion thereof) described above with respect to the interbody device 100. In this manner, the relative insertion heights and implantation heights of the portions of the interbody device 600 may be as described with respect to interbody device 100, and upon implantation, the device 600 may orient the vertebral bodies of the adjacent vertebrae at an acute angle such that the vertebrae are realigned to follow the normal curvature (e.g., lordosis) of the spine. In other embodiments, the overall distances between the opposite sides of the interbody device 600, the overall distances between the opposite sides of the main body 610, and the overall distances between the opposite sides of the arm 620 may have one or more of the various relationships and configurations described above with respect to the interbody device 200. In this manner, the relative insertion heights and implantation heights of the portions of the interbody device 600 may be as described with respect to interbody device 200, and upon implantation, the device 600 may orient the vertebral bodies of the adjacent vertebrae parallel (i.e., at a zero-degree angle) or substantially parallel to one another such that the vertebrae are realigned to follow the normal curvature of the spine.

Additional differences between the interbody device 600 and the interbody devices 100, 200, 400, 500 described above will be appreciated from the respective drawings. Further, it will be appreciated that the different features and functionality of the interbody device 600 may be incorporated into the above-described interbody devices in a similar manner.

The interbody device 600 may be formed of various biocompatible materials. In some embodiments, the main body 610 and the arm 620 may be formed of polyether ether ketone (PEEK), although other suitable polymers may be used. In some embodiments, the main body 610 and the arm 620 may be formed of titanium, although other suitable metals may be used. As compared to other materials often used for interbody devices, titanium may provide the necessary strength required to accommodate the open architecture of the interbody device 600. In some embodiments, the pin 630 may be formed of stainless steel, although other suitable metals or polymers may be used. In some embodiments, at least portions of the main body 610 and the arm 620 may be formed of a porous material having small pores that mimic the mechanical structure of bone and encourage bone growth therein. In some embodiments, the main body 610 and the arm 620 may be formed by direct metal laser sintering (DMLS), although other manufacturing techniques may be used. As compared to other manufacturing techniques often used to form interbody devices, DMLS may ease creation of the open architecture of the interbody device 600.

FIGS. 7A-7F illustrate an expandable interbody device 700 (which also may be referred to as an "interbody spacer," an "interbody cage," a "spacer," or a "cage") according to one or more embodiments of the disclosure. The interbody device 700 may be configured for implantation within an intervertebral space between two adjacent vertebrae to provide structural support and stabilization of the vertebrae. The interbody device 700 generally may be configured and used in a manner similar to the interbody devices 100, 200, 400, 500, 600 described above, although certain differences in the configuration and use of the interbody device 700 are described below. Corresponding features of the interbody device 700 may be indicated by corresponding reference numbers in the drawings.

One difference between the interbody device 700 and the interbody devices 100, 200, 400, 500 relates to engagement features configured for engaging mating features of an instrument system used for implanting the device 600 within the intervertebral space IS. Similar to the interbody device 600, a main body 710 of the device 700 may include a port 781 (which also may be referred to as a "hole" or a "thru hole") defined in the second end 712 of the main body 710 and having a generally rectangular cross-sectional shape with rounded or otherwise contoured corners, when viewed from an end of the port 781. The port 781 may be spaced apart from each of the first side 713, the second side 714, the third side 715, and the fourth side 716 of the main body 710 and in direction communication with a channel 782 defined in the main body 782. Similar to the interbody device 600, the port 781 of the device 700 may include one or more internal lips 795 positioned along one or more internal surfaces of the port 781 and extending inward toward the longitudinal axis $A_L$ of the device 700, one or more internal recesses 796 positioned adjacent the internal lips 795 and between the internal lips 795 and the first end 711 of the main body 710 in the direction of the longitudinal axis $A_L$ of the device 700, and one or more lead-in surfaces 797 positioned along the second end 712 of the main body 710 and extending inward toward the longitudinal axis $A_L$ of the device 700 in a direction from the second end 712 toward the first end 711 of the main body 710. In some embodiments, as shown, the port 781 may include a pair of internal lips 795 positioned opposite one another along respective sides of the port 781, and a pair of internal recesses 796 positioned opposite one another along respective sides of the port 781 and corresponding to the pair of internal lips 795. The internal lips 795, the internal recesses 796, and the lead-in surfaces 797 of the port 781 may be configured for engaging mating features of an instrument system, such as the instrument system 800 described below, during implantation of the interbody device 700.

Another difference between the interbody device 700 and the interbody devices 100, 200, 400, 500, 600 relates to features configured for facilitating expansion of the device 700 from the compact configuration to the expanded configuration and for engaging the respective vertebrae $V_1$, $V_2$ to help maintain the device 700 in the implanted position within the intervertebral space IS (i.e., to prevent migration of the device 700 within the intervertebral space IS). Similar to the interbody devices 100, 200, 400, the main body 710 of the device 700 may include a first plurality of teeth 791 (which also may be referred to as "ridges") positioned along the third side 715 of the main body 710, and a second plurality of teeth 792 (which also may be referred to as "ridges") positioned along the fourth side 716 of the main body 710. In contrast to the interbody devices 100, 200, 400, the third side 725 and the fourth side 726 of the arm 720 of the device 700 may be formed as smooth surfaces, devoid of any teeth therealong. The smooth surfaces of the third side 725 and the fourth side 726 of the arm 720 may allow the interbody device 700 to be expanded with minimal resistance from the respective vertebrae $V_1$, $V_2$, while the teeth 791, 792 of the main body 710 securely engage the respective vertebrae $V_1$, $V_2$ and maintain the position of the main body 710 within the intervertebral space IS.

Yet another difference between the interbody device 700 and the interbody devices 100, 200, 400, 500, 600 relates to features that cooperate with the vertebrae $V_1$, $V_2$ to facilitate insertion of the device 700 into the intervertebral space IS and positioning of the device 700 therein. In particular, portions of the first end 701, the first side 703, and/or the second side 704 of the interbody device 700 may include one or more polished surfaces 798 (identified by "+" symbols in FIGS. 7E and 7F) configured for reducing friction between the device 700 and the vertebrae $V_1$, $V_2$ as the device 700 is inserted into and positioned within the intervertebral space IS. In some embodiments, as shown, the first end 711 of the main body 710 may include one or more polished surfaces 798. In some embodiments, as shown, the first end 721 of the arm 720 may include one or more polished surfaces 798. In some embodiments, as shown, a curved portion 761 of the first side 723 of the arm 720 may include one or more polished surfaces 798. In some embodiments, as shown, a curved portion 763 of the second side 714 of the main body 710 may include one or more polished surfaces 798. In other embodiments, additional portions of the main body 710 and/or the arm 720 of the device 700 may include one or more polished surfaces 798. It will be appreciated that the polished surfaces 798 of the interbody device 700 may be particularly beneficial during initial insertion of the device 700 between the vertebrae $V_1$, $V_2$ and initial distraction of the intervertebral space IS via the device 700.

Another difference between the interbody device 700 and the interbody devices 100, 200, 400 relates to the relationship between the second overall distance $D_2$ (between the first side 703 and the second side 704 of the device 700) and the third overall distance $D_3$ (between the third side 705 and the fourth side 706 of the device 700) at the second end 702 of the device 700. Similar to the interbody device 500, the second overall distance $D_2$ of the interbody device 700 may be less than the third overall distance $D_3$. In this manner, the device 700 does not over-distract the posterior portion of the intervertebral space IS upon insertion of the device 700 therein. Instead, the device 700 may provide partial distraction of the posterior portion of the intervertebral space IS upon insertion of the device 700 therein and then further distraction of the posterior portion of the intervertebral space IS upon rotation of the device 700 therein.

In some embodiments, the overall distances between the opposite sides of the interbody device 700, the overall distances between the opposite sides of the main body 710, and the overall distances between the opposite sides of the arm 720 may have one or more of the various relationships (i.e., greater than, less than, or equal) and configurations (i.e., varying or remaining constant along a portion thereof) described above with respect to the interbody device 100. In this manner, the relative insertion heights and implantation heights of the portions of the interbody device 700 may be as described with respect to interbody device 100, and upon implantation, the device 700 may orient the vertebral bodies of the adjacent vertebrae at an acute angle such that the vertebrae are realigned to follow the normal curvature (e.g., lordosis) of the spine. In other embodiments, the overall distances between the opposite sides of the interbody device 700, the overall distances between the opposite sides of the main body 710, and the overall distances between the opposite sides of the arm 720 may have one or more of the various relationships and configurations described above with respect to the interbody device 200. In this manner, the relative insertion heights and implantation heights of the portions of the interbody device 700 may be as described with respect to interbody device 200, and upon implantation, the device 700 may orient the vertebral bodies of the adjacent vertebrae parallel (i.e., at a zero-degree angle) or substantially parallel to one another such that the vertebrae are realigned to follow the normal curvature of the spine.

Additional differences between the interbody device 700 and the interbody devices 100, 200, 400, 500, 600 described above will be appreciated from the respective drawings. Further, it will be appreciated that the different features and functionality of the interbody device 700 may be incorporated into the above-described interbody devices in a similar manner.

The interbody device 700 may be formed of various biocompatible materials. In some embodiments, the main body 710 and the arm 720 may be formed of polyether ether ketone (PEEK), although other suitable polymers may be used. In some embodiments, the main body 710 and the arm 720 may be formed of titanium, although other suitable metals may be used. In some embodiments, the pin 730 may be formed of stainless steel, although other suitable metals or polymers may be used. In some embodiments, the main body 710 and/or the arm 720, or at least portions thereof, may be formed of a porous material configured to facilitate bone growth therein.

Instrument Systems for Implantation of Expandable Interbody Devices

Figure 8A:
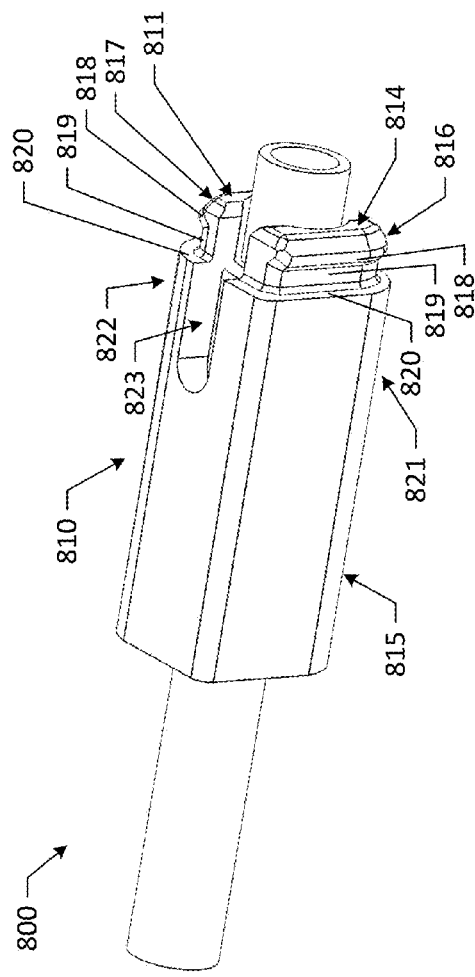
FIG. 8A shows a top perspective view of a distal portion of an instrument system for inserting and positioning an expandable interbody device in an intervertebral space, rotating the interbody device within the intervertebral space, expanding the interbody device within the intervertebral space, and delivering bone graft into a cavity of the expanded interbody device, the instrument system in an assembled configuration.
Figure 8B:
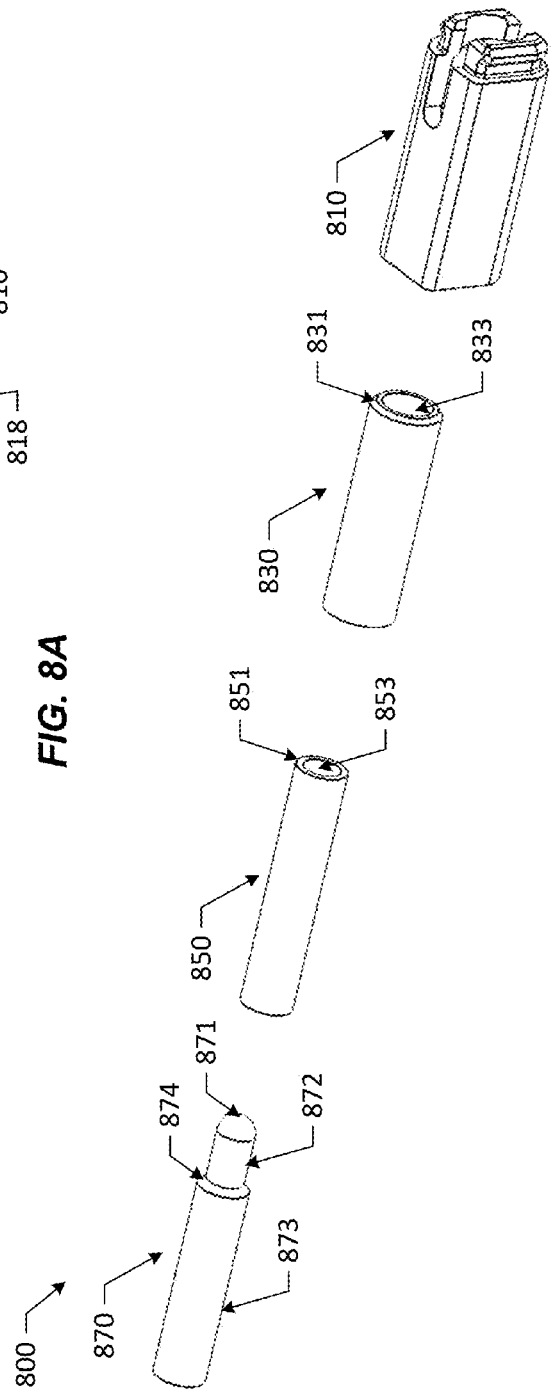
FIG. 8B shows an exploded perspective view of the distal portion of the instrument system of FIG. 8A in a disassembled configuration.

FIGS. 8A and 8B illustrate an instrument system 800 (which also may be referred to simply as an "instrument") for implantation of an expandable interbody device, according to one or more embodiments of the disclosure. In particular, the instrument system 800 may be configured for inserting and positioning the expandable interbody device in an intervertebral space, rotating the interbody device within the intervertebral space, expanding the interbody device within the intervertebral space, and delivering bone graft or a bone graft substitute into a cavity of the expanded interbody device. The instrument system 800 may be configured for use with the interbody device 600 and the interbody device 700 described above, although the other interbody devices described above may be modified to include similar mating features for use with the instrument system 800. FIGS. 8C-8G illustrate use of the instrument system 800 with the interbody device 700 and how certain features of the instrument system 800 interact with mating features of the device 700. It will be understood that the instrument system 300 may be used in a similar manner with the interbody device 600 or modified versions of the other interbody devices described above.

The instrument system 800 may have an elongated shape defining a longitudinal axis $A_{IS}$. As shown, the instrument system 800 may include an outer tube 810, an intermediate tube 830, an inner tube 850, and a bone graft plunger 870. It will be appreciated that only a distal portion of the instrument system 800 is shown in FIGS. 8A-8G for illustration purposes, and that a proximal portion of the instrument system 800 may include additional features and/or components for manipulation by a user. As described below, certain portions of the outer tube 810, the intermediate tube 830, the inner tube 850, and the bone graft plunger 870 may be configured to cooperate with one another and to interact with an expandable interbody device, such as the interbody device 700, to insert and position the interbody device in an intervertebral space, to rotate the interbody device within the intervertebral space, to expand the interbody device within the intervertebral space, and to deliver bone graft or a bone graft substitute into a cavity of the expanded interbody device.

The outer tube 810 may have an elongated shape extending along a longitudinal axis $A_{OT}$ of the outer tube 810. When the instrument system 800 is assembled for use, the longitudinal axis $A_{OT}$ of the outer tube 810 may coincide with the longitudinal axis $A_{IS}$ of the instrument system 800. The outer tube 810 may include a first end 811 (which also may be referred to as a "distal end"), a second end (which also may be referred to as a "proximal end") disposed opposite the first end 811 in the direction of the longitudinal axis $A_{OT}$ of the outer tube 810, and a cannula 813 (which also may be referred to as a "central aperture" or an "aperture") extending through the outer tube 810 along the longitudinal axis $A_{OT}$ from the first end 811 to the second end thereof. As shown, the outer tube 810 may include an interbody device interface 814 (which also may be referred to as a "device interface") extending along the longitudinal axis $A_{OT}$ from the first end 811 toward the second end of the outer tube 810, and a tubular body 815 extending from the interbody device interface 814 toward the second end of the outer tube 810.

As shown, the interbody device interface 814 may include a plurality of protrusions configured for releasably engaging mating features of an expandable interbody device. In particular, the interbody device interface 814 may include a first protrusion 816 and a second protrusion 817 (which also may be referred to as a "first tab" and a "second tab") spaced apart from one another. The first protrusion 816 and the second protrusion 817 each may be spaced apart from the longitudinal axis $A_{OT}$. As shown, the first protrusion 816 and the second protrusion 817 each may include an external lip 818 positioned at or near the first end 811 of the outer tube 810, and a base 819 positioned adjacent the external lip 818 and between the external lip 818 and the tubular body 815 of the outer tube 810 in the direction of the longitudinal axis $A_{OT}$. The tubular body 815 may include a pair of shoulders 820 positioned adjacent the respective bases 819 of the protrusions 816, 817. As shown, when the instrument system 300 is used with the interbody device 700, the protrusions 816, 817 may engage and be received within the port 781 of the device 700. In particular, the external lips 818 of the protrusions 816, 817 may engage and be received within the respective internal recesses 796 of the port 781, and the bases 819 of the protrusions 816, 817 may engage the respective internal lips 795 of the port 781, while the shoulders 820 of the outer tube 810 abut the second end 712 of the main body 710.

As shown, a distal portion of the outer tube 810 may have a split configuration, similar to a collet. In particular, the distal portion of the outer tube 810 may include a first part 821 and a second part 822 that are separated from one another via a slot 823 extending therebetween. As shown, the first part 821 may include the first protrusion 816, and the second part 822 may include the second protrusion 817. The slot 823 may extend parallel to the longitudinal axis $A_{OT}$ of the outer tube 810. In this manner, the first part 821 and the second part 822 may be configured to resiliently deflect toward one another and toward the longitudinal axis $A_{OT}$ of the outer tube 810. Such deflection may facilitate insertion of the protrusions 816, 817 of the interbody device interface 814 into the port 781 of the interbody device 700. In some embodiments, as shown, the slot 823 may extend axially through the interbody device interface 814 and partially through the tubular body 815 of the outer tube 810. The cannula 813 of the outer tube 810 may include a first portion 824 extending from the first end 811 toward the second end of the outer tube 810 and having a first inner diameter $ID_1$, a second portion 825 extending from the first portion 824 toward the second end of the outer tube 810 and having a second inner diameter $ID_2$, and an internal shoulder 826 positioned at an interface of the first portion 824 and the second portion 825. As shown, the first inner diameter $ID_1$ may be less than the second inner diameter $ID_2$.

The intermediate tube 830 (which also may be referred to as a "locking tube" or a "locking member") may have an elongated shape extending along a longitudinal axis $A_{MT}$ of the intermediate tube 830. When the instrument system 800 is assembled for use, the longitudinal axis $A_{MT}$ of the intermediate tube 830 may coincide with the longitudinal axis $A_{IS}$ of the instrument system 800. The intermediate tube 830 may include a first end 831 (which also may be referred to as a "distal end"), a second end (which also may be referred to as a "proximal end") disposed opposite the first end 831 in the direction of the longitudinal axis $A_{MT}$ of the intermediate tube 830, and a cannula 833 (which also may be referred to as a "central aperture" or an "aperture") extending through the intermediate tube 830 along the longitudinal axis $A_{MT}$ from the first end 831 to the second end thereof. As shown, the cannula 833 of the intermediate tube 830 may have a third inner diameter $ID_3$, which may be constant along the length of the intermediate tube 830. In some embodiments, as shown, the third inner diameter $ID_3$ may be equal to the first inner diameter $ID_1$ of the cannula 813 of the outer tube 810. As shown, the intermediate tube 830 may have a first outer diameter $OD_1$, which may be constant along the length of the intermediate tube 830. In some embodiments, as shown, the first outer diameter $OD_1$ may be slightly less than second inner diameter $ID_2$ of the cannula 813 of the outer tube 810 and greater than the first inner diameter $ID_1$ of the cannula 813 of the outer tube 810. In this manner, the intermediate tube 830 may be inserted into and received within the second portion 825 of the cannula 813 until the first end 831 of the intermediate tube 830 abuts the internal shoulder 826 of the cannula 813, as shown.

When the intermediate tube 830 is received within the first portion 824 of the cannula 813, the intermediate tube 830 may inhibit the first part 821 and the second part 822 of the outer tube 810 from deflecting toward one another and toward the longitudinal axis $A_{OT}$ of the outer tube 810. In this manner, the intermediate tube 830 may lock the interbody device interface 814 of the outer tube 810 with respect to the port 781 of the interbody device 700 when the intermediate tube 830 is received within the first portion 824 of the cannula 813. As a result of the engagement between the protrusions 816, 817 of the interbody device interface 814 and the locking of the interbody device interface 814 via the intermediate tube 830, the interbody device 700 may be axially coupled to the interbody device interface 814 (i.e., the interbody device 700 may be restrained from axial movement with respect to the interbody device interface 814). Further, as a result of the engagement between the protrusions 816, 817 of the interbody device interface 814, the interbody device 700 may be rotatably coupled to the interbody device interface 814 (i.e., the interbody device 700 may be restrained from rotational movement with respect to the interbody device interface 814). In this manner, when the interbody device 700 is attached to the locked interbody device interface 814, the interbody device 700 may be positioned and rotated via the outer tube 810. Following implantation of the interbody device 700, the intermediate tube 830 may be removed from the first portion 824 of the cannula 813, thereby unlocking the interbody device interface 814 with respect to the port 781 of the device 700 and allowing the outer tube 810 (and the entire instrument system 800) to be removed from the implanted device 700.

The inner tube 850 (which also may be referred to as an "expansion tube," an "expansion member," or a "bone graft tube") may have an elongated shape extending along a longitudinal axis $A_{IT}$ of the inner tube 850. When the instrument system 800 is assembled for use, the longitudinal axis $A_{IT}$ of the inner tube 850 may coincide with the longitudinal axis $A_{IS}$ of the instrument system 800. The inner tube 850 may include a first end 851 (which also may be referred to as a "distal end"), a second end (which also may be referred to as a "proximal end") disposed opposite the first end 851 in the direction of the longitudinal axis $A_{IT}$ of the inner tube 850, and a cannula 853 (which also may be referred to as a "central aperture" or an "aperture") extending through the inner tube 850 along the longitudinal axis $A_{IT}$ from the first end 851 to the second end thereof. As shown, the cannula 853 of the inner tube 850 may have a fourth inner diameter $ID_4$, which may be constant along the length of the inner tube 850. As shown, the inner tube 850 may have a second outer diameter $OD_2$, which may be constant along the length of the inner tube 850. In some embodiments, as shown, the second outer diameter $OD_2$ may be slightly less than third inner diameter $ID_3$ of the cannula 833 of the intermediate tube 830 and slightly less than the first inner diameter $ID_1$ of the cannula 813 of the outer tube 810. In this manner, the inner tube 850 may be inserted through and received within the cannula 833. The inner tube 850 also may be configured for insertion through the port 781 of the interbody device 700 and into at least a portion of the channel 782 of the device 700, such that the first end 851 engages the actuator portion 785 of the hinge tab 735. In this manner, the inner tube 850 may facilitate expansion of the interbody device 700 from the compact configuration to the expanded configuration and also may facilitate delivery of bone graft or a bone graft substitute into the cavity 740 of the expanded interbody device 700.

The bone graft plunger 870 (which also may be referred to simply as a "plunger") may have an elongated shape extending along a longitudinal axis $A_{BP}$ of the bone graft plunger 870. When the instrument system 800 is assembled for use, the longitudinal axis $A_{BP}$ of the bone graft plunger 870 may coincide with the longitudinal axis $A_{IS}$ of the instrument system 800. The bone graft plunger 870 may include a first end 871 (which also may be referred to as a "distal end") and a second end (which also may be referred to as a "proximal end") disposed opposite the first end 871 in the direction of the longitudinal axis $A_{BP}$. The bone graft plunger 870 may formed as a shaft extending along the longitudinal axis $A_{BP}$. As shown, the bone graft plunger 870 may include a first portion 872 extending from the first end 871 toward the second end of the bone graft plunger 870 and having a third outer diameter $OD_3$, a second portion 873 extending from the first portion 872 toward the second end of the bone graft plunger 870 and having a fourth outer diameter $OD_4$, and an external shoulder 874 positioned at an interface of the first portion 872 and the second portion 873. As shown, the third outer diameter $OD_3$ may be less than the fourth outer diameter $OD_4$. In some embodiments, as shown, the third outer diameter $OD_3$ may be slightly less than fourth inner diameter $ID_4$ of the cannula 853 of the inner tube 850, and the fourth outer diameter $OD_4$ may be greater than fourth inner diameter $ID_4$ of the cannula 853. In this manner, the first portion 872 of the bone graft plunger 870 may be inserted into and received within the cannula 853 of the inner tube 850 to push bone graft or a bone graft substitute out of the cannula 853 and into the cavity 740 of the expanded interbody device 700.

Many modifications of the embodiments of the present disclosure will come to mind to one skilled in the art to which the disclosure pertains upon having the benefit of the teachings presented herein through the foregoing descriptions and the associated drawings. Therefore, it is to be understood that the present invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. An interbody device for implantation within an intervertebral space between a first vertebra and a second vertebra, the interbody device comprising:
    a main body having an elongated shape; and
    an arm movably connected to the main body and having an elongated shape;
    wherein the interbody device has a first end, a second end disposed opposite the first end of the interbody device in a direction of a longitudinal axis of the interbody device, a first side, a second side disposed opposite the first side of the interbody device in a direction of a first transverse axis of the interbody device, a third side, and a fourth side disposed opposite the third side of the interbody device in a direction of a second transverse axis of the interbody device;
    wherein the first transverse axis of the interbody device is perpendicular to the longitudinal axis of the interbody device;
    wherein the second transverse axis of the interbody device is perpendicular to each of the longitudinal axis and the first transverse axis of the interbody device;
    wherein a first overall distance between the first side and the second side of the interbody device increases along at least a majority of a length of the interbody device in a direction from the first end toward the second end of the interbody device;
    wherein the main body has a first side, a second side disposed opposite the first side of the main body in the direction of the first transverse axis of the interbody device, a third side, and a fourth side disposed opposite the third side of the main body in the direction of the second transverse axis of the interbody device;
    wherein the arm has a first side, a second side disposed opposite the first side of the arm in the direction of the first transverse axis of the interbody device, a third side, and a fourth side disposed opposite the third side of the arm in the direction of the second transverse axis of the interbody device; and
    wherein a second overall distance between the third side and the fourth side of the main body is greater than a third overall distance between the third side and the fourth side of the arm.

2. The interbody device of claim 1, wherein the arm is pivotally connected to the main body via a hinge connection defining a pivot axis, wherein the arm is pivotable about the pivot axis with respect to the main body from a compact position to an expanded position, and wherein the pivot axis is parallel to the second transverse axis of the interbody device.

3. The interbody device of claim 2, wherein the hinge connection is positioned closer to the second end of the interbody device than the first end of the interbody device.

4. The interbody device of claim 2, wherein the hinge connection comprises:
    a hinge recess defined between a pair of hinge supports of the main body; and
    a hinge tab of the arm movably disposed within the hinge recess.

5. The interbody device of claim 4, wherein the main body further comprises:
    a port extending from the second end of the interbody device toward the first end of the interbody device; and
    a channel in communication with the port, wherein the channel extends from the port toward the first end of the interbody device.

6. The interbody device of claim 5, wherein a portion of the hinge tab is movably disposed within the channel.

7. The interbody device of claim 2, wherein the main body comprises a first plurality of teeth positioned on the third side of the main body and a second plurality of teeth positioned on the fourth side of the main body.

8. The interbody device of claim 7, wherein each of the first plurality of teeth extends in the direction of the first transverse axis of the interbody device, and wherein each of the second plurality of teeth extends in the direction of the first transverse axis of the interbody device.

9. The interbody device of claim 2, wherein the interbody device has a second overall distance between the first side and the second side of the interbody device at the second end of the interbody device, wherein the interbody device has a third overall distance between the third side and the fourth side of the interbody device at the second end of the interbody device, and wherein the second overall distance is greater than the third overall distance.

10. The interbody device of claim 1, wherein the first transverse axis of the interbody device is perpendicular to the longitudinal axis of the interbody device, and wherein the second transverse axis of the interbody device is perpendicular to each of the longitudinal axis and the first transverse axis of the interbody device.

11. An interbody device for implantation within an intervertebral space between a first vertebra and a second vertebra, the interbody device comprising:
  a main body having an elongated shape; and
  an arm pivotally connected to the main body via a hinge connection defining a pivot axis and having an elongated shape;
  wherein the arm is pivotable about the pivot axis with respect to the main body from a compact position to an expanded position;
  wherein the interbody device has a first end, a second end disposed opposite the first end of the interbody device in a direction of a longitudinal axis of the interbody device, a first side, a second side disposed opposite the first side of the interbody device in a direction of a first transverse axis of the interbody device, a third side, and a fourth side disposed opposite the third side of the interbody device in a direction of a second transverse axis of the interbody device;
  wherein the first transverse axis of the interbody device is perpendicular to the longitudinal axis of the interbody device;
  wherein the second transverse axis of the interbody device is perpendicular to each of the longitudinal axis and the first transverse axis of the interbody device;
  wherein the pivot axis is parallel to the second transverse axis of the interbody device;
  wherein a first overall distance between the first side and the second side of the interbody device increases along at least a majority of a length of the interbody device in a direction from the first end toward the second end of the interbody device;
  wherein the main body has a first side, a second side disposed opposite the first side of the main body in the direction of the first transverse axis of the interbody device, a third side, and a fourth side disposed opposite the third side of the main body in the direction of the second transverse axis of the interbody device; and
  wherein the main body comprises a first plurality of teeth positioned on the third side of the main body and a second plurality of teeth positioned on the fourth side of the main body.

12. The interbody device of claim 11, wherein each of the first plurality of teeth extends in the direction of the first transverse axis of the interbody device, and wherein each of the second plurality of teeth extends in the direction of the first transverse axis of the interbody device.

13. The interbody device of claim 11, wherein the main body further comprises a port extending from the second end of the interbody device toward the first end of the interbody device, and a channel in communication with the port, wherein the channel extends from the port toward the first end of the interbody device.

14. The interbody device of claim 11, wherein the hinge connection is positioned closer to the second end of the interbody device than the first end of the interbody device, and wherein the hinge connection comprises:
  a hinge recess defined between a pair of hinge supports of the main body; and
  a hinge tab of the arm movably disposed within the hinge recess.

15. The interbody device of claim 11, wherein the arm has a first side, a second side disposed opposite the first side of the arm in the direction of the first transverse axis of the interbody device, a third side, and a fourth side disposed opposite the third side of the arm in the direction of the second transverse axis of the interbody device, and wherein the third side and the fourth side of the arm are devoid of any teeth.

16. The interbody device of claim 15, wherein a second overall distance between the third side and the fourth side of the main body is greater than a third overall distance between the third side and the fourth side of the arm.

17. An interbody device for implantation within an intervertebral space between a first vertebra and a second vertebra, the interbody device comprising:
  a main body having an elongated shape; and
  an arm pivotally connected to the main body via a hinge connection defining a pivot axis and having an elongated shape;
  wherein the arm is pivotable about the pivot axis with respect to the main body from a compact position to an expanded position;
  wherein the interbody device has a first end, a second end disposed opposite the first end of the interbody device in a direction of a longitudinal axis of the interbody device, a first side, a second side disposed opposite the first side of the interbody device in a direction of a first transverse axis of the interbody device, a third side, and a fourth side disposed opposite the third side of the interbody device in a direction of a second transverse axis of the interbody device;
  wherein the first transverse axis of the interbody device is perpendicular to the longitudinal axis of the interbody device;
  wherein the second transverse axis of the interbody device is perpendicular to each of the longitudinal axis and the first transverse axis of the interbody device;
  wherein the pivot axis is parallel to the second transverse axis of the interbody device;
  wherein the interbody device has a first overall distance between the first side and the second side of the interbody device at the first end of the interbody device;
  wherein the interbody device has a second overall distance between the first side and the second side of the interbody device at the second end of the interbody device;
  wherein the interbody device has a third overall distance between the third side and the fourth side of the interbody device at the second end of the interbody device;
  wherein the first overall distance is than each of the second overall distance and the third overall distance; and
  wherein the second overall distance is greater than the third overall distance.

18. The interbody device of claim 17, wherein the hinge connection is positioned closer to the second end of the interbody device than the first end of the interbody device, and wherein the hinge connection comprises:
  a hinge recess defined between a pair of hinge supports of the main body; and
  a hinge tab of the arm movably disposed within the hinge recess.

19. The interbody device of claim 17, wherein the main body comprises:
  a port extending from the second end of the interbody device toward the first end of the interbody device; and a channel in communication with the port, wherein the channel extends from the port toward the first end of the interbody device.

20. The interbody device of claim 17, wherein the main body has a first side, a second side disposed opposite the first side of the main body in the direction of the first transverse axis of the interbody device, a third side, and a fourth side disposed opposite the third side of the main body in the direction of the second transverse axis of the interbody device, and wherein the main body comprises a first plurality of teeth positioned on the third side of the main body and a second plurality of teeth positioned on the fourth side of the main body.

* * * * *